US008865400B2

(12) United States Patent
Gudmundsson et al.

(10) Patent No.: US 8,865,400 B2
(45) Date of Patent: Oct. 21, 2014

(54) GENETIC VARIANTS CONTRIBUTING TO RISK OF PROSTATE CANCER

(75) Inventors: Julius Gudmundsson, Reykjavik (IS); Patrick Sulem, Reykjavik (IS)

(73) Assignee: deCODE Genetics ehf., Reykjavik (IE)

(*) Notice: Subject to any disclaimer, the term of this patent is extended or adjusted under 35 U.S.C. 154(b) by 757 days.

(21) Appl. No.: 12/442,171

(22) PCT Filed: Feb. 7, 2008

(86) PCT No.: PCT/IS2008/000003
§ 371 (c)(1),
(2), (4) Date: Mar. 20, 2009

(87) PCT Pub. No.: WO2008/096375
PCT Pub. Date: Aug. 14, 2008

(65) Prior Publication Data
US 2010/0041037 A1     Feb. 18, 2010

(30) Foreign Application Priority Data

Feb. 7, 2007   (IS) ............................... 8604
Jun. 22, 2007  (IS) ............................... 8654

(51) Int. Cl.
*C12Q 1/68*   (2006.01)
*C12P 19/34*  (2006.01)
*C07H 21/02*  (2006.01)
*C07H 21/04*  (2006.01)

(52) U.S. Cl.
CPC ........ *C12Q 1/6886* (2013.01); *C12Q 2600/172* (2013.01); *C12Q 2600/156* (2013.01); *C12Q 2600/106* (2013.01)
USPC .......................... 435/6.1; 435/91.2; 536/24.3

(58) Field of Classification Search
CPC ............... C12Q 1/6886; C12Q 1/6883; C12Q 2600/112; C12Q 2600/118; C12Q 2600/156; G06F 19/18; G06F 19/00; G06F 19/3431
See application file for complete search history.

(56) References Cited

U.S. PATENT DOCUMENTS

| | | | |
|---|---|---|---|
| 4,376,110 A | 3/1983 | David et al. |
| 5,223,409 A | 6/1993 | Ladner et al. |
| 5,288,644 A | 2/1994 | Beavis et al. |
| 5,445,934 A | 8/1995 | Fodor et al. |
| 5,700,637 A | 12/1997 | Southern |
| 5,744,305 A | 4/1998 | Fodor et al. |
| 5,945,334 A | 8/1999 | Besemer et al. |
| 6,054,270 A | 4/2000 | Southern |
| 6,300,063 B1 | 10/2001 | Lipshutz et al. |
| 6,355,623 B2 | 3/2002 | Seidman et al. |
| 6,429,027 B1 | 8/2002 | Chee et al. |
| 6,733,977 B2 | 5/2004 | Besemer et al. |
| 6,858,394 B1 | 2/2005 | Chee et al. |
| 7,364,858 B2 | 4/2008 | Barany et al. |

| | | | |
|---|---|---|---|
| 2005/0136407 A1 | 6/2005 | Cramer et al. |
| 2005/0255507 A1 | 11/2005 | Jenkins et al. |
| 2006/0051763 A1 | 3/2006 | Loukola et al. |
| 2009/0317799 A1 | 12/2009 | Amundadottir et al. |
| 2010/0129799 A1 | 5/2010 | Guomundsson et al. |
| 2011/0053281 A1 | 3/2011 | Thorlacius et al. |

FOREIGN PATENT DOCUMENTS

| | | |
|---|---|---|
| WO | WO-90/02809 A1 | 3/1990 |
| WO | WO-91/17271 A1 | 11/1991 |
| WO | WO-92/01047 A1 | 1/1992 |
| WO | WO-92/09690 A2 | 6/1992 |
| WO | WO-92/15679 A1 | 9/1992 |
| WO | WO-92/18619 A1 | 10/1992 |
| WO | WO-92/20791 A1 | 11/1992 |
| WO | WO-93/01288 A1 | 1/1993 |
| WO | WO-99/64590 | 12/1999 |
| WO | WO-2004/028346 | 4/2004 |
| WO | WO-2006/063285 | 6/2006 |

OTHER PUBLICATIONS

Andiappan (BMC Genetics. 2010. 11: 36).*
Sotos et al. Statistics Education Research Journal Nov. 2009, 8(2):33-55.*
Langdahl (Journal of Bone and Mineral Research 2000 vol. 15, No. 3, pp. 402-414.*
Wall (Nature Reviews Genetics (2003) vol. 4, pp. 587-597).*
Terwilliger and Hiekkalinna European Journal of Human Genetics (2006) 14, 426-437.*
Panter et al (Cultural Diversity and Ethnic Minority Psychology 15(1):51-66 [2009]).*
Dyson et al (Ethnicity and Health 11(2):169-189 [May 2006]).*
NCBI, National Center for Biotechnology Information, dbSNP database: rs7501939, ss43985207, submitted Jul. 18, 2005.*
NCBI, National Center for Biotechnology Information, dbSNP database: rs7501939, ss67583123, submitted Nov. 16, 2006.*
NCBI, National Center for Biotechnology Information, dbSNP database: rs4430796, ss43986967, submitted Jul. 18, 2005.*
NCBI, National Center for Biotechnology Information, dbSNP database: rs4430796, ss67335670, submitted Nov. 16, 2006.*
Agami et al., RNAi and related mechanisms and their potential use for therapy, Curr. Opin. Chem. Biol., 6:829-34 (2002).
Altschul et al., Gapped BLAST and PSI-BLAST: a new generation of protein database search programs, Nucleic Acids Res., 25:3389-402 (1997).
Amarzguioui et al., Approaches for chemically synthesized siRNA and vector-mediated RNAi, FEBS Lett., 579:5974-81 (2005).
Amundadottir et al., A common variant associated with prostate cancer in European and African populations, Nat. Genet., 38:652-8 (2006).
Amundadottir et al., Cancer as a complex phenotype: pattern of cancer distribution within and beyond the nuclear family, PLoS Med., 1:e65 (2004).
Bellanne-Chantelot et al., Large genomic rearrangements in the hepatocyte nuclear factor-1beta (TCF2) gene are the most frequent cause of maturity-onset diabetes of the young type 5, Diabetes, 54:3126-32 (2005).

(Continued)

*Primary Examiner* — Jehanne Sitton
(74) *Attorney, Agent, or Firm* — Marshall, Gerstein & Borun LLP

(57) ABSTRACT

The present invention is characterized by certain genetic variants being susceptibility variants for prostate cancer. The invention relates to methods of determining increased susceptibility to prostate cancer, as well as methods of determining decreased susceptibility to prostate cancer, using such variants. The invention further relates to kits for determining a susceptibility to prostate cancer.

14 Claims, 1 Drawing Sheet

(56) References Cited

OTHER PUBLICATIONS

Bennett, Efficiency of antisense oligonucleotide drug discovery, Antisense Nucleic Acid Drug Dev., 12:215-24 (2002).
Bonnycastle et al., Common variants in maturity-onset diabetes of the young genes contribute to risk of type 2 diabetes in Finns, Diabetes, 55:2534-40 (2006).
Bosher et al., RNA interference: genetic wand and genetic watchdog, Nat. Cell Biol., 2:E31-6 (2000).
Brummelkamp et al., A system for stable expression of short interfering RNAs in mammalian cells, Science, 296:550-3 (2002).
Camp et al., Meta-analysis of associations of the Ser217Leu and Ala541Thr variants in ELAC2 (HPC2) and prostate cancer, Am. J. Hum. Genet., 71:1475-8 (2002).
Carpten et al., Germline mutations in the ribonuclease L gene in families showing linkage with HPC1, Nat. Genet., 30:181-4 (2002).
Casey et al., RNASEL Arg462Gln variant is implicated in up to 13% of prostate cancer cases, Nat. Genet., 32:581-3 (2002).
Chang et al., Linkage and association of CYP17 gene in hereditary and sporadic prostate cancer, Int. J. Cancer, 94:354-9 (2001).
Chen et al., Clinical development of antisense oligonucleotides as anti-cancer therapeutics, Methods Mol. Med., 75:621-36 (2003).
Chen et al., Fluorescence polarization in homogeneous nucleic acid analysis, Genome Res., 9:492-8 (1999).
Chen et al., The evolution of gene regulaton by transcrpton factors and microRNAs, Nat. Rev. Genet., 8:93-103 (2007).
Chi et al., Genomewide view of gene silencing by small interfering RNAs, Proc. Natl. Acad. Sci. USA, 100:6343-6 (2003).
Church et al., Genomic sequencing, Proc. Natl. Acad. Sci. USA, 81:1991-5 (1984).
Cookson, Prostate cancer: screening and early detection, Cancer Control, 8:133-40 (2001).
Cotton et al., Reactivity of cytosine and thymine in single-base-pair mismatches with hydroxylamine and osmium tetroxide and its application to the study of mutations, Proc. Natl. Acad. Sci. USA, 85:4397-401 (1988).
Cunningham et al., Genome linkage screen for prostate cancer susceptibility loci: Results from the Mayo Clinic familial prostate cancer study, The Prostate, 57:335-46 (2003).
Daly et al., High-resolution haplotype structure in the human genome, Nat. Genet., 29:229-32 (2001).
Dawson et al., A first-generation linkage disequilibrium map of human chromosome 22, Nature, 418:544-8 (2002).
Dempster et al., Manual likelihood from incomplete data via the EM algorithm, J. Royal Stat. Soc. B, 39:1-38 (1977).
Devlin et al., Genomic control for association studies, Biometrics, 55:997-1004 (1999).
Dias et al., Antisense oligonucleotides: basic concepts and mechanisms, Mol. Cancer Ther., 1:347-55 (2002).
Drivdahl et al., Suppression of growth and tumorigenicity in the prostate tumor cell line M12 by overexpression of the transcription factor SOX9, Oncogene, 23:4584-93 (2004).
Duggan et al., Two genome-wide association studies of aggressive prostate cancer implicate putative prostate tumor suppressor gene DAB2IP, J. Natl. Cancer Inst., 99:1836-44 (2007).
Edghill et al., Mutations in hepatocyte nuclear factor-1beta and their related phenotypes, J. Med. Genet., 43:84-90 (2005).
Falk et al., Haplotype relative risks: an easy reliable way to construct a proper control sample for risk calculations, Ann. Hum. Genet., 51:227-33 (1987).
Fire et al., Potent and specific genetic interference by double-stranded RNA in *Caenorhabditis elegans*, Nature, 391:806-11 (1998).
Flavell et al., Analysis of the beta-delta-globin gene loci in normal and Hb Lepore DNA: direct determination of gene linkage and intergene distance, Cell, 15:25-41 (1978).
Frayling et al., Genome-wide association studies provide new insights into type 2 diabetes aetiology, Nat. Rev. Genet., 8:657-62 (2007).
Freedman et al., Admixture mapping identfies 8q24 as a prostate cancer risk locus in African-Amercan men, Proc. Nat. Acad. Sci. USA, 103:14068-73 (2006).
Fuchs et al., Targeting recombinant antibodies to the surface of *Escherichia coli*: fusion to a peptidoglycan associated lipoprotein, Bio/Technology, 9:1369-74 (1991).
Gabriel et al., The structure of haplotype blocks in the human genome, Science, 296:2225-9 (2002).
Galfre et al., Antibodies to major histocompatibility antigens produced by hybrid cell lines, Nature, 266:550-2 (1977).
Geever et al., Direct identification of sickle cell anemia by blot hybridization, Proc. Natl. Acad. Sci. USA, 78:5081-5 (1981).
Grant et al., Variant of transcription factor 7-like 2 (TCF7L2) gene confers risk of type 2 diabetes, Nat. Genet., 38:320-3 (2006).
Gretarsdottir et al., The gene encoding phosphodiesterase 4D confers risk of ischemic stroke, Nat. Genet., 35:131-8 (2003).
Griffiths et al., Human anti-self antibodies with high specificity from phage display libraries, EMBO J., 12:725-34 (1993).
Gudmundsson et al., Genome-wide association study identifies a second prostate cancer susceptibility variant at 8q24, Nat. Genet., 39:631-7 (2007).
Gudmundsson et al., Two variants on chromosome 17 confer prostate cancer risk, and the one in TCF2 protects against type 2 diabetes, Nat. Genet., 39:977-83 (2007).
Gulcher et al., Protection of privacy by third-party encryption in genetic research in Iceland, Eur. J. Hum. Genet., 8:739-42 (2000).
Haiman et al., Multiple regions within 8q24 independently affect risk for prostate cancer, Nat. Genet., 39:638-44 (2007).
Hay et al., Bacteriophage cloning and *Escherichia coli* expression of a human IgM Fab, Hum. Antibodies Hybridomas, 3:81-5 (1992).
Hedelin et al., Dietary intake of phytoestrogens, estrogen receptor-beta polymorphisms and the risk of prostate cancer, Prostate, 66:1512-20 2006.
Helgadottir et al., A common variant on chromosome 9p21 affects the risk of myocardial infarction, Science, 316:1491-3 (2007).
Hill et al., Theor. Appl. Genet., 22:226-31 (1968).
Hill-Harfe et al., Fine mapping of chromosome 17 translocation breakpoints > or = 900 Kb upstream of SOX9 in acampomelic campomelic dysplasia and a mild, familial skeletal dysplasia, Am. J. Hum. Genet., 76:663-74 (2005).
Hunter, Genetics: a touch of elegance with RNAi, Curr. Biol., 9:R440-2 (1999).
Huse et al., Generation of a large combinatorial library of the immunoglobulin repertoire in phage lambda, Science, 246:1275-81 (1989).
International Preliminary Report on Patentability for corresponding International Application No. PCT/IS2008/000003, dated Aug. 11, 2009.
International Search Report and Written Opinion for corresponding International Application No. PCT/IS2008/000003, dated Oct. 31, 2008.
Janer et al., Genomic scan of 254 hereditary prostate cancer families, The Prostate, 57:309-19 (2008).
Jeffreys et al., Intensely punctate meiotic recombination in the class II region of the major histocompatibility complex, Nat. Genet., 29:217-22 (2001).
Jemal et al., Cancer statistics, 2002, CA Cancer J. Clin., 52:23-47 (2002).
Karlin et al., Applications and statistics for multiple high-scoring segments in molecular sequences, Proc. Natl. Acad. Sci. USA, 90:5873-7 (1993).
Kasper et al., A meta-analysis of diabetes mellitus and the risk of prostate cancer, Cancer Epidemiol. Biomarkers Prev., 15:2056-62 (2006).
Kohler et al., Continuous cultures of fused cells secreting antibody of predefined specificity, Nature, 256:495-7 (1975).
Koopman, Sex determination: a tale of two Sox genes, Trends Genet., 21:367-70 (2005).
Kozbor et al., The production of monoclonal antibodies from human lymphocytes, Immunol. Today, 4:72-9 (1983).
Kraft et al., Genetic variation in the HSD17B1 gene and risk of prostate cancer, PLoS Genet., 1:e68 (2005).

(56) References Cited

OTHER PUBLICATIONS

Kurreck, Antisense technologies. Improvement through novel chemical modifications, Eur. J. Biochem., 270:1628-44 (2003).
Kutyavin et al., A novel endonuclease IV post-PCR genotyping system, Nucleic Acids Res., 34:e128 (2006).
Lange et al., Fine-mapping the putative chromosome 17q21-22 prostate cancer susceptibility gene to a 10 cM region based on linkage analysis, Hum. Genet., 121:49-55 (2007).
Lange et al., Genome-wide scan for prostate cancer susceptibility genes using families from the University of Michigan prostate cancer genetics project finds evidence for linkage on chromosome 17 near BRCA1, Prostate, 57:326-34 (2003).
Lavery et al., Antisense and RNAi: powerful tools in drug target discovery and validation, Curr. Opin. Drug Discov. Devel., 6:561-9 (2003).
Leipoldt et al., Two novel translocation breakpoints upstream of SOX9 define borders of the proximal and distal breakpoint cluster region in campomelic dysplasia, Clin. Genet., 71:67-75 (2007).
Lerner, How to make a hybridoma, Yale J. Biol. Med., 54:385-402 (1981).
Lewontin, The interaction of selection and linkage. II. Optimum models, Genetics, 50:757-82 (1964).
Lichtenstein et al., Environmental and heritable factors in the causation of cancer—analyses of cohorts of twins from Sweden, Denmark, and Finland, N. Engl. J. Med., 343:78-85 (2000).
Lindmark et al., Analysis of the macrophage scavenger receptor 1 gene in Swedish hereditary and sporadic prostate cancer, Prostate, 59:132-40 (2004).
Maier et al., Mutation screening and association study of RNASEL as a prostate cancer susceptibility gene, Br. J. Cancer, 92:1159-64 (2005).
Makridakis et al., Association of mis-sense substitution in SRD5A2 gene with prostate cancer in African-American and Hispanic men in Los Angeles, USA, Lancet, 354:975-8 (1999).
Maniatis et al., The first linkage disequilibrium (LD) maps: delineation of hot and cold blocks by diplotype analysis, Proc. Natl. Acad. Sci USA, 99:2228-33 (2002).
Mantel et al., Statistical aspects of the analysis of data from retrospective studies of disease, J. Natl. Cancer Inst., 22:719-48 (1959).
Marchini et al., A new multipoint method for genome-wide association studies by imputation of genotypes, Nat. Genet., 39:906-13 (2007).
Marques et al., A structural basis for discriminating between self and nonself double-stranded RNAs in mammalian cells, Nat. Biotechnol., 24:559-65 (2006).
May et al., Crossover clustering and rapid decay of linkage disequilibrium in the Xp/Yp pseudoautosomal gene SHOX, Nat. Genet., 31:272-5 (2002).
McManus et al., Gene silencing in mammals by small interfering RNAs, Nat. Rev. Genet., 3:737-47 (2002).
Miller et al., Germ-line mutations of the macrophage scavenger receptor 1 gene: association with prostate cancer risk in African-American men, Cancer Res., 63:3486-9 (2003).
Mistry et al., Meta-analysis of prostate-specific antigen and digital rectal examination as screening tests for prostate carcinoma, J. Am. Board Fam. Pract., 16:95-101 (2003).
Myers et al., A fine-scale map of recombination rates and hotspots across the human genome, Science, 310:321-4 (2005).
Myers et al., Detection of single base substitutions by ribonuclease cleavage at mismatches in RNA:DNA duplexes, Science, 230:1242-6 (1985).
Myers et al., The distribution and causes of meiotic recombination in the human genome, Biochem. Soc. Trans., 34:526-30 (2006).
Nam et al., V89L polymorphism of type-2, 5-alpha reductase enzyme gene predicts prostate cancer presence and progression, Urology, 57:199-204 (2001).
Nelson et al., Prostate cancer, N. Eng. J. Med., 349:366-81 (2003).
Nicolae et al., Measuring the relative information in allele-sharing linkage studies, Biometrics, 60:368-75 (2004).
Nicolae, Testing untyped alleles (TUNA)-applications to genome-wide association studies, Genet. Epidemiol., 30:718-27 (2006).
Nielsen et al., Peptide nucleic acid (PNA). A DNA mimic with a peptide backbone, Bioconjug. Chem., 5:3-7 (1994).
Nielsen et al., Sequence-selective recognition of DNA by strand displacement with a thymine-substituted polyamide, Science, 254:1497-500 (1991).
Nwosu et al., Heterogeneity of genetic alterations in prostate cancer: evidence of the complex nature of the disease, Hum. Mol. Genet., 10:2313-8 (2001).
Orita et al., Detection of polymorphisms of human DNA by gel electrophoresis as single-strand conformation polymorphisms, Proc. Natl. Acad. Sci. USA, 86:2766-70 (1989).
Ostrander et al., Genetics of prostate cancer: too many loci, too few genes, Am. J. Hum. Genet., 67:1367-75 (2000).
Parkin et al., Global cancer statistics, 2002, CA Cancer J. Clin., 55:74-108 (2005).
Patil et al., Blocks of limited haplotype diversity revealed by high-resolution scanning of human chromosome 21, Science, 294:1719-23 (2001).
Pe'er et al., Evaluating and improving power in whole-genome association studies using fixed marker sets, Nat. Genet., 38:663-7 (2006).
Pearson et al., Improved tools for biological sequence comparison, Proc. Natl. Acad. Sci. USA, 85:2444-8 (1988).
Peschel et al., Surgery, brachytherapy, and external-beam radiotherapy for early prostate cancer, Lancet Oncol., 4:233-41 (2003).
Phillips et al., Chromosome-wide distribution of haplotype bocks and the role of recombination hot spots, Nat. Genet. 33:382-7 (2003).
Plasterk et al., The silence of the genes, Curr. Opin. Genet. Dev., 10:562-7 (2000).
Punglia et al., Effect of verification bias on screening for prostate cancer by measurement of prostate-specific antigen, N. Engl. J. Med., 349:335-42 (2003).
Rebbeck et al., Association of HPC2/ELAC2 genotypes and prostate cancer, Am. J. Hum. Genet., 67:1014-9 (2000).
Rebouissou et al., Germline hepatocyte nuclear factor 1alpha and 1beta mutations in renal cell carcinomas, Hum. Mol. Genet., 14:603-14 (2005).
Reich et al., Linkage disequilibrium in the human genome, Nature, 411:199-204 (2001).
Rennert et al., A novel founder mutation in the RNASEL gene, 471delAAAG, is associated with prostate cancer in Ashkenazi Jews, Am. J. Hum. Genet., 71:981-4 (2002).
Reynolds et al., Rational siRNA design for RNA interference, Nat. Biotechnol., 22:326-30 (2004).
Ries et al. (eds). Cancer Incidence and Survival among Children and Adolescents: United States SEER Program 1975-1995, National Cancer Institute, SEER Program. NIH Pub. No. 99-4649. Bethesda, MD, 1999.
Risch et al., The future of genetic studies of complex human diseases, Science, 273:1516-7 (1996).
Risch et al., The relative power of family-based and case-control designs for linkage disequilibrium studies of complex human diseases I. DNA pooling, Genome Res., 8:1273-88 (1998).
Roeder et al., Using linkage genome scans to improve power of association in genome scans, Am. J. Hum. Genet., 78:243-52 (2006).
Rokman et al., Germline alterations of the RNASEL gene, a candidate HPC1 gene at 1q25, in patients and families with prostate cancer, Am. J. Hum. Genet., 70:1299-304 (2002).
Sanger et al., DNA sequencing with chain-terminating inhibitors, Proc. Natl. Acad. Sci. USA, 74:5463-7 (1977).
Schleutker et al., Genome-wide scan for linkage in finnish hereditary prostate cancer (HPC) families identifies novel susceptibility loci at 11q14 and 3p25-26, The Prostate, 57:280-9 (2003).
Seppala et al., Germ-line alterations in MSR1 gene and prostate cancer risk, Clin. Cancer Res., 9:5252-6 (2003).
Severi et al., ELAC2/HPC2 polymorphisms, prostate-specific antigen levels, and prostate cancer, J. Natl. Cancer Inst., 95:818-24 (2003).
Shea et al., ELAC2 and prostate cancer risk in Afro-Caribbeans of Tobago, Hum. Genet., 111:398-400 (2002).
Sheffield et al., Attachment of a 40-base-pair G + C-rich sequence (GC-clamp) to genomic DNA fragments by the polymerase chain reaction results in improved detection of single-base changes, Proc. Natl. Acad. Sci. USA, 86:232-6 (1989).
Shi, Mammalian RNAi for the masses, Trends Genet., 19:9-12 (2003).
Shuey et al., RNAi: gene-silencing in therapeutic intervention, Drug Discov. Today, 7:1040-6 (2002).

(56) References Cited

OTHER PUBLICATIONS

Silander et al., Genetic variation near the hepatocyte nuclear factor-4 alpha gene predicts susceptibility to type 2 diabetes, Diabetes, 53:1141-9 (2004).
Simard et al., Perspective: prostate cancer susceptibility genes, Endocrinology, 143:2029-40 (2002).
Siolas et al., Synthetic shRNAs as potent RNAi triggers, Nat. Biotechnol., 23:227-31 (2005).
Smith et al., A high-density admixture map for disease gene discovery in african americans, Am. J. Hum. Genet., 74:1001-13 (2004).
Stacey et al., Common variants on chromosomes 2q35 and 16q12 confer susceptibility to estrogen receptor-positive breast cancer, Nat. Genet., 39:865-9 (2007).
Stanford et al., Association of HPC2/ELAC2 polymorphisms with risk of prostate cancer in a population-based study, Cancer Epidemiol. Biomarkers Prev., 12:876-81 (2003).
Stephens et al., Antisense oligonucleotide therapy in cancer, Curr. Opin. Mol. Ther., 5:118-22 (2003).
Stumpf et al., Demography, recombination hotspot intensity, and the block structure of linkage disequilibrium, Curr. Biol., 13:1-8 (2003).
Suarez et al., Polymorphisms in the prostate cancer susceptibility gene HPC2/ELAC2 in multiplex families and healthy controls, Cancer Res., 61:4982-4 (2001).
Tavtigian et al., A candidate prostate cancer susceptibility gene at chromosome 17p, Nat. Genet., 27:172-80 (2001).
Terasawa et al., Epigenetic inactivation of TCF2 in ovarian cancer and various cancer cell lines, Br. J. Cancer, 94:914-21 (2006).
Terwilliger et al., A haplotype-based 'haplotype relative risk' approach to detecting allelic associations, Hum. Hered., 42:337-46 (1992).
Thompson et al., Prevalence of prostate cancer among men with a prostate-specific antigen level < or =4.0 ng per milliliter, N. Engl. J. Med., 350:2239-46 (2004).
Thompson, Applications of antisense and siRNAs during preclinical drug development, Drug Discov. Today, 7:912-7 (2002).
Torelli et al., ADVANCE and ADAM: two algorithms for the analysis of global similarity between homologous informational sequnces. CABIOS, 10:3-5 (1984).
Velagaleti et al., Position effects due to chromosome breakpoints that map approximately 900 Kb upstream and approximately 1.3 Mb downstream of SOX9 in two patients with campomelic dysplasia, Am. J. Hum. Genet., 76:652-62 (2005).
Vesprini et al., HPC2 variants and screen-detected prostate cancer, Am. J. Hum. Genet., 68:912-7 (2001).
Vickers et al., Efficient reduction of target RNAs by small interfering RNA and RNase H-dependent antisense agents. A comparative analysis, J. Biol. Chem., 278:7108-18 (2003).
Wall et al., Haplotype blocks and linkage disequilibrium in the human genome, Nat. Rev. Genet., 4:487-97 (2003).
Wang et al., Analysis of the RNASEL gene in familial and sporadic prostate cancer, Am. J. Hum. Genet., 71:116-23 (2002).
Wang et al., Antisense anticancer oligonucleotide therapeutics, Curr. Cancer Drug Targets, 1:177-96 (2001).
Wang et al., Distribution of recombination crossovers and the origin of haplotype blocks: the interplay of population history, recombination, and mutation, Am. J. Hum. Genet., 71:1227-34 (2002).
Wang et al., No association of germline alteration of MSR1 with prostate cancer risk, Nat. Genet., 35:128-9 (2003).
Wang et al., Role of HPC2/ELAC2 in hereditary prostate cancer, Cancer Res., 61:6494-9 (2001).
Wang et al., SOX9 is expressed in normal prostate basal cells and regulates androgen receptor expression in prostate cancer cells, Cancer Res. 67:528-36 (2007).
White et al., Prohibitin mutations are uncommon in prostate cancer families linked to chromosome 17q, Prostate Cancer Prostatic Dis., 9:298-302 (2006).
Wiklund et al., Genetic analysis of the RNASEL gene in hereditary, familial, and sporadic prostate cancer, Clin. Cancer Res., 10:7150-6 (2004).
Winckler et al., Evaluation of common variants in the six known maturity-onset diabetes of the young (MODY) genes for association with type 2 diabetes, Diabetes, 56:685-93 (2007).
Winklund et al., Genome-wide scan of Swedish families with hereditary prostate cancer: Suggestive evidence of linkage at 5q11.2 and 19p13.3, The Prostate, 57:290-7 (2003).
Witte et al., Genome-wide scan of brothers: Replication and fine mapping of prostate cancer susceptibility and aggressiveness loci, The Prostate, 57:298-308 (2003).
Xia et al., siRNA-mediated gene silencing in vitro and in vivo, Nat. Biotechnol., 20:1006-10 (2002).
Xu et al., Germline mutations and sequence variants of the macrophage scavenger receptor 1 gene are associated with prostate cancer risk, Nat. Genet., 32:321-5 (2000).
Xu et al., A combined genomewide linkage scan of 1,233 families for prostate cancer-susceptibility genes conducted by the international consortium for prostate cancer genetics, Am. J. Hum. Genet., 77:219-29 (2005).
Xu et al., Genome-wide scan for prostate cancer susceptibility genes in the Johns Hopkins hereditary prostate cancer families, The Prostate, 57:320-5 (2003).
Yeager et al., Genome-wide association study of prostate cancer identifies a second risk locus at 8q24, Nat. Genet., 39:645-9 (2007).
Zhang et al., A dynamic programming algorithm for haplotype block partitioning, Proc. Natl. Acad. Sci. USA, 99:7335-9 (2002).
Zuhlke et al. Tuncating BRCA1 mutations are uncommon in a cohort of hereditary prostate cancer families with evidence of linkage to 17q markers, Clin. Cancer Res., 10:5975-80 (2004).
"Division of Genomic Medicine: A Catalog of Published Genome-Wide Association Studies," National Human Genome Research Institute (2013). Retrieved from the Internet on Feb. 12, 2013: URL:http://www.genome.gov/gwastudies/.
"Good Laboratory Practices for Molecular Genetic Testing for Heritable Diseases and Conditions," Morbidity and Mortality Weekly Report, vol. 58, No. RR-6, Department of Health and Human Services Centers for Disease Control and Prevention (Jun. 12, 2009).
Bitton et al., "The Framingham Heart Study's Impact on Global Risk," Prog Cardiovasc Dis., 53(1):68-78 (2010).
Elliott et al., "Evaluation of Association of HNF1B Variants with Diverse Cancers: Collaborative Analysis of Date from 19 Genome-Wide Association Studies," PLOS ONE, 5(5):e10858 (2010).
Grys, "Actuarial Considerations on Genetic Testing," Phil. Trans. R. Soc. Lond. B, 352:1057-1061 (1997).
Han et al., "Implication of Genetic Variants Near SLC30A8, HHEX, CDKAL1, CDKN2S/B, IGF2BP2, FTO, TCF2, KCNQ1, and WFS1 in Type 2 Diabetes in a Chinese Population," BMC Medical Genetics, 11:81 (2010).
Issue Brief, American Academy of Actuaries, "Genetic Information and Voluntary Life Insurance," (1998).
Levin et al., "Chromosome 17q12 Variants Contribute to Risk of Early-Onset Prostate Cancer," Cancer Res., 68:6492-6495 (2008).
NCBI dbSNP database of short genetic variations summary, RefSNP clusters in the human genome, www.ncbi.nlm.nih.gov/projects/SNP/snp_summary.cgi http://www.ncbi.nlm.nih.gov/projects/SNP/snp_summary.cgi accessed Feb. 12, 2013.
Setiawan et al., "HNF1B and Endometrial Cancer Risk: Results from the PAGE Study," PLOS ONE, 7(1):e30390 (2012).
Silberberg, Chemistry the Molecular Nature of Matter and Change, Fourth Edition, p. G-12 (2006).
Stevens et al., "HNF18 and JAZF1 Genes, Diabetes, and Prostate Cancer Risk," Prostate, 70(6):601-607 (2010).
The International HapMap Consortium, "A Haplotype Map of the Human Genome," Nature, 437:1299-1320 (2005).
Zhang et al., "Association of Single Nucleotide Polymorphisms in TCF2 with Type 2 Diabetes Susceptibility in a Han Chinese Population," PLOS ONE, 7(12):e52938 (2012).
Zick et al., "Genetic Testing for Alzheimer's Disease and its Impact on Insurance Purchasing Behavior," Health Affairs, 24(2):481-490 (2005).

\* cited by examiner

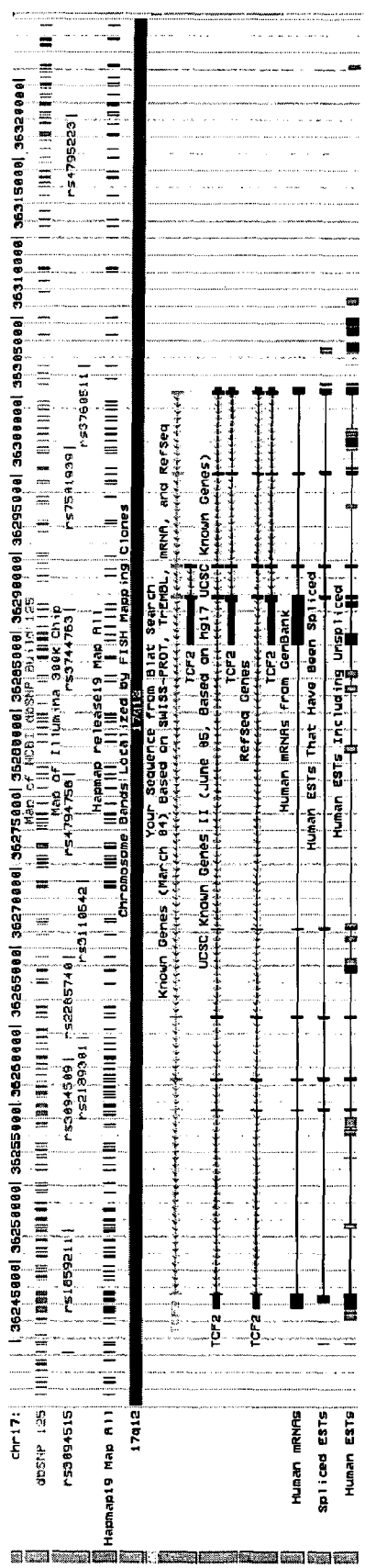

SEQUENCE LISTING

<160> NUMBER OF SEQ ID NOS: 362

<210> SEQ ID NO 1
<211> LENGTH: 600
<212> TYPE: DNA
<213> ORGANISM: Homo sapiens

<400> SEQUENCE: 1

```
tcagtgaagg gaaagtaacc cagttaaatc aaggaaaaga ttttttttaca gcatgtatct    60
gtggcttgta caaagttttt acttttgact ggctattttg atgttgttag aaatagtgag   120
gatccacttc tagaaatact ggatattaga aactgttttg atgacagtgg tatcactctg   180
aagttagaga tatagccatt ccctggtttc ctcactattc aattcacttg caaaaggact   240
ctgcagaaca gattaacagt acattgttct gtaattctct ggttactcta acagggtcgg   300
rgtaaatttg taaagaaatg caaaccagct tgaggcagca ctgcccaatt tgatcaaaac   360
taaatgcaac catcgtgggt tcaagtttgg tggtccaaaa cattggaatg tttcaaagac   420
atctaaatgc aatgccagtg ttgttttatt tggtttgggg tttgctatcc ctttatgtta   480
aacaggagtt cagaaaaatt gcacaaaaga ctcactgtct gtttctatga atgcctacat   540
actcagtagc caatgttact gataaatgaa aacatcaaat atacatgaac aaagtcttta   600
```

<210> SEQ ID NO 2
<211> LENGTH: 600
<212> TYPE: DNA
<213> ORGANISM: Homo sapiens

<400> SEQUENCE: 2

```
ggcgtgaacc cgggaggcgg agcttgcagt gagccgagat cgcgccactg cactccagtc    60
tgggtggcag agcgagaccc cgtctcaaaa agttaaataa ataaataaat aaataaaaca   120
aaaataacaa taacaacaat ctcttgaaga ggctgttgta tttgtaaaac gtcccttcct   180
cagcatcttg agaaactttc tggacctctg tcttttgaga agtttccagt ctgcctttcc   240
tgcctccttc tcctttctga agaaattctc attgaataca gagaggcagc acagactgga   300
ratgctgcat aaagcttaaa ttgggcaggg cccaagcgtt gttgggtctt tggagacaat   360
```

```
ggctcctgag aattttttta ggctttccag gaactacaga gagttgcttc atgtcaggaa      420
cacaaattct taaagagcta gtcaccaagt atggggggcc aacccattct tggaaaggtc      480
tctcgctcta agcagcaaac agctctcatg ttgcttcttc caatctattc atgtaatgct      540
cccaacaaaa gcacaaacac cacaatatga aatgaacacc taaaaccatt cctttcacca      600

<210> SEQ ID NO 3
<211> LENGTH: 600
<212> TYPE: DNA
<213> ORGANISM: Homo sapiens

<400> SEQUENCE: 3
tggtttcaac tttgccaata tcttttcttg cttattgaac agatgctttg aaaagagaga       60
tataatttaa aactagaaat taaaatagtg tgcagcacag aacaaaagta ctaaagaagc      120
aatatataca tgtttactat ttatttaatg caggtacata tttaacttac aaaaaccagc      180 acccccattac tgtatgttga tatatatatt agcttgatag aacaagaaaa aaaacggaag      240
ggaaaactag tttcaggtga aacaaaaaag aaaacggtgt agaggctgaa atagatacag      300
yattgcaaca taataagcaa ttttatttct aaatggcgcc tttaaatatg tcaaataaaa      360
ttaattctgt ttaatgaata aaaatccagt aatcgaacat attttataag catttgggta      420
gttgtgatta ttttattaag actttgatat taaactcgtg agaacacagg ctttgataga      480 gatgttttg agaaatgcaa acttttttata ttaattatat ataagaacga atttctcaag      540
tatttacaaa ggtaatttcc aagtacacaa tatgaggaag taacaagaag aacaaaaaat      600

<210> SEQ ID NO 4
<211> LENGTH: 600
<212> TYPE: DNA
<213> ORGANISM: Homo sapiens

<400> SEQUENCE: 4
gcagtatttt gttaatcttt gctgcccttta tttactgtgg gagaggcgct ttggttttttc       60 ctcttcttcc tttggtatag cactaatgta ttttatatgt ctttaatctc agttccagtt      120
ctgtcaatat ttgagcttat cttaaaccga agaactccaa aggagagtca agaaagtaa      180 attctcaccc cggaaggcaa ataacaatta tttcattaaa cattcaaatc acaaagaaca      240
ccttggacca gttcttgata taaataagag gctgcagact tttccaaatc cctgcccgtg      300
kgatgaacac tttaaaggtc ccaagatttc taataatggg gctaaatttc ccaaaatgtg      360
tttttctgct aaaaaatcca gtaacaagga actgtacaaa ttctaatctc tgtatgagtc      420
ttcatctttg gaatgcctat tcctgaagat gagagatgga tagtaggaac ctatgtatcg      480
atctgggtta gccactggg ctcattaatg aaatatcact gggaggagca gcccagcatc      540
ctatacgtga gccaagcatt tagaattgcc tttaggattc ttcacactgt tagcagccaa      600

<210> SEQ ID NO 5
<211> LENGTH: 180
<212> TYPE: DNA
<213> ORGANISM: Homo sapiens

<400> SEQUENCE: 5
tcacaaatgt catatatcca tatattgaga cacacacaca cacacacaca cacacacaca       60
catatatata cacatacata cagtcttgct atcatcgcta aaattttgt catcatctaa      120 ctcatttttg gctttttttt tctggctttc atacttttcc ttatctcatc tgttagattg      180
```

```
<210> SEQ ID NO 6
<211> LENGTH: 600
<212> TYPE: DNA
<213> ORGANISM: Homo sapiens

<400> SEQUENCE: 6
tctgtcttcc agaacctcac atttattctt ccttctctgt ggaataccct ttcactactt    60
ttactggcta atcctatttt atcctttaga tgtcaaatta catggcattt cctccaagaa   120 acttttctc ttcttcctag cctcatatag attagttccc tgtactatga gctagcagag   180
ccgactgaat ccccactatc ataaaaaata cttagtacat tttgttggaa tgtataatgt   240
ctcctcaata cactgagagt tccataaaga caggagctat ttctgatttg ctcaacccac   300
rtaccctgag gtagcagaat tcttggccta aagttctgaa tagctttatc acagctaaag   360
cacagttgta aggatggagg cactagatca gtgcaaatac ttgactattt atctaccagg   420
ttaaacctag atggaaaaat acagcttaaa taactcaaaa ttttactgat tgaaacatga   480
tgaaggcccc ttcttcatat attaagtact aagatttaat tcagaattag aaaaaggtca   540
atgtaaatag tcttggacag caagtgtttc tgggaaaggt ttccttgctc taaatcaaat   600

<210> SEQ ID NO 7
<211> LENGTH: 600
<212> TYPE: DNA
<213> ORGANISM: Homo sapiens

<400> SEQUENCE: 7
ctctagctag ggctggttta aatgctccct ccgtgagtgg acatcagcaa gtttggtccc    60
gttttgcttt ctgctataac agggcagcat tgagttcatt gcctcacaac tgttgcacac   120
cccctctcct cagtgcacag aaatactctc cacacgacac tgccactgct gggggacagg   180
agtgggtggc actggtgttt caagactgtt tttctacctc ttcagtgtct cttttagcaa   240
tatgaagttg aaaccaggta ctgtgagtga tcacctgatt tttggttttg ctgaaggtgt   300
ytctttgtgt agataattgt taaattagtg tccttgtagc gggggatgat cattggggcc   360
ttctattctg tcatcttgct ccacttccca tgatcacttt tgtcagcagg cagtgaatcc   420
tgccaggact gagtctgtct caccagggta atggattccc ttctggccca gggtggatct   480
agaaatgcca cctaggagta aagacctata accaggggct tcaggaatct gccttgcact   540
ttattgtact atgactaagt taacacccaa gttgcaagac aaagttttct ttactattcc   600

<210> SEQ ID NO 8
<211> LENGTH: 600
<212> TYPE: DNA
<213> ORGANISM: Homo sapiens

<400> SEQUENCE: 8
tggttggctt aaacagcagt cacagttttg gagactggaa agtccaagtc accagcagat    60
ttggtgtctg gtgagggtct gcttcatggt ttagagatgg cagtcttctc acagtgtcct   120
cacctgcttg agaaaggaag ccagcattct ctggactctt acaaggacac taatccatta   180
ataaggagtc tagcctcatg acctcatcta agcctaatta cttccaaaa actatctcct   240 agtaccatct cattaagggt tagggtttca acttacgaat tttaggggga cacaagcatc   300
magttcataa caaatatctt ttcttgagtg tatttgatat ctgtctgtcc tctttggtga   360
aatgtctgtc agtgcctttt gcccattttc taattaagtt atttgctatt gcattattat   420
tgatttccta caagttaact ttaatctctc tagttttggt tcctgactga agtttatttt   480
```

```
gtcctggagg aggaacattt ggcaatgtct atatatgcct tyagttgtca cacgagaaga    540
aaggaaatgt tactggcatc tagtggaatt atttgtgtag actgggttca tttcttcttt    600

<210> SEQ ID NO 9
<211> LENGTH: 180
<212> TYPE: DNA
<213> ORGANISM: Homo sapiens

<400> SEQUENCE: 9
aaaagtcaaa gaagtagaat taatgagata gaatagaaat gaatcataac tggttccctc     60
ctccctcaaa tcagaaagaa gtaactcact rgtttgattt ttttttccta aaaggcaaaa    120
ggaactgcaa atattaacac caacctggat tttctatttc aacagaactt aaaggcacgt    180

<210> SEQ ID NO 10
<211> LENGTH: 180
<212> TYPE: DNA
<213> ORGANISM: Homo sapiens

<400> SEQUENCE: 10
ttggcccctc agctgaatgc tcaaagtttc ctggagaacc cacaaacaac agaaaacatc     60
ttctctgaca cctctcatta gtctacccaa stgaagactt ctaaaacctt cctctattta    120
tcagctgata ggtaatcagt ttacctccaa atcatggaga agacatgatc tattgttcct    180

<210> SEQ ID NO 11
<211> LENGTH: 180
<212> TYPE: DNA
<213> ORGANISM: Homo sapiens

<400> SEQUENCE: 11
aatttgggct taaggaagtt gggctggatg aaaataattt taattgaaaa caaaaacttt     60
atcccaaagt tctcacacca ctggtacttc sttttcactg gttgaacaat aaaaaaattg    120
cagaaatgaa cctagtttgt tctcatcctt gactgcatgg tagaatcatc tgtgatatcc    180

<210> SEQ ID NO 12
<211> LENGTH: 180
<212> TYPE: DNA
<213> ORGANISM: Homo sapiens

<400> SEQUENCE: 12
taagactctt tatccagaac atagaaagaa ctcttacaac ttagcaacac aaaaagaaaa     60
atagattgaa aaatgggtga aggactagta ycaacatttc tccaaagata tgcaaaatgc    120
agttaccaac aattacatga gaagattctc agcgtcatta gttattagga aaatgcaaga    180

<210> SEQ ID NO 13
<211> LENGTH: 180
<212> TYPE: DNA
<213> ORGANISM: Homo sapiens

<400> SEQUENCE: 13
tttcccctct attcagacct tttctgcaaa ggagttcaca gtgggtgtct gtttctttct     60
aaaaacccta tttcacacca tgctaaagat rtttataggt ttggcaacta gtccagctca    120
tctcaggctg aattttgggg attcattggg gtttacagtt gaaaaatgct tgtagatacc    180

<210> SEQ ID NO 14
<211> LENGTH: 180
<212> TYPE: DNA
```

-continued

<213> ORGANISM: Homo sapiens

<400> SEQUENCE: 14

```
tcagaccttt tctgcaaagg agttcacagt gggtgtctgt ttctttctaa aaaccctatt        60
tcacaccatg ctaaagatat ttataggttt kgcaactagt ccagctcatc tcaggctgaa       120
ttttggggat tcattggggt ttacagttga aaaatgcttg tagataccat ctactcggcg       180
```

<210> SEQ ID NO 15
<211> LENGTH: 180
<212> TYPE: DNA
<213> ORGANISM: Homo sapiens

<400> SEQUENCE: 15

```
ttcaactccc acttacgagt gagaacatgt ggtgtttgat tttctgttct tgtgttagtt        60
tactgagaat gatggtctcc agcatcatcc rtgtcattgc aaaggacatt aactcatcct       120
ttttatatgg ctgcatagta ttccatggtg tatatgtgcc acattttctt tatctaatct       180
```

<210> SEQ ID NO 16
<211> LENGTH: 180
<212> TYPE: DNA
<213> ORGANISM: Homo sapiens

<400> SEQUENCE: 16

```
ggctgaagat acactttcaa ggagcaggaa gctattcctg aagttcccat gtgtgtagta        60
aaacttcagc tcatgtggac taagttatac rtccatcctg gcaaatgccg acacccctgg       120
agggttagac cctaataatt cagttccctg gtaaaaacag tgttgtatac acctgcggga       180
```

<210> SEQ ID NO 17
<211> LENGTH: 180
<212> TYPE: DNA
<213> ORGANISM: Homo sapiens

<400> SEQUENCE: 17

```
tgaagtcaaa ccagcctctt tctgtctctc tgtgactttg atcaacttgt tcaaatgaca        60
agcttcaatt tcttcacctg aagaggaca rtaatcatga ataccttgca atgtgggtat       120
gaggctgaaa tgagaaactg tatgtaaaga ttttagcact ctgatacaac aagtagctat       180
```

<210> SEQ ID NO 18
<211> LENGTH: 180
<212> TYPE: DNA
<213> ORGANISM: Homo sapiens

<400> SEQUENCE: 18

```
attaaattaa acaacacac atatattatg tcacccaatt tctcaggatt gggtggttct        60
ggctcagcat gcctcctgag attttagtca ygctattgac aagggttatg gttttctcaa       120
ggcttgactg gggctggaga agccatttcc aaactcatgc atatggtttt tggcaggctt       180
```

<210> SEQ ID NO 19
<211> LENGTH: 180
<212> TYPE: DNA
<213> ORGANISM: Homo sapiens

<400> SEQUENCE: 19

```
gattagaatg tattttatta tgttctttct aaatgttaaa gaagcttaga aaacacattg        60
agttattaat tttaattact tttacattgc rtatgaagat gttcaataaa actcaagtcc       120
tctactaaaa aaaaactgaa gtattttact aatttaatat aactagttaa gcttaggacc       180
```

<210> SEQ ID NO 20
<211> LENGTH: 180
<212> TYPE: DNA
<213> ORGANISM: Homo sapiens

<400> SEQUENCE: 20
tttaaacagt tccttatgtt ccctagcata agtattttat agatattcaa acataataac    60 taaacccta ggtcgatgat cattaaaata kttttgctat tcagtttgcc cactttataa   120
aaaggtacta tgtgccaagg ctaaacattc tctaaggtaa catttgaact ctaaaattca   180

<210> SEQ ID NO 21
<211> LENGTH: 180
<212> TYPE: DNA
<213> ORGANISM: Homo sapiens

<400> SEQUENCE: 21
tgcagcctgg ccatgcggta gaaaagaaga acccattttc tgatgaggaa ttgaagctga    60
ctgaataaat ttgcataagt aaggaggagg ygaatgttga tagccaagga tgggtaaaat   120
gcctcaaaga catttagaga tctttgcttc agccccttcc atcagagggc cggggccta   180

<210> SEQ ID NO 22
<211> LENGTH: 180
<212> TYPE: DNA
<213> ORGANISM: Homo sapiens

<400> SEQUENCE: 22
aattttgttt gttgttagtc tgaggcccag ggtgtggtgg aacataaggg atgaggaata    60
tttgctctga ctcatgatgt cttttccaaa rtactttatc catgctatga gtcctttcta   120
tttactgaga gccagaaaca ggcagaaaga gcactctgcc ttgtattgtc acatcccttc   180

<210> SEQ ID NO 23
<211> LENGTH: 180
<212> TYPE: DNA
<213> ORGANISM: Homo sapiens

<400> SEQUENCE: 23
cttaagtctt tttaaaatat ctattttctc cagtataagg tttctcaaag aacttccaga    60
atttaaacta tttctatatt gtcaacatgt rtctacaatg aaattcttct aaatgatgga   120
ctgcatctgt actcgttgaa gattatttca gacaaccatg atatacataa tggtttgtgc   180

<210> SEQ ID NO 24
<211> LENGTH: 180
<212> TYPE: DNA
<213> ORGANISM: Homo sapiens

<400> SEQUENCE: 24
aacacataga aaatgataat tttgtacagt gcattagagt aggcggaaga agtttcatga    60
ggctgaaggt gatctactga agtctccatg mccaacctgc tgctgggagg accgtatctt   120
ggaacaccta taacccatga caactgagtg tgccatggct gaaaaggcga aaggtctggc   180

<210> SEQ ID NO 25
<211> LENGTH: 180
<212> TYPE: DNA
<213> ORGANISM: Homo sapiens

<400> SEQUENCE: 25

```
acacacacac atctttaatg aaaaaatatc ctctaaaagt aaaatattct ctagagaaaa    60
aatattctct aaaatttgtg gaaacaaggg ytctaactat aggtttcaca gaggttggaa   120
tttataactt gtactttatt ttatttaaaa tattctttcc atcctttagc gtttgtctgc   180

<210> SEQ ID NO 26
<211> LENGTH: 180
<212> TYPE: DNA
<213> ORGANISM: Homo sapiens

<400> SEQUENCE: 26
ttgacttcta tgcacatgca ggctcaactg ccaaggcttg gggcttccac cctctgaagc    60
cacagcctaa gctgtacatt ggccccttc mgccacgcag gcaccaagtc ccaaagctgc   120
acagagcaca gggaccctgg gcctggccca tgaaaccatt tttacctcct gggcttctag   180

<210> SEQ ID NO 27
<211> LENGTH: 180
<212> TYPE: DNA
<213> ORGANISM: Homo sapiens

<400> SEQUENCE: 27
tttgtcttta tatttgagtt tctgttcggt ggaaaagcat acctcctcct acatctgtag    60
acaaattcaa acattactt gaccatgtag mctccatgaa gcttttccag aagaagttta   120
acaaaaaatg tgccccgcaa ccccattaaa aattccaaat gcatttatcc taccaatgaa   180

<210> SEQ ID NO 28
<211> LENGTH: 180
<212> TYPE: DNA
<213> ORGANISM: Homo sapiens

<400> SEQUENCE: 28
atggataaga aaattgagtc agagtggtta aattactatt aaatagaaaa gttagtattt    60 tatttttgcca agtgtaacat taaaaacaaa mctactttct actatcttcc atatttacta   120
aataaaatga cattttgctg cctaagaaat aagatatttg aaatcataga aaatttagct   180

<210> SEQ ID NO 29
<211> LENGTH: 180
<212> TYPE: DNA
<213> ORGANISM: Homo sapiens

<400> SEQUENCE: 29
tcactacatt tccttaattt gcctcattct agtgaaaact tcattgtaga ccatggaaaa    60
gttttagggc ttctctagac ttattattct stggcttatc catttaagga gacagacaac   120
ttaaggcttt ttatatttat ttatttattt attttttgag atggagtctc actctgtcgc   180

<210> SEQ ID NO 30
<211> LENGTH: 180
<212> TYPE: DNA
<213> ORGANISM: Homo sapiens

<400> SEQUENCE: 30
atggcctaat cacctctcat taggccctac ctaccaagac tgttgcatca gggattaacc    60
taacacatgt tttttagggg acaggttcaa mccataatag gggtggtcct caagagaaat   120
gctggaattt acaacacacc caaaggtgaa tagaattact tcattttgcc tttgctgaaa   180

<210> SEQ ID NO 31
<211> LENGTH: 180
```

<212> TYPE: DNA
<213> ORGANISM: Homo sapiens

<400> SEQUENCE: 31

```
agaaggactt atgttacata aactcctatg aatgactaca cattgtgtgt gtttgtcaca    60
gtgtatatgt gtgtgaaatt acaattctta yggatttctc atgtaatcgt ctttcaattt   120
ttttttttct ttttgagat gaagtcttgc ttttgttgct cagcctggag tacaatggca    180
```

<210> SEQ ID NO 32
<211> LENGTH: 180
<212> TYPE: DNA
<213> ORGANISM: Homo sapiens

<400> SEQUENCE: 32

```
aatgattaaa agtgattgat aataaattct cttctaataa agtaggtagg cttttccttg    60
ttgacttctg ctatttgaag atatgaaata mggttttctt ttttgatcat tcaataatag   120
atgagaacac catctataga caagctttta agctcaagtt tttaaggtca agaaaagaca   180
```

<210> SEQ ID NO 33
<211> LENGTH: 180
<212> TYPE: DNA
<213> ORGANISM: Homo sapiens

<400> SEQUENCE: 33

```
cttaagacaa aaacctactt ctagacagaa ctaatcaact ctattatttt gtaaagagaa    60
aaaaaaaaga cccaaattgt taaaaactaa saaagaaaag cctgactgaa tgaaatagct   120
attccatgtt ttaaatccca cattgctggg ttaaaattag agcaattggt attttaagca   180
```

<210> SEQ ID NO 34
<211> LENGTH: 180
<212> TYPE: DNA
<213> ORGANISM: Homo sapiens

<400> SEQUENCE: 34

```
aggttacagt cgtgtaaatt tagttgttct gcttcagtta caattttaaa tgatgaaatt    60
cttaaatcta taaaaatagt tattaaattc rtattcttct gttttgtaaa aaataaaata   120
acagaaatta aagggactg ttaaaaagac ttaaaaatcc taaggtagag aaaatttatg    180
```

<210> SEQ ID NO 35
<211> LENGTH: 180
<212> TYPE: DNA
<213> ORGANISM: Homo sapiens

<400> SEQUENCE: 35

```
gagtcaataa atctcaaggt taagacataa agatgtaatt ttaaaataaa agcagatgtc    60
tctatatata ccatggaata ctatgcagtc rtaaaaagaa tgaaatcatg tcctttgcag   120
caatatggat ggaattggag gccattatag taaacaattt gatgtaggaa cagaaaaaca   180
```

<210> SEQ ID NO 36
<211> LENGTH: 180
<212> TYPE: DNA
<213> ORGANISM: Homo sapiens

<400> SEQUENCE: 36

```
aaaattaacc ctcccttagg tgtacccttg tagacagact ccggttttta ctgctcttcc    60
aaaatgtccc tgcacttttc tttaggaaac rttcacatct cttccattgg gactttgttg   120
```
cctggtgcct cattcctctt ttctgtccaa cccttccaaa tgcacaatgt ttccagaaaa    180

<210> SEQ ID NO 37
<211> LENGTH: 180
<212> TYPE: DNA
<213> ORGANISM: Homo sapiens

<400> SEQUENCE: 37
taaagaaagg ataaatgctt gaggtgatag atacccaatt tgtcctgatg tgattagtat    60
gaatttaaaa tatcaaaata cctcatctag rtacatacta tgtacccaca acatttaaaa    120
ataaaaaaat caacataaat aaataaagga aatgctaacg ttttacagtg tgtgatttg    180

<210> SEQ ID NO 38
<211> LENGTH: 180
<212> TYPE: DNA
<213> ORGANISM: Homo sapiens

<400> SEQUENCE: 38
aaatatgtcc atatactggg aaggtgacat gccccaactc catgagcaca gaagcgcctg    60
tgcttaggac cctcccagac cttcccctac rtaccttttc acttggctgt ttatgggtac    120
ccttctttat agcatttatt agtaaactgg taaatgtatg taaagtgttt ccccaagttc    180

<210> SEQ ID NO 39
<211> LENGTH: 179
<212> TYPE: DNA
<213> ORGANISM: Homo sapiens

<400> SEQUENCE: 39
ggtgatcact gccagtccgg cccttgaaat atgcccatgg tcactgttga ttacactatt    60
aatattctca gtttctaac taggtcttat rttactgctt cttttgcac aatccatgct    120 gctccttact ctagaaaact tggaggaaat aatgacttca tatgggaacc agcaatagg    179

<210> SEQ ID NO 40
<211> LENGTH: 180
<212> TYPE: DNA
<213> ORGANISM: Homo sapiens

<400> SEQUENCE: 40
tctagaaaac ttggaggaaa taatgacttc atatgggaac cagcaatagg aaagaggaga    60
aaaagagaaa tctcatatta ctacttattg ytgccataat ttcttcctct tattctgttc    120
atcaacttgc aaaccacgcc ccttatctct cttctttctg catcagaata tgtaagctga    180

<210> SEQ ID NO 41
<211> LENGTH: 180
<212> TYPE: DNA
<213> ORGANISM: Homo sapiens

<400> SEQUENCE: 41
agaaaaagct agttatttta taatctcctg ggattcattt caaattatat attttatctc    60
attttgttca gatcctatct cttatcttct staggtctcc agagagtatc agtccatatt    120
cacagctttt agctacctca ggcttcttgt tctaaatttt acattcctag ataattcatt    180

<210> SEQ ID NO 42
<211> LENGTH: 180
<212> TYPE: DNA
<213> ORGANISM: Homo sapiens

<400> SEQUENCE: 42

```
gacttactta atacacatga gaggaatgat tttaggactg agattagtag aactgatgtg    60
atgctgatgg tgatggtgac tgccatgaag ytgctgctgc tgataaactg tcttccaaga   120
caaaattgtt cagcaggcaa agttaatttt ggagataatt ttatccttt tccatttccat   180
```

<210> SEQ ID NO 43
<211> LENGTH: 180
<212> TYPE: DNA
<213> ORGANISM: Homo sapiens

<400> SEQUENCE: 43

```
cgactcatca gaatttggtg ttgtcagtct tttaaaattt agccacgagt caatgtataa    60
tgctgtcttg tcattttatt tacaattctc rgacaagtaa tgatgttgag cacattttca   120
taggcttatt aaatgcctgt atttatattt ttgtaaagta ttttccaaa tcttttggcc    180
```

<210> SEQ ID NO 44
<211> LENGTH: 180
<212> TYPE: DNA
<213> ORGANISM: Homo sapiens

<400> SEQUENCE: 44

```
ttattccagc atgatttgtt gaaaaacttg tctttccctg ctaaatttat ttggtacttt    60
cataaaaaat ttatgtgttg gtacctttc yggattcttg attctgttct actgatttag   120
ttttctatcc ttttgtcaat accacacttg aatattgcaa cttttactca ggtctagaaa   180
```

<210> SEQ ID NO 45
<211> LENGTH: 180
<212> TYPE: DNA
<213> ORGANISM: Homo sapiens

<400> SEQUENCE: 45

```
ttagataaaa cagatgttaa gtcagaaact gtcaaaagag acaaaaaggt aattgtataa    60
taataaagag gtcaattcag caaaaggata waaaaatagt aaacgtatat gcaaccatca   120
ttggaacacc ccaatatagg aagcaaatat taatagggcc aaaaggtgag atagaatgaa   180
```

<210> SEQ ID NO 46
<211> LENGTH: 180
<212> TYPE: DNA
<213> ORGANISM: Homo sapiens

<400> SEQUENCE: 46

```
tcacatcaag tattctttct gaccacaaca aagtaaaaga acatttaaaa acctcaataa    60
taagagggac tttgaaaact gcacaaaaac rtggaaatta acaacattc tcctgaacaa   120 tcaatgggtc agtgaagaca ttaagaagga aatttaaaaa tgtatttact tatgtggagc   180
```

<210> SEQ ID NO 47
<211> LENGTH: 180
<212> TYPE: DNA
<213> ORGANISM: Homo sapiens

<400> SEQUENCE: 47

```
tttgaaaaat aacttataca aattctattc aaactatttc ccaaaataga agaggaagaa    60
gtgctttcaa actcaatata tgaggccact rctaccctga taccaaaacc agacaaggat   120
aaaacaaaca gaaaacctat gggccaatat cactgatgaa catatatgta aaaccctga   180
```

<210> SEQ ID NO 48

```
<211> LENGTH: 180
<212> TYPE: DNA
<213> ORGANISM: Homo sapiens

<400> SEQUENCE: 48
attatgttaa gtaaaataag ccaagtacag aaaaataaat atcacatgtg ttcttatatg    60
tgggagccaa aaaagtggat ttcatgtagg wagagagtag aatggtggtt attataggta   120
aggaatagaa tgaaggagag gaggatgaag agaaattggt taatgaatac aaaaatgcag   180

<210> SEQ ID NO 49
<211> LENGTH: 180
<212> TYPE: DNA
<213> ORGANISM: Homo sapiens

<400> SEQUENCE: 49
agtattttct cagaatcatg ttcctacata acactgactt ctcctcatat cccattagga    60
tgtcttgcca tgtgctcatt cctaaactag rcattgacaa ggggaaaata gaatcactgc   120
ccatggctca gaccactggc tttcaatcct gtttgcatat tagaatgccc cagagagttt   180

<210> SEQ ID NO 50
<211> LENGTH: 180
<212> TYPE: DNA
<213> ORGANISM: Homo sapiens

<400> SEQUENCE: 50
caagaaaaga aagaaataca agctcatcaa tttagtgaaa aataagtcaa atgatttgac    60
tgaatagatc ttctgttagt caaagagggc ycaaattgtt ggctggggag atagacatag   120
ccaaagaaca actggggcaa ttccatacac aatttcccta atgttctact gatgagttaa   180

<210> SEQ ID NO 51
<211> LENGTH: 180
<212> TYPE: DNA
<213> ORGANISM: Homo sapiens

<400> SEQUENCE: 51
acattagaga gggctaaaca agggcagtga gaagactggc aggcagcaga aatcattttc    60
tttttgatct cacacaccag ggcattcccc staagaggca gtgagatgta gcctggccct   120
ggaactagaa acagaggtgg ctgctgtgct agtgcctgag atgcacgatg ctggggtcaa   180

<210> SEQ ID NO 52
<211> LENGTH: 180
<212> TYPE: DNA
<213> ORGANISM: Homo sapiens

<400> SEQUENCE: 52
tgagtgctcc tgtgtgctgg gccctggcct ggattagaat gcctctgctg tgggctttgg    60
gtttgtcagg atggaatcct acagcctcct yggggaaag cacacctcat gctgagcgct   120
gtgttaggca caggctggga tggagcactt cttctggtcc ttcattcttc tggcaaagct   180

<210> SEQ ID NO 53
<211> LENGTH: 180
<212> TYPE: DNA
<213> ORGANISM: Homo sapiens

<400> SEQUENCE: 53
tttgcggggt acgtggcttg ggttttgttt ttagtgagag gtgatgcaca ggctggtagt    60
taggagcctg caagcctgca ggctgggctc rtgtccaggc tcctgcccca agtccacatg   120
```

```
actttgggca agtcacttca ccagtctgaa cctcagtttc ttcatctgta aaatggaggt    180

<210> SEQ ID NO 54
<211> LENGTH: 180
<212> TYPE: DNA
<213> ORGANISM: Homo sapiens

<400> SEQUENCE: 54
tgcctcagga ttcaatccct cccactatcc tccaagaaca gggtgaagtt ctgaatatat    60
ctctctatac aaatgcattc tattgttgat rcttttttcca gagaggagga aattaacagt   120
aatagtaatc aatattattg actgcaacga aatgtcttct ttggaaattg actgatggtc    180

<210> SEQ ID NO 55
<211> LENGTH: 180
<212> TYPE: DNA
<213> ORGANISM: Homo sapiens

<400> SEQUENCE: 55
tatgctcctc cccagaagct ttaggtctgt gtgtggtgga agcaaagaag cccctttccc    60
tgttcttcta caggtcaggt cctagcttgc mggtttgggc gcgcttccgc cgccctcccc    120
tcctgcccgt caccaggggg gaagcaggtg aaactccaat agtgctgcaa ggcctatggc    180

<210> SEQ ID NO 56
<211> LENGTH: 180
<212> TYPE: DNA
<213> ORGANISM: Homo sapiens

<400> SEQUENCE: 56
agttttatct ttgactttgt gttgtgtaga tgaagctgat gggacaatag agcgtatgcc    60
aggggcttag tctcagttca tgtggtcccc scttctgctg cctccttgcc tttctggcat    120
gggtttcagg tcccagctct ccatccactg atgcccctgg cctggccagg cctctctctt    180

<210> SEQ ID NO 57
<211> LENGTH: 180
<212> TYPE: DNA
<213> ORGANISM: Homo sapiens

<400> SEQUENCE: 57
aattaggcct gctacaacag ccatcttact aagtcttctc ttcaccatca ttctgggagc    60
tctcttcaca tcttccatat tgcataaatt sctacatatt ccttctttat aaattaatgc    120
cttggagtgt gacaccagaa gcttcctaga aaagaagcg tggctggtca ttttttttgag    180

<210> SEQ ID NO 58
<211> LENGTH: 180
<212> TYPE: DNA
<213> ORGANISM: Homo sapiens

<400> SEQUENCE: 58
ttattaatcc ttccagatat aaaaactttc tacaagcttc aatatttcta acctttaaca    60
aagaacttcc aaaatattac aaaaaactag staagtgaaa acattttcct tctttttaaa    120
tatcaaactt gttttgtctt tctgaaatag ttaatgtgaa tatatatttt aaaactatt    180

<210> SEQ ID NO 59
<211> LENGTH: 180
<212> TYPE: DNA
<213> ORGANISM: Homo sapiens
```

<400> SEQUENCE: 59
ttttaggtca tttctgactt agggcaattg cagtcagagc tatcatgaat atcctcatgc    60
atgcatcgtt ttgacatggc tcagagtttc rttttttgtt ggttttaaat aaattatata   120
cttagaaatg gactttctgg gttataagac atgcacattt ttagttttgc tagttattac   180

<210> SEQ ID NO 60
<211> LENGTH: 180
<212> TYPE: DNA
<213> ORGANISM: Homo sapiens

<400> SEQUENCE: 60
caagagcctt tataaaacat ttaatttctg cttaacaact cattggcgga cagaaaattt    60
ttcagtgatc tatttttcaa tgaacacaga sagccagaat gtcaaacaaa gactaaaatt   120
taggggatct gacttcagtc tggccagttt agcccataac actgtgaatg ccacatgcc    180

<210> SEQ ID NO 61
<211> LENGTH: 180
<212> TYPE: DNA
<213> ORGANISM: Homo sapiens

<400> SEQUENCE: 61
tgcaacactt gactgagaaa aatcagaaga cttaaataat atacagtgca catggataat    60
ttattctctg atgacaaggg tatcaatata ytcattcttt tctctcttcc atctcatcaa   120
attccatctt tctttaagtg actaaataag tgacatccta ggctgtggac tctctgccta   180

<210> SEQ ID NO 62
<211> LENGTH: 180
<212> TYPE: DNA
<213> ORGANISM: Homo sapiens

<400> SEQUENCE: 62
gacagtgtga acattcagtt ggtttgcaga ttccacactc tgagggcaga ttccacacat    60
tgtcttgact cttttttcctt ctcattcttt ytgcttttac accactgatg accctgtctc   120
catcctgctg ggaagtaatt agtgctgaag gaatgacaac tctagcacat aagtggcagg   180

<210> SEQ ID NO 63
<211> LENGTH: 180
<212> TYPE: DNA
<213> ORGANISM: Homo sapiens

<400> SEQUENCE: 63
acaactctag cacataagtg gcagggccat gaggatgaga agcaaaaaaa gaaaaaacgg    60
aaggggccat gggggaacta aatcaaggca rctggaggca ggggcacctt cctctggatg   120
ctgcgaatgg aatagccatc cgggtgcccc gaaggtcaag tactgagatc ctgaatttac   180

<210> SEQ ID NO 64
<211> LENGTH: 180
<212> TYPE: DNA
<213> ORGANISM: Homo sapiens

<400> SEQUENCE: 64 gctagcccctt catttttaatg tatcctgtat gcattggtta attagctttg ctataacaaa    60
aaaaaatcaa tatacagtga cttaaagaag rgagatattg gccgggtgca gtggctcacg   120
cttgtaatcc cagcactttg ggaggccaag gcgggcagat cacgaggtca ggagttcgag   180

```
<210> SEQ ID NO 65
<211> LENGTH: 180
<212> TYPE: DNA
<213> ORGANISM: Homo sapiens

<400> SEQUENCE: 65
gccgagattg tgccactgca ctccagcctg ggcgacagag ctagactcta tctcaaaaaa      60
taaaaaaaga gagatattta tttctcctcc rtatcacttc tctgagttga gcagttcagg     120
ttgatgtgat ggcttggctg tatgaggttt gtcccgcgct ccactttttt ctgtcttta     180

<210> SEQ ID NO 66
<211> LENGTH: 180
<212> TYPE: DNA
<213> ORGANISM: Homo sapiens

<400> SEQUENCE: 66
caacaaacaa aattccatac tcaggtattg gttcccttt gatgctccga aagcactaa      60 ttaatgtttt agaaaaggta taaggatac rctacatcag ggagttctgg aatgaaagag     120
aaccattcca ctgaatttat aatcttgcag gtacgtggta gctattgttg tagttacaat     180

<210> SEQ ID NO 67
<211> LENGTH: 180
<212> TYPE: DNA
<213> ORGANISM: Homo sapiens

<400> SEQUENCE: 67
ggcatgttga atttggggta cctctgaaaa aaaataggaa tgggagaaaa gttagtccag      60
ggacaggcct aggaaagcag gtatttgtct watctgatgt ttattggaag ccatgagaat     120
caatgaatgt atccagaaag tgagactatg aacaagacaa atctgatggt aacattttta     180

<210> SEQ ID NO 68
<211> LENGTH: 180
<212> TYPE: DNA
<213> ORGANISM: Homo sapiens

<400> SEQUENCE: 68
agttttattg gaacaaccac attcatttat tcacaaatca actatggctg ctgccatgtg      60
ctgtaactgc agaactatgt gttttccaca kaacaccagg cccacaaatc ctaaaagact     120
tactaactgg cccttaccat gaaaagtgtg atgatttctg gagtagcatt taaggacatg     180

<210> SEQ ID NO 69
<211> LENGTH: 180
<212> TYPE: DNA
<213> ORGANISM: Homo sapiens

<400> SEQUENCE: 69
gtcttctaga ttggggctgt gttgtatcaa ctccatgaga caaacagcaa agacaacttt      60
gctcatgggg tagaatggtt gacatctcca rgtgagaaaa atggcctcaa aagtcccaga     120
gtctttggga actgcatcaa acaaccaagg aatttatgtc caaactctgt aaacacacat     180

<210> SEQ ID NO 70
<211> LENGTH: 180
<212> TYPE: DNA
<213> ORGANISM: Homo sapiens

<400> SEQUENCE: 70
agggcagggt gctaaacaaa gaaaggaatt aaagaaatta agtaatgctt tgtcaaatgg      60
```

<210> SEQ ID NO 71
<211> LENGTH: 180
<212> TYPE: DNA
<213> ORGANISM: Homo sapiens

<400> SEQUENCE: 71

```
tgatgttgga cctgcaccat gagggatatg ragatagtgt cattccctgg ccctctgccc    120
ttcattatgt tttctaaaaa gggaccagaa gatttactta aaaagcagcc ataactataa    180
```

<210> SEQ ID NO 71
<211> LENGTH: 180
<212> TYPE: DNA
<213> ORGANISM: Homo sapiens

<400> SEQUENCE: 71

```
acctgcagat gtttaatctg ggcacctctt ggcccaagtc attttgacac aaaaagttag     60
ccatggcatg tactaaaact gaaatcatac yaagagtgta ttctttagta ctccatggat    120
gtcttccttc aaagtttagc tatttaagat ttatgtcatt atataaacaa tagagaatta    180
```

<210> SEQ ID NO 72
<211> LENGTH: 180
<212> TYPE: DNA
<213> ORGANISM: Homo sapiens

<400> SEQUENCE: 72

```
aagtttttatt atcctcttag actgaagaag acactgagac aagaagcggt taaattacag     60
tatcaggacc ccagatggct aaagctggag sctgaatccc ctacctgggt gcctattttt    120
aggtatttag gtataacaac atgttctaga gataatcagt acacaacagt gacaacatga    180
```

<210> SEQ ID NO 73
<211> LENGTH: 180
<212> TYPE: DNA
<213> ORGANISM: Homo sapiens

<400> SEQUENCE: 73

```
acttttccat accctccttg cccccttat ccctagtaca agagttaaaa aactctcagt     60
gctaaacacc cagaaagctg agaaaattat rtgggtgcac acaggcacag ctaaatcact    120
agtgatttca caaccctagg aaatctctct taatatatta ggctactgtg ggttatttag    180
```

<210> SEQ ID NO 74
<211> LENGTH: 180
<212> TYPE: DNA
<213> ORGANISM: Homo sapiens

<400> SEQUENCE: 74

```
tgaagtgcag cggcacaatg atagctcact gcggcctcga cctcctgggc tcaagtgatc     60
ctcccacttc agccttccaa gtagatggga ytacacattt gtgccaccat gctcagctaa    120
ttttttttaaa aaaaattttg tagtgacaag atcatgctat gttacttagg ctgttctcaa    180
```

<210> SEQ ID NO 75
<211> LENGTH: 180
<212> TYPE: DNA
<213> ORGANISM: Homo sapiens

<400> SEQUENCE: 75

```
cacaaaagta tttaaacaaa tagtgatgtg acattctgtt tgatattttc ctggaataac     60
aaaacttccc actgctttga gaaaaaaaaa mactcgccaa tattttttatg atcaaataaa    120
aaatacatga acataattac ttatcatggg cttcctagag gaccaatgtg taggatgatc    180
```

<210> SEQ ID NO 76
<211> LENGTH: 180
<212> TYPE: DNA
<213> ORGANISM: Homo sapiens

<400> SEQUENCE: 76
ataacaaaac ttcccactgc tttgagaaaa aaaaaaactc gccaatattt ttatgatcaa    60
ataaaaaata catgaacata attacttatc rtgggcttcc tagaggacca atgtgtagga   120
tgatcatgtg atctatctcc aatgtataaa ccagacagga taacaatacc atatctggac   180

<210> SEQ ID NO 77
<211> LENGTH: 180
<212> TYPE: DNA
<213> ORGANISM: Homo sapiens

<400> SEQUENCE: 77
ttccaatctt ctccctcttc tctactttgc ttctctttcc atcttcatct gaatctgtct    60
tgaggaaaaa gttactcgca ttctagataa saggacaccc cagctcgctc ctgatcggtc   120
ttcacctgca cttcctgtgt tacaaacata aaaatcctgc acaatttcac aacaaattcc   180

<210> SEQ ID NO 78
<211> LENGTH: 180
<212> TYPE: DNA
<213> ORGANISM: Homo sapiens

<400> SEQUENCE: 78
ccctcttctc tactttgctt ctctttccat cttcatctga atctgtcttg aggaaaaagt    60
tactcgcatt ctagataaga ggacacccca rctcgctcct gatcggtctt cacctgcact   120
tcctgtgtta caaacataaa aatcctgcac aatttcacaa caaattcctt ggatccttat   180

<210> SEQ ID NO 79
<211> LENGTH: 180
<212> TYPE: DNA
<213> ORGANISM: Homo sapiens

<400> SEQUENCE: 79
cctgcacttc ctgtgttaca aacataaaaa tcctgcacaa tttcacaaca aattccttgg    60
atccttatgc tttctctcat aattcctgac macactctct atacaatttg ttcactatgt   120
agtatataag ttttatgtag tgttagagcc gttaaagtga catttagag ggaaaaaa      180

<210> SEQ ID NO 80
<211> LENGTH: 180
<212> TYPE: DNA
<213> ORGANISM: Homo sapiens

<400> SEQUENCE: 80
ctgaatttag ctatgatgtt acatctttag ctgtagaaaa tttctaataa gggtggcctg    60
ttttcctttg ccactgaagg gttcatacac ragattcagc atttccgagt aggggcccag   120
ttggagccac catgaagcat tctttggaaa gaaactccct gtttctttaa cttttttcccc   180

<210> SEQ ID NO 81
<211> LENGTH: 180
<212> TYPE: DNA
<213> ORGANISM: Homo sapiens

<400> SEQUENCE: 81
gctcctatac aacattctgg atgtgtacac tttaagataa aatagaaatt aaaactaatt    60
tggcttaaga tccactgaac agtcaatcca yactttagtg gccttgagaa gtaaaacctt   120
tgctacaatg gaagctaatg tcttaaaagg accaaagagt tctttatgta atcactcaga   180

<210> SEQ ID NO 82
<211> LENGTH: 180
<212> TYPE: DNA
<213> ORGANISM: Homo sapiens

<400> SEQUENCE: 82
attttaacgt cttaggaaga ctgttttct cttcattctt tatgccttga aagaagatta    60
acaggaactt gatttccccc tagcaaaaaa katatattgg agttgatcat attacactag   120
gtatctaaat aagtggctta catcttatat tctcactagg atacagatat gctggcatta   180

<210> SEQ ID NO 83
<211> LENGTH: 180
<212> TYPE: DNA
<213> ORGANISM: Homo sapiens

<400> SEQUENCE: 83 tatactttt atattttatg atatatatta tggacaaaag agaagagact gaatcaaata    60
acaattgtcc ccaaaatggt atacctttt ktgtcaaaca gctaaagtga aggggtaatc   120
tcttctatct cactaggagt taagctgggt agtggatcag tagcagcttt ggttagttcc   180

<210> SEQ ID NO 84
<211> LENGTH: 180
<212> TYPE: DNA
<213> ORGANISM: Homo sapiens

<400> SEQUENCE: 84
tgttctacct accctggtac cttccagatt ctctcttgtc attccagcct agggtaaacc    60
ttcaacaaga gtcttctcat tatggaaaaa yctctgtgac tgtggctggc cattgcccta   120
cccatgccac aggtcgaatt cttgggaagc aggctctgag atggagccca atgtgcagta   180

<210> SEQ ID NO 85
<211> LENGTH: 180
<212> TYPE: DNA
<213> ORGANISM: Homo sapiens

<400> SEQUENCE: 85
aactgcctca gcaagccaca cagagagcta tgtgactgaa atgcctgtta gattttcct     60 acatcgtgca aaaatgccca gacctttata ytcctgcctc agtcagtcat aaaatgtggc   120
tgctttggga agggcaaggt gactgtagct gaagcaactt ctagagggtt gacagtgctc   180

<210> SEQ ID NO 86
<211> LENGTH: 180
<212> TYPE: DNA
<213> ORGANISM: Homo sapiens

<400> SEQUENCE: 86
caggtttcat actgttggag aaataggtta taagtaagga agttgggaa ggcaagaata     60 agccttgtgg tggactgaaa tcagaggtgt rtgaatttat tttaaaaatc tagacagaca   120
aatatgcatg tacatacaca tatttcctag ctccaccaac taagagggcc tcaaaacaat   180

<210> SEQ ID NO 87
<211> LENGTH: 180
<212> TYPE: DNA
<213> ORGANISM: Homo sapiens

<400> SEQUENCE: 87
gataaaattc aaagctaaac ctgggatccg taactcagag agaaaagctc cttttcttcc    60

```
ttcaaataag taacatgcat attcgcttgt yggtgtcttc tcaaaataaa tattcccagg      120
aaagaagata gtccattttt cctgaattgt aactttctaa ggttcttatc aggaagtatt      180

<210> SEQ ID NO 88
<211> LENGTH: 180
<212> TYPE: DNA
<213> ORGANISM: Homo sapiens

<400> SEQUENCE: 88
tccagtcaat ttgcttctgc aatgctggcc atacagatgt tggaatgaag catgtgttta       60
caaagctaaa gatatgtgca gtatagacag mggaaaattt tttcacagtc gacaaaatat      120
agcattactt actgtgtaga gtgaaatcca ttgataaaac agtgagtttt gaaaaaaata      180

<210> SEQ ID NO 89
<211> LENGTH: 180
<212> TYPE: DNA
<213> ORGANISM: Homo sapiens

<400> SEQUENCE: 89
tagtgtattt tatgtgtggc ccaaaacaat actccttcta acgtggccca gggaagccaa       60
aagacgagac accactggtt tttacaaata ycttcttatt tcaatttggt gttttaaacc      120
aaaattcagc tccttatagc ttacttattt tgtattatta ttgttcttta accatttaac      180

<210> SEQ ID NO 90
<211> LENGTH: 180
<212> TYPE: DNA
<213> ORGANISM: Homo sapiens

<400> SEQUENCE: 90
acaaaaccat ccatttaacg gtataaacta aattatgttt cacaaactgg gtttccattg       60
tggtaatatg atgcatacaa acatggttaa rtagaagaca taggaagaga tgcaaatagc      120
agcttcccat gctttcttag caaaaaaaag agcactgtac actcaatggt atattatgcc      180

<210> SEQ ID NO 91
<211> LENGTH: 180
<212> TYPE: DNA
<213> ORGANISM: Homo sapiens

<400> SEQUENCE: 91
cttcatatat tcatagagac aacagactaa aaattagatt cttttttat tcttaatcca       60 tggagaagtc ctttaatgtc caagcgacat yaggtgtttt agtacagaga aaaggatca      120 aactcaattt cattacatac tgaaaaggcc aagaatagaa ataaccccga tatcatggtc      180

<210> SEQ ID NO 92
<211> LENGTH: 180
<212> TYPE: DNA
<213> ORGANISM: Homo sapiens

<400> SEQUENCE: 92 cttttttactt cattcgttta cttcatacat ggaacaacat agataaccct taaaatcatt       60
atgcaaagtg aaagaagcta gacacaaaag wgtacttagc gcaggattcc atttccatga      120
aatattcaga aaatgtgaat ctacagagac agtaagttag tgcttgcctg ggaagggcag      180

<210> SEQ ID NO 93
<211> LENGTH: 180
<212> TYPE: DNA
```

<213> ORGANISM: Homo sapiens

<400> SEQUENCE: 93

| ttaacaccaa tgagagaaaa cactaccttg tttagcatca ttgtcctaaa tatttttgta | 60 |
| gtagcaaaac aggataactt gtaaaaggca watcataagg aaagcactag tcattagagg | 120 |
| catatatgtg atatcagatt tgttgaactg ttgcttatgg agtatcctca cacaaccatg | 180 |

<210> SEQ ID NO 94
<211> LENGTH: 180
<212> TYPE: DNA
<213> ORGANISM: Homo sapiens

<400> SEQUENCE: 94

| catccatttt gggacttaaa ttatcttcat tcctgcttat atttaactaa ttgtctaaaa | 60 |
| tgttgaccca acacaaaacc ataagggaga mtcatggatg attatttatt tatttgtgtt | 120 |
| tgccatgccc tctctgcacc atcagatgtt ttacagatta agaagactgg aggggaaagt | 180 |

<210> SEQ ID NO 95
<211> LENGTH: 180
<212> TYPE: DNA
<213> ORGANISM: Homo sapiens

<400> SEQUENCE: 95

| tgttatgcca ggataagtct gtatgaaaac ccttggagag ccaggtgaag acactgagca | 60 |
| ttggatgagg agtatttagc caaaaagctc rttctggaag ggaaagagga gccgggtagc | 120 |
| tccctgaaga cctctgtgtt gaatgattta aggctacctg taggaaatgc cttctgcttt | 180 |

<210> SEQ ID NO 96
<211> LENGTH: 179
<212> TYPE: DNA
<213> ORGANISM: Homo sapiens

<400> SEQUENCE: 96

| gtatgaaaac ccttggagag ccaggtgaag acactgagca ttggatgagg agtatttagc | 60 |
| caaaaagctc attctggaag ggaaagagga rccgggtagc tccctgaaga cctctgtgtt | 120 |
| gaatgattta aggctacctg taggaaatgc cttctgcttt attgcttttt agtctccct | 179 |

<210> SEQ ID NO 97
<211> LENGTH: 180
<212> TYPE: DNA
<213> ORGANISM: Homo sapiens

<400> SEQUENCE: 97

| gagtatttag ccaaaaagct cattctggaa gggaaagagg agccgggtag ctccctgaag | 60 |
| acctctgtgt tgaatgattt aaggctacct rtaggaaatg ccttctgctt tattgctttt | 120 |
| tagtctccct tcttttggg ggggcggaaa aagaagcaca acacagatct ttccttcctt | 180 |

<210> SEQ ID NO 98
<211> LENGTH: 180
<212> TYPE: DNA
<213> ORGANISM: Homo sapiens

<400> SEQUENCE: 98

| ggtagctccc tgaagacctc tgtgttgaat gatttaaggc tacctgtagg aaatgccttc | 60 |
| tgctttattg cttttagtc tcccttcttt ytgggggggc ggaaaaagaa gcacaacaca | 120 |
| gatctttcct tcctttgact cacattagta ttccgcagaa tgtttgagta aaacctccat | 180 |

```
<210> SEQ ID NO 99
<211> LENGTH: 180
<212> TYPE: DNA
<213> ORGANISM: Homo sapiens

<400> SEQUENCE: 99
catatcacaa ataaaaaata agtgagtcag gaaaaacact gaatggcaga taatgagaca      60
gcattcataa catgccttct tagagagagt ktattggtgt ctcagagatt tactttaaca     120
gacgaaggtt tctcaaccta agaaccgctg acatttgggg tccaatcatt ctttgccatt     180

<210> SEQ ID NO 100
<211> LENGTH: 180
<212> TYPE: DNA
<213> ORGANISM: Homo sapiens

<400> SEQUENCE: 100
tgaatggcag ataatgagac agcattcata acatgccttc ttagagagag tttattggtg      60
tctcagagat ttactttaac agcgaaggt wtctcaacct aagaaccgct gacatttggg     120
gtccaatcat tctttgccat tagaaatgtc ctgtgcatga taaatctttA gcaacagata     180

<210> SEQ ID NO 101
<211> LENGTH: 180
<212> TYPE: DNA
<213> ORGANISM: Homo sapiens

<400> SEQUENCE: 101
gtactaacat tttgaacttg ttgagaaaaa taatgttcca cagaaaacta aaggtaaata      60
aatgttcaag aaaatatatt ctatttccca yaaagctgct cttttcttat gtgcccaggg     120
aatattagta gtgaggtcat aaagtttgga gcctcactga ctggatttga atccaggatt     180

<210> SEQ ID NO 102
<211> LENGTH: 180
<212> TYPE: DNA
<213> ORGANISM: Homo sapiens

<400> SEQUENCE: 102
aaagtaaatc agtattttaa gaaagtgcat ttgtgatttt ggacttgttg tattaaggtg      60
aaatataatg tggtttgtca tcaatctctc ygtgtggcat aaaagggctg acttgttgaa     120
atttcatagg ttttatttta cagagaaaac aagaccctgt tctgcccaga gtcctatcag     180

<210> SEQ ID NO 103
<211> LENGTH: 180
<212> TYPE: DNA
<213> ORGANISM: Homo sapiens

<400> SEQUENCE: 103
tttatagaca gttctatagc ttcttacctt atattttaac gtggtatttg gtttaatcaa      60
attgatatta gtatggatta tctaatagga ytctgaaaac catccctaat gtcaatagaa     120
taaacataac tcaatgagga ctctaagcca tcagattctt tgctctctca tctctaatga     180

<210> SEQ ID NO 104
<211> LENGTH: 180
<212> TYPE: DNA
<213> ORGANISM: Homo sapiens

<400> SEQUENCE: 104
```

```
ttctttttct ttaaaatggc acccactgct ctataaaatg atctattggg acttcaaagc    60
tgtggcaatt gcatgtggca caggatgtac rcaattaatt atgtgatgct taaatgacag   120
ggtataggaa aaataagaga gaagaagaaa aagttttttt tttttttaaa aaaaaagcaa   180

<210> SEQ ID NO 105
<211> LENGTH: 180
<212> TYPE: DNA
<213> ORGANISM: Homo sapiens

<400> SEQUENCE: 105
aaaaaaaaaa tccaaagtaa actgaaagac ctggttgtct gcctgccaaa aaccagtagc    60
agataaggcc tccagttgct gtggaaactc rggcctccag gagccagaat ccaatttcag   120
aaaccacaaa atcaacataa acgtgtgcaa aaataaaaag gtttgtttgg caagtaataa   180

<210> SEQ ID NO 106
<211> LENGTH: 180
<212> TYPE: DNA
<213> ORGANISM: Homo sapiens

<400> SEQUENCE: 106
gtcctttgat gagtgaacaa tttttaattc attcttatat tctcagaaat tatctttcct    60
tcttttcctt taaagaataa atgtgctctt wtacttagtt catcaatagg ttgataaatc   120
atttgcttgg ataagaccaa cctgtatttc atctaacact aaatgtagag gattttcaat   180

<210> SEQ ID NO 107
<211> LENGTH: 180
<212> TYPE: DNA
<213> ORGANISM: Homo sapiens

<400> SEQUENCE: 107
ggaggatgaa atgtaaaata tataattcca cttcctggga atagactgta ttgtatatca    60
tttgcatcga aaatgcctca ttcttgccgc wgagattctg ctaaatgcct atcacatcac   120
ttctgtcatc tcttgggcca acagctaagc cctgtctctt tgtaactgca ttctgttcaa   180

<210> SEQ ID NO 108
<211> LENGTH: 180
<212> TYPE: DNA
<213> ORGANISM: Homo sapiens

<400> SEQUENCE: 108
agacaggtca gccacagtga tgagattttt tctttttttct tttttcctgg aaactgtaaa    60
tggcagagaa aactcagcct taagcaattc kgcattgtgc tgtcttcgga catacaagta   120
tctgttctta tgcgcaaggt ttgctcaata taaaattctc tcaggagtgg agaaaaaata   180

<210> SEQ ID NO 109
<211> LENGTH: 180
<212> TYPE: DNA
<213> ORGANISM: Homo sapiens

<400> SEQUENCE: 109
ttttcacaac cacttacagc attataaaaa aggaaacctg atattgaaga agtgttcatt    60
tgactcagtt tataggtata ttatgccaca waattttctc actggaagtt gcaactttga   120
tttgtttttg ttattaattc acttacaata atatcttctt gttaaacata ttaacggtac   180

<210> SEQ ID NO 110
<211> LENGTH: 180
```

```
<212> TYPE: DNA
<213> ORGANISM: Homo sapiens

<400> SEQUENCE: 110
aaacatatta acggtacatt tatataaaga aatttgaaga ccataaaaac atgttttttga      60 agaatattta atgactaaag aaagttttga yatattgtaa gtgaaaaaaa tcaggatata     120
taatttaaat cttacaataa aatatttgat aaagaggtta aaataaatat atacacaaaa     180

<210> SEQ ID NO 111
<211> LENGTH: 180
<212> TYPE: DNA
<213> ORGANISM: Homo sapiens

<400> SEQUENCE: 111
tgtgcttcac agagtgagag tgtgtgtgtg tgtgtgtgtg cgtgcgtgtg tgtgtgtgtg      60
tgtgcgtgtg tgtgtgtgtg tgtgtgtgcc ygtaagcaca tacggtacat ggtgattttt     120
atactgtaga aaactgctga gctaaaaatc tttctgcaag gaaaagaggg catggttttc     180

<210> SEQ ID NO 112
<211> LENGTH: 180
<212> TYPE: DNA
<213> ORGANISM: Homo sapiens

<400> SEQUENCE: 112
ttctggcttc gctcactttt ctgccattct ccagaatgtc tttgtgtgat acttgtacta      60
taaaagaatg ccagattaga aaatcaaaat mttggaacca aagttataaa tctggacacc     120
acagagagcc agagtataag ggtattttt tctaatgttt tgttgccact aaggcatatt     180

<210> SEQ ID NO 113
<211> LENGTH: 180
<212> TYPE: DNA
<213> ORGANISM: Homo sapiens

<400> SEQUENCE: 113
gaatgtcttt gtgtgatact tgtactataa aagaatgcca gattagaaaa tcaaatatt      60 ggaaccaaag ttataaatct ggacaccaca sagagccaga gtataagggt attttttct     120 aatgttttgt tgccactaag gcatattatt tcttaaaaca gaagtacaac tcttgaagat     180

<210> SEQ ID NO 114
<211> LENGTH: 180
<212> TYPE: DNA
<213> ORGANISM: Homo sapiens

<400> SEQUENCE: 114
gcacgtattt atacggtaca tgcgatattt tgatatcagc atacaaattt taattatcaa      60
atcaagtaat tggggtaccc attgccttaa rtatttatca cttcttcata ttgggaatgc     120
gaagttttct cttctagcta ttttttgtttt tagacggagt cttgccctgt cgcccaggct    180

<210> SEQ ID NO 115
<211> LENGTH: 180
<212> TYPE: DNA
<213> ORGANISM: Homo sapiens

<400> SEQUENCE: 115
tgcgatattt tgatatcagc atacaaattt taattatcaa atcaagtaat tggggtaccc      60
attgccttaa atatttatca cttcttcata ytgggaatgc gaagttttct cttctagcta    120
```

```
tttttgttttt tagacggagt cttgccctgt cgcccaggct gcagtgcagt ggcatgatct    180

<210> SEQ ID NO 116
<211> LENGTH: 180
<212> TYPE: DNA
<213> ORGANISM: Homo sapiens

<400> SEQUENCE: 116
tttctgagtt tggtatatga aagttttaaa ccaagacaat ccctatgagt tgataaaaag    60
gatagaagac acagattgcc ttggtagaaa rgagtatggt gggcaccaat caagagtttc    120
agaaccttga atgatgagat gaggtttcag gaataggtct caggccaaag gtggaaggca    180

<210> SEQ ID NO 117
<211> LENGTH: 180
<212> TYPE: DNA
<213> ORGANISM: Homo sapiens

<400> SEQUENCE: 117
gtttaatgtg ctcacagaca tatcagatag cattcctcca gctgcatcca acagtgctct    60
cttttattgg ttctagttct ggataaaatt kagttacctt tggcagatct agcattgctg    120
caataggaag gaaaggagag aggaccagaa aagattccaa gtgcaaaatg tgcccttagg    180

<210> SEQ ID NO 118
<211> LENGTH: 180
<212> TYPE: DNA
<213> ORGANISM: Homo sapiens

<400> SEQUENCE: 118
ccatctaatt tacttaatcc tattattgtt atttcatgtg gttagtgttc agtaacactt    60
agaacatttt ttaaaaatga attgattata yaattatttc atatattatg tacgtgagcc    120
cagaagttct catcattaag tatattagat gtctgtgatt actatacttt atgagaaaga    180

<210> SEQ ID NO 119
<211> LENGTH: 180
<212> TYPE: DNA
<213> ORGANISM: Homo sapiens

<400> SEQUENCE: 119
atccttttat atatctttcc catccaagcc tatcttgctt gtccttttgca agaccctaat    60 tcaaacccat tatcctttca tgcatgttca kttgcaggat ccttgtaact ggactctttt    120
tccatccaag tggccctgca ttccaccagt agatcaacct tctttaagca tcattttgat    180

<210> SEQ ID NO 120
<211> LENGTH: 180
<212> TYPE: DNA
<213> ORGANISM: Homo sapiens

<400> SEQUENCE: 120
ggtggtgagt tcaacaacca aagggtcatg tgattaaata cattttgaaa tgactgcctg    60
ccctagcctc ttaaaaaaat tcacaatgct yattagcaca acaatgactt gaataaatct    120
cccaatagaa aaatctgctt cattttactt aacacactca tgtctcaaat tagttgaata    180

<210> SEQ ID NO 121
<211> LENGTH: 180
<212> TYPE: DNA
<213> ORGANISM: Homo sapiens

<400> SEQUENCE: 121
```

```
ctcattagca caacaatgac ttgaataaat ctcccaatag aaaaatctgc ttcattttac    60
ttaacacact catgtctcaa attagttgaa yacgaaaacc tgttttttt tttaatttat   120 gtaaacatta ttaacatttc tcagattgaa tattttaaat aacatacata ctttgggaaa   180

<210> SEQ ID NO 122
<211> LENGTH: 180
<212> TYPE: DNA
<213> ORGANISM: Homo sapiens

<400> SEQUENCE: 122
tttcagtcta ttctctctga ccactcttac tatccctcca ttaacttttt tttgaatgaa    60
ctctcactct gtcacaggct ggagtggatc rtgcagtggc acaatctccc gagtagctgg   120
gattacaggg gcccaccacc atgcctggct attttttgt attttagta gagacagggt   180

<210> SEQ ID NO 123
<211> LENGTH: 180
<212> TYPE: DNA
<213> ORGANISM: Homo sapiens

<400> SEQUENCE: 123
atctggtttg aggcaataat actaatgcta ccatttataa aaataagtaa tttctaaagg    60
gtggtagtaa aacacaggaa attgatagca ygtaaattgg aggatatcag gtccttacaa   120
ggttgtcaca ttgttgtatg aattcaagat caatcaaaaa taataattat aaatggaaat   180

<210> SEQ ID NO 124
<211> LENGTH: 180
<212> TYPE: DNA
<213> ORGANISM: Homo sapiens

<400> SEQUENCE: 124
aaatgtgtgt tacctttta ctgctttgta agtaaatcat agaatcactt ttttagtatc    60
atttcacttt tatgagtatt ttttaaaaac ycctctgcta atgcctggaa tctctccatt   120
cagagttaga gtcataatca gatttggcca gttgatacca aggcaactgc ctgtgtgttt   180

<210> SEQ ID NO 125
<211> LENGTH: 180
<212> TYPE: DNA
<213> ORGANISM: Homo sapiens

<400> SEQUENCE: 125
ctgcctgtgt gttttctttt gactgtatca cgggacacag aacacagctt aagaaacagt    60
caggaaaatg aggcctgttt ttttgagggg mtaattaaga aagacaaagt caattaacat   120
ctgattcctc acaggtttct ccaagcaaat tgttccaatt acccaaaacc agtgagcaaa   180

<210> SEQ ID NO 126
<211> LENGTH: 180
<212> TYPE: DNA
<213> ORGANISM: Homo sapiens

<400> SEQUENCE: 126
catgcaagat tattcaaatg acccttgatg tccatgattt ttagaaggat acaaacaaaa    60
caggtaatgt ttggccagaa tggtgaataa sttaaaggga aaattacttg gaaaataaat   120
tcgaagtcat agaattgttt aaggttgaga aaacaagcca gttagcctca aatacttgaa   180

<210> SEQ ID NO 127
```

```
<211> LENGTH: 180
<212> TYPE: DNA
<213> ORGANISM: Homo sapiens

<400> SEQUENCE: 127
gtgccactgc gctccagcct ggtgacagag caagactcca tctcaaaaag aaagaaagaa      60
agaaacaaac aaacaaaaaa cagctgcaag rccaatatgg tcaaataaag caaaacaaaa     120
cttttgaatt ttacaataga aatttatgtg atcgaactat gtatgaccta taaaaaatt     180

<210> SEQ ID NO 128
<211> LENGTH: 180
<212> TYPE: DNA
<213> ORGANISM: Homo sapiens

<400> SEQUENCE: 128
ccttaatgct ccagctatca tctcaatagc ttatataaag ttaattaagg ctatccgaaa      60
tgcagccttt ccaggactgt atctcttgag sctccatcaa aactgccttg tcataaagta     120
gaagaaacta gcatgttaat aagaagaaga gaaatctgtc caacttctaa tagtcttatg     180

<210> SEQ ID NO 129
<211> LENGTH: 180
<212> TYPE: DNA
<213> ORGANISM: Homo sapiens

<400> SEQUENCE: 129
cacagctgaa taaaattgcc ttagtgcatg aatcactctt aggttttatt caggttcatt      60
actatgtgtt atttctctcg gctacccttc ycaatccttg ctcaccatgc tatttggaaa     120
tctctaaagg aagggtgggg tgaatcccat gactcctgct ctcttgccat ttttagctgc     180

<210> SEQ ID NO 130
<211> LENGTH: 180
<212> TYPE: DNA
<213> ORGANISM: Homo sapiens

<400> SEQUENCE: 130
atccttgctc accatgctat ttggaaatct ctaaaggaag ggtggggtga atcccatgac      60
tcctgctctc ttgccatttt tagctgcctg maaccttttcc tggctgccag aatttataga     120
cttgggctga gtggccttgc caaataacaa gcgtctggct catgaatccc gaggtggact     180

<210> SEQ ID NO 131
<211> LENGTH: 180
<212> TYPE: DNA
<213> ORGANISM: Homo sapiens

<400> SEQUENCE: 131
tcttagtttt ttatttttct cattgttgta aagaaggcaa agagataaag agacgtagtc      60
atagagagaa acttaattgg cactactgta rgctcagcat ctattttttc ctatgcttta     120
aacaataaca tctgccagcg tataataaga ctatcaagaa aaagcatttt ggaaatactt     180

<210> SEQ ID NO 132
<211> LENGTH: 180
<212> TYPE: DNA
<213> ORGANISM: Homo sapiens

<400> SEQUENCE: 132
tatctatttt tgccttattt ttactagaga catgtggcaa gacaatgcta tcagggagaa      60
ttgaatttgt tcgtttataa aggctttcta yatggaaaga ttaaagtaaa actagaacaa     120
```
aagacctaaa atccattttt gaactagggc tataagatta tagaaattat cctcatttgt    180

<210> SEQ ID NO 133
<211> LENGTH: 180
<212> TYPE: DNA
<213> ORGANISM: Homo sapiens

<400> SEQUENCE: 133
atcaggaaaa taggtctgtg gttaagggaa gtaatcaact gacaggaacc tacagaaggg    60
tgccaaatat tgcactctca ctctcctcgt yatcactaat ctgccaagcc tctcctttgg    120
ctgaatctaa cgagaaccca gaaggcacga aagccatgtg acggcattca tatagattat    180

<210> SEQ ID NO 134
<211> LENGTH: 180
<212> TYPE: DNA
<213> ORGANISM: Homo sapiens

<400> SEQUENCE: 134
ctttagccta agatataatg agtgctttct cttatttgta acaaagctaa ttttgattta    60
agcagaaaag ttctggcaac ttcaaaatat ragtagtaag tctctggctg taaagtcaga    120
ggaggaggag gggcatccac actgtcttat tcagccatgg ttctttctga tgaagcaatg    180

<210> SEQ ID NO 135
<211> LENGTH: 180
<212> TYPE: DNA
<213> ORGANISM: Homo sapiens

<400> SEQUENCE: 135
aaataaatta ggacataaac caagaaattc tttgaaatca atgaaaacaa agatacaaca    60
tatcagaatc tctgggatac acacaaagca stgataagag ggacgttaat agcactaaac    120
gttcaaattg aaaagttaga aagatctcaa attaacaatc taacattgga actagaggaa    180

<210> SEQ ID NO 136
<211> LENGTH: 180
<212> TYPE: DNA
<213> ORGANISM: Homo sapiens

<400> SEQUENCE: 136
tgaatccagg agttcatttt ttgaaaataa gatagatagt tagctggact aataaagcaa    60
aaaaagagaa aacatccaaa taaatttaat yagaaatcac aaaggagaca ttaccactga    120
ccccacagga aaacaaaaca aaacaaaaca aaaaccatcg ggagactatt atgaataccc    180

<210> SEQ ID NO 137
<211> LENGTH: 180
<212> TYPE: DNA
<213> ORGANISM: Homo sapiens

<400> SEQUENCE: 137
catcggagac tattatgaat acctctctgc acacgaactt taaaacccca gaagaaaacg    60
ataaattact ggacatatag aacctcccga rattgaacct gcaagaaatt gaatccctaa    120
aaagaccaat aataagcttc aaaattgaat cagtaataaa aaacctgcca accaaaaaaa    180

<210> SEQ ID NO 138
<211> LENGTH: 180
<212> TYPE: DNA
<213> ORGANISM: Homo sapiens

<400> SEQUENCE: 138
ttgctactac ctaaatactg cttttgggt ctcactttcc aattatgaag ttatctgagc      60
tcatctctga cccctttctg gattccctct rttcagttca tgagcccaga ggaagtaaga    120
gcacaacaaa ccggataaag tcaaggtcta actagtgcta agcatcacag aaagctgagt    180

<210> SEQ ID NO 139
<211> LENGTH: 179
<212> TYPE: DNA
<213> ORGANISM: Homo sapiens

<400> SEQUENCE: 139
tacacctagt ttttctcata ttgaagcttt cttgggtgag caccatactt gctaattata     60
ctccatgccc catcctccac aacaaaaaaa wttccaaaga aaacagttga aatttcacca    120
tgaccagtgt ctggatgaag ctgtcttgag aattgtggaa taagcagctc cctcggtgt     179

<210> SEQ ID NO 140
<211> LENGTH: 180
<212> TYPE: DNA
<213> ORGANISM: Homo sapiens

<400> SEQUENCE: 140
ttttatatat atacatatat gcatataaat atgtatatgg atatatacat acatgtgtat     60
attatatgtg cacataaata tatatgacat rggaattcca ctgttaactt actcaatggt    120
ttctactgta caactcacaa atgcaaagta tatcattcaa attctgattt tatgcttcta    180

<210> SEQ ID NO 141
<211> LENGTH: 180
<212> TYPE: DNA
<213> ORGANISM: Homo sapiens

<400> SEQUENCE: 141
gtgcttaaag tgtcccctta cagaaaaaaa aaattactat gttcaagtat aaccccattc     60
atatatatct acccaagtgc tttcgtctat raaatgagta tttgactgat aaatacatac    120
atatttaatt ttgtaactt ccccacaata aattatttgt ataaaacaga aaaattttta    180

<210> SEQ ID NO 142
<211> LENGTH: 180
<212> TYPE: DNA
<213> ORGANISM: Homo sapiens

<400> SEQUENCE: 142
gcacaatgaa tttcatatac ttcactcaaa ttagagcctc caagtccctc cctcaaatgt     60
tatatatttt cactttatac tagattctct ygatgtgtat cataatagca aagaattcac    120
ttagcaaaga atccacttgg agaacacaca cagaaaatga aagactaaac aaaatttaa    180

<210> SEQ ID NO 143
<211> LENGTH: 180
<212> TYPE: DNA
<213> ORGANISM: Homo sapiens

<400> SEQUENCE: 143
aaagtagtta aaactgaaag ttgtagagta agactttaaa aattacctag tatagtttct     60
tcattttaca aagcagaaaa ctgaaattct sagagaccac taagtgaata acgtacattc    120
aatcaatttt tttaaaggga aactaattta tcacctaaag ctaacatcaa gccatatcga    180

<210> SEQ ID NO 144
<211> LENGTH: 180
<212> TYPE: DNA
<213> ORGANISM: Homo sapiens

<400> SEQUENCE: 144
cctgaagtgg cctcccaaag tgctgggatt acaggcatgg gccaccacac ctggcctaat      60 aacatttta aaaatcaaaa ttaatgcaaa maattccaag atgaaaaaat atccaaattt     120
taaataaaga cagacatttg tttgtgtgat ggatctgtaa tggcaatagt catttccaaa     180

<210> SEQ ID NO 145
<211> LENGTH: 180
<212> TYPE: DNA
<213> ORGANISM: Homo sapiens

<400> SEQUENCE: 145
gaaatagaat gccattaaag actataatac tacatgggta ccacctatta ctactgtata      60
taaacatatg aatacatatg tttgtcaagt rtggtaaaaa tattttcacc tcattagcag     120
acttactttg tgggatccag tgtgggaccc cacaaattca tatgcattct ttacaaatct     180

<210> SEQ ID NO 146
<211> LENGTH: 180
<212> TYPE: DNA
<213> ORGANISM: Homo sapiens

<400> SEQUENCE: 146
agcactcaat attaattgaa aagttttcta caaaatgtag gcattaaatt attactatgg      60
caaacaagtt tataatgtga taggtcaaat rctcgtttat taaagtgtta gggatatata     120
tctatatata tatatatata tagatatata tacacacata tatatgtgtt gcatttcagg     180

<210> SEQ ID NO 147
<211> LENGTH: 180
<212> TYPE: DNA
<213> ORGANISM: Homo sapiens

<400> SEQUENCE: 147
tggtacataa atttgggata agtgtcagga tttgagaatt tgaggaagta aaatttgaag      60
atgtgaggcc agaagatatt tttctagtct ygaatttaac aatatctata taataacaca     120
attcaatatt ttttgttcat gtatctctgg atccaaagga ataaaagaga tttccacttc     180

<210> SEQ ID NO 148
<211> LENGTH: 180
<212> TYPE: DNA
<213> ORGANISM: Homo sapiens

<400> SEQUENCE: 148
cctcaagata tctacccacc ttggcctccc aaagtgctgg gattacaagc atgagccacc      60
atgtctggcc aaacacaagg ttttcaactt yaagcaccag tgattcattg agtaaagatt     120
ctctcggctg cattttttgat ttgcaagatg aaaagacaaa agttactaat ctgaaaaatg     180

<210> SEQ ID NO 149
<211> LENGTH: 180
<212> TYPE: DNA
<213> ORGANISM: Homo sapiens

<400> SEQUENCE: 149
aaaggaattg tacaccatca ccaaatatgg catataccag gtatgtgagg ctggttcaat      60

```
atttgaaaac cagtcactgt aatacaccct rttaacaaac taaggatgaa aaatgtacat    120
gatcataaca atcaatggag aaaaagcatt tgacaaaact caatactaat tcataaccct    180

<210> SEQ ID NO 150
<211> LENGTH: 180
<212> TYPE: DNA
<213> ORGANISM: Homo sapiens

<400> SEQUENCE: 150
ccagcctggg tgacagagcg agactccatc tcaaaagaa agaaagaaag aaagaaatcc     60
atagatggac acagaaaaat tagccttaac ytagttgaca taccttatac aaaaattaac   120
tcaaaatggg caatgaattt aaatataaaa tataaggta taaaatttta aaataaaaac    180

<210> SEQ ID NO 151
<211> LENGTH: 180
<212> TYPE: DNA
<213> ORGANISM: Homo sapiens

<400> SEQUENCE: 151
atttcttaca aatgtttatg aatcaacagt tatctcaaaa taaatgtaa ttcaaagcaa     60 acaaaaaaca aatcaaacaa tatgaaaggt yagatcttcc tagtagcact aacttaccca   120
acattgatta ggtataattc ttgggctgct ggctagtgtt ctaaatgtac actttattat   180

<210> SEQ ID NO 152
<211> LENGTH: 180
<212> TYPE: DNA
<213> ORGANISM: Homo sapiens

<400> SEQUENCE: 152
ttacccaaca ttgattaggt ataattcttg gctgctggc tagtgttcta aatgtacact     60
ttattatgag gcatgaaaca tgttgggaag ycaggcgcgc tgactcacac ctgtaatccc   120
agcactttgg gaggtctaag tgggcagatc accggggtc aagagttcga gaccagccta    180

<210> SEQ ID NO 153
<211> LENGTH: 180
<212> TYPE: DNA
<213> ORGANISM: Homo sapiens

<400> SEQUENCE: 153
tctcaaaaaa cgaaaacatg ttgagaaagt aatgctgtta tgcaaatcct atgtttcact    60
ttcttgagtt atggatgatt aaatttgtaa wcttaaaatt gcactgccat gtgagtctaa   120
aatttaataa actggttcca caaacaaagg gaaaaggatg gtattccttt taaaacatga   180

<210> SEQ ID NO 154
<211> LENGTH: 180
<212> TYPE: DNA
<213> ORGANISM: Homo sapiens

<400> SEQUENCE: 154
actcgtatga aaataagcag taaatattta cattgtcttt aaatgttaaa atacttatgg    60
aatgggatat ggggtagcag tgtgcagcta ygctttttaa aattttattt catgatctaa   120
ttaaaaatat ccccagataa aaatcaaaca cacaaaatct gcaatatgga gtggctatca   180

<210> SEQ ID NO 155
<211> LENGTH: 180
<212> TYPE: DNA
<213> ORGANISM: Homo sapiens
```

```
<400> SEQUENCE: 155
gtcatatgta taagtacatt ctcctcagtg gaatatatcc ctagaaagta ggaactatat      60
ctcattttgt gatatgtcta gccatctagc rtagtgcttg aaatgtacta aatattcaac     120
acgtttctta ttattgatgg acatattcta tcctttgaga gctgactatc ttaaatggat    180

<210> SEQ ID NO 156
<211> LENGTH: 180
<212> TYPE: DNA
<213> ORGANISM: Homo sapiens

<400> SEQUENCE: 156
ttggcattta cacaatgcca ggatatgcag taaaaggagg aaaatataat gaaacatctt      60
gataacttat aatacagcat gttctactat wtggcaacat cccaatgact aactgaagtt     120
tttacctttc atctagctat tttggtactg tatagacaca gttcaataac tggaacagta    180

<210> SEQ ID NO 157
<211> LENGTH: 180
<212> TYPE: DNA
<213> ORGANISM: Homo sapiens

<400> SEQUENCE: 157
ggagttagcc ttaaaagtct tactcagaaa gacttttttt aaaaattgaa cttgcttttt      60
tttactccct atttaaatgg aatatacttg ytattgacat ggtggtaaac ataaaataca     120
agaaatcacc cttattccat ttcccaaaag caaccatcta aattcatgat gcatgtcaca    180

<210> SEQ ID NO 158
<211> LENGTH: 180
<212> TYPE: DNA
<213> ORGANISM: Homo sapiens

<400> SEQUENCE: 158
tacattgaaa gggtcatgga tctacttcat gagggatttt ttttttcagg gtgattttt      60 ttttcagttt gttctccaag caagaaataa ytctccaaac aaaagggaac ttaattctga     120
ggcattaccg tagcacatca aacatcaaaa acagagataa tataagatag aatgctccag    180

<210> SEQ ID NO 159
<211> LENGTH: 180
<212> TYPE: DNA
<213> ORGANISM: Homo sapiens

<400> SEQUENCE: 159
gttaataaat gcagagtact taaagaacag actttgagaa tgtgtacaag caaacttaa      60 gaatattttg tgctgggcac agtggctgaa rcccttaatc ccagcacttt gcgaggccaa     120
ggctgttgga tcacctgagg tcaggagttc agaccagcc tggccaacat gacggagccc    180

<210> SEQ ID NO 160
<211> LENGTH: 180
<212> TYPE: DNA
<213> ORGANISM: Homo sapiens

<400> SEQUENCE: 160
tttcttctga aaggtatata tagttttttg taagaactga tcaacttctg agctgaactg      60
cttttcagaa atgttcatag gaacctctat rcattttaat gttatatttt tatccacttt     120
aataagtcta gaggtcttat ctggatattc acattgatgc ttttctttat cattttggct    180
```

```
<210> SEQ ID NO 161
<211> LENGTH: 180
<212> TYPE: DNA
<213> ORGANISM: Homo sapiens

<400> SEQUENCE: 161
caacttctga gctgaactgc ttttcagaaa tgttcatagg aacctctatg cattttaatg      60
tttatatttt atccactttta ataagtctag rggtcttatc tggatattca cattgatgct    120
tttctttatc attttggctg tggatagcat ttgtgttttg ttttgttttt ctctccttca    180

<210> SEQ ID NO 162
<211> LENGTH: 180
<212> TYPE: DNA
<213> ORGANISM: Homo sapiens

<400> SEQUENCE: 162
gaaaatcacg actatataag atattctggt ttcagtgaaa ctagacattt accagatgtt      60
gggcacttga agtcttccat ctgtaacata stgtgtcttg atttcaattc tcacatctgt    120
tacttagctg agtacttatt ccttctattc ttcagtcagc tcatctctta aacagagata    180

<210> SEQ ID NO 163
<211> LENGTH: 174
<212> TYPE: DNA
<213> ORGANISM: Homo sapiens

<400> SEQUENCE: 163
ttgctgggaa ataattcctt atatataatc ttaaagctac tctccctccc ccaagccctc      60
tgcttctgat tcccacttat gttgcaaata satgatagaa cagggaaata tattgcggtt    120
tcacactttc ggggatttta tggtcactta ttcctaacta ggagatagag acac             174

<210> SEQ ID NO 164
<211> LENGTH: 180
<212> TYPE: DNA
<213> ORGANISM: Homo sapiens

<400> SEQUENCE: 164
agcttaacag ccatccctaa tcatggcgta cgttcgttaa tgcatacata aggaaaagaa      60
tgcaagctgt gttgtgaaga agttaaggca wcagactttc taagtacaac tgctggcttt    120
actagtattt gatgcacgtt cttgaacaag ttacttagca gctctgggcc ttaagttccc    180

<210> SEQ ID NO 165
<211> LENGTH: 180
<212> TYPE: DNA
<213> ORGANISM: Homo sapiens

<400> SEQUENCE: 165 catggggggcg gttacctcca tgctgttctc atgatagtga gtgagttctc acaagatttg      60
atggttttat aagggggcttt tccaccactt ygctctgaac ctcttcctgc caccatgtga    120
aggatgtgtt tgcttctgct cctgccatga ttgtaagttt cctgaggcct cccagccaag    180

<210> SEQ ID NO 166
<211> LENGTH: 180
<212> TYPE: DNA
<213> ORGANISM: Homo sapiens

<400> SEQUENCE: 166
aaagattaaa atgatactta aaacaacat caataacaaa aaaactaatt ataaatgtca      60
```

```
tcttttaaat ctacaatagg gaaaaagaat staaaatacc ttggaataaa tgtttacgtc    120
ttactacaac tataacgcaa tcacctttc tcccattccc aatagtttca agcaaaaaat    180

<210> SEQ ID NO 167
<211> LENGTH: 180
<212> TYPE: DNA
<213> ORGANISM: Homo sapiens

<400> SEQUENCE: 167
gtagcaaatc aaggcctttc tgaggagcag aaacaaccca gggaggctaa cgaacataaa     60
aatctggcat cctcttatag ctatcataaa rgtgaagaaa aacatcctag aggaattagc    120
tttgagaccc aagacggtta aggttgctag aacagaaaaa caagaaagac aaattttaa    180

<210> SEQ ID NO 168
<211> LENGTH: 180
<212> TYPE: DNA
<213> ORGANISM: Homo sapiens

<400> SEQUENCE: 168
ggaatgggaa aatttctgag atagagagta tagagaaaga aatggagagt aatgggaacc     60
actgggtaat gaaacttggg ttagataatc rttttatctg cctttggctc ttctataatg    120
catatgacta ccatttctgt agagtgaggc caactatagt acgggtgaat ttaataataa    180

<210> SEQ ID NO 169
<211> LENGTH: 180
<212> TYPE: DNA
<213> ORGANISM: Homo sapiens

<400> SEQUENCE: 169
atgaaacttg ggttagataa tcattttatc tgcctttggc tcttctataa tgcatatgac     60
taccatttct gtagagtgag gccaactata stacgggtga atttaataat aaattataag    120
aaaaatgttc caccattgta ttcacattac atgagtgtga gcatcccttg cacatccta    180

<210> SEQ ID NO 170
<211> LENGTH: 180
<212> TYPE: DNA
<213> ORGANISM: Homo sapiens

<400> SEQUENCE: 170
cgggtgaatt taataataaa ttataagaaa aatgttccac cattgtattc acattacatg     60
agtgtgagca tcccttgcac atccctagta stccctaaaa actgaaggag aaactaatta    120
taatgtattt atttgtattg actatgaaac gttttgttcc ccaaatgctt gattttctct    180

<210> SEQ ID NO 171
<211> LENGTH: 180
<212> TYPE: DNA
<213> ORGANISM: Homo sapiens

<400> SEQUENCE: 171
ggcatgagcc actgtgccag gccctgtgtt tttaactttc ttgagtgttc cagtaagtta     60
attagaaagt ccagcatgct ccataagcac kgtgttggat tgttatctct ctttagcatt    120
aattaagcac atatattcag catacagaaa ggggctttca tatctatgag tcaatgcaat    180

<210> SEQ ID NO 172
<211> LENGTH: 180
<212> TYPE: DNA
```

<213> ORGANISM: Homo sapiens

<400> SEQUENCE: 172

| | | | | | |
|---|---|---|---|---|---|
| cttcttaaat | tcaagcatgt | ttgtggacag | aacttgcttt | atgaataatt | gtagaagaca | 60 |
| acatcgattt | cacctggtat | gatctgaatt | yaagagtcct | ttctggcagg | gcatggtggc | 120 |
| tcgtgcctgt | aatcccagca | cattgggagg | ccaaggtggg | tggatcagga | gatcaagaga | 180 |

<210> SEQ ID NO 173
<211> LENGTH: 180
<212> TYPE: DNA
<213> ORGANISM: Homo sapiens

<400> SEQUENCE: 173

| | | | | | |
|---|---|---|---|---|---|
| ttttgataca | ttcatattat | gtataaagat | taaatcaggg | taattgagat | atccatcacc | 60 |
| ttaaatattc | accttttctt | tatgctagga | wtgttcaaat | tattttcttc | tagcaatttt | 120 |
| gaaatgtata | ctagattatt | gactatagtc | accctactga | tctgtcgaac | actaggcttt | 180 |

<210> SEQ ID NO 174
<211> LENGTH: 180
<212> TYPE: DNA
<213> ORGANISM: Homo sapiens

<400> SEQUENCE: 174

| | | | | | |
|---|---|---|---|---|---|
| aatttgcact | aaatacactg | gtcttttgta | tgcgctgtct | ggatggcatg | gacagtactt | 60 |
| gattattttt | catcctacat | tctgagtagt | rcactatagt | actagcagta | aacatttatg | 120 |
| gagagactag | tataccaaca | ctaatgtcta | atgataaccc | tttgaggtag | gttttgtttt | 180 |

<210> SEQ ID NO 175
<211> LENGTH: 180
<212> TYPE: DNA
<213> ORGANISM: Homo sapiens

<400> SEQUENCE: 175

| | | | | | |
|---|---|---|---|---|---|
| ttcaggtgtg | atatcatttt | cttacaaaat | aaatttagtt | aaaaagcaaa | aggtgtaaaa | 60 |
| aatggcagac | taggaagctc | taagccctca | wactcccaca | aaaacaccca | aaaaaacccc | 120 |
| taaatttgta | ggagctcttg | aaaacagtga | aagatttaca | gctaccaagc | taacatcaaa | 180 |

<210> SEQ ID NO 176
<211> LENGTH: 180
<212> TYPE: DNA
<213> ORGANISM: Homo sapiens

<400> SEQUENCE: 176

| | | | | | |
|---|---|---|---|---|---|
| cagtccttgt | ggcctagact | ctttcaagtt | tacttaggac | cctgctgtag | gggttggggg | 60 |
| gtcctttaat | ccgttttggt | gaggcttgtg | rgaattcaag | ttctgactgc | cgggttcatt | 120 |
| gattcccctc | tagctagggc | tggtttaaat | gctccctccg | tgagtggaca | tcagcaagtt | 180 |

<210> SEQ ID NO 177
<211> LENGTH: 180
<212> TYPE: DNA
<213> ORGANISM: Homo sapiens

<400> SEQUENCE: 177

| | | | | | |
|---|---|---|---|---|---|
| attcaactct | cctatttggc | ttgtgcagaa | gacagatgga | tgttggagaa | tgacagttaa | 60 |
| ttatcataat | acttcatcaa | gtggtgattc | yaattgcagc | cgctgtacca | gatgtttcat | 120 |
| tacttgagca | aattaacaca | ccttctgcta | cctggtatac | agctattgat | cgggctttga | 180 |

<210> SEQ ID NO 178
<211> LENGTH: 180
<212> TYPE: DNA
<213> ORGANISM: Homo sapiens

<400> SEQUENCE: 178

```
taccatggaa tactatgcat ccagtataaa gaacgagatc atgtcccttg cagggacatg      60
gatggaactg gagaccatta ttcttggcaa wccaaaacag gaacagaaga ccaaatacca     120
cgtgttctca cttataagtg ggagctaaat gatgaaaaca catggacaca tagaggggaa     180
```

<210> SEQ ID NO 179
<211> LENGTH: 180
<212> TYPE: DNA
<213> ORGANISM: Homo sapiens

<400> SEQUENCE: 179

```
gtatcaggag aatatcacca atgcttttta caaatgcctt tatgcagcca tgatgcaaaa      60
tgaaatcaat aaaatatcaa ttattgcaaa rttaaaaata gtgtactttt tgactaattt     120
ttgaccaaaa agaaaactct gttaaatatt tcaataagtt tattctgagc caatgtgtca     180
```

<210> SEQ ID NO 180
<211> LENGTH: 180
<212> TYPE: DNA
<213> ORGANISM: Homo sapiens

<400> SEQUENCE: 180

```
atcattttgg tgtattgggc aagaattcat ttatcggagt ggtgagtatg gagtgaaccct     60
caacctcaaa tctgtccttt aatctcaagg stcttttcct gctatcccgt caccaaactt    120
tccttctttc tctatccagg gtctcttact gtctctgtgt gtcaaatgtg caggaatttt    180
```

<210> SEQ ID NO 181
<211> LENGTH: 180
<212> TYPE: DNA
<213> ORGANISM: Homo sapiens

<400> SEQUENCE: 181

```
tggcagctga aaagcaagca cctctgcaag aagcagagaa tttcggaaat gagcaaaata      60
tcgcctataa tacaccaaaa aggaagaagg magatagata gggaaagtga agaaataaca     120
gaaacactat tcccaatcgg gagggaagca gttcccagta cacaaccctg attgggaccc     180
```

<210> SEQ ID NO 182
<211> LENGTH: 180
<212> TYPE: DNA
<213> ORGANISM: Homo sapiens

<400> SEQUENCE: 182

```
tttacaacag ggaccaagag gaggcccaaa agcaagagaa aaagctcagg agaaggacag      60
aggctctggt agcagatttg caggcttgca ragtccagca tccccaaggt gcatccgcta     120
gttgctatcg tgtgtggcagg ctagagcatt ttaggaagga atgcccaggc agcaagatga    180
```

<210> SEQ ID NO 183
<211> LENGTH: 180
<212> TYPE: DNA
<213> ORGANISM: Homo sapiens

<400> SEQUENCE: 183

```
cagacatttt cttaccactc atggatctac tataaaaata tcaccaggaa attaggttat    60
tatcctcagt ttttcttcca cgagaaatag magggatgca ttgtaaggaa catcaaaagg   120
aaacaaataa ggtagtcaaa ggagatagat tagctgacca agcagctaaa tcagaggcaa   180

<210> SEQ ID NO 184
<211> LENGTH: 180
<212> TYPE: DNA
<213> ORGANISM: Homo sapiens

<400> SEQUENCE: 184
acgagaaata gcagggatgc attgtaagga acatcaaaag gaaacaaata aggtagtcaa    60
aggagataga ttagctgacc aagcagctaa rtcagaggca aggaagcctc aaggcatcaa   120
cacacttcaa gcccctccta atctaggaag gctccataag aaaaactaaa cctcagtatt   180

<210> SEQ ID NO 185
<211> LENGTH: 180
<212> TYPE: DNA
<213> ORGANISM: Homo sapiens

<400> SEQUENCE: 185
tctcttgagg ggggaataat aaagttatta aggaataatt ttaggcagat agagaaggta    60
aaaggagtta tcagtgaggc ttttttttt waaaaataga aacagctcct gaaacatttc   120
ttaacagaaa ggcggcttga aaaaccagg cagacaagta ttgatatgca aatgcaggcg   180

<210> SEQ ID NO 186
<211> LENGTH: 180
<212> TYPE: DNA
<213> ORGANISM: Homo sapiens

<400> SEQUENCE: 186
agataatgct tatgaactag gtactattat gatcctcaac attagattag aaaactgcag    60
atcagggagg taaggtaact tggctgagat yacatggata gtaaatggtt gagccagttt   120
tcattcatgg taatgtggac tcccaaacct cattcgtttt acttgactgc caccacttag   180

<210> SEQ ID NO 187
<211> LENGTH: 180
<212> TYPE: DNA
<213> ORGANISM: Homo sapiens

<400> SEQUENCE: 187
atatcaatgt aaactggact tggagtgtta caaaaatcct gctcaaaagc atatactaaa    60
ccattaccat tttcttgtaa gtacaaatca rttttatga gacacagtct tgctttgtca   120
ccaaggctgg agcgcagtgg tgtgaccaca gctcactgca gcctcgacct acagagctca   180

<210> SEQ ID NO 188
<211> LENGTH: 180
<212> TYPE: DNA
<213> ORGANISM: Homo sapiens

<400> SEQUENCE: 188
gggtaatttt ctaccatcta agataaattg cttcactgtg cttcacatcc caagtccttc    60
caccctctca ggctcttttt ccactgatta mtacatcttc ctataccttc aaggctttcc   120
ctctgtaagg gttcctcccc attaacaaat aaaggtgccc aagtctctga cacctagaaa   180

<210> SEQ ID NO 189
<211> LENGTH: 180
```

```
<400> SEQUENCE: 189
atttatcttc cattaaagag agcctcagta ccccaagtgg gaggctctcc cagatagtca    60
gaagggtgaa actggaggta gagagtaaag kgatcagggc ccatacacaa agtcatacat   120
ttacacatgg aaacaaacag catgcttccg aatgaatcac caatcaaggg attgggtgag   180

<210> SEQ ID NO 190
<211> LENGTH: 180
<212> TYPE: DNA
<213> ORGANISM: Homo sapiens

<400> SEQUENCE: 190
tgtcctctct ctacactctc tactggatga tctcatttat atcctcttca cctactgccc    60
atgcactgat gactccaaaa tctacatctc yggctcattc ttctttccta ggctgcacat   120
cagggtatct ccggcctttt gaacatctcc aagttaatgc cccttgggta ccagaaattc   180

<210> SEQ ID NO 191
<211> LENGTH: 180
<212> TYPE: DNA
<213> ORGANISM: Homo sapiens

<400> SEQUENCE: 191
tattttgaga aacagatttg tactttgttt acctatactt aaatgtgttg ttgtaatatt    60
tcttttcaaa acagtggcac catatttctt yagaaagtgc aacggcactc actgtttagc   120
agcataaaaa atattatttg tgaaattaca atgtactcca aatagagaaa atatttcag   180

<210> SEQ ID NO 192
<211> LENGTH: 180
<212> TYPE: DNA
<213> ORGANISM: Homo sapiens

<400> SEQUENCE: 192
cgtaggtggg aattgaataa tgagaacaca tggacacagg aagggaaca tcacactctg    60 ggtacacttt gattttttaaa agactcccgc ygtgagactc ccgcaaggtc acttgctgct   120
ctctcacctc tctctctggt cctcctgtcc tcttggccag gaaatggcat cccatcgcca   180

<210> SEQ ID NO 193
<211> LENGTH: 180
<212> TYPE: DNA
<213> ORGANISM: Homo sapiens

<400> SEQUENCE: 193
ctccatctca aaaacaaac aaacaaacaa aaaactaaga agtatactt aacaggcaat    60 atttctcagg gttctcaaat tcacaaacac rcaaatgatg ttaaacaact agggaaaact   120
gcattacaat caggagcaag acaagtctgc ctactatcaa aaatgttatt aagtattgtc   180

<210> SEQ ID NO 194
<211> LENGTH: 180
<212> TYPE: DNA
<213> ORGANISM: Homo sapiens

<400> SEQUENCE: 194
ttaaagtgag caagccggga agtggtggag ctgggatcca caccctggtc tgtcttgagt    60
ccaagggtaa tcgtcttgca ttcactatgg matgtttccc ttacgttaag agttgctgac   120
```

```
atagacagtg catgtcattc cttttggtgt ggccttcctc ctttctagct tttttctgcc    180

<210> SEQ ID NO 195
<211> LENGTH: 180
<212> TYPE: DNA
<213> ORGANISM: Homo sapiens

<400> SEQUENCE: 195
agacatcagg ctagcccaca agggaagata gtttacttac caataacact gtgtacccac    60
aggctcaggc cacttttgtc agaagcagaa yaggctttcc aaggtcacca cgctgtacta    120
aaacttcacc taatcattag agaaagacaa catggcacat acacgtgatg tttggtatca    180

<210> SEQ ID NO 196
<211> LENGTH: 180
<212> TYPE: DNA
<213> ORGANISM: Homo sapiens

<400> SEQUENCE: 196
tctcttaact acaatatcag aatatataat aattgctgtt tcagggccca ccatgtatga    60
ggtgcttgac atatcttact gatagttttc wtaaaatccc tgtgacataa gtttctttct    120
tccagtttca cagatgagga aatttaggct cagaggggta gattacttgt ccctgttcac    180

<210> SEQ ID NO 197
<211> LENGTH: 180
<212> TYPE: DNA
<213> ORGANISM: Homo sapiens

<400> SEQUENCE: 197
ggcagggaca gaaggggcag ccccagcatc tgagcccttc acactgagaa tgacaccgtc    60
ttacctggaa gtgtcctcca ttgttgctgt yacacttgaa gctgcctgtt ctcacagcta    120
cattgtaatc agtcttccct acacaatatt tagcattctc accactgtgc gtttagctat    180

<210> SEQ ID NO 198
<211> LENGTH: 180
<212> TYPE: DNA
<213> ORGANISM: Homo sapiens

<400> SEQUENCE: 198
tcttctctgc ctacactcat taccttggtg atcttttcca gtattgtggt gtcttatgtg    60
atctacactc tcatcactgt ccagtttaga kagctgacct agattccaca gtctatttcc    120
aattacccac ctggcaagta cacatgcatg ttaaataaac attttgattt taactgtgta    180

<210> SEQ ID NO 199
<211> LENGTH: 180
<212> TYPE: DNA
<213> ORGANISM: Homo sapiens

<400> SEQUENCE: 199
cagagctgtt cctattcggc catcttggct cctcccccta gctgttgttt cctacagatc    60
tttcttaact tcctctaatt ttttccatgc ygttataatc ttctgacata cagtaggatg    120
taattattca ttttatttac tgtttgtata attacatgga aatatgagtt ccatgagggt    180

<210> SEQ ID NO 200
<211> LENGTH: 180
<212> TYPE: DNA
<213> ORGANISM: Homo sapiens

<400> SEQUENCE: 200
```

```
gaaggaaggc tgaaaataat taaattccca ctgaacatat atatttagct catatagaag      60
cctaggcacc ttagtacact ctagatgtta ragtgaggat atttggctcc aggaacacac     120
ataggcagct aagtggaatg gtaagagact agatattaag atcagaaatg tttgggccaa     180
```

```
<210> SEQ ID NO 201
<211> LENGTH: 180
<212> TYPE: DNA
<213> ORGANISM: Homo sapiens

<400> SEQUENCE: 201
tctatcctca tgattagatt caatttatac attttgtct ggaatagcac aaaatgatag       60
tattttcttc tcaatgcatt acatctgttg rcaaagtact tatttattcc ataactggta    120
atgtcaaatt taatcactta attaatgttg tattcagcag gttatgtcaa gtaaagttac    180
```

```
<210> SEQ ID NO 202
<211> LENGTH: 180
<212> TYPE: DNA
<213> ORGANISM: Homo sapiens

<400> SEQUENCE: 202
tggtgcacag agacagaaaa taaggggata cagaaaactt aagatggtaa agaaagtaaa      60
gcttgattaa caaatagaaa attacccagc wtgtgtgtgt ttgaaggagg gagtggctat    120
ggaggtgaga ggaggcttgt taagttcaga ggacctggag gaattttctg tgtctggaat    180
```

```
<210> SEQ ID NO 203
<211> LENGTH: 180
<212> TYPE: DNA
<213> ORGANISM: Homo sapiens

<400> SEQUENCE: 203
aatagaaaat tacccagcat gtgtgtgttt gaaggaggga gtggctatgg aggtgagagg      60
aggcttgtta agttcagagg acctggagga rttttctgtg tctggaatta gaaagggatg    120
caggctggga gttgaggtga gaaattagaa agtcgaaacc tcaagaaaat aagccactta    180
```

```
<210> SEQ ID NO 204
<211> LENGTH: 180
<212> TYPE: DNA
<213> ORGANISM: Homo sapiens

<400> SEQUENCE: 204
gaggaagctc acaagtgcat ggaaattaaa taacacgctt tgaaacaatt attatgtcaa      60
agaagaaatt gaagatgaaa ttagaaaata yattgagaca aggaaaaacc aaaacacaac    120
acagtgaaac ataacatgca gccaaatcag cactaagaag gaagtttata acaataaatg    180
```

```
<210> SEQ ID NO 205
<211> LENGTH: 180
<212> TYPE: DNA
<213> ORGANISM: Homo sapiens

<400> SEQUENCE: 205
ttttactgta tgtgaaatct aaaattgtta accatataga agcagatagt agaatggtag      60
tggccagggg ctgagggaag ggagaaatgc rggtggggtg ttggttaagc gatacaaagt    120
ttcagttatg tgtaataaat aacatctgta ggtctagtgt ataatacaga acctatgatt    180
```

```
<210> SEQ ID NO 206
```

```
<211> LENGTH: 180
<212> TYPE: DNA
<213> ORGANISM: Homo sapiens

<400> SEQUENCE: 206
ctgcaagcag acagtttgat ttcttacttc ccagtttgta taacttttat ttccttttct    60
tgtcttattg cattggcaaa attttccaat maaaattcaa aaagagtag tgatagtgaa    120 catccttctt ttttttcttg atcttagggg gaaaacatct agtttcttgt gattaactat   180

<210> SEQ ID NO 207
<211> LENGTH: 180
<212> TYPE: DNA
<213> ORGANISM: Homo sapiens

<400> SEQUENCE: 207
tggggatttg gggcctcagg gttgggaagg gcagacaagg accctgattt caggggtttc    60
atcatcttct gggggaggca tacaacaagt maagaatctt caaccctgat gaatgtgcag   120
tgtgatagaa ttcagtgggc tctaatggca tgtggcagga aactataacc ttgtttaggg   180

<210> SEQ ID NO 208
<211> LENGTH: 180
<212> TYPE: DNA
<213> ORGANISM: Homo sapiens

<400> SEQUENCE: 208
tgaacatctc tatttaggta tctgcctttg agcattttat cttaatgtat tagtttgttc    60
aaatatataa tcccacaggt atgtattata wtccaataac ctaaccagtc tctctcctag   120
aaatccattg gttttgattc cacaaaaatg tcaatccttt agctgtaact tttcatccac   180

<210> SEQ ID NO 209
<211> LENGTH: 180
<212> TYPE: DNA
<213> ORGANISM: Homo sapiens

<400> SEQUENCE: 209
cagtaattgg gggaatgcaa actaaaaccc caatgagaca ccactacata cctattacaa    60
tgtctacaat ttaaaaagtc tgaccatacc ragtgttata agaatgtgga agaactagaa   120
ctctcatatg ctcccagttg aaatgtaaaa ttgcacagcc actttggaaa acagttttt   180

<210> SEQ ID NO 210
<211> LENGTH: 180
<212> TYPE: DNA
<213> ORGANISM: Homo sapiens

<400> SEQUENCE: 210 ttcacttta cttttctctg agctctcctg ggtctctccc atacatgtgc atattttccc    60
agtcacacag gatatatgaa gacctactgt kgtgcattca ttttcaaaat ctctttatta   120
aattcctctc tgatcctctg cttgccccac tgtaacctca aacttaggca accaaatgga   180

<210> SEQ ID NO 211
<211> LENGTH: 180
<212> TYPE: DNA
<213> ORGANISM: Homo sapiens

<400> SEQUENCE: 211
aataacccag cttttcacca tctgacccaa atggaattca cccactggga gaaaagctgc    60
taaattgttt tggtcggcac atactgtaaa mctatccttc tcaccttggg atctaaggag   120
```

```
attgagggt gggctggatg gaagaagccc catgcaagga cacagattct tttacacaca    180

<210> SEQ ID NO 212
<211> LENGTH: 180
<212> TYPE: DNA
<213> ORGANISM: Homo sapiens

<400> SEQUENCE: 212
acagacaggc agaagaaaat ccagttgcca taaaatcttc catcagagga gaaggatcta    60
tccactttta attcctgggg ttcttatgag raaaatagag gtctcttgcc tcatacatgc   120
atcgagagtg gcaagacaaa atcaagaaaa ataattcagc tgactgagaa caaaaaacct   180

<210> SEQ ID NO 213
<211> LENGTH: 180
<212> TYPE: DNA
<213> ORGANISM: Homo sapiens

<400> SEQUENCE: 213
tatgagtggt tgcttgactt tgggtaattt ccttaataca tttatggctt tacagtttca    60
caactaaaaa atactactag atacagttga sacttgaaca acatgggctt gaactgcatg   120
ggttcactta tatgcatatt tctttcaacc aaaagcagat aaaaaataca gcatctggga   180

<210> SEQ ID NO 214
<211> LENGTH: 180
<212> TYPE: DNA
<213> ORGANISM: Homo sapiens

<400> SEQUENCE: 214
agtatttgat acactcaata gatgttccaa aggtattcag taataattaa acacctattc    60
tcatttttta aaatatatat acttaaagta rattctagta ggctatattg aggtgatttt   120
tttccctgta aaaaagcac agaatggttt tatacaacca gaggaaattt cattaaaatc    180

<210> SEQ ID NO 215
<211> LENGTH: 180
<212> TYPE: DNA
<213> ORGANISM: Homo sapiens

<400> SEQUENCE: 215
atgggaaaaa agttatgagg taagccagcc ttttaatgat aatagcaggc aaaaccttat    60
ttctagaaca cgagggccat aacttactga ytgaataaaa tcccaatcaa aatgccaatg   120 gaatttatt tgtagagctt tacataacca tgttaatatt cacgtattag aataactagg   180

<210> SEQ ID NO 216
<211> LENGTH: 180
<212> TYPE: DNA
<213> ORGANISM: Homo sapiens

<400> SEQUENCE: 216
gaacatagtg tttttcagca ggtgagtacc tgatctaagt tgtaaatgct gtctaccact    60
gaaaaatgcc ataacaaaca acagcactca rtgaagtaat tggttagaca aggcacagtg   120
gtagtgtgcg agcataggct cgggagccag aaaaacttga attccaatcc caaatactat   180

<210> SEQ ID NO 217
<211> LENGTH: 180
<212> TYPE: DNA
<213> ORGANISM: Homo sapiens
```

```
<400> SEQUENCE: 217
agtagcttgt ccaaggttac acagctatta ctggtggga atgtgactgg aatgcagata      60
tgtattagga taaagctcga gattactata ycatgcagaa gaagaataaa aaacacagca     120
gactgggtgc agtggctcat gcctgtaatc ccagcacttt gggaggctga ggtaggtgga    180

<210> SEQ ID NO 218
<211> LENGTH: 180
<212> TYPE: DNA
<213> ORGANISM: Homo sapiens

<400> SEQUENCE: 218
gtatgctgct ggaattgagg ctccaaatgt ttaagtagct tgtccaaggt tacacagcta     60
ttaactggtg ggaatgtgac tggaatgcag ratgtatta ggataaagct cgagattact    120
atatcatgca gaagaagaat aaaaaacaca gcagactggg tgcagtggct catgcctgta    180

<210> SEQ ID NO 219
<211> LENGTH: 180
<212> TYPE: DNA
<213> ORGANISM: Homo sapiens

<400> SEQUENCE: 219
caataagaaa aaggggaagg ggccaggtgg aatcacttgg gaataataaa gttaaggatt     60
gcctatactg catcccacgt tggctttagc rttaaaaaac aagctccctt tagagtcctg    120
gccctccctt acactagctg tgtgacactg ggctgttacg taacttacct agatcttaat    180

<210> SEQ ID NO 220
<211> LENGTH: 180
<212> TYPE: DNA
<213> ORGANISM: Homo sapiens

<400> SEQUENCE: 220
gtgccacttg ctaatctcct ccttttgag ttggtctaga aaaggccaag taagtatcct     60 tttttcatgaa atattagaat gactccaggg ytttctgatg gcttttgaat tagaacaaaa    120
caaaaaaatc aattcttagt ttcttatagg aacaattaat gattaaagac aaaatatcct    180

<210> SEQ ID NO 221
<211> LENGTH: 180
<212> TYPE: DNA
<213> ORGANISM: Homo sapiens

<400> SEQUENCE: 221
cctggaacta catgtgtacc ctcagggcaa ctggtctgtg gagtctcttt cagtacactg     60
tatcccacta gtaagtaaat aatctctctc ratcttgttt ggtgtccttg ggggaaaaag    120
ggcatcagcc ccatcttcca gtgctttgaa gaaagcttca gggtgtgaat tataccagtc    180

<210> SEQ ID NO 222
<211> LENGTH: 180
<212> TYPE: DNA
<213> ORGANISM: Homo sapiens

<400> SEQUENCE: 222
gcacataata ttgagcctta actttaggtc ttatactgca gatacataaa gtgtgtcaca     60
cacaattgga atttctttac aggcaacttg rcaattgcac aaaacaggca agtaaattaa    120
aaaaaaagcc aaggatgatt ccttctgagg cataggttgt tattggaaac aagtaaagct    180
```

```
<210> SEQ ID NO 223
<211> LENGTH: 180
<212> TYPE: DNA
<213> ORGANISM: Homo sapiens

<400> SEQUENCE: 223
tgacataatt gtgtatgttg aaaattctca agaagcaata aaataagtct tggaactaat      60
aagcaattat agcaaggtca cgggatacaa ktataatata cataagtcca ttgctttctt     120
atatacccac aatgaaatat ttgaatttga aatttaaaat acaataccat ttacattttc     180

<210> SEQ ID NO 224
<211> LENGTH: 180
<212> TYPE: DNA
<213> ORGANISM: Homo sapiens

<400> SEQUENCE: 224 aattttctt gatatttagt atattcttga tatttagtat aagtttaggt tatattcttg       60
gcattttgca taatatcttg ttagaatctg rgtcctatta atatcctctg gagagtgctg    120 aattttttg ggttggactt agctagacca acatggctag attcagacta aatgttctgt    180

<210> SEQ ID NO 225
<211> LENGTH: 180
<212> TYPE: DNA
<213> ORGANISM: Homo sapiens

<400> SEQUENCE: 225
ttttaaaaaa tacatattta actttctcaa tataaaaagc taatttgaaa aataatctcc     60
ttatacaagt ctatagcaga tagctcctcc yccttcctgt gattctcttg ggggtaacat    120
gacttctttc ccagtatcta agtccttgag ctagaatttt aaaacaattt taagcattgt    180

<210> SEQ ID NO 226
<211> LENGTH: 180
<212> TYPE: DNA
<213> ORGANISM: Homo sapiens

<400> SEQUENCE: 226
cctagtaccc attattttaa cccagtacag tacactattg cctctccatt tgtgaaaaga     60
aaaaaaaaaa gacggaaagt ccttttata yggaaataca gataggattt taaaaacagg    120
ccccagaaaa ccttacacaa cactttctgc tattaaacca ttctctttcc ttcttcccct    180

<210> SEQ ID NO 227
<211> LENGTH: 180
<212> TYPE: DNA
<213> ORGANISM: Homo sapiens

<400> SEQUENCE: 227
tcacctatca ttaccaatca tcactctaag ggggacagcc ctcatccgtg cacacactat     60
tcagtgccca gggcctgagt attttgagga wcccaagaag cagtgttgta ttttgcatgt    120
agtagaaata attaggccat tacacccagc atacagggaa acccaccttc ttttcacgtc    180

<210> SEQ ID NO 228
<211> LENGTH: 180
<212> TYPE: DNA
<213> ORGANISM: Homo sapiens

<400> SEQUENCE: 228
ctcttttgaa ttagcactgt aaccatagac aaccagaaaa aaacctaagt atttatcaaa     60
```

```
gtgggcaatg gttaaaagaa ttattctata yccatgaaat tgagtatcat ggagatatta    120
gaaatggtga tgcaatcata tattgacatt aaaattatat tcatcttcta aggtcaaatg    180
```

<210> SEQ ID NO 229
<211> LENGTH: 180
<212> TYPE: DNA
<213> ORGANISM: Homo sapiens

<400> SEQUENCE: 229

```
taaaataggg aaacatatca tctgtaatgc catcattcag agatgttcag tcaacaattt     60
ttgtgtgttt atatctctct aaacttctaa statgcattt gcatgtgtac acacacatct    120
ctgtttcaaa agctgctttt ctcatttgac cttagaagat gaatataatt ttaatgtcaa    180
```

<210> SEQ ID NO 230
<211> LENGTH: 180
<212> TYPE: DNA
<213> ORGANISM: Homo sapiens

<400> SEQUENCE: 230

```
ctgtttgcta agagacagaa aagaaaaaag aagctacagc aaagggtata tgtgctttct     60
gagatacaag aaatacagag tgctttgaga yagcacagga tggaaatccc tgctagttta    120
cgctggcctc ttggaggaag agatttatca gctgagactt gaaggaacag taaaaagaca    180
```

<210> SEQ ID NO 231
<211> LENGTH: 180
<212> TYPE: DNA
<213> ORGANISM: Homo sapiens

<400> SEQUENCE: 231

```
ctgtctcaaa gcactctgta tttcttgtat ctcagaaagc acatataccc tttgctgtag     60
cttctttttt cttttctgtc tcttagcaaa yagcacaaac ccagcatgaa gcttgttcat    120
ttttgcatct tagaatctaa catgataccc agccagcagg tttgggaaaa tctatctcat    180
```

<210> SEQ ID NO 232
<211> LENGTH: 180
<212> TYPE: DNA
<213> ORGANISM: Homo sapiens

<400> SEQUENCE: 232

```
agccagcagg tttgggaaaa tctatctcat ttgggtcaca aagaccaata caaaaacttt     60
gttcccatca tttcctcatc atccaacata ygttagagct gtttgaaagg cataaataaa    120
ggagttgact ttttggtgga tggaaaatgg taaaagttta ttactaatat ctgaagtgga    180
```

<210> SEQ ID NO 233
<211> LENGTH: 180
<212> TYPE: DNA
<213> ORGANISM: Homo sapiens

<400> SEQUENCE: 233

```
aaaacacatt ggttttctca ttactcaagg tttaatcaaa taaacaaaac cagcaggaga     60
tatacatata cacacacata cacattcaag kgactggctt acataattgt gggggctggc    120
tatataagtc caaagtccat agaatagtca gtcaggaagt aaagatcacg agtaggctag    180
```

<210> SEQ ID NO 234
<211> LENGTH: 180
<212> TYPE: DNA
<213> ORGANISM: Homo sapiens

<400> SEQUENCE: 234
tttcccagat cttggtcatt cacgtaccat ctttaggatt tttaacatat ccaaatacca      60
cctgaataat cattcgatta atatttccat kgaaaccata taaactttaa atttaaatac     120
agtttaaaag aagccccaca tcatgatcaa gaatggaaaa ctaatgtttc atatcataga    180

<210> SEQ ID NO 235
<211> LENGTH: 180
<212> TYPE: DNA
<213> ORGANISM: Homo sapiens

<400> SEQUENCE: 235
gtatgagtga cattactggc aaagagagag atcagcatac tggaagcagc acagggcttt     60
gaggcagtca gatttggggc tgaaaaactc yagcgctaac tagctgtgtt ttcttgagca    120
agttgcttaa catccactta ttccttaaag gaatgtgtat tgagtgcttg ccatatacca    180

<210> SEQ ID NO 236
<211> LENGTH: 180
<212> TYPE: DNA
<213> ORGANISM: Homo sapiens

<400> SEQUENCE: 236
ttctgagaga gaaaaaattc atcgtttaca atatcttgct gtcagccaaa gattgtgttc     60
tgaggagggt cctttattgc agaaatggtt yctggttgaa agaatgcaaa tcacaacctt    120
agattctgct tctgtaaaaa cagatgacag aaggggagga cagaaggatg gcttctattc    180

<210> SEQ ID NO 237
<211> LENGTH: 180
<212> TYPE: DNA
<213> ORGANISM: Homo sapiens

<400> SEQUENCE: 237
tattccaagt tcacgcctac aacaaggcca tctgttttca tttggaactt aaaggtgcac     60
ttcccctggc tctgctttca ctttccatca ygcttccttc tcctttcaga ctcaccataa    120
agtgaaatag ttgatcccag cctgttggct tcagagcagc aattttgagc tctttcctag    180

<210> SEQ ID NO 238
<211> LENGTH: 180
<212> TYPE: DNA
<213> ORGANISM: Homo sapiens

<400> SEQUENCE: 238
tataaaattt aatatggcag agagaacgag aaattatttc tggttcagct gtatccaagt     60
gtggctcaaa aatgcaaatg gaaacagaca yggcaaaagt cacaatggag caaaatatat    120
cttcctctgt ggagattctc atcaacgttg gcatatgagt agtattcata gacctctagg    180

<210> SEQ ID NO 239
<211> LENGTH: 180
<212> TYPE: DNA
<213> ORGANISM: Homo sapiens

<400> SEQUENCE: 239
aatatgtcga ttttagccct aatcccattg tgctgtaaac agtggtaacg tgtatgtctt     60
attaactgaa ctgtgagctt ccagaggcca sgaaatgtat ttattcttgt ttattcctct    120
ttttattccc agcacccatg acagtgccag gcacatagag gacattcaat aaatggttct    180

<210> SEQ ID NO 240
<211> LENGTH: 180
<212> TYPE: DNA
<213> ORGANISM: Homo sapiens

<400> SEQUENCE: 240
accagactaa taatactctg attctactgt gtacaggagt catttctcat cttcctggta    60
accctgaaag gtggatttta ttatctctaa yttacacaaa ggcaaataag ctcagaggag   120
tgcaagatca tgtccagagt cacaaaacca gtaagtgatg atcaagggta tttatgaatc   180

<210> SEQ ID NO 241
<211> LENGTH: 180
<212> TYPE: DNA
<213> ORGANISM: Homo sapiens

<400> SEQUENCE: 241
ttacatttag ggcaagggac ttgagattta aggaaaggt aatgttaggg aaactgggtt     60
gtaattttag tcctgggagt cagttggagg sggagcgtag aaggtaggt catctttgtg    120 atggactggt tcggttttgt ctcagggtta catgaatctg tggagagaag ccagcagtct   180

<210> SEQ ID NO 242
<211> LENGTH: 180
<212> TYPE: DNA
<213> ORGANISM: Homo sapiens

<400> SEQUENCE: 242
taactttagt ttcctaacaa tgtaattata agtcctcata gtgcagaaca cctaataaat    60
aaaagaagcc ttttcagtag atgtgaagat rcagatgaga agatggaaat ggcaccagcc   120
ctgcgcccac ctcccatttc cttacctatg accccagggg agaccaggtt cccaggggtc   180

<210> SEQ ID NO 243
<211> LENGTH: 180
<212> TYPE: DNA
<213> ORGANISM: Homo sapiens

<400> SEQUENCE: 243
ccagcacaac agtcctctgc ttgcattctc acacacagaa accagcctag catgcttaaa    60
ctgtatgcca agttaaaagg gtgcttggca stcttgaaca tgagtcttta accaaactga   120
tgaatgattt gcacatggct tagagaagca aaaattatca gaacacgctt taaaagtcat   180

<210> SEQ ID NO 244
<211> LENGTH: 180
<212> TYPE: DNA
<213> ORGANISM: Homo sapiens

<400> SEQUENCE: 244
ccatctaccc acaacctaga ttcaatgatt cttaacatt tgttgtatgt acctatatgc     60
gacaactgta gacagaacag taattcgata rgaattacat gtatctatat gcatgcatat   120
gtgcatacat tttttcaaaa acatttaaag taagatacat acattaatgc catgttgtct   180

<210> SEQ ID NO 245
<211> LENGTH: 180
<212> TYPE: DNA
<213> ORGANISM: Homo sapiens

<400> SEQUENCE: 245 agcttttct catcaactgt ggatggacta ttttttctcc cttaaaggca ggatacatgc      60

```
tttattcttt tactttaatt atcattttgc rgaataaaga gttggagtaa tagaaatctc    120
caattatgaa acattattct ccctttttct atctttctct ctctttctct gggtataact    180

<210> SEQ ID NO 246
<211> LENGTH: 180
<212> TYPE: DNA
<213> ORGANISM: Homo sapiens

<400> SEQUENCE: 246
catattttaa attttagttt tctcttgttt ttctactttc ttgatgtgag accttaggtt     60 attttaaaa acattttctc attcactgct rtaaattttc tcagcatttc tttagttgca    120
tcctacatat attgatatgt tgtcttttat tctcatcagt tgtatgtatt ttaattttaa    180

<210> SEQ ID NO 247
<211> LENGTH: 180
<212> TYPE: DNA
<213> ORGANISM: Homo sapiens

<400> SEQUENCE: 247
ttgaggctgg tacccaatag ctctatgtat ctcttaagct ttcttcactt tttcattact     60
cttctgtctc tgcttaagtt cctgctggta scacctggaa aaagaaggt gcttcctttt    120 gccttccaag tatcataaag tgagttatgg ggaatccaaa gcaatggtgc agaaagtgtt    180

<210> SEQ ID NO 248
<211> LENGTH: 180
<212> TYPE: DNA
<213> ORGANISM: Homo sapiens

<400> SEQUENCE: 248
tgaatgaatc aagatcgcat tcactattag ggaagggtaa gcgagaacag actgtgaggg     60
caagatgttt atgggaaatg ttttcttatt yttaaaaaca aaaacaaaaa caaaaaaact    120
gcactaaagg gaaaaccagc gactcttatt ctgttggacc ctattgtgcc tggatatggt    180

<210> SEQ ID NO 249
<211> LENGTH: 180
<212> TYPE: DNA
<213> ORGANISM: Homo sapiens

<400> SEQUENCE: 249
cctgtgaatt acattttctc tgaaaggacc actgacagac aagctgtggt tattcagacg     60
tgggtatgtg aaagatgtct tgaagataaa yaaagggagc tttgtttcaa caaaaacgac    120
ttacagcatt tactgccaat gataaaactg gactcgaaca aaaattagaa ttttggaaa     180

<210> SEQ ID NO 250
<211> LENGTH: 180
<212> TYPE: DNA
<213> ORGANISM: Homo sapiens

<400> SEQUENCE: 250
atgttgtagt atgcatcaga atttcgttcc ttcctaaggc agaataatat tctattgtat     60
gtataaacta catttgattt gatttttatt ytaagaatct catgggtgga taaaaataaa    120
gagatctatc tggtcaaatg tatttttctta aaatactaaa acattattgc gcatttccat    180

<210> SEQ ID NO 251
<211> LENGTH: 180
<212> TYPE: DNA
```

<213> ORGANISM: Homo sapiens

<400> SEQUENCE: 251

| cacccagcta atttttttgt attttagta gaaatgggat ttcaccgtgt tggccaggct | 60 |
| ggtctcgaac tcctgacctc aggtaatcca ygcgtcttgg cctcccaaag tcctgggatt | 120 |
| acaggtgtaa gccactgtcc ccggctatgg ttaaacttta tgttaacagg atttccatta | 180 |

<210> SEQ ID NO 252
<211> LENGTH: 180
<212> TYPE: DNA
<213> ORGANISM: Homo sapiens

<400> SEQUENCE: 252

| taacaggatt tccattaaac tgtctgacac atacatattg ttcaaatata gttattgaac | 60 |
| agataatttt atgcaggatt tgcttattca rtcagcattt atgaaacata taatatgtgt | 120 |
| ctgaaactgt cctgggcaca caggattcac aaatacatta gacaggttta ttgcttttca | 180 |

<210> SEQ ID NO 253
<211> LENGTH: 180
<212> TYPE: DNA
<213> ORGANISM: Homo sapiens

<400> SEQUENCE: 253

| tcaccaagag tttccttatg gttctttgta gtctataccc ctcacctcta tttctagcct | 60 |
| gctctgatcc cagccccaga taatcactta ygggctcttt gtttgtataa attggttggc | 120 |
| attttctaga atttcatata aatggaatca aacagtgtgt cctctttat ctggcatctt | 180 |

<210> SEQ ID NO 254
<211> LENGTH: 180
<212> TYPE: DNA
<213> ORGANISM: Homo sapiens

<400> SEQUENCE: 254

| ctagtttgca gctactaaaa taaagctggt atgagtattt aaatgtacat gttcgttcac | 60 |
| atggtaaata ggtactttca ttactcttgg mtaaatacc agagttgtaa agtctggatt | 120 |
| atatgatagg tattggtata acttttttaa aaactgccaa accttttacc aaagtggttg | 180 |

<210> SEQ ID NO 255
<211> LENGTH: 180
<212> TYPE: DNA
<213> ORGANISM: Homo sapiens

<400> SEQUENCE: 255

| ctagttctgt ggcttaccct ttctttcatt taatgatgtc ttttgaagga cagaagttct | 60 |
| tagttttaat gaattccaat ttgtcacttt yctttatca agttttttga gtttcatata | 120 |
| agaaattgtt gcctactgta tggtcacaaa gattttccca tattttcttc tagaagtgta | 180 |

<210> SEQ ID NO 256
<211> LENGTH: 180
<212> TYPE: DNA
<213> ORGANISM: Homo sapiens

<400> SEQUENCE: 256

| ttgcaaatat tatctcctat tccattctgt gggttggctc ttcactttgt tgattgtttt | 60 |
| cattgctgta cagaagcttt ctaacttgat rtcatcccat ttgttcattt ttgctttggt | 120 |
| tgtctgtgct tattgggtat tattcaagaa attttttgccc agagaaatgt cctggagagt | 180 |

<210> SEQ ID NO 257
<211> LENGTH: 180
<212> TYPE: DNA
<213> ORGANISM: Homo sapiens

<400> SEQUENCE: 257
ttttgacaaa agtaggatat ttgttcacct ttacactatc gcatgaaata acaatttcac    60
tgccctaaaa attacctaca ttccaccaat ycatcccttc ttcccaccct gggaatcctt   120
tgaaagcact ggtcttttca ctgtctctac agttttgctc tttccagaat gtcatatagt   180

<210> SEQ ID NO 258
<211> LENGTH: 180
<212> TYPE: DNA
<213> ORGANISM: Homo sapiens

<400> SEQUENCE: 258
agaagttata ctaagttaag acggtcactc tttttctatt ggacactgtt gtacttgcat    60
gtgatcctga aacactttt gtagacatgc yaatcctaac tgggatatct ctctgatgct   120
gacagcaagc tctcagggcc ttctacaggc aggaatctgc caccttgtaa tgatgagggt   180

<210> SEQ ID NO 259
<211> LENGTH: 180
<212> TYPE: DNA
<213> ORGANISM: Homo sapiens

<400> SEQUENCE: 259
tgtgttttac caagtgaacc ttgacacaga aactagataa ggataattta agaatggcaa    60
atttcaaagc aatctgtctc agaaacatac rtgaaaatat cacatgcaag gtacttgttt   120
aaaaagctag caatatcttt ttattttag ttttagtttt ttttttttt tttgagatgg   180

<210> SEQ ID NO 260
<211> LENGTH: 180
<212> TYPE: DNA
<213> ORGANISM: Homo sapiens

<400> SEQUENCE: 260
tagtgtgata ttgctgggta taaggtcaat atcacaaaat tcaattgaat ttgtatatcc    60
tggcattaaa catgtaaaga gacaactttt maatgtcatt tctcatagta tcagaacaca   120
tcaaatgcct aggaacaaat ctagcaaaga ttcccaagac ctctgcccgg aagtctacac   180

<210> SEQ ID NO 261
<211> LENGTH: 180
<212> TYPE: DNA
<213> ORGANISM: Homo sapiens

<400> SEQUENCE: 261
atttgcaata tacatatgta tataccacaa atgtctgatg tacagaatgt aatacccct    60 aaaatcaaga ggggaaaaga ataatgcaac raaacattgg caaaatattt gaacagcacc   120
ttcacaaaac aggacatcca gcggactaat agacaaacag acaaacagct gctcaacctc   180

<210> SEQ ID NO 262
<211> LENGTH: 180
<212> TYPE: DNA
<213> ORGANISM: Homo sapiens

<400> SEQUENCE: 262

```
tccacaaaac tgtgggcaat aatcttgtta aactttcggc cactacctag cagggatctc    60
cctttctcca gtttacaatg acgcgttcct ycctccttct gaaccctcat cagcagtgtc   120
ctgaaaagtc agacttctac taactgtctg tccatggcaa tgaaacctt cccaaggcga    180
```

<210> SEQ ID NO 263
<211> LENGTH: 180
<212> TYPE: DNA
<213> ORGANISM: Homo sapiens

<400> SEQUENCE: 263

```
atcttctctc agtttcagta ttttaaatat tttaccgttt gtccaattcc tctaagtttt    60
tgatttattg gcatgatggt ctctaacggt rtgcctccca gttttgattc ctgatattac   120
caatttgtgt gtttatttct tttatcttca caagtctcac ccgtggttta tgagttttat   180
```

<210> SEQ ID NO 264
<211> LENGTH: 180
<212> TYPE: DNA
<213> ORGANISM: Homo sapiens

<400> SEQUENCE: 264

```
tttccccagg agaggaagt atgtacctgg gccatctgct gctgctggtt ggagggccag     60
gagctacaga cctggctctc ttctactggg rgaagcgttg gatatctctc ttccactggg   120
ggaagcgtcg ggagattctg caactggttc accttctgtt gcagaataga tgtctggaaa   180
```

<210> SEQ ID NO 265
<211> LENGTH: 180
<212> TYPE: DNA
<213> ORGANISM: Homo sapiens

<400> SEQUENCE: 265

```
ccttctttgt tagacagaaa tcttctctga taagaaactt ctctcatccc ctacttggta    60
atcaagtatt atagtttata tgccaaacac atgttaactg tttcaatttt tgcctctgtt   120
tacccagttt caaaataatg aatttattcc ctagcatcta atattttta gatattttc    180
```

<210> SEQ ID NO 266
<211> LENGTH: 180
<212> TYPE: DNA
<213> ORGANISM: Homo sapiens

<400> SEQUENCE: 266

```
gtctaaggtg catcagattg acagaaggta aaacacattt ggaatcccag cagcaaaact    60
ctaggaaatg gaggcttaag cttttctagcc wtctcagcac agagaagctt atttgtgaat  120
ggggctggaa catacgccaa gagaaccaat ataaggcaca gtgttcttaa ctctatgttc   180
```

<210> SEQ ID NO 267
<211> LENGTH: 180
<212> TYPE: DNA
<213> ORGANISM: Homo sapiens

<400> SEQUENCE: 267

```
atcaaaatgc ctcaaatata tgtaaatcca ataattcaca attatccctt ttaaaatcct    60
tatttgtcat gtgtgtagga ttctagggaa scaactcatt atttttttaaa gctcctaaat  120 aacacgaaag aatcaagcac ttttcctgca tttccttttgc aatctatatc tgaaagtaac  180
```

<210> SEQ ID NO 268
<211> LENGTH: 180

<212> TYPE: DNA
<213> ORGANISM: Homo sapiens

<400> SEQUENCE: 268
ggctacagac tcatatattt catgagtccc tccctaccca ttccttgcct ctcccttcag      60
ttgctgggtt tctgaatttc tgtatagtta mcccttatct tgcctcccat tgttcaata      120 gaaatgatca cttttacttg aatcttttgg tagaattgta taccatgtgt tcctgtctag    180

<210> SEQ ID NO 269
<211> LENGTH: 180
<212> TYPE: DNA
<213> ORGANISM: Homo sapiens

<400> SEQUENCE: 269
cagcatcggc gcttagctgc ctccgcggtg cagctaaggt tcgtgtcgct accccttggc      60
ccttcgctct tgctgcctta accccgccgg yggagcccgc tcttctggcc tgttgagccc    120
gctccctcac tgccacacag caagttccga gaccatggat tcgggcagca gcagcagcga    180

<210> SEQ ID NO 270
<211> LENGTH: 180
<212> TYPE: DNA
<213> ORGANISM: Homo sapiens

<400> SEQUENCE: 270
gtgggtagtg ccttaggcac agcagtatac ctggagagag agacagtttg ctttgctgtc      60
aaacctcata tcatgagct agttgaatag ktgtggggac tgctggcaca acaccctggg    120
ctcattcatg ctcaggtaaa ggcaatgtat ccttctacat tgtccctttg tgtgtacatg    180

<210> SEQ ID NO 271
<211> LENGTH: 180
<212> TYPE: DNA
<213> ORGANISM: Homo sapiens

<400> SEQUENCE: 271
tgctagcaaa taagtattat ttttctcatg cccctagttt tcctccaggc cttgaatagt      60
gtgccatcca tggaggcaaa cagttcttcc ygacttaaca tttggtcact atgatgtttt    120
actccccacg aagatcttgg gaagccacat ttcgtctggc tgcaatcatc atcctttaag    180

<210> SEQ ID NO 272
<211> LENGTH: 180
<212> TYPE: DNA
<213> ORGANISM: Homo sapiens

<400> SEQUENCE: 272
cagctttgac ttctttgtct tatggaatga atctgatata cattcattcc ctagccacct      60
ccaagctcag ctcagattct gctagcaaat magtattatt tttctcatgc ccctagtttt    120
cctccaggcc ttgaatagtg tgccatccat ggaggcaaac agttcttcct gacttaacat    180

<210> SEQ ID NO 273
<211> LENGTH: 180
<212> TYPE: DNA
<213> ORGANISM: Homo sapiens

<400> SEQUENCE: 273
actgttataa tattcttatt aacactaagt actatcccgc ttatattcaa ttcttaaatt      60
ctttaaattc tgctaaaatg taatactcca maggggcata gatttttgcc tgttttgttt    120

```
ttattctatg tacatcatct agaatactac tgtcacatgg tacactctaa ataaatgttt    180
```

<210> SEQ ID NO 274
<211> LENGTH: 180
<212> TYPE: DNA
<213> ORGANISM: Homo sapiens

<400> SEQUENCE: 274

```
ttatgaagca tgcaaattat gagatatgta agacatttgt acccatgatt gcttggatat    60
aggttgtcac ataagaagtg ctggatttaa ygtaggggaa ttacacaatc tcttgcattt   120
accctattac tctgagaaaa cagaacaata cttctcttcag ggtttgtcag gatatatgca  180
```

<210> SEQ ID NO 275
<211> LENGTH: 180
<212> TYPE: DNA
<213> ORGANISM: Homo sapiens

<400> SEQUENCE: 275

```
gcccctatcc tgtacccatg taaaccccaa accccaggct ccacaagcag aagagtggaa    60
gagcacaaga gcagcagaat gacacagcat rgaaggagaa aagagaagga gtggccatcc   120
cacagccaat ctcctctcca accatccctg gaggagttgg aggagttcgg ctggggatgg   180
```

<210> SEQ ID NO 276
<211> LENGTH: 180
<212> TYPE: DNA
<213> ORGANISM: Homo sapiens

<400> SEQUENCE: 276

```
attcagtctc tcttttgacc tctcacaatt tttgtagttg caatttaatg tggtgctgcc    60
tcagttaagg ggacatgcat agggtgagtg ragatcctcc caggtgtcca gagccctgcc   120
ctgtggcttg gcattcccac ccttcccctc cctgcaccca cactcaggcc ctctcctgtg   180
```

<210> SEQ ID NO 277
<211> LENGTH: 180
<212> TYPE: DNA
<213> ORGANISM: Homo sapiens

<400> SEQUENCE: 277

```
cccagccagt tcctcctttt aaagaaaaaa aggtgggaaa taaccctctt tcaggcactc    60
cattggtttt atggtgcctc cacttgtgag rgtttgtgta aaatggaaat attatggtct   120
ttttgtgaac aattacatca agaaaaaga gctctaaggt tgacctgcaa actatagagt    180
```

<210> SEQ ID NO 278
<211> LENGTH: 180
<212> TYPE: DNA
<213> ORGANISM: Homo sapiens

<400> SEQUENCE: 278

```
aaagcatgga ctagcctcat tataattctc ttttaggagg cccaggatac agtgtggact    60
ctccccagag ctcggaggtc caattaaaag rtggagaata aaattagaac tacctatcta   120
aataaaatgt ctctccttac acaatcttat gataaatttc tatacttta tgcttaactt    180
```

<210> SEQ ID NO 279
<211> LENGTH: 180
<212> TYPE: DNA
<213> ORGANISM: Homo sapiens

<400> SEQUENCE: 279

```
aggatacagt gtggactctc cccagagctc ggaggtccaa ttaaaaggtg gagaataaaa        60
ttagaactac ctatctaaat aaaatgtctc yccttacaca atcttatgat aaatttctat       120
acttttatgc ttaacttgca atgaaatttg ctttatttcc ctctagcata ccaggctttt      180
```

<210> SEQ ID NO 280
<211> LENGTH: 180
<212> TYPE: DNA
<213> ORGANISM: Homo sapiens

<400> SEQUENCE: 280

```
agtattgtat ctaactgggg gattttttccc ctatctagta ctataaaact gaagacatgt       60
acatctgctc tttgagaact gttgcttgga ytcactaaat gaaaagtagt atgattccct      120
gagcccacaa aatatagcct aaagggtgga gtgctagttg agacaaatcc tccactttat      180
```

<210> SEQ ID NO 281
<211> LENGTH: 180
<212> TYPE: DNA
<213> ORGANISM: Homo sapiens

<400> SEQUENCE: 281

```
cagtgttcct ctcttgtaac acaattctca gcaagtgtga gcatccacgc aagtccacct       60
tcatcacccc cgtggggctt ggagggcata yagagccagt gcaaacagga ggctctggca      120 actactttg ttgaaaggaa taaagtcctt tgcctctgac ccagagggtt tctgtcttct       180
```

<210> SEQ ID NO 282
<211> LENGTH: 180
<212> TYPE: DNA
<213> ORGANISM: Homo sapiens

<400> SEQUENCE: 282

```
cataacagat tctttctatc atgatctttc tgaaacacca ttgttcttcc tgacatgcat       60
tgtcctttat tgccatgaat agtaaaccca rcttatttaa ctacttgtgc attcctggca      120
ctctttggct ggaggacatt ggcatataca catgctgatc ttcttccagt ttatcaacat      180
```

<210> SEQ ID NO 283
<211> LENGTH: 180
<212> TYPE: DNA
<213> ORGANISM: Homo sapiens

<400> SEQUENCE: 283

```
gggcactcag tattcatcat ttctttattc tacaaataat tattgcattg atctaggatc       60
caaagttaaa actgtccaag tcctggtcct yatggagatt ccattttagt cagaaaagat      120
aacataagaa atgactaagt cccttaacaa atatttattg agcaactcct agaaactgca      180
```

<210> SEQ ID NO 284
<211> LENGTH: 180
<212> TYPE: DNA
<213> ORGANISM: Homo sapiens

<400> SEQUENCE: 284

```
tgttcattgt agtaagtttt ttatctgagc aaggtggaga gccattggag attgttgagc       60
aaagtaggaa attaacttac atttgaacag ratttctctg gctgttgtga ggagtactga      120
ctcaagagtg gaaggtgagg gactacagtg atagggaaat taggtaaaag gctactcaat      180
```

<210> SEQ ID NO 285

```
<211> LENGTH: 180
<212> TYPE: DNA
<213> ORGANISM: Homo sapiens

<400> SEQUENCE: 285
ggattgtcag attatgtatt ttatcttggt tgggttttgg taagttgtga ttttttgagg    60
aatgtgtctt tttcttctat gccatcaaac raatgaacat aaagttgtcc atactattac   120
ttattatctt tttaattatg taagctctac agtggtatcc catttcattc ccgatattgg   180

<210> SEQ ID NO 286
<211> LENGTH: 180
<212> TYPE: DNA
<213> ORGANISM: Homo sapiens

<400> SEQUENCE: 286
attacttatt atcttttttaa ttatgtaagc tctacagtgg tatcccattt cattcccgat    60
attggtgatt tgtgcttttt tattttgttt wtctatcaag aggtttatta attgtactgg   120
cttttttgtc atagaactto cttttggtga tgtttgcagt gtatatcttt ttccatgctt   180

<210> SEQ ID NO 287
<211> LENGTH: 180
<212> TYPE: DNA
<213> ORGANISM: Homo sapiens

<400> SEQUENCE: 287
gtcatgagac accctactcc tacaggttgc tcccacagcc ctgggatccc ttactagttt    60
gccttcttct ttctaccttt cagagatctt ktttgattgc ttcttgcatt cgtcacatag   120
tatatagttg tacttagcag taaggagcag ggaaaaaagt gagtccacgg actggatgtt   180

<210> SEQ ID NO 288
<211> LENGTH: 180
<212> TYPE: DNA
<213> ORGANISM: Homo sapiens

<400> SEQUENCE: 288
gattacaggt gtgagccact gtgcccggcc agttataact attaaatatc cttctttatc    60
catgtaatat tcttggctct aaaatgtact ytgtctcctc caaatttagc ctctctggct   120
ttctttgcac taaagttaac gtggcatatc tttgtcacat cttttagttt tattatattt   180

<210> SEQ ID NO 289
<211> LENGTH: 180
<212> TYPE: DNA
<213> ORGANISM: Homo sapiens

<400> SEQUENCE: 289
cgtgcaatag atagcatata gttgtgtctt acatttttat tcagtctgcc aatctctgac    60
tttaaattgg ggtgttcaga cctgttacat ytaatgtcat ttattactat gatttggttt   120
gagtctagta ttttttttatt tgtcccacct gctctttgtt ccctttttccc tgttttctgt   180

<210> SEQ ID NO 290
<211> LENGTH: 180
<212> TYPE: DNA
<213> ORGANISM: Homo sapiens

<400> SEQUENCE: 290
ctttatttta aaatcagcgc cattttttcc tgaatttctg atagaattgt tactcctata    60
tagctctgtt cccccttcct gattttttgta rtattatttg tatacatatc atatccatat   120
```

```
gtattacaaa cccaataata ctttattatg attattactg tacatactct cgggccttgt    180
```

<210> SEQ ID NO 291
<211> LENGTH: 180
<212> TYPE: DNA
<213> ORGANISM: Homo sapiens

<400> SEQUENCE: 291

```
ttctttaagc gtggtttccc atggttcttt gtatgtatgc ataaaggctg attaaacatt    60
ttttctgtta tatctgacat ctaggccatc ycaccggcaa tttctgttgc ctccttctaa    120
ttcctgtgca tgggtcagac acttctgttt gtttgcatgt ctcatcattt ttttgtaaaa    180
```

<210> SEQ ID NO 292
<211> LENGTH: 180
<212> TYPE: DNA
<213> ORGANISM: Homo sapiens

<400> SEQUENCE: 292

```
gtgacttcaa ggtcaaggct tttttttttt tttttttttg gttcttttaa agtataagca    60
aagaagcaga aaccttagag ccctaagagg yataggcact tgtccaaatg atgttctttt    120
tttttttttt ttttaactct aaacaaaatt acacatcatt tagatactat tgcacaggtt    180
```

<210> SEQ ID NO 293
<211> LENGTH: 180
<212> TYPE: DNA
<213> ORGANISM: Homo sapiens

<400> SEQUENCE: 293

```
ttgatttgtc atttcagggt gtttgtcggg ctgatctctc cattgtagct tttcccacca    60 accttcttc tgttggtttt agcagccatt ratgataatt gcctagattc attatttctg    120
tagaggttga aaaatggtga tatttaattc tttcaatctt tctgcattat taactggaat    180
```

<210> SEQ ID NO 294
<211> LENGTH: 180
<212> TYPE: DNA
<213> ORGANISM: Homo sapiens

<400> SEQUENCE: 294

```
tgtggtcatt ttttaatgct taaacagtgt catcttataa attaggagcc ccttctgttt    60
tcacttctat gttttttttc acattatctc sttagtcttt gttggcgtcc ttgcttttg    120 gcataagcta ttttaggctc atcatgtaca ctccctgccc caccccctgga attagccatt    180
```

<210> SEQ ID NO 295
<211> LENGTH: 180
<212> TYPE: DNA
<213> ORGANISM: Homo sapiens

<400> SEQUENCE: 295

```
aatttcccta ttctgaacat ttcatataac tagagtcttg aaatatgtgg ccttctgtgt    60
ctcacttctt ccagttagca tagtgttttc raagtttatc catattatag catgtcttag    120
tatttccatt ccttttcatg gctgaaagat attccattgt atgagtatac caccttttat    180
```

<210> SEQ ID NO 296
<211> LENGTH: 180
<212> TYPE: DNA
<213> ORGANISM: Homo sapiens

```
<400> SEQUENCE: 296
agtaccttag aatcttagta actgaagcct tgtagtaagt tttgatattg ggaagtatga      60
ctcctccaac tttgttccac gttttcaaaa rgtgttttga ccatttttgag ttacttccat    120 tttagtatta attttagggt cagcttgtct gtttctgcac agaaggtatt tagaattttca   180

<210> SEQ ID NO 297
<211> LENGTH: 180
<212> TYPE: DNA
<213> ORGANISM: Homo sapiens

<400> SEQUENCE: 297
cattttcaaa cacatctgta tctatgagca atatatagta tttttgtatg ttttaagttt      60
atataaatgg tatattatgt gattgttctg waactcactt ttctcaatca gcattatgtt    120
tttaagatga cactgatata tattgatgtg atttcttcat tttcactgcc atattaaatt    180

<210> SEQ ID NO 298
<211> LENGTH: 180
<212> TYPE: DNA
<213> ORGANISM: Homo sapiens

<400> SEQUENCE: 298
tgagatattt ccaaaataac accaatacca attaaagttt ataggagatg aggaaagagg      60
aaaaaaaaaa aaggtagtac ctggagaaag rtgcagaaat ctggaggaga aattactttc    120
aaggtggtaa aaactcaaat agatttaact actggtggga aggagcctag ggagagggag    180

<210> SEQ ID NO 299
<211> LENGTH: 180
<212> TYPE: DNA
<213> ORGANISM: Homo sapiens

<400> SEQUENCE: 299
tcaccttgtt tctttaccat ttctcaagga ttattggccc tcactacctg atatctattg      60
ttgtgagaat aatttgcttt ttaattttttc wacaagttgg gtaaatggtc cctgttattc    120
catcttgccc agaagtgcaa gttcagctga gagtttaaaa agtgttaaga ttctcataag    180

<210> SEQ ID NO 300
<211> LENGTH: 180
<212> TYPE: DNA
<213> ORGANISM: Homo sapiens

<400> SEQUENCE: 300
gtaaaattgt agccctctta gcaggttggt tttgaggaat ttaacttact agattcaagt      60
tacgtgattc ctgctatccc atgagttttg ytggctgcag gccagggatt ggctgtttac    120
tactttccgc tgtctcagtg ctgtaatacc ctggcctaat ggctctaatt aactccatat    180

<210> SEQ ID NO 301
<211> LENGTH: 180
<212> TYPE: DNA
<213> ORGANISM: Homo sapiens

<400> SEQUENCE: 301
taattaactc catatatttg ttccagaaag atgaagaggt tctgtatagt taagaatcaa      60
taaaatacaa attgttgctt aggaaacccc rtgtactctt agtgtcagta attaacttttt    120 tttctggaga agtttaagaa acaggcccaa gccattcaat agccatttgt gaagctgata   180
```

```
<210> SEQ ID NO 302
<211> LENGTH: 180
<212> TYPE: DNA
<213> ORGANISM: Homo sapiens

<400> SEQUENCE: 302
tccagatcct gcacaataat aaatctctta atttattagt agctgctttc ttaaaaggat    60
ttatgaacat aactttctgc tttactaata magagctgaa gcagacttag gaccgatgag   120
aagaatgtaa actaaaaatc atgtctttat gaaaatagga atttcttcct aagatctggg   180

<210> SEQ ID NO 303
<211> LENGTH: 180
<212> TYPE: DNA
<213> ORGANISM: Homo sapiens

<400> SEQUENCE: 303
tttagtagta ggaaaagctt tattttcaac attgtgattt ggggactttg ttgtttgaat    60
gctttggttt gctccacttt ctcatgtctt ytttctcacc ttctacatgt agtatacttg   120
ctatagcttt aagttccaat tgcatatctt ctttatgtaa aatgatataa tcttgagtcc   180

<210> SEQ ID NO 304
<211> LENGTH: 180
<212> TYPE: DNA
<213> ORGANISM: Homo sapiens

<400> SEQUENCE: 304
ccataactat agagctaaat gaaatgtcac aaagtgtttt tggtttattt atgtaatttg    60
tgaataattt ttttcccttt tccttatacc kccagaattt gatgtctttc tatgtaaaat   120
aaaatagaat ttcttttctg aaataatctc tttttttta dacagagtct tgctctgtcg   180

<210> SEQ ID NO 305
<211> LENGTH: 180
<212> TYPE: DNA
<213> ORGANISM: Homo sapiens

<400> SEQUENCE: 305
atttctgttt ggaggttttt gtatattcat tgtaaaagat tatctttgat gacaaataaa    60
atttgagctc tagattaaaa acatttccat rttcattaca ctgaaaggat ctctttccat   120
ctccgctata aattttctaa tgttttgaa ggtctgttat ctccagatac cctttcccac   180

<210> SEQ ID NO 306
<211> LENGTH: 180
<212> TYPE: DNA
<213> ORGANISM: Homo sapiens

<400> SEQUENCE: 306
gaagtttaat cttactcagc atcagaaaat acagagtggc aggaatctta ttaatgtaat    60
gtgtgtggga aagtctttat gagaaaatca sgtcttggta aaaatgaaaa aaagattctt   120
tgtaaaagtt aaaatagtta ccacataatt acacgcctgc cagtgtgcca agcactacaa   180

<210> SEQ ID NO 307
<211> LENGTH: 180
<212> TYPE: DNA
<213> ORGANISM: Homo sapiens

<400> SEQUENCE: 307
cagcaaacac tgatacaaat taacatcaag tctaaacaag gatattgcat tgccactacc    60
```

```
ccagattcct cctttccctg aactaggaat wcaaattctg aatgggtaga gttaccatgg      120
tacagtaggt gaaaattaat caggagtaga aaaacaccct ttgatgaaaa aatttagaat      180
```

<210> SEQ ID NO 308
<211> LENGTH: 180
<212> TYPE: DNA
<213> ORGANISM: Homo sapiens

<400> SEQUENCE: 308

```
aaaagcagga gtgttagtct atttgaagtt cttccactta gaaacatgag aagtaaagat      60
taagtgttcc ctctaacata gctcagtgat rtattcagta ttgccatgtg cttgaacttg     120
tctatctctt caggaccaaa aatatcataa ttttgctgtg acacgaaagg tattaggata     180
```

<210> SEQ ID NO 309
<211> LENGTH: 180
<212> TYPE: DNA
<213> ORGANISM: Homo sapiens

<400> SEQUENCE: 309

```
gtgctactct ggaccaatct gcctctgggg tggccctgct ctgtctatgg agcagtcact      60
tggctgtaca ctgttgctca ataaacttg mtttctttca ttgtcaaaaa aaaaaaaata     120
aataaaaaaa taaaagaaa gagggtttaa ttgactcaca gttctgcatg cttgggagg      180
```

<210> SEQ ID NO 310
<211> LENGTH: 180
<212> TYPE: DNA
<213> ORGANISM: Homo sapiens

<400> SEQUENCE: 310

```
tacaaggata actcctcatg actctaacca caaggaactt ctgagcataa agacaagtta      60
gaaaaggaga ttaaccttct ttcaaaggat rgatgtttaa ggcttggggt agatattcac     120
aggattggtt cccagccagg gggcttccaa gactatagta agtgttagag taattgtgct     180
```

<210> SEQ ID NO 311
<211> LENGTH: 180
<212> TYPE: DNA
<213> ORGANISM: Homo sapiens

<400> SEQUENCE: 311

```
gctgggatta caggcgtgag ccactgcacc tggctgacaa aatttttttaa acaatgaccg      60 ctctattgta gctaaatacc agagaagact rtacctctac ccctactagc aaaggccaac     120
tagagagact tccacccttg ccagcctgta ataagacctc tagttccctg atagagtggt     180
```

<210> SEQ ID NO 312
<211> LENGTH: 180
<212> TYPE: DNA
<213> ORGANISM: Homo sapiens

<400> SEQUENCE: 312

```
ggatatccat agctctgaca cccgccccccc tgcccctcc ccgctgccaa atgaacttca      60
gcttaaactt cacacctcat taaaacttaa wctcaaatgg atgacagaca tcaatgtaaa     120
aattaaaacc ataaaacttt tagaagatat tgtaggagaa aattgtgagg tactagggct     180
```

<210> SEQ ID NO 313
<211> LENGTH: 180
<212> TYPE: DNA
<213> ORGANISM: Homo sapiens

<400> SEQUENCE: 313

```
tcagaaatat aaattaaaac cataaggaga taccaataaa tacacataag attggcaaaa    60
aaaaaaaaaa aaaggaaaag tcttgtagag yatgtcagtc ttactcctgg gcttctggtg   120
tcacggaaat aaagacaaac attaattatt aaagtataag aatacatgta caagtatttt   180
```

<210> SEQ ID NO 314
<211> LENGTH: 180
<212> TYPE: DNA
<213> ORGANISM: Homo sapiens

<400> SEQUENCE: 314

```
gcacccttttg ggaaaaggtc actgtgcaac atgatgcagt tattcttcat acaaacaaaa    60
gtgcattcac tcctttccaa agcaagaaaa scaaaagtct cataagctgt tgcatgcaga   120
tccaaatcca gggataattg ttcatcctaa tttagcaggg attttgaata aggacatgtg   180
```

<210> SEQ ID NO 315
<211> LENGTH: 180
<212> TYPE: DNA
<213> ORGANISM: Homo sapiens

<400> SEQUENCE: 315

```
tttgtcagct ttactgaagt ttgatcaatt ttattgatat tttcaaagaa ccagcttttg    60
ttgcattgat gttctgtata attttcttgt wttcaatatt attgttttct attctcgtct   120
ttattattac tttccttctg catgttttag gttcaattta ctcttctttt tctagttact   180
```

<210> SEQ ID NO 316
<211> LENGTH: 180
<212> TYPE: DNA
<213> ORGANISM: Homo sapiens

<400> SEQUENCE: 316

```
tctctgataa acattgatac aaaaattttc tataaaatat tagcaaaccc aagttcaaca    60
acacatcaaa aagattatac atcatgactg ytatgatttg aatgtcttct ccaaaactca   120
tgttgaaact caatccccag tgtgacaata ttgagaagta gagcctttaa gaggtgaata   180
```

<210> SEQ ID NO 317
<211> LENGTH: 180
<212> TYPE: DNA
<213> ORGANISM: Homo sapiens

<400> SEQUENCE: 317

```
ggcaacttaa ataaaaagac tgatgggagg cctcttgaac tctgttagtt tccctactct    60
ttacttttct ttttatgttt catgcaccat sctcaggtgc tgtgaaacca gttcctggtt   120
tttaatctag tctcacagta agcaggttgt cctcatttag ctaccatttt acttctcaat   180
```

<210> SEQ ID NO 318
<211> LENGTH: 180
<212> TYPE: DNA
<213> ORGANISM: Homo sapiens

<400> SEQUENCE: 318

```
aagaaataaa tgtgaattgc ccttgaaaaa aaaagacaat agaggtattg aaataaaata    60
ctaaaaatgt ttgattatcc ccaaataagt raggaatgtg agacagagga ataataaaca   120
aatgagacaa aaagaaaaca aatagcaaat gacagactga atcgcatcta taattacatt   180
```

<210> SEQ ID NO 319
<211> LENGTH: 180
<212> TYPE: DNA
<213> ORGANISM: Homo sapiens

<400> SEQUENCE: 319
tgctggggaa ggacagaagg gcaaggcaga cttggatatc acagcaggat ctgttatggg      60
gcttgtcttc ctctcatagc agctctggga rgtggatgtc agcatcttca ttttacagac     120
aagaagctga ggcatagaca tacatattgc atgaactaga caaagccaca gagctagtaa     180

<210> SEQ ID NO 320
<211> LENGTH: 180
<212> TYPE: DNA
<213> ORGANISM: Homo sapiens

<400> SEQUENCE: 320
aaagaacaaa gctggaggca tcgtgctatt tgacttcaaa ctatactaca gggtgacaat      60
aagcaaacca gcatggtact gctacaaaag yagactaatg gaatacaata gtaaactcag     120
aaattagacc acacatctac agccaactga tctttgacaa acctgttgaa aacaagcaat     180

<210> SEQ ID NO 321
<211> LENGTH: 180
<212> TYPE: DNA
<213> ORGANISM: Homo sapiens

<400> SEQUENCE: 321
gaaccaaaaa gaaatgctca agatcaaaaa cattgtaaca gaaataaaga atgcctttgt      60
tgggtttatt agtagacagg atacaactga rtaaagaatc tctgagcttg aggatatatc     120
attagaaact tcaaaaacta aaaaagcaaa gagaacagaa actgaaataa acaacagaa      180

<210> SEQ ID NO 322
<211> LENGTH: 180
<212> TYPE: DNA
<213> ORGANISM: Homo sapiens

<400> SEQUENCE: 322
ttcttatcta tagagtaaca aagataagaa ttacttccaa ctcctcaaaa accatgcaaa      60
caagaagaga gcggagcaaa atattcaaag kgttgaggga aaaatccacc aacctagaat     120
tgcatatttt gcaaaattat ccttcaaaag tgaaggatga agactttctt agagaaacaa     180

<210> SEQ ID NO 323
<211> LENGTH: 180
<212> TYPE: DNA
<213> ORGANISM: Homo sapiens

<400> SEQUENCE: 323
tacacagtga gcccatctct aacaacccta cctaacactg taaccccctc atccttccca      60
gctcacttcc acaccttaca tttctcctta ytgcttatca ccattaaaat cctatgcatt     120
ttatttattt agattttta tctatcttct tcaattataa tataaacttc acaagttcag      180

<210> SEQ ID NO 324
<211> LENGTH: 180
<212> TYPE: DNA
<213> ORGANISM: Homo sapiens

<400> SEQUENCE: 324
ttgtgtttct acctattcaa ggaacaatga ggacactacc tcacagaagt ctggctggta      60

```
tttattcttc tgtggtgaac acctctaaac raaaaggatt ttgagttgat ctcttgccta    120
tccataaatg ggatcaagtc caggggttca gagagaaaag ataatgggga gcatcaccag    180
```

<210> SEQ ID NO 325
<211> LENGTH: 180
<212> TYPE: DNA
<213> ORGANISM: Homo sapiens

<400> SEQUENCE: 325

```
ttgaaatcaa taataagaat ttgggaaact cacatatatg tgaaaattaa gcaagatact     60
cccaaataac caatgggtca agaacaaaat saaaggggaa attagataat ctcttgaaat    120
gaataacatg acgacataga ataacaaaat ttatgcaatg caacaaactc ggtgcttaga    180
```

<210> SEQ ID NO 326
<211> LENGTH: 180
<212> TYPE: DNA
<213> ORGANISM: Homo sapiens

<400> SEQUENCE: 326

```
cacaggcaaa aaagcaaaaa tagacaactt ggttatatca aactaaaaag cttctttaca     60
gtaaagaaaa caatgaacag ggtgaagagc rggcaaatat atttgcaaac tattcatctg    120
acaagagatt aatatccaga ctatacaatg aactcaaaaa cctcaacagg aaaaaaacag    180
```

<210> SEQ ID NO 327
<211> LENGTH: 180
<212> TYPE: DNA
<213> ORGANISM: Homo sapiens

<400> SEQUENCE: 327

```
gtaagtcaat taaacctctt ttcttttataa attacccagt cttgggtatt tcctcatagc     60
agtgtgagaa caaactaata cactctccaa yaataattta cagtatattt ttaaacagtt    120
agaaacaagg attttgaatg ttcccaacac aaagaaattg taaatgtttg aggtgatata    180
```

<210> SEQ ID NO 328
<211> LENGTH: 180
<212> TYPE: DNA
<213> ORGANISM: Homo sapiens

<400> SEQUENCE: 328

```
acatttattg aaatatcact tcctactcca taaatatgta tgattattat gtgtcaatta     60
aaagaaaatt tccaaaaaat tgtttgacta ygtatgcagg ggattattc tggactgtct    120 attctattcc attggtctat gtgtctgtct ttatgccagt accaacacta ttgattactg    180
```

<210> SEQ ID NO 329
<211> LENGTH: 180
<212> TYPE: DNA
<213> ORGANISM: Homo sapiens

<400> SEQUENCE: 329

```
atttatattg attccatgtc tttgctattg tgaatagtgc tgcaatgaac atttgcatgc     60
atatattttt atggtagaat gatctgtatt kttttgggtg tatacccggt aatgtcattg    120
cggggttgaa tggtagttct gctttttaact ctttaaggaa ttaccatact gcttttcaaa    180
```

<210> SEQ ID NO 330
<211> LENGTH: 180
<212> TYPE: DNA

<213> ORGANISM: Homo sapiens

<400> SEQUENCE: 330

```
gagattttcc ttaaaattcc tttggtatat tgctaaaagt aggattgctg gatcgtgcgg      60
taaatcagtt ttcagtttct tgaggaacaa ytatactctg tctcttttt  ttattatgct    120
ttaagtttta gggtgcatgt gcacaacgtg cagcttagtt acatatgtat acatgtgcca    180
```

<210> SEQ ID NO 331
<211> LENGTH: 180
<212> TYPE: DNA
<213> ORGANISM: Homo sapiens

<400> SEQUENCE: 331

```
aagagtttat agttttaggt cttatgttta ggtctttaat ccattttag ttaattttg      60
tatatggctt aaggttagga ttccactta wcctttttct gcttaagaga agcggtttca    120
ctttgtcacc cacactggag tacagtggcc taatcaaagc tcattgcagc cttgaactct    180
```

<210> SEQ ID NO 332
<211> LENGTH: 180
<212> TYPE: DNA
<213> ORGANISM: Homo sapiens

<400> SEQUENCE: 332

```
tctaacagat gaaatgctaa tagatgaaac tgttgatcca agagaagaat gagagcttca      60
caccctaaa tcacgaaata gtatggaatt kttaaccat tccctggatt cctctcttcc     120
acatcttcta attcagtcct ttcaaagtgc agctcttgtc ttgtcttttt cttgacaatt    180
```

<210> SEQ ID NO 333
<211> LENGTH: 180
<212> TYPE: DNA
<213> ORGANISM: Homo sapiens

<400> SEQUENCE: 333

```
agtgtccttg tctggctttg atatatcact gctgctgcct cacaacaagt ttgaaagagt      60
tctctcctct taacatttgt ataagagttc ragaaggact tttattattt cttctctaaa    120
tggttggtag aattcaccta agaagacatg tccttggctt tttaataatg ggagattttt    180
```

<210> SEQ ID NO 334
<211> LENGTH: 180
<212> TYPE: DNA
<213> ORGANISM: Homo sapiens

<400> SEQUENCE: 334

```
ctggctttga tatatcactg ctgctgcctc acaacaagtt tgaaagagtt ctctcctctt      60
aacatttgta taagagttca agaaggactt ktattatttc ttctctaaat ggttggtaga    120
attcaccta agaacatgt ccttggcttt taataatgg gagattttg agtactgatt      180
```

<210> SEQ ID NO 335
<211> LENGTH: 180
<212> TYPE: DNA
<213> ORGANISM: Homo sapiens

<400> SEQUENCE: 335

```
cattttttat tttattaact tgtgtctttt tctttgttag tctagctaag ggtttgtcaa      60
atatttaatt ttttcagaaa accaacaact raagttttat ttttatggtg ttttttagtc    120
tctattatac ttatttatgt tctgatctgt gttatttcct ttctttact aactttggac    180
```

<210> SEQ ID NO 336
<211> LENGTH: 180
<212> TYPE: DNA
<213> ORGANISM: Homo sapiens

<400> SEQUENCE: 336
cccttcccct ttgatggact gcttatgatt tcctgtcttg aattttacct tctctaaggt      60
atcttttggg tgattctgga tcttgaaaaa mctacttgcc accgctttgg agacatctca     120
tgcatctctg gttaagtcat aatcttggtt aaggcacttg ggaggatacc tttggtaaag     180

<210> SEQ ID NO 337
<211> LENGTH: 180
<212> TYPE: DNA
<213> ORGANISM: Homo sapiens

<400> SEQUENCE: 337
agacgaatgc ataattgact gtccccactc ctctcttttc acatgtaaaa tgtgaattca      60
gtgagcacaa atcaaagcct cacaagaatg yaacacttgg ttcaccacct accccacttt     120
ttctttcttt gtttccttc cttttcctcc tgcccactct ttcccctta aatactgaag     180

<210> SEQ ID NO 338
<211> LENGTH: 180
<212> TYPE: DNA
<213> ORGANISM: Homo sapiens

<400> SEQUENCE: 338
ctccttacag ccactgacgt ttggtgtttt cttgtcctaa attgacagtg attctgggtt      60
gttcaccctg gaacctatgg gaagaatgtt sttgtcatta catcaggaag agaaggcagc     120
ccgttgactc agtagtgctg ctctgggcag ggttgggagc tgagcaatag acttttcatt     180

<210> SEQ ID NO 339
<211> LENGTH: 180
<212> TYPE: DNA
<213> ORGANISM: Homo sapiens

<400> SEQUENCE: 339
tggtaatgaa acttgaaaat caagagcctt ttcaaaatat caaaatgcaa tattccctgc      60
aattaatgtc cttttgggtg atctctttga rgaatataat gcaaaccgta atccttcaaa     120
gggaatttac aaggctaact acctcctgaa ctcatcttaa aggaaatgga agggaaatac     180

<210> SEQ ID NO 340
<211> LENGTH: 180
<212> TYPE: DNA
<213> ORGANISM: Homo sapiens

<400> SEQUENCE: 340
agaagactag ggggacacac aacctactga gacaacaacc aggatcctaa gggagttctg      60
gcatcacccc ttccctcacc ccaggctgca sagcgtgtag ctccaaaaga ggtcccttcc     120
taataactga ggagagaaga gggaagagtg aggaggagtt tctcttgcat cttggatacc     180

<210> SEQ ID NO 341
<211> LENGTH: 599
<212> TYPE: DNA
<213> ORGANISM: homo sapiens

<400> SEQUENCE: 341

```
tagtggtctt tctcaaatat ttacagttcc ctttacatgc cttctcttcc attcctttat    60
ggctgcacct gtaggccttt tatctagaat aacactcatc atagtttaca gtgcatctac   120
tccacatctc catcatagag aggaggaaac agacacaaag gatttaggta gtttgcccaa   180
ggttacccca tgagttaggt gtcagccagg actggaactt gagcccatgt gcttcacccc   240
cccggcccat gggctgcccg atggtggcag aaccnctgag gattatcaag gtcccttggr   300
gaataaggac ctcagtgtgg aacaggagcc ctgccaggtg tggggtaccc ctgcaggac    360 tgggggattg gctgacctaa ctcaagttat atctcacttg agatctaact caagtgactc   420
ttcccatgtg aagatccctc ccagactgcc aaagcaaaga ctattactct aactttttgt   480
ttttgttttt tcttttttg cgggggatgg agtctctctc tgccacccta aattcatgct    540
aaagatttct agtgtcttac catatgctag gaaatgtgga tagagtagta aacaagagc    599
```

<210> SEQ ID NO 342
<211> LENGTH: 180
<212> TYPE: DNA
<213> ORGANISM: Homo sapiens
<400> SEQUENCE: 342

```
ctaaatgctc cctctttggg caccaacagc actctgccct atattgtgtt ccactgtgcc    60
agggtagcac tgagtttcaa tgcaaagtcc ygaactcact ttaactttcc ctcctccaag   120
cacacagatt cttactccat gctgtgctgc ctagggttgg gggaggggtg atatgggcaa   180
```

<210> SEQ ID NO 343
<211> LENGTH: 180
<212> TYPE: DNA
<213> ORGANISM: Homo sapiens
<400> SEQUENCE: 343

```
acttcacatt taaaaagtgg aatcacattc cttccaaggt atacgaacta agttgtctta    60
ttgttgagtt aggaaacaga tatttctggc kttccttccc tttgaaacat ttctccttca   120
gctttcaagg cttatttctg cagagtcaca gcacagttta aacacacccc aaaaagcatg   180
```

<210> SEQ ID NO 344
<211> LENGTH: 180
<212> TYPE: DNA
<213> ORGANISM: Homo sapiens
<400> SEQUENCE: 344

```
tgccttgtat tgtcacatcc cttctctgaa gttaaaaagt tctatagcaa agcctaacta    60
tctgaagggg ttgaggacta aaggaataaa sgatatgctg tatgggtttg ggtagatagg   120
ggcagacatt catattacta aatgacattt tattttatgt tttgtaaata tttaacattt   180
```

<210> SEQ ID NO 345
<211> LENGTH: 180
<212> TYPE: DNA
<213> ORGANISM: Homo sapiens
<400> SEQUENCE: 345

```
atacttaaat ctctcttaga caatttggat ttacaaagag actgacaaac aaatggacag    60
atagtctttg agaacttaat gtgaatgcca stgtatttgg ggtactgttc tctgcttcag   120
aatgaatagt ctattgaaat ctcagttcct actggctaat ttgaagcaca agtgttgaga   180
```

<210> SEQ ID NO 346
<211> LENGTH: 180

```
<212> TYPE: DNA
<213> ORGANISM: Homo sapiens

<400> SEQUENCE: 346
cctttcaggg ctctcttggc ctctgagctc ccaggatcca ttgtgtttct gttgcctggg    60
gcccgaactg tggagttcaa cttgctagaa rctttgtctt acttctcatt ctctagcaaa   120
attacttgcc cagaaagcag tgccctcagt ccttactttt tatgacgaac tattctattc   180

<210> SEQ ID NO 347
<211> LENGTH: 180
<212> TYPE: DNA
<213> ORGANISM: Homo sapiens

<400> SEQUENCE: 347
agatgaagga atatatttag aggatttggc acaatacctc accacagaaa aggttcaata    60
aatgtgaacc gttattgtgt ctgttcacat yaaatgaaaa aatctcacat tgctcccagg   120
cccttgggat gatccacact ggctttcgcc attggtgact ctactggtgc cacacagggc   180

<210> SEQ ID NO 348
<211> LENGTH: 180
<212> TYPE: DNA
<213> ORGANISM: Homo sapiens

<400> SEQUENCE: 348
cacgtgtgtt caccgggaag agccgggaga gctggttatt tttgtttgtt tgtttgaaaa    60
cacagctcag gttcagaggt tccctaacac sgagaaaggc accggtcccg aagagggcct   120
gcggccattg tgtcccaagc gcaggtgtca aacgccggcc gcggcgcccg cagggtccgt   180

<210> SEQ ID NO 349
<211> LENGTH: 180
<212> TYPE: DNA
<213> ORGANISM: Homo sapiens

<400> SEQUENCE: 349
tgaattgatt atgaaaatga aggtagaatg aaatggatga aaacagcaca aggccagaga    60
agaatatctt tctgcacttt taatattgtc rtcccgtgct aacattttt tttttttga    120 gatggagtct ccctctgttg cccaggctgg agttcagtgg catgatcttg gctcactgca   180

<210> SEQ ID NO 350
<211> LENGTH: 180
<212> TYPE: DNA
<213> ORGANISM: Homo sapiens

<400> SEQUENCE: 350
ccagtttagc cataacact gtgaatggcc acatgcctca ccttgctcct ggactttgac    60
agtaaatatt tgaatggtag aaccggtgag racctgaata gtaaatattt tatgagagga   120
aataggaact ccccttttct ctgtccttcc cttacattaa acatattaat ttatattaac   180

<210> SEQ ID NO 351
<211> LENGTH: 180
<212> TYPE: DNA
<213> ORGANISM: Homo sapiens

<400> SEQUENCE: 351
cacttttcta tcacttattt cactcccagt attctgcgtc gcactcattt gctgcataca    60
gcagaaaatg gttactattt ctacttttg yggtgctaat gcattttctc tgacaatatt   120
```
cgtagagaaa ttgtaagaag gaaaaaaaat catcgctcaa atatgaaag caatttcata    180

<210> SEQ ID NO 352
<211> LENGTH: 180
<212> TYPE: DNA
<213> ORGANISM: Homo sapiens

<400> SEQUENCE: 352
aaatgaaagt aaattttcct gtgcaatata ccatgtattt atggcatgaa ttttacgtgt    60
cttgcattac atggtagtga aattcaccca ratgaggaaa agctttgtct acataaagtt    120
gaagaacata aacacattta tggattactg tcttagattt ctaaagtatt acaggtttag    180

<210> SEQ ID NO 353
<211> LENGTH: 180
<212> TYPE: DNA
<213> ORGANISM: Homo sapiens

<400> SEQUENCE: 353
gtatttatgg catgaatttt acgtgtcttg cattacatgg tagtgaaatt cacccagatg    60
aggaaaagct ttgtctacat aaagttgaag wacataaaca catttatgga ttactgtctt    120
agatttctaa agtattacag gtttagaaac ctgtaatagt ctgcacatag attacagata    180

<210> SEQ ID NO 354
<211> LENGTH: 180
<212> TYPE: DNA
<213> ORGANISM: Homo sapiens

<400> SEQUENCE: 354
tttatgcagg acaaaaggtg attacacatt tccagtcaat ttgcttctgc aatgctggcc    60
atacagatgt tggaatgaag catgtgttta yaaagctaaa gatatgtgca gtatagacag    120
aggaaaattt tttcacagtc gacaaaatat agcattactt actgtgtaga gtgaaatcca    180

<210> SEQ ID NO 355
<211> LENGTH: 180
<212> TYPE: DNA
<213> ORGANISM: Homo sapiens

<400> SEQUENCE: 355
caagaaagac caaaccaag gaaggatag ccatcgtaga tccatgattg tttcagtctg    60
ccaaaataaa aggcttttca atggtttatc mcagatgaca gctgatttct aaagaagtag    120
ccggattttt ttttctatat ctctgcacac aaagtgaaca cagttcatag gtaaagaaca    180

<210> SEQ ID NO 356
<211> LENGTH: 180
<212> TYPE: DNA
<213> ORGANISM: Homo sapiens

<400> SEQUENCE: 356
atttttaagt gtattgcttt catttaaata caaaaataaa tgcaacatct ttgcaaagtg    60
tgttcagtat atatgttgtc acagccagaa yattttacaa cagtgtggaa taaaagatag    120
actccactgt tactgtttat agtctgtaat aggcaacata aaaacaaagt ccacattagt    180

<210> SEQ ID NO 357
<211> LENGTH: 180
<212> TYPE: DNA
<213> ORGANISM: Homo sapiens

<400> SEQUENCE: 357

```
cctggctgac agtcacttaa ctgccagata tgaaagtgat cccatctgag gcaagggatc      60
cagccaggtg agtccagccc aactaaacca ycaactccaa gactcacgat tttgaaaatt     120
cttatcttct tttgccacac agatttgata tgatttgcta tgtagtattg ctgtgacaat     180
```

<210> SEQ ID NO 358
<211> LENGTH: 180
<212> TYPE: DNA
<213> ORGANISM: Homo sapiens

<400> SEQUENCE: 358

```
ccaactggct accacagcta gagctaatta atcaactggt tagttaatat gttattgcta      60
gagctgcatc tatgcccagc acgatagcta ygttttaggg atactgatag gtttaaccat     120
gcacactgga gaactactgc aaaaaggtat cctgtgcata ctttagcaaa tttaatttct     180
```

<210> SEQ ID NO 359
<211> LENGTH: 180
<212> TYPE: DNA
<213> ORGANISM: Homo sapiens

<400> SEQUENCE: 359

```
acaagcattt atgtcattta tatgtaccca attttcccat ttctaacagt ttatttagat      60
tacttctgaa aattgagata ttacacaaag ktggtcatta tttaaagtta tttccctgtt     120
aaccatttta aagcctgtaa acattaggtg tttaagtaag aaccttaaac atatgggcat     180
```

<210> SEQ ID NO 360
<211> LENGTH: 180
<212> TYPE: DNA
<213> ORGANISM: Homo sapiens

<400> SEQUENCE: 360

```
attcctccct cattcaaatc caagcaatag aatattacca agggctcctt taacattctt      60
ttgccatgaa gtcaaagaac tgctcctgca ragaaaaggg ttaattgaga ccacagagaa     120
gaacagttca ccaagcatac tagagtttct gccctggtaa aacatacccca aagatgatgg    180
```

<210> SEQ ID NO 361
<211> LENGTH: 180
<212> TYPE: DNA
<213> ORGANISM: Homo sapiens

<400> SEQUENCE: 361

```
atgttaagtg tagaattcag tggcattacc tacacttctc ttgttgtaca ccatcatctc      60
tatccatacc cagaatattt tatcaaacca mactgaagct ctgttcccat taacctataa     120
ctccccatta ccccagctcc tggtagaaca gaatcataaa gatagactat atcatagaga    180
```

<210> SEQ ID NO 362
<211> LENGTH: 180
<212> TYPE: DNA
<213> ORGANISM: Homo sapiens

<400> SEQUENCE: 362

```
ggaggttgga atggggcagg tgtaatgtca ttatggaaga taggtacatg atggaagtga      60
gaaggctggt gtatgtctgt gtgtctatgt rtgctgggga aaatgagaag tgtgtctctt     120
tgtgaggaca gatggataca gtgagcatgg gtaatcacag tcaatgaaaa tgtgataatt    180
```

GENETIC VARIANTS CONTRIBUTING TO RISK OF PROSTATE CANCER

RELATED APPLICATIONS

This application is the U.S. National Stage of International Application No. PCT/IS2008/000003, filed Feb. 7, 2008, published in English, and claims priority under 35 U.S.C. §119 or 365 to Iceland Application No. 8654, filed Jun. 22, 2007 and Iceland Application No. IS 8604, filed Feb. 7, 2007.

BACKGROUND OF THE INVENTION

Cancer, the uncontrolled growth of malignant cells, is a major health problem of the modern medical era and is one of the leading causes of death in developed countries. In the United States, one in four deaths is caused by cancer (Jemal, A. et al., *CA Cancer J. Clin.* 52:23-47 (2002)).

The incidence of prostate cancer has dramatically increased over the last decades and prostate cancer is now a leading cause of death in the United States and Western Europe (Peschel, R. E. and J. W. Colberg, *Lancet* 4:233-41 (2003); Nelson, W. G. et al., *N. Engl. J. Med.* 349 (4):366-81 (2003)). Prostate cancer is the most frequently diagnosed noncutaneous malignancy among men in industrialized countries, and in the United States, 1 in 8 men will develop prostate cancer during his life (Simard, J. et al., *Endocrinology* 143 (6):2029-40 (2002)). Although environmental factors, such as dietary factors and lifestyle-related factors, contribute to the risk of prostate cancer, genetic factors have also been shown to play an important role. Indeed, a positive family history is among the strongest epidemiological risk factors for prostate cancer, and twin studies comparing the concordant occurrence of prostate cancer in monozygotic twins have consistently revealed a stronger hereditary component in the risk of prostate cancer than in any other type of cancer (Nelson, W. G. et al., *N. Engl. J. Med.* 349 (4):366-81 (2003); Lichtenstein P. et al., *N. Engl. J. Med.* 343 (2):78-85 (2000)). In addition, an increased risk of prostate cancer is seen in $1^{st}$ to $5^{th}$ degree relatives of prostate cancer cases in a nation wide study on the familiarity of all cancer cases diagnosed in Iceland from 1955-2003 (Amundadottir et al., *PLoS Medicine* 1 (3):e65 (2004)). The genetic basis for this disease, emphasized by the increased risk among relatives, is further supported by studies of prostate cancer among particular populations: for example, African Americans have among the highest incidence of prostate cancer and mortality rate attributable to this disease: they are 1.6 times as likely to develop prostate cancer and 2.4 times as likely to die from this disease than European Americans (Ries, L. A. G. et al., *NIH Pub. No. 99-4649* (1999)).

An average 40% reduction in life expectancy affects males with prostate cancer. If detected early, prior to metastasis and local spread beyond the capsule, prostate cancer can be cured (e.g., using surgery). However, if diagnosed after spread and metastasis from the prostate, prostate cancer is typically a fatal disease with low cure rates. While prostate-specific antigen (PSA)-based screening has aided early diagnosis of prostate cancer, it is neither highly sensitive nor specific (Punglia et al., *N Engl J Med.* 349 (4):335-42 (2003)). This means that a high percentage of false negative and false positive diagnoses are associated with the test. The consequences are both many instances of missed cancers and unnecessary follow-up biopsies for those without cancer. As many as 65 to 85% of individuals (depending on age) with prostate cancer have a PSA value less than or equal to 4.0 ng/mL, which has traditionally been used as the upper limit for a normal PSA level (Punglia et. al., *N Engl J Med.* 349 (4):335-42 (2003); Cookston, M. S., *Cancer Control* 8 (2):133-40 (2001); Thompson, I. M. et al., *N Engl J. Med.* 350:2239-46 (2004)). A significant fraction of those cancers with low PSA levels are scored as Gleason grade 7 or higher, which is a measure of an aggressive prostate cancer.

In addition to the sensitivity problem outlined above, PSA testing also has difficulty with specificity and predicting prognosis. PSA levels can be abnormal in those without prostate cancer. For example, benign prostatic hyperplasia (BPH) is one common cause of a false-positive PSA test. In addition, a variety of noncancer conditions may elevate serum PSA levels, including urinary retention, prostatitis, vigorous prostate massage and ejaculation.

Subsequent confirmation of prostate cancer using needle biopsy in patients with positive PSA levels is difficult if the tumor is too small to see by ultrasound. Multiple random samples are typically taken but diagnosis of prostate cancer may be missed because of the sampling of only small amounts of tissue. Digital rectal examination (DRE) also misses many cancers because only the posterior lobe of the prostate is examined. As early cancers are nonpalpable, cancers detected by DRE may already have spread outside the prostate (Mistry K. J., *Am. Board Fam. Pract.* 16 (2):95-101 (2003)).

Thus, there is clearly a great need for improved diagnostic procedures that would facilitate early-stage prostate cancer detection and prognosis, as well as aid in preventive and curative treatments of the disease. In addition, there is a need to develop tools to better identify those patients who are more likely to have aggressive forms of prostate cancer from those patients that are more likely to have more benign forms of prostate cancer that remain localized within the prostate and do not contribute significantly to morbidity or mortality. This would help to avoid invasive and costly procedures for patients not at significant risk.

The incidence of prostate cancer has dramatically increased over the last decades. Prostate cancer is a multifactorial disease with genetic and environmental components involved in its etiology. It is characterized by heterogeneous growth patterns that range from slow growing tumors to very rapid highly metastatic lesions.

Although genetic factors are among the strongest epidemiological risk factors for prostate cancer, the search for genetic determinants involved in the disease has been challenging. Studies have revealed that linking candidate genetic markers to prostate cancer has been more difficult than identifying susceptibility genes for other cancers, such as breast, ovary and colon cancer. Several reasons have been proposed for this increased difficulty including: the fact that prostate cancer is often diagnosed at a late age thereby often making it difficult to obtain DNA samples from living affected individuals for more than one generation; the presence within high-risk pedigrees of phenocopies that are associated with a lack of distinguishing features between hereditary and sporadic forms; and the genetic heterogeneity of prostate cancer and the accompanying difficulty of developing appropriate statistical transmission models for this complex disease (Simard, J. et al., *Endocrinology* 143 (6):2029-40 (2002)).

Various genome scans for prostate cancer-susceptibility genes have been conducted and several prostate cancer susceptibility loci have been reported. For example, HPC1 (1q24-q25), PCAP (1q42-q43), HCPX (Xq27-q28), CAPB (1p36), HPC20 (20q13), HPC2/ELAC2 (17p11) and 16q23 have been proposed as prostate cancer susceptibility loci (Simard, J. et al., *Endocrinology* 143(6):2029-40 (2002); Nwosu, V. et al., *Hum. Mol. Genet.* 10 (20):2313-18 (2001)). In a genome scan conducted by Smith et al., the strongest evidence for linkage was at HPC1, although two-point analysis also revealed a LOD score of ≥1.5 at D4S430 and LOD scores≥1.0 at several loci, including markers at Xq27-28 (Ostrander E. A. and J. L. Stanford, *Am. J. Hum. Genet.* 67:1367-75 (2000)). In other genome scans, two-point LOD scores of ≥1.5 for chromosomes 10q, 12q and 14q using an autosomal dominant model of inheritance, and chromosomes 1q, 8q, 10q and 16p using a recessive model of inheritance, have been reported, as well as nominal evidence for linkage to chr 2q, 12p, 15q, 16q and 16p. A genome scan for prostate cancer predisposition loci using a small set of Utah high risk prostate cancer pedigrees and a set of 300 polymorphic markers provided evidence for linkage to a locus on chromosome 17p (Simard, J. et al., *Endocrinology* 143 (6):2029-40 (2002)). Eight new linkage analyses were published in late 2003, which depicted remarkable heterogeneity. Eleven peaks with LOD scores higher than 2.0 were reported, none of which overlapped (see Actane consortium, Schleutker et al., Wiklund et al., Witte et. al., Janer et. al., Xu et. al., Lange et al., Cunningham et al.; all of which appear in *Prostate*, vol. 57 (2003)).

As described above, identification of particular genes involved in prostate cancer has been challenging. One gene that has been implicated is RNASEL, which encodes a widely expressed latent endoribonuclease that participates in an interferon-inducible RNA-decay pathway believed to degrade viral and cellular RNA, and has been linked to the HPC locus (Carpten, J. et al., *Nat. Genet.* 30:181-84 (2002); Casey, G. et al., *Nat. Genet.* 32 (4):581-83 (2002)). Mutations in RNASEL have been associated with increased susceptibility to prostate cancer. For example, in one family, four brothers with prostate cancer carried a disabling mutation in RNASEL, while in another family, four of six brothers with prostate cancer carried a base substitution affecting the initiator methionine codon of RNASEL. Other studies have revealed mutant RNASEL alleles associated with an increased risk of prostate cancer in Finnish men with familial prostate cancer and an Ashkenazi Jewish population (Rokman, A. et al., *Am J. Hum. Genet.* 70:1299-1304 (2002); Rennert, H. et al., *Am J. Hum. Genet.* 71:981-84 (2002)). In addition, the Ser217Leu genotype has been proposed to account for approximately 9% of all sporadic cases in Caucasian Americans younger than 65 years (Stanford, J. L., *Cancer Epidemiol. Biomarkers Prev.* 12 (9):876-81 (2003)). In contrast to these positive reports, however, some studies have failed to detect any association between RNASEL alleles with inactivating mutations and prostate cancer (Wang, L. et al., *Am. J. Hum. Genet.* 71:116-23 (2002); Wiklund, F. et al., *Clin. Cancer Res.* 10 (21):7150-56 (2004); Maier, C. et al., *Br. J. Cancer* 92 (6):1159-64 (2005)).

The macrophage-scavenger receptor 1 (MSR1) gene, which is located at 8p22, has also been identified as a candidate prostate cancer-susceptibility gene (Xu, J. et al., *Nat. Genet.* 32:321-25 (2002)). A mutant MSR1 allele was detected in approximately 3% of men with nonhereditary prostate cancer but only 0.4% of unaffected men. However, not all subsequent reports have confirmed these initial findings (see, e.g., Lindmark, F. et al., *Prostate* 59 (2):132-40 (2004); Seppala, E. H. et al., *Clin. Cancer Res.* 9 (14):5252-56 (2003); Wang, L. et al., *Nat. Genet.* 35 (2):128-29 (2003); Miller, D. C. et al., *Cancer Res.* 63 (13):3486-89 (2003)). MSR1 encodes subunits of a macrophage-scavenger receptor that is capable of binding a variety of ligands, including bacterial lipopolysaccharide and lipoteicholic acid, and oxidized high-density lipoprotein and low-density lipoprotein in serum (Nelson, W. G. et al., *N. Engl. J. Med.* 349 (4):366-81 (2003)).

The ELAC2 gene on Chr17p was the first prostate cancer susceptibility gene to be cloned in high risk prostate cancer families from Utah (Tavtigian, S. V., et al., *Nat. Genet.* 27 (2):172-80 (2001)). A frameshift mutation (1641InsG) was found in one pedigree. Three additional missense changes: Ser217Leu; Ala541Thr; and Arg781His, were also found to associate with an increased risk of prostate cancer. The relative risk of prostate cancer in men carrying both Ser217Leu and Ala541Thr was found to be 2.37 in a cohort not selected on the basis of family history of prostate cancer (Rebbeck, T. R., et al., *Am. J. Hum. Genet.* 67 (4):1014-19 (2000)). Another study described a new termination mutation (Glu216X) in one high incidence prostate cancer family (Wang, L., et al., *Cancer Res.* 61 (17):6494-99 (2001)). Other reports have not demonstrated strong association with the three missense mutations, and a recent metaanalysis suggests that the familial risk associated with these mutations is more moderate than was indicated in initial reports (Vesprini, D., et al., *Am. J. Hum. Genet.* 68(4):912-17 (2001); Shea, P. R., et al., *Hum. Genet.* 111 (4-5):398-400 (2002); Suarez, B. K., et al., *Cancer Res.* 61 (13):4982-84 (2001); Severi, G., et al., *J. Natl. Cancer Inst.* 95 (11):818-24 (2003); Fujiwara, H., et al., *J. Hum. Genet.* 47 (12):641-48 (2002); Camp, N. J., et al., *Am. J. Hum. Genet.* 71 (6):1475-78 (2002)).

Polymorphic variants of genes involved in androgen action (e.g., the androgen receptor (AR) gene, the cytochrome P-450c17 (CYP17) gene, and the steroid-5-α-reductase type II (SRD5A2) gene), have also been implicated in increased risk of prostate cancer (Nelson, W. G. et al., *N. Engl. J. Med.* 349 (4):366-81 (2003)). With respect to AR, which encodes the androgen receptor, several genetic epidemiological studies have shown a correlation between an increased risk of prostate cancer and the presence of short androgen-receptor polyglutamine repeats, while other studies have failed to detect such a correlation. Linkage data has also implicated an allelic form of CYP17, an enzyme that catalyzes key reactions in sex-steroid biosynthesis, with prostate cancer (Chang, B. et al., *Int. J. Cancer* 95:354-59 (2001)). Allelic variants of SRD5A2, which encodes the predominant isozyme of 5-α-reductase in the prostate and functions to convert testosterone to the more potent dihydrotestosterone, have been associated with an increased risk of prostate cancer and with a poor prognosis for men with prostate cancer (Makridakis, N. M. et al., *Lancet* 354:975-78 (1999); Nam, R. K. et al., *Urology* 57:199-204 (2001)).

In short, despite the effort of many groups around the world, the genes that account for a substantial fraction of prostate cancer risk have not been identified. Although twin studies have implied that genetic factors are likely to be prominent in prostate cancer, only a handful of genes have been identified as being associated with an increased risk for prostate cancer, and these genes account for only a low percentage of cases. Thus, it is clear that the majority of genetic risk factors for prostate cancer remain to be found. It is likely that these genetic risk factors will include a relatively high number of low-to-medium risk genetic variants. These low-to-medium risk genetic variants may, however, be responsible for a substantial fraction of prostate cancer, and their identification, therefore, a great benefit for public health. Furthermore, none of the published prostate cancer genes have been reported to predict a greater risk for aggressive prostate cancer than for less aggressive prostate cancer.

Extensive genealogical information for a population containing cancer patients has in a recent study been combined with powerful gene sharing methods to map a locus on chromosome 8q24.21, which has been demonstrated to play a major role in cancer. Various cancer patients and their relatives were genotyped with a genome-wide marker set including 1100 microsatellite markers, with an average marker density of 3-4 cM. (Amundadottir L. T., *Nature Genet.* 38 (6): 652-658 (2006)). Association was detected to a single LD block within the locus between positions 128.414 and 128.506 Mb (NCBI build 34) in Utah CEPH HapMap samples.

SUMMARY OF THE INVENTION

The present invention relates to methods of determining an increased or decreased susceptibility to prostate cancer (e.g., aggressive prostate cancer), by evaluating certain markers that have been found to be associated with increased or decreased susceptibility of prostate cancer (e.g., aggressive prostate cancer). Various applications based on the association of particular polymorphic markers to prostate cancer are described herein.

In a first aspect, the present invention relates to a determining a susceptibility to prostate cancer in a human individual, comprising determining the presence or absence of at least one allele of at least one polymorphic marker in a nucleic acid sample obtained from the individual, wherein the at least one polymorphic marker is selected from the polymorphic markers set forth in Tables 11-15, and markers in linkage disequilibrium therewith, and wherein the presence of the at least one allele is indicative of a susceptibility to prostate cancer.

In another aspect, the invention relates to a method for determining a susceptibility to prostate cancer in a human individual, comprising determining the presence or absence of at least one allele of at least one polymorphic marker in a genotype dataset derived from the individual, wherein the at least one polymorphic marker is selected from the polymorphic markers set forth in Tables 11-15, and markers in linkage disequilibrium therewith, and wherein the presence of the at least one allele is indicative of a susceptibility to prostate cancer. The genotype dataset derived from the individual contains a set of genotypes that are based on an analysis of nucleic acid sample from that individual. In other words, the genotypes are characteristic of the individual. In one embodiment, the at least one marker is selected from the group of markers listed in Tables 7-11, and markers in linkage disequilibrium therewith.

In another aspect, the invention relates to a method of predicting aggressive prostate in a human individual who has been diagnosed with, or presents symptoms for, prostate cancer, by determining the presence or absence of at least one allele of at least one polymorphic marker in a nucleic acid sample obtained from the individual, or in a genotype dataset derived from the individual, wherein the at least one polymorphic marker is selected from the polymorphic markers set forth in Tables 11-15, and markers in linkage disequilibrium therewith, and wherein the presence of the at least one allele is indicative of aggressive prostate cancer. In one embodiment, the at least one polymorphic marker is selected from the markers set forth in Table 11, and markers in linkage disequilibrium therewith. In another embodiment, the at least one polymorphic marker is selected from rs2710646, and markers in linkage disequilibrium therewith.

In another embodiment, the at least one marker is selected from the group of markers listed in Tables 7-11. In another embodiment, the at least one marker is selected from the markers set forth in SEQ ID NO:1-362. In another embodiment, the at least one marker is selected from the group of markers listed in Tables 1, 4a and 4b, and markers in linkage disequilibrium therewith. In another embodiment, the at least one marker is selected from marker rs3923603 (SEQ ID NO:1), rs4430796 (SEQ ID NO:2), rs7501939 (SEQ ID NO:3), rs1859962 (SEQ ID NO:4), D17S1350 (SEQ ID NO:5), rs5945572 (SEQ ID NO:6), rs5945605 (SEQ ID NO:7), rs2710646 (SEQ ID NO:8), rs3760511 (SEQ ID NO:56), rs7214479 (SEQ ID NO:134), rs6501445 (SEQ ID NO:146), rs983085 (SEQ ID NO:150), rs5945605 (SEQ ID NO:178) and rs721048 (SEQ ID NO:344), and markers in linkage disequilibrium therewith. In one embodiment, the at least one polymorphic marker is selected from rs2710646 (SEQ ID NO:8) and rs721048 (SEQ ID NO:344), and markers in linkage disequilibrium therewith. In one such embodiment, the at least one polymorphic marker is selected from the markers set forth in Table 11. In another embodiment, the at least one polymorphic marker is rs3923603 (SEQ ID NO:1), or markers in linkage disequilibrium therewith. In one such embodiment, the at least one polymorphic marker is selected from the markers set forth in Table 7. In another embodiment, the at least one polymorphic marker is rs7501939 (SEQ ID NO:3), or markers in linkage disequilibrium therewith. In one such embodiment, the at least one polymorphic marker is selected from the group of markers set forth in Table 8. In a further embodiment, the at least one polymorphic marker is rs1859962 (SEQ ID NO:4), or markers in linkage disequilibrium therewith. In one such embodiment, the at least one polymorphic marker is selected from the group of markers set forth in Table 9. In yet another embodiment, the at least one polymorphic marker is rs5945572 (SEQ ID NO:6), or markers in linkage disequilibrium therewith. In one such embodiment, the at least one polymorphic marker is selected from the group of markers set forth in Table 10. In certain embodiments, the method further comprises assessing frequency of at least one haplotype in the individual, wherein the presence of the at least one haplotype is indicative of a susceptibility to prostate cancer.

In one embodiment, the at least one marker is selected from the group of markers listed in Table 7, and markers in linkage disequilibrium therewith. In another embodiment the at least one marker is selected from the group of markers listed in Table 8, and markers in linkage disequilibrium therewith. In another embodiment the at least one marker is selected from the group of markers listed in Table 9, and markers in linkage disequilibrium therewith. In another embodiment the at least one marker is selected from the group of markers listed in Table 10, and markers in linkage disequilibrium therewith. In another embodiment the at least one marker is selected from the group of markers listed in Table 11, and markers in linkage disequilibrium therewith.

In another embodiment, the present invention relates to a method of determining a susceptibility to prostate cancer in a human individual, comprising analyzing a nucleic acid sample obtained from the individual for the presence or absence at least one allele of at least one polymorphic marker associated with LD block C02, LD block C04a, the TCF2 gene, LD block C17b and LD block C0Xa, wherein the presence of the at least one allele is indicative of a susceptibility to prostate cancer. In one embodiment, the at least marker is selected from the group of markers located within LD block C04a, the TCF2 gene, LD block C17b and/or LD block C0Xa.

In another embodiment, the at least one polymorphism is selected from rs3923603, rs7501939, rs1859962, rs5945572, rs2710646, rs3760511, rs4430796, rs7214479, rs6501455, rs983085, rs5945605, and rs721048, and wherein the presence of allele A in marker rs3923603, allele C in rs7501939, allele G in rs1859962, allele A in rs5945572, allele A in rs2710646, allele C in rs3760511, allele A in rs4430796, allele T in rs7214479, allele A in rs6501455, allele C in rs983085, allele T in rs5945605, or allele A in rs721048 is indicative of increased susceptibility to prostate cancer.

Certain applications of the present invention relate to the TCF2 gene. In one embodiment, the at least one polymorphic marker associated with susceptibility of prostate cancer is associated with the TCF2 gene. In other words, the marker is in linkage disequilibrium with the TCF2 gene. The at least one marker is in one embodiment selected from the group of markers listed in Table 13. In one preferred embodiment, the at least one marker is selected from the markers set forth in Table 4a, Table 4b and/or Table 8. The at least one marker is in another embodiment selected from markers rs7501939 (SEQ ID NO:3) and rs4430796 (SEQ ID NO:2), and markers in linkage disequilibrium therewith. In another embodiment, the at least one polymorphic marker is selected from rs7501939 (SEQ ID NO:3) and rs4430796 (SEQ ID NO:2), and wherein the presence of allele C in marker rs7501939 or allele A in marker rs4430796 is indicative of increased susceptibility of prostate cancer.

In one embodiment, the at least one polymorphic marker is associated with LD block C04a, wherein the presence of the at least one allele is indicative of a susceptibility to prostate cancer. In one embodiment, the marker is selected from the markers within LD block C04a as set forth in Table 12. In another embodiment, the marker is selected from the group of markers within LD block C04a set forth in Table 7. In one preferred embodiment, the marker is marker rs3923603 (SEQ ID NO:1), and markers in linkage disequilibrium therewith. In another preferred embodiment, the marker is marker rs3923603, and wherein the presence of allele 1 in rs3923603 is indicative of increased susceptibility of prostate cancer.

In another embodiment, the at least one polymorphic marker is associated with LD block C17b, wherein the presence of the at least one allele is indicative of a susceptibility to prostate cancer. In one embodiment, the marker is selected from the markers within LD block C17b as set forth in Table 14. In another embodiment, the marker is selected from the markers within LD block C17b set forth in Table 9. In one preferred embodiment, the at least one polymorphic marker is selected from markers rs1859962 (SEQ ID NO:4) and D17S1350 (SEQ ID NO:5), and markers in linkage disequilibrium therewith. In another preferred embodiment, the marker is selected from markers rs1859962 and D17S1350, and wherein the presence of allele G in marker rs1859962 and allele 0 or allele 2 in marker D17S1350 is indicative of increased susceptibility of prostate cancer. In yet another embodiment, the at least one haplotype is a haplotype comprising allele G at marker rs17763769 and allele 0 or allele 2 at marker D17S1350.

Another embodiment of the invention relates to a method of determining a susceptibility to prostate cancer in an individual, comprising analyzing a nucleic acid sample obtained from the individual for the presence or absence at least one allele of at least one polymorphic marker associated with LD Block C0Xa, wherein the presence of the at least one allele is indicative of a susceptibility to prostate cancer. In one embodiment, the at least one polymorphic marker is selected from markers within LD block C0Xa as set forth in Table 15. In another embodiment, the at least one polymorphic marker is selected from markers within LD block C0Xa set forth in Table 10. In one preferred embodiment, the marker is marker rs5945572 (SEQ ID NO:6), and markers in linkage disequilibrium therewith. In another preferred embodiment, the presence of allele 1 in marker rs5945572 is indicative of increased susceptibility of prostate cancer.

In another embodiment, the at least one polymorphic marker is associated with LD Block C02, wherein the presence of the at least one allele is indicative of a susceptibility to prostate cancer. In one embodiment, the marker is selected from the markers within LD block C02 as set forth in Table 16. In another embodiment, the marker is selected from the markers within LD block C02 set forth in Table 11. In one preferred embodiment, the at least one polymorphic marker is marker rs2710646 (SEQ ID NO:8) or marker rs721048 (SEQ ID NO:344), and markers in linkage disequilibrium therewith. In another preferred embodiment, the marker is selected from markers rs2710646 or marker rs721048, and wherein the presence of allele A in marker rs2710646 or allele A in marker rs721048 is indicative of increased susceptibility of prostate cancer.

In another aspect, the present invention relates to a method of diagnosing or determining a susceptibility of prostate cancer in an individual, the method comprising determining the identity of at least one allele of at least one polymorphic marker in a nucleic acid sample obtained from the individual, wherein the at least one marker is selected from the group of markers located within the TCF2 gene, and markers in linkage disequilibrium therewith, wherein the presence of the at least one allele is indicative of a susceptibility of prostate cancer. In one embodiment, the at least one marker is selected from the markers set forth in Table 13. In another embodiment, the at least one marker is selected from the markers set forth in Table 6, and markers in linkage disequilibrium therewith. In another embodiment, the at least one marker is selected from marker rs7501939 (SEQ ID NO:3), rs3760511 (SEQ ID NO:56) and rs4430796 (SEQ ID NO:2), and markers in linkage disequilibrium therewith.

Another aspect of the invention relates to a method of identification a marker for use in assessing susceptibility to prostate cancer, the method comprising identifying at least one polymorphism in linkage disequilibrium with at least one of the polymorphisms listed in Tables 7-11, and determining the genotype status of a sample of individuals diagnosed with, or having a susceptibility to, prostate cancer, and a control sample, wherein significant association to prostate cancer, or a susceptibility to prostate cancer, of at least one allele in the at least one polymorphism is indicative of the polymorphism being useful for assessing susceptibility to prostate cancer. In one embodiment, linkage disequilibrium is characterized by numerical values of $r^2$ of greater than 0.2.

Another aspect of the invention relates to a method of identification of a marker for use in assessing susceptibility to prostate cancer, the method comprising (a) identifying at least one polymorphic marker in linkage disequilibrium with at least one of the markers set forth in any of the Tables 7, 8, 9, 10 or 11 (SEQ ID NO:1-362); (b) determining the genotype status of a sample of individuals diagnosed with, or having a susceptibility to, prostate cancer; and (c) determining the genotype status of a sample of control individuals; wherein a significant difference in frequency of at least one allele in at least one polymorphism in individuals diagnosed with, or having a susceptibility to, prostate cancer, as compared with the frequency of the at least one allele in the control sample is indicative of the at least one polymorphism being useful for assessing susceptibility to prostate cancer. In one embodiment, an increase in frequency of the at least one allele in the at least one polymorphism in individuals diagnosed with, or having a susceptibility to, prostate cancer, as compared with the frequency of the at least one allele in the control sample is indicative of the at least one polymorphism being useful for assessing increased susceptibility to prostate cancer. In another embodiment, a decrease in frequency of the at least one allele in the at least one polymorphism in individuals diagnosed with, or having a susceptibility to, prostate cancer, as compared with the frequency of the at least one allele in the control sample is indicative of the at least one polymorphism being useful for assessing decreased susceptibility to, or protection against, prostate cancer.

A further aspect relates to a method of genotyping a nucleic acid sample obtained from a human individual at risk for, or diagnosed with, prostate cancer, comprising determining the presence or absence of at least one allele of at least one polymorphic marker in the sample, wherein the at least one marker is selected from the group consisting of the markers set forth in Tables 7-11 (SEQ ID NO:1-362), and markers in linkage disequilibrium therewith, and wherein the presence or absence of the at least one allele of the at least one polymorphic marker is indicative of a susceptibility of prostate cancer. In one embodiment, genotyping comprises amplifying a segment of a nucleic acid that comprises the at least one polymorphic marker by Polymerase Chain Reaction (PCR), using a nucleotide primer pair flanking the at least one polymorphic marker. In another embodiment, genotyping is performed using a process selected from allele-specific probe hybridization, allele-specific primer extension, allele-specific amplification, nucleic acid sequencing, 5'-exonuclease digestion, molecular beacon assay, oligonucleotide ligation assay, size analysis, and single-stranded conformation analysis. In a preferred embodiment, the process comprises allele-specific probe hybridization. In another preferred embodiment, the process comprises DNA sequencing. In a preferred embodiment, the method comprises the steps of (1) contacting copies of the nucleic acid with a detection oligonucleotide probe and an enhancer oligonucleotide probe under conditions for specific hybridization of the oligonucleotide probe with the nucleic acid; wherein (a) the detection oligonucleotide probe is from 5-100 nucleotides in length and specifically hybridizes to a first segment of the nucleic acid whose nucleotide sequence is given by any one of SEQ ID NO:1-SEQ ID NO:362; (b) the detection oligonucleotide probe comprises a detectable label at its 3' terminus and a quenching moiety at its 5' terminus; (c) the enhancer oligonucleotide is from 5-100 nucleotides in length and is complementary to a second segment of the nucleotide sequence that is 5' relative to the oligonucleotide probe, such that the enhancer oligonucleotide is located 3' relative to the detection oligonucleotide probe when both oligonucleotides are hybridized to the nucleic acid; and (d) a single base gap exists between the first segment and the second segment, such that when the oligonucleotide probe and the enhancer oligonucleotide probe are both hybridized to the nucleic acid, a single base gap exists between the oligonucleotides; (2) treating the nucleic acid with an endonuclease that will cleave the detectable label from the 3' terminus of the detection probe to release free detectable label when the detection probe is hybridized to the nucleic acid; and measuring free detectable label, wherein the presence of the free detectable label indicates that the detection probe specifically hybridizes to the first segment of the nucleic acid, and indicates the sequence of the polymorphic site as the complement of the detection probe.

Another aspect of the invention relates to the use of an oligonucleotide probe in the manufacture of a reagent for diagnosing and/or assessing susceptibility to prostate cancer in a human individual, wherein the probe hybridizes to a segment of a nucleic acid whose nucleotide sequence is given by any one of SEQ ID NO:1-SEQ ID NO:362, and wherein the probe is 15-500 nucleotides in length.

A further aspect of the invention relates to a method of assessing an individual for probability of response to a therapeutic agent for preventing and/or ameliorating symptoms associated with prostate cancer, comprising: determining the presence or absence of at least one allele of at least one polymorphic marker in a nucleic acid sample obtained from the individual, wherein the at least one polymorphic marker is selected from the group consisting of the polymorphic markers set forth in Tables 7-11 (SEQ ID NO:1-362), and markers in linkage disequilibrium therewith, wherein the presence of the at least one allele of the at least one marker is indicative of a probability of a positive response to the therapeutic agent.

Yet another aspect relates to method of predicting prognosis of an individual diagnosed with, cancer, the method comprising determining the presence or absence of at least one allele of at least one polymorphic marker in a nucleic acid sample obtained from the individual, wherein the at least one polymorphic marker is selected from the group consisting of the polymorphic markers set forth in Tables 7-11, and markers in linkage disequilibrium therewith, wherein the presence of the at least one allele is indicative of a worse prognosis of the cancer in the individual.

A further aspect of the invention relates to a method of monitoring progress of a treatment of an individual undergoing treatment for prostate cancer, the method comprising determining the presence or absence of at least one allele of at least one polymorphic marker in a nucleic acid sample obtained from the individual, wherein the at least one polymorphic marker is selected from the group consisting of the polymorphic markers listed in Tables 7-11 (SEQ ID NO:1-362), and markers in linkage disequilibrium therewith, wherein the presence of the at least one allele is indicative of the treatment outcome of the individual.

Certain embodiments of the methods of the invention further comprise assessing at least one biomarker in a sample from the individual. The sample is in certain embodiments a blood sample or a cancer biopsy sample. Other embodiments include a further step of analyzing a sample comprising genomic DNA from a human individual or a genotype dataset derived from a human individual for the presence or absence of at least one at-risk allele of at least one at-risk variant for prostate cancer not in linkage disequilibrium with any one of the markers set forth in Tables 7-11. In one such embodiment, the at least one at-risk variant for prostate cancer is selected from rs10505483, rs1447295, rs6983267 and rs10896450, and markers in linkage disequilibrium therewith. In one such embodiment the presence of allele A in rs10505483, allele A in rs1447295, allele G in rs6983267 and allele G in rs10896450 is indicative of increased susceptibility of prostate cancer.

In certain embodiments, the invention comprises determining the presence or absence of at least one allele of at least two polymorphic markers selected from the group of polymorphic markers set forth in Tables 7-11, and markers in linkage disequilibrium therewith, and wherein the presence of the at least one allele of the at least two polymorphic markers is indicative of an increased susceptibility to prostate cancer. In one embodiment, the method comprises determining the presence of an at-risk allele of markers rs10505483, rs1447295, rs1859962, rs2710646, rs4430796, rs5945572, and rs6983267. In another embodiment, the method comprises determining the presence of an at-risk allele of markers rs10505483, rs1447295, rs1859962, rs2710646, rs4430796, rs5945572, rs6983267 and rs10896450. In one such embodiment, the at-risk allele is allele A in rs10505483, allele A in rs1447295, allele G in rs6983267, allele G in rs10896450, allele G in rs1859962, allele A in rs2710646, allele A in rs4430796, and allele A in rs5945572.

Certain embodiments further comprise analyzing non-genetic information to make risk assessment, diagnosis, or prognosis of the individual. The non-genetic information is in some embodiments selected from age, gender, ethnicity, socioeconomic status, previous disease diagnosis, medical history of subject, family history of cancer, biochemical measurements, and clinical measurements.

The invention also relates to kits for assessing susceptibility to prostate cancer in a human individual. In one embodiment, the kit comprises reagents necessary for selectively detecting at least one allele of at least one polymorphic marker in the genome of the individual, wherein the at least one polymorphic marker is selected from the group consisting of the polymorphic markers listed in Tables 12-16, and markers in linkage disequilibrium therewith, and wherein the presence of the at least one allele is indicative of a susceptibility to prostate cancer. In one embodiment, the at least one polymorphic marker is selected from the markers set forth in Tables 7-11. In another embodiment, the at least one polymorphic markers is selected from the group of markers associated with the TCF2 gene. In another embodiment, the kit comprises reagents for selectively detecting at least one allele of at least one polymorphic marker in the genome of the individual, wherein the polymorphic marker is selected from the markers set forth in Tables 7-11 (SEQ ID NO:1-362), and markers in linkage disequilibrium therewith, and wherein the presence of the at least one allele is indicative of a susceptibility to prostate cancer. In one embodiment, the reagents comprise at least one contiguous oligonucleotide that hybridizes to a fragment of the genome of the individual comprising the at least one polymorphic marker, a buffer and a detectable label. In another embodiment, the reagents comprise at least one pair of oligonucleotides that hybridize to opposite strands of a genomic nucleic acid segment obtained from the subject, wherein each oligonucleotide primer pair is designed to selectively amplify a fragment of the genome of the individual that includes one polymorphic marker, and wherein the fragment is at least 30 base pairs in size. In one preferred embodiment, the at least one oligonucleotide is completely complementary to the genome of the individual. In one embodiment, the oligonucleotide is about 18 to about 50 nucleotides in length. In another embodiment, the oligonucleotide is 20-30 nucleotides in length.

In a preferred embodiment, the kit comprises: (a) a detection oligonucleotide probe that is from 5-100 nucleotides in length; (b) an enhancer oligonucleotide probe that is from 5-100 nucleotides in length; and (c) an endonuclease enzyme; wherein the detection oligonucleotide probe specifically hybridizes to a first segment of the nucleic acid whose nucleotide sequence is given by any one of SEQ ID NO:1-SEQ ID NO:362; and wherein the detection oligonucleotide probe comprises a detectable label at its 3' terminus and a quenching moiety at its 5' terminus; wherein the enhancer oligonucleotide is from 5-100 nucleotides in length and is complementary to a second segment of the nucleotide sequence that is 5' relative to the oligonucleotide probe, such that the enhancer oligonucleotide is located 3' relative to the detection oligonucleotide probe when both oligonucleotides are hybridized to the nucleic acid; wherein a single base gap exists between the first segment and the second segment, such that when the oligonucleotide probe and the enhancer oligonucleotide probe are both hybridized to the nucleic acid, a single base gap exists between the oligonucleotides; and wherein treating the nucleic acid with the endonuclease will cleave the detectable label from the 3' terminus of the detection probe to release free detectable label when the detection probe is hybridized to the nucleic acid.

The kit can in another embodiment comprise at least one detection oligonucleotide probe that is from 5-100 nucleotides in length and specifically hybridizes (under stringent conditions) to all or a portion of the TCF2 gene, the LD block C02, the LD block C17b, the LD block C0Xa or the LD block C04a, and wherein at least one of said at least one oligonucleotide probes comprises a polymorphism selected from the group of polymorphisms listed in Tables 7-11, and polymorphisms in linkage disequilibrium therewith.

Another aspect relates to a kit comprising at least one reagent for determining the presence in a human nucleic acid of at least one at-risk allele of at least one marker in the TCF2 gene, the LD block C02, the LD block C17b, the LD block C0Xa or the LD block C04a, wherein the presence of the at least one at-risk allele correlates with an increased prevalence of prostate cancer in humans. In one embodiment the at least one reagent comprises at least one contiguous nucleotide sequence that is fully complementary to a region of human nucleic acid that comprises the at least one marker. In another embodiment, the kit comprises at least one allele-specific nucleotide that differentially hybridizes to single-stranded human nucleic acid molecules that contain different alleles of the marker, wherein the marker is selected from the group of markers set forth in any of the Tables 7-11, and wherein the allele-specific oligonucleotide is from 15-200 nucleotides in size.

A further method of the invention relates to detecting the presence of at least one allele of at least one polymorphic marker associated with prostate cancer, the method comprising a step of contacting at least one oligonucleotide probe that specifically hybridizes to an oligonucleotide sequence comprising said polymorphic marker with a test sample comprising genomic DNA from a human individual, and determining whether the at least one oligonucleotide probe hybridizes to the genomic DNA from the test sample. In one embodiment of such a method, the oligonucleotide probe comprises a label. In one preferred embodiment, the label is a fluorescent label. In another embodiment, the oligonucleotide probe further comprises a quencher. In another embodiment, the method comprises contacting two oligonucleotide probes with the test sample, wherein at least one of the oligonucleotide probes contains a fluorescent label and a quencher. The oligonucleotide probes are in preferred embodiments from 15 to 100 nucleotides in size, such as from 18-50 nucleotides, such as 20-30 nucleotides in size.

In certain methods, uses and kits of the invention, the presence of the at least one allele or haplotype is indicative of increased susceptibility to prostate cancer. In some embodiments, the increased susceptibility is characterized by a relative risk of at least 1.1, including a relative risk of at least 1.15, a relative risk of at least 1.2, a relative risk of at least 1.25, a relative risk of at least 1.3, a relative risk of at least 1.4, a relative risk of at least 1.5, a relative risk of at least 1.6, a relative risk of at least 1.7, and a relative risk of at least 2.0.

In other methods and kits, the presence of the at least one allele or haplotype is indicative of decreased susceptibility to prostate cancer. In some embodiments, the decreased susceptibility is characterized by a relative risk of less than 0.9, including a relative risk of less than 0.85, a relative risk of less than 0.8, a relative risk of less than 0.75, a relative risk of less than 0.7, a relative risk of less than 0.6, and a relative risk of less than 0.5.

The various aspects (i.e., uses, methods, kits, media, and apparatus) of the invention can, in a general sense, be reduced to practice using any one or a plurality of the markers described herein to be associated with a susceptibility of prostate cancer. Thus in certain embodiments, the at least one marker to be assessed is selected from the group of markers listed in Tables 7-11, and markers in linkage disequilibrium therewith. In another embodiment, the at least one marker is selected from the group of markers listed in Tables 7-11. In certain other embodiments, the at least one marker is selected from the markers set forth in SEQ ID NO:1-362. In other embodiments, the at least one marker is selected from the group of markers listed in Tables 1, 4a and 4b, and markers in linkage disequilibrium therewith. In other embodiments, the at least one marker is selected from marker rs3923603 (SEQ ID NO:1), rs4430796 (SEQ ID NO:2), rs7501939 (SEQ ID NO:3), rs1859962 (SEQ ID NO:4), D17S1350 (SEQ ID NO:5), rs5945572 (SEQ ID NO:6), rs5945605 (SEQ ID NO:7), rs2710646 (SEQ ID NO:8), rs3760511 (SEQ ID NO:56), rs7214479 (SEQ ID NO:134), rs6501445 (SEQ ID NO:146), rs983085 (SEQ ID NO:150), rs5945605 (SEQ ID NO:178) and rs721048 (SEQ ID NO:344), and markers in linkage disequilibrium therewith. In some embodiments, the at least one polymorphic marker is selected from rs2710646 (SEQ ID NO:8) and rs721048 (SEQ ID NO:344), and markers in linkage disequilibrium therewith. In particular embodiment, the at least one polymorphic marker is selected from the markers set forth in Table 11. In other particular embodiments, the at least one polymorphic marker is rs3923603 (SEQ ID NO:1), or markers in linkage disequilibrium therewith. In certain such embodiments, the at least one polymorphic marker is selected from the markers set forth in Table 7. In certain other embodiments, the at least one polymorphic marker is rs7501939 (SEQ ID NO:3), or markers in linkage disequilibrium therewith. In some of such embodiments, the at least one polymorphic marker is selected from the group of markers set forth in Table 8. In some further embodiments, the at least one polymorphic marker is rs1859962 (SEQ ID NO:4), or markers in linkage disequilibrium therewith. In certain such embodiments, the at least one polymorphic marker is selected from the group of markers set forth in Table 9. In other embodiments, the at least one polymorphic marker is rs5945572 (SEQ ID NO:6), or markers in linkage disequilibrium therewith. In particular embodiments, the at least one polymorphic marker is selected from the group of markers set forth in Table 10. In one embodiment, the at least one marker is selected from the group of markers listed in Table 7, and markers in linkage disequilibrium therewith. In other embodiments, the at least one marker is selected from the group of markers listed in Table 8, and markers in linkage disequilibrium therewith. In other embodiments, the at least one marker is selected from the group of markers listed in Table 9, and markers in linkage disequilibrium therewith. In other embodiments, the at least one marker is selected from the group of markers listed in Table 10, and markers in linkage disequilibrium therewith. In other embodiments, the at least one marker is selected from the group of markers listed in Table 11, and markers in linkage disequilibrium therewith. In other embodiments, the at least one marker is selected from markers associated with LD block C02, LD block C04a, the TCF2 gene, LD block C17b or LD block C0Xa, as described herein. In certain such embodiments, the at least marker is selected from the group of markers located within LD block C04a, the TCF2 gene, LD block C17b or LD block C0Xa.

The prostate cancer phenotype applicable for assessment by the methods, uses and kits of the invention is in certain embodiments aggressive prostate cancer, as described further herein. In other words, the markers of the invention are in certain embodiments predictive of aggressive prostate cancer, as defined herein, in an individual. In one embodiment, markers associated with LD block C02 are predictive of aggressive prostate cancer, such as markers selected from the markers set forth in Table 11, or markers in linkage disequilibrium therewith. In certain embodiments, the invention pertains individuals with specific age at onset of disease. In certain embodiments, age at onset of disease is the age at which first diagnosis of the disease is made. In certain other embodiments, age at onset is the age of first symptoms of the disease, which may occur at an earlier age than the actual disease diagnosis. In certain embodiments, age at onset of prostate cancer is early—also sometimes called young onset disease. In particular embodiments, age at onset is before age 70. In other embodiments, age at onset is before age 65. In certain other embodiments, age at onset is before age 60. In other embodiments, age at onset of disease is before age 55.

In certain embodiments of the invention, linkage disequilibrium is characterized by particular cutoff values of the linkage disequilibrium measures $r^2$ and/or |D'|, as discussed in more detail herein. In one embodiment, linkage disequilibrium is characterized by numerical values of $r^2$ of greater than 0.1. In another embodiment, linkage disequilibrium is characterized by values of $r^2$ of greater than 0.2. In other embodiments, linkage disequilibrium is characterized by values of $r^2$ of greater than 0.3, 0.4, 0.5, 0.6, 0.7, 0.8, 0.9, 0.95 or 0.99. In other embodiments, linkage disequilibrium is characterized by numerical values of |D'| of greater than 0.5, such as values of greater than 0.6, values greater than 0.7, values greater than 0.8, values greater than 0.9, or values greater than 0.95. Other non-integer cutoff values in the range of 0.01-1.0 for $r^2$ or |D'| are also contemplated and are also encompassed by the present invention. In particular embodiments, a cutoff of a particular value for $r^2$ and a cutoff of a particular value of |D'| are characteristic of the linkage disequilibrium. In one such embodiment, linkage disequilibrium is characterized by values of $r^2$ of greater than 0.2 and/or |D'| of greater than 0.8. It should be appreciated that other combinations and permutations of the cutoff values of $r^2$ and |D'| are contemplated and are also within the scope of the present invention.

BRIEF DESCRIPTION OF THE DRAWINGS

The foregoing and other objects, features and advantages of the invention will be apparent from the following more particular description of preferred embodiments of the invention.

FIG. 1 shows the genomic structure of the TCF2 gene. The gene is characterized by the presence of several splice variants, varying in length from about 5 kb (2 exons) to almost 60 kb (9 exons) of genomic sequence. The positions of SNP markers (dbSNP125, Illumina 300k chip, and HapMap Release 19) are indicated by vertical bars.

DETAILED DESCRIPTION OF THE INVENTION

A description of preferred embodiments of the invention follows.

The present invention discloses polymorphic variants and haplotypes that have been found to be associated with prostate cancer. Particular alleles at polymorphic markers (e.g., the markers of Tables 12-16, e.g., the markers of Tables 7-11, e.g., markers rs3923603 (SEQ ID NO:1), rs4430796 (SEQ ID NO:2), rs7501939 (SEQ ID NO:3), rs1859962 (SEQ ID NO:4), D17S1350 (SEQ ID NO:5), rs5945572 (SEQ ID NO:6), rs5945605 (SEQ ID NO:7), rs2710646 (SEQ ID NO:8), rs721048 (SEQ ID NO:344) and markers in linkage disequilibrium therewith) and haplotypes comprising such alleles have been found to be associated with prostate cancer. Such markers and haplotypes are useful for diagnostic purposes, as described in further detail herein. Further applications of the present invention includes methods for assessing response to prostate cancer therapeutic agents utilizing the polymorphic markers of the invention, as well as kits for assessing susceptibility of an individual to prostate cancer.

DEFINITIONS

The following terms shall, in the present context, have the meaning as indicated:

A "polymorphic marker", sometimes referred to as a "marker", as described herein, refers to a genomic polymorphic site. Each polymorphic marker has at least two sequence variations characteristic of particular alleles at the polymorphic site. Thus, genetic association to a polymorphic marker implies that there is association to at least one specific allele of that particular polymorphic marker. The marker can comprise any allele of any variant type found in the genome, including single nucleotide polymorphisms (SNPs), microsatellites, insertions, deletions, duplications and translocations.

An "allele" refers to the nucleotide sequence of a given locus (position) on a chromosome. A polymorphic marker allele thus refers to the composition (i.e., sequence) of the marker on a chromosome. Genomic DNA from an individual contains two alleles (e.g., allele-specific sequences) for any given polymorphic marker, representative of each copy of the marker on each chromosome. Sequence codes for nucleotides used herein are: A=1, C=2, G=3, T=4.

Sequence conucleotide ambiguity as described herein is as proposed by IUPAC-IUB. These codes are compatible with the codes used by the EMBL, GenBank, and PIR databases.

| IUB code | Meaning |
|---|---|
| A | Adenosine |
| C | Cytidine |
| G | Guanine |
| T | Thymidine |
| R | G or A |
| Y | T or C |
| K | G or T |
| M | A or C |
| S | G or C |
| W | A or T |
| B | C G or T |
| D | A G or T |
| H | A C or T |
| V | A C or G |
| N | A C G or T (Any base) |

A nucleotide position at which more than one sequence is possible in a population (either a natural population or a synthetic population, e.g., a library of synthetic molecules) is referred to herein as a "polymorphic site".

A "Single Nucleotide Polymorphism" or "SNP" is a DNA sequence variation occurring when a single nucleotide at a specific location in the genome differs between members of a species or between paired chromosomes in an individual. Most SNP polymorphisms have two alleles. Each individual is in this instance either homozygous for one allele of the polymorphism (i.e. both chromosomal copies of the individual have the same nucleotide at the SNP location), or the individual is heterozygous (i.e. the two sister chromosomes of the individual contain different nucleotides). The SNP nomenclature as reported herein refers to the official Reference SNP (rs) ID identification tag as assigned to each unique SNP by the National Center for Biotechnological Information (NCBI).

A "variant", as described herein, refers to a segment of DNA that differs from the reference DNA. A "marker" or a "polymorphic marker", as defined herein, is a variant. Alleles that differ from the reference are referred to as "variant" alleles.

A "microsatellite" is a polymorphic marker that has multiple small repeats of bases that are 2-8 nucleotides in length (such as CA repeats) at a particular site, in which the number of repeat lengths varies in the general population.

An "indel" is a common form of polymorphism comprising a small insertion or deletion that is typically only a few nucleotides long.

A "haplotype," as described herein, refers to a segment of genomic DNA within one strand of DNA that is characterized by a specific combination of alleles arranged along the segment. For diploid organisms such as humans, a haplotype comprises one member of the pair of alleles for each polymorphic marker or locus. In a certain embodiment, the haplotype can comprise two or more alleles, three or more alleles, four or more alleles, or five or more alleles. Haplotypes are described herein in the context of the marker name and the allele of the marker in that haplotype, e.g., "A rs3923603" refers to the A allele of marker rs3923603 being in the haplotype, and is equivalent to "rs3923603 allele A". Furthermore, allelic codes in haplotypes are as for individual markers, i.e. 1=A, 2=C, 3=G and 4=T.

The term "susceptibility", as described herein, refers to an individual (or group of individuals) being prone to developing a certain state (e.g., a certain trait, phenotype or disease), or being less able to resist a particular state than the average individual. The term encompasses both increased susceptibility and decreased susceptibility. Thus, particular alleles at polymorphic markers and/or haplotypes of the invention as described herein may be characteristic of increased susceptibility (i.e., increased risk) of prostate cancer, as characterized by a relative risk (RR) or odds ratio (OR) of greater than one for the particular allele or haplotype. Alternatively, the markers and/or haplotypes of the invention are characteristic of decreased susceptibility (i.e., decreased risk) of prostate cancer, as characterized by a relative risk of less than one.

The term "and/or" shall in the present context be understood to indicate that either or both of the items connected by it are involved. In other words, the term herein shall be taken to mean "one or the other or both".

The term "look-up table", as described herein, is a table that correlates one form of data to another form, or one or more forms of data to a predicted outcome to which the data is relevant, such as phenotype or trait. For example, a look-up table can comprise a correlation between allelic data for at least one polymorphic marker and a particular trait or phenotype, such as a particular disease diagnosis, that an individual who comprises the particular allelic data is likely to display, or is more likely to display than individuals who do not comprise the particular allelic data. Look-up tables can be multidimensional, i.e. they can contain information about multiple alleles for single markers simultaneously, or the can contain information about multiple markers, and they may also comprise other factors, such as particulars about diseases diagnoses, racial information, biomarkers, biochemical measurements, therapeutic methods or drugs, etc.

A "computer-readable medium", is an information storage medium that can be accessed by a computer using a commercially available or custom-made interface. Exemplary compute-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

A "nucleic acid sample" is a sample obtained from an individual that contains nucleic acid (DNA or RNA). In certain embodiments, i.e. the detection of specific polymorphic markers and/or haplotypes, the nucleic acid sample comprises genomic DNA. Such a nucleic acid sample can be obtained from any source that contains genomic DNA, including as a blood sample, sample of amniotic fluid, sample of cerebrospinal fluid, or tissue sample from skin, muscle, buccal or conjunctival mucosa, placenta, gastrointestinal tract or other organs.

The term "prostate cancer therapeutic agent" refers to an agent that can be used to ameliorate or prevent symptoms associated with prostate cancer.

The term "prostate cancer-associated nucleic acid", as described herein, refers to a nucleic acid that has been found to be associated to prostate cancer. This includes, but is not limited to, the markers and haplotypes described herein and markers and haplotypes in strong linkage disequilibrium (LD) therewith. In one embodiment, a prostate cancer-associated nucleic acid refers to an LD-block found to be associated with prostate cancer through at least one polymorphic marker located within the LD block or associated with the LD block.

"Aggressive prostate cancer", as described herein, refers to prostate cancer with combined Gleason grades of 7 or higher OR stage T3 or higher OR node positive OR metastasis positive disease OR death because of prostate cancer. Note that it is sufficient to have one of these criteria to be determined aggressive prostate cancer. These clinical parameters are well known surrogates for increased aggressiveness of the disease.

The term "LD block C04a", as described herein, refers to the Linkage Disequilibrium (LD) block on Chromosome 4 between positions 145,601,002 and 145,805,005 of NCBI (National Center for Biotechnology Information) Build 34. The position of the LD block in NCBI Build 35 is between positions 145,380,980 and 145,584,983, and in NCBI Build 36, the LD block is between positions 145,242,825 and 145,446,828. In all these sequence builds, the LD block spans 204,004 bp.

The term "LD block C17b", as described herein, refers to the Linkage Disequilibrium (LD) block on Chromosome 17 between positions 69,665,200 and 69,843,150 of NCBI (National Center for Biotechnology Information) Build 34. The position of the LD block in NCBI Build 35 and in NCBI Build 36 is between positions 66,579,672 and 66,757,622. In all these sequence builds, the LD block spans 177,951 bp.

The term "LD block C0Xa, as described herein, refers to the Linkage Disequilibrium (LD) block on Chromosome X between positions 50,084,494 and 50,695,908 of NCBI (National Center for Biotechnology Information) Build 34, spanning markers rs972635 and rs4986573. The LD Block is located between positions 51,000,724 and 51,612,138 in NCBI Build 35, while in NCBI Build 36, the LD block is located between positions 51,184,428 and 51,795,842. The block spans 611,414 bp in all these sequence builds.

The term "TCF2", or "TCF2 gene" as described herein, refers to the human transcription factor 2 gene on chromosome 17q12. Other names for this gene include Hepatocyte nuclear factor 1-beta (HNF-1beta or HNF-1B), Variant hepatic nuclear factor 1 (VHNF1) and Homeoprotein (LFB3)). The TCF2 gene is characterized by several splice variants, the longest of which stretches across a 64 kb region, between positions 36,235,927 and 36,324,014 in NCBI Build 34, and between position 33,114,490 and 33,202,577 in NCBI Build 35.

The term "LD block C02", as described herein, refers to the Linkage Disequilibrium (LD) block on Chromosome 2 between positions 62,767,002 and 63,881,002 of NCBI (National Center for Biotechnology Information) Build 34. The position of the LD block in NCBI Build 35 is between positions 62,704,119 and 63,818,119, and in NCBI Build 36, the LD block spans positions 62,645,972 and 63,759,972. In all these sequence builds, the LD block spans 1,114,000 bp.

Through association analysis of a population of individuals diagnosed with prostate cancer, it has been discovered that certain alleles at certain polymorphic markers are associated with prostate cancer. A genome-wide analysis for variants associated with prostate cancer (e.g., aggressive prostate cancer) revealed association of prostate cancer to five regions of the genome, on chromosome 2 (2p15), chromosome 4 (4q31.21), chromosome 17 (17q12 and 17q24.3) and chromosome X (Xp11.22). Particular markers have been found to be associated with an increased risk of prostate cancer in these four regions, as shown herein.

As indicated in Table 1, the A allele of marker rs3923603 (SEQ ID NO:1) on chromosome 4q31.21 (also called rs3923603 A allele) was found to be associated with an increased risk of prostate cancer. The marker is located in a linkage disequilibrium region which we call LD block C04a between positions 145,601,002 and 145,805,005 bp on chromosome 4 (NCBI Build 34). On chromosome 17q12, markers rs7501939 2 allele (SEQ ID NO:3) and rs4430796 A allele (SEQ ID NO:2), residing within the TCF2 gene between positions 36,235,927 and 36,324,014 (NCBI Build 34) on chromosome 17 were found to be associated with prostate cancer. Furthermore, rs1859962 3 allele on chromosome 17q24.3 (SEQ ID NO:4) was found to be associated with an increased risk of prostate cancer. A haplotype defined by markers D17S1350 (SEQ ID NO:5; alleles 0 and 2 combined together) and rs1859962 G allele (SEQ ID NO:4) refined the association signal and increases the risk and decreases the P value. Both these markers are located in what we call LD block C17b between positions 69,665,200 and 69,843,150 bp on chromosome 17 (NCBI Build 34). The marker rs5945572 A allele (SEQ ID NO:6) on chromosome Xp11.22 has been found to be associated with an increased risk of prostate cancer. The marker is located in what we call LD block C0Xa between positions 50,084,494 and 50,695,908 bp (NCBI Build 34) on chromosome X. Marker rs2710646 A allele (SEQ ID NO:8) on chromosome 2 has also been found to be associated with increased risk of prostate cancer. This marker is located within a region on chromosome 2 with extensive linkage disequilibrium, between position 62,767,002 and 63,881,002 (NCBI Build 34), which we denote LD block C02.

These markers, and markers that are correlated with these markers are useful in the methods of the present invention. Thus, there are many polymorphic markers at each locus either within or close to the LD blocks defined herein that are in strong LD with the SNP markers shown herein to be associated with prostate cancer (e.g., aggressive prostate cancer). These correlated markers, including known SNPs or other polymorphic markers such as microsatellites or indels, as well as other correlated SNPs or other polymorphic markers, could therefore be used, alone or in combination, as surrogate markers for detecting the association to prostate cancer described herein.

Given that a significant percentage of prostate cancer is a non-aggressive form that will not spread beyond the prostate and cause morbidity or mortality, and treatments of prostate cancer including prostatectomy, radiation, and chemotherapy all have side effects and significant cost, it would be valuable to have diagnostic markers, such as those described herein, that show greater risk for aggressive prostate cancer as compared to the less aggressive form(s).

Replication analysis of the association of markers within the five chromosomal regions (e.g., 2p15, 4q31.21, 17q12, 17q24.3 and Xp11.23) with cancer (e.g., prostate cancer (e.g., aggressive prostate cancer)) shows that the results are applicable to other populations. Several cohorts of Caucasian origin from Nijmegen, the Netherlands, (Radboud University Nijmegen Medical Centre (RUNMC)), Chicago, U.S. (Northwestern University), and Zaragoza, Spain (Zaragoza University Hospital) all showed association of the variants described herein with prostate cancer, with associated risk (measured as odds ratio, OR) being similar or even higher than found in the Icelandic population.

Transcription Factor 2 Gene (TCF2) Association with Prostate Cancer

The present invention in one aspect relates to identification of a prostate cancer-associated gene encoding transcription factor 2 (official gene symbol is TCF2, but other names for this gene are: Hepatocyte nuclear factor 1-beta (HNF-1beta) (HNF-1B), Variant hepatic nuclear factor 1 (VHNF1) and Homeoprotein (LFB3)). Several markers within intron 1 and 2 of TCF2, as well as markers in front of exon 1, such as the SNP markers rs4430796, rs7501939 and rs3760511, have been found to be associated with prostate cancer. The original observation, first found in an Icelandic cohort, of the association of rs7501939 ($P=6.8 \times 10^{-5}$; Relative risk=1.20; Population attributable risk=20.7%) and of marker rs3760511 ($P=2.5 \times 10^{-5}$; Relative risk=1.22; Population attributable risk=20.7%) was subsequently replicated in a Dutch prostate cancer cohort and a United States Caucasian cohort.

The TCF2 (HNF1beta) is the only known gene that maps to the region on chromosome 17q12 of the human genome within which an association to prostate cancer has been found. The underlying variation in markers or haplotypes associated with region and cancer may affect expression of the TCF2 gene. It is however also possible that the expression and/or function of the nearby genes, such as DDX52, AP1GBP1, TBC1D3/TBC1D3B (PRC17), are affected by the variants found to be associated to prostate cancer, or variants in linkage disequilibrium therewith. For example, such variation may affect RNA or protein stability or may have structural consequences, such that the region is more prone to somatic rearrangement in haplotype/allele carriers. Thus, the underlying variation could affect uncharacterized genes directly linked to the markers and/or haplotypes described herein, or could possibly also influence neighbouring genes that are not directly associated to the markers and/or haplotypes described herein.

As a result of the discoveries disclosed herein, methods are now available for diagnosis of an increased susceptibility to prostate cancer, as well as for diagnosis of a decreased susceptibility to prostate cancer and/or a protection against prostate cancer. In preferred embodiments of the invention, diagnostic assays are used to identify the presence of particular alleles at chromosomal regions 2p15, 4q31.21, 17q12, 17q24.3 and Xp11.23, in particular the regions defined by LD block C02, LD block C04a, the TCF2 gene, LD block C17b and LD block C0Xa. In additional embodiments of the invention, other markers or SNPs, identified using the methods described herein, can be used for diagnosis of an increased susceptibility to prostate cancer, and also for diagnosis of a decreased susceptibility to prostate cancer or for identification of an allele that is protective against prostate cancer. The diagnostic assays presented below can be used to identify the presence or absence of these particular alleles.

Assessment for Markers and Haplotypes

The genomic sequence within populations is not identical when individuals are compared. Rather, the genome exhibits sequence variability between individuals at many locations in the genome. Such variations in sequence are commonly referred to as polymorphisms, and there are many such sites within each genome For example, the human genome exhibits sequence variations which occur on average every 500 base pairs. The most common sequence variant consists of base variations at a single base position in the genome, and such sequence variants, or polymorphisms, are commonly called Single Nucleotide Polymorphisms ("SNPs"). These SNPs are believed to have occurred in a single mutational event, and therefore there are usually two possible alleles possible at each SNP site; the original allele and the mutated allele. Due to natural genetic drift and possibly also selective pressure, the original mutation has resulted in a polymorphism characterized by a particular frequency of its alleles in any given population. Many other types of sequence variants are found in the human genome, including microsatellites, insertions, deletions, inversions and copy number variations. A polymorphic microsatellite has multiple small repeats of bases (such as CA repeats, TG on the complimentary strand) at a particular site in which the number of repeat lengths varies in the general population. In general terms, each version of the sequence with respect to the polymorphic site represents a specific allele of the polymorphic site. These sequence variants can all be referred to as polymorphisms, occurring at specific polymorphic sites characteristic of the sequence variant in question. In general terms, polymorphisms can comprise any number of specific alleles. Thus in one embodiment of the invention, the polymorphism is characterized by the presence of two or more alleles in any given population. In another embodiment, the polymorphism is characterized by the presence of three or more alleles. In other embodiments, the polymorphism is characterized by four or more alleles, five or more alleles, six or more alleles, seven or more alleles, nine or more alleles, or ten or more alleles. All such polymorphisms can be utilized in the methods and kits of the present invention, and are thus within the scope of the invention. In some instances, reference is made to different alleles at a polymorphic site without choosing a reference allele. Alternatively, a reference sequence can be referred to for a particular polymorphic site. The reference allele is sometimes referred to as the "wild-type" allele and it usually is chosen as either the first sequenced allele or as the allele from a "non-affected" individual (e.g., an individual that does not display a disease or abnormal phenotype).

Alleles for SNP markers as referred to herein refer to the bases A, C, G or T as they occur at the polymorphic site in the SNP assay employed. The allele codes for SNPs used herein are as follows: 1=A, 2=C, 3=G, 4=T. The person skilled in the art will however realise that by assaying or reading the opposite DNA strand, the complementary allele can in each case be measured. Thus, for a polymorphic site (polymorphic marker) containing an A/G polymorphism, the assay employed may either measure the percentage or ratio of the two bases possible, i.e. A and G. Alternatively, by designing an assay that determines the opposite strand on the double-stranded DNA template, the percentage or ratio of the complementary bases T/C can be measured. Quantitatively (for example, in terms of relative risk), identical results would be obtained from measurement of either DNA strand (+ strand or − strand).

Polymorphic sites (polymorphic markers) can allow for differences in sequences based on substitutions, insertions or deletions. For example, a polymorphic microsatellite has multiple small repeats of bases (such as CA repeats) at a particular site in which the number of repeat lengths varies in the general population. Each version of the sequence with respect to the polymorphic site represents a specific allele of the polymorphic site.

Typically, a reference sequence is referred to for a particular sequence. Alleles that differ from the reference are referred to as "variant" alleles. For example, the genomic DNA sequence from position 145,601,002 to position 145,805,005 bp on Chromosome 4 of NCBI Build 34 ("LD block C04a") represents a reference sequence. Other reference sequences related to the present invention include the genomic DNA sequence from position 36,235,927 to position 36,324,014 bp on Chromosome 17 of NCBI Build 34 ("TCF2 gene"), the genomic DNA sequence from position 69,665,200 to position 69,843,150 bp on Chromosome 17 of NCBI Build 34 ("LD block C17b"), the genomic DNA sequence from position 50,084,494 to position 50,695,908 bp on Chromosome X of NCBI Build 34 ("LD block C0Xa"), and the genomic DNA sequence from position 62,767,002 to 63,881,002 bp on Chromosome 2 of NCBI Build 34 ("LD block C02"). A variant sequence, as used herein, refers to a sequence that differs from the reference sequence but is otherwise substantially similar. Alleles at the polymorphic genetic markers that define the haplotypes described herein are variants. Additional variants can include changes that affect a polypeptide, e.g., a polypeptide encoded by the sequences represented by LD block C02, LD block C04a, the TCF2 gene sequence, LD block C17b, or and LD block C0Xa. Sequence differences, when compared to a reference nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence, as described in detail herein. Such sequence changes alter the polypeptide encoded by the nucleic acid. For example, if the change in the nucleic acid sequence causes a frame shift, the frame shift can result in a change in the encoded amino acids, and/or can result in the generation of a premature stop codon, causing generation of a truncated polypeptide. Alternatively, a polymorphism associated with prostate cancer or a susceptibility to prostate cancer can be a synonymous change in one or more nucleotides (i.e., a change that does not result in a change in the amino acid sequence). Such a polymorphism can, for example, alter splice sites, affect the stability or transport of mRNA, or otherwise affect the transcription or translation of an encoded polypeptide. It can also alter DNA to increase the possibility that structural changes, such as amplifications or deletions, occur at the somatic level. The polypeptide encoded by the reference nucleotide sequence is the "reference" polypeptide with a particular reference amino acid sequence, and polypeptides encoded by variant alleles are referred to as "variant" polypeptides with variant amino acid sequences.

A haplotype refers to a segment of DNA that is characterized by a specific combination of alleles arranged along the segment. For diploid organisms such as humans, a haplotype comprises one member of the pair of alleles for each polymorphic marker or locus. In a certain embodiment, the haplotype can comprise two or more alleles, three or more alleles, four or more alleles, or five or more alleles, each allele corresponding to a specific polymorphic marker along the segment. Haplotypes can comprise a combination of various polymorphic markers, e.g., SNPs and microsatellites, having particular alleles at the polymorphic sites. The haplotypes thus comprise a combination of alleles at various genetic markers.

Detecting specific polymorphic markers and/or haplotypes can be accomplished by methods known in the art for detecting sequences at polymorphic sites. For example, standard techniques for genotyping for the presence of SNPs and/or microsatellite markers can be used, such as fluorescence-based techniques (Chen, X. et al., Genome Res. 9 (5): 492-98 (1999); Kutyavin et al., Nucleic Acid Res. 34:e128 (2006)), including PCR, LCR, Nested PCR and other techniques for nucleic acid amplification. Specific methodologies available for SNP genotyping include, but are not limited to, TaqMan genotyping assays and SNPlex platforms (Applied Biosystems), mass spectrometry (e.g., MassARRAY system from Sequenom), minisequencing methods, real-time PCR, Bio-Plex system (BioRad), CEQ and SNPstream systems (Beckman), Molecular Inversion Probe array technology (e.g., Affymetrix GeneChip), and BeadArray Technologies (e.g., Illumina GoldenGate and Infinium assays). By these or other methods available to the person skilled in the art, one or more alleles at polymorphic markers, including microsatellites, SNPs or other types of polymorphic markers, can be identified.

In certain methods described herein, an individual who is at an increased susceptibility (i.e., at risk) for prostate cancer is an individual in whom at least one specific allele at one or more polymorphic marker or haplotype conferring increased susceptibility for prostate cancer is identified (i.e., at-risk marker alleles or haplotypes). In one aspect, the at-risk marker or haplotype is one that confers a significant increased risk (or susceptibility) of prostate cancer. In one embodiment, significance associated with a marker or haplotype is measured by a relative risk (RR). In another embodiment, significance associated with a marker or haplotype is measured by an odds ratio (OR). In a further embodiment, the significance is measured by a percentage. In one embodiment, a significant increased risk is measured as a risk (relative risk and/or odds ratio) of at least 1.2, including but not limited to: at least 1.2, at least 1.3, at least 1.4, at least 1.5, at least 1.6, at least 1.7, 1.8, at least 1.9, at least 2.0, at least 2.5, at least 3.0, at least 4.0, and at least 5.0. In a particular embodiment, a risk (relative risk and/or odds ratio) of at least 1.2 is significant. In another particular embodiment, a risk of at least 1.3 is significant. In yet another embodiment, a risk of at least 1.4 is significant. In a further embodiment, a risk of at least 1.5 is significant. In another further embodiment, a significant increase in risk is at least 1.7 is significant. However, other cutoffs are also contemplated, e.g., at least 1.15, 1.25, 1.35, and so on, and such cutoffs are also within scope of the present invention. In other embodiments, a significant increase in risk is at least about 20%, including but not limited to about 25%, 30%, 35%, 40%, 45%, 50%, 55%, 60%, 65%, 70%, 75%, 80%, 85%, 90%, 95%, 100%, 150%, 200%, 300%, and 500%. In one particular embodiment, a significant increase in risk is at least 20%. In other embodiments, a significant increase in risk is at least 30%, at least 40%, at least 50%, at least 60%, at least 70%, at least 80%, at least 90% and at least 100%. Other cutoffs or ranges as deemed suitable by the person skilled in the art to characterize the invention are however also contemplated, and those are also within scope of the present invention. In certain embodiments, a significant increase in risk is characterized by a p-value, such as a p-value of less than 0.05, less than 0.01, less than 0.001, less than 0.0001, less than 0.00001, less than 0.000001, less than 0.0000001, less than 0.00000001, or less than 0.000000001.

An at-risk polymorphic marker or haplotype of the present invention is one where at least one allele of at least one marker or haplotype is more frequently present in an individual at risk for prostate cancer (affected), compared to the frequency of its presence in a healthy individual (control), and wherein the presence of the marker or haplotype is indicative of increased susceptibility to prostate cancer. The control group may in one embodiment be a population sample, i.e. a random sample from the general population. In another embodiment, the control group is represented by a group of individuals who are disease-free, i.e. individuals who have not been diagnosed with prostate cancer. Such disease-free control may in one embodiment be characterized by the absence of one or more specific symptoms characteristic of prostate cancer. In another embodiment, the disease-free control group is characterized by the absence of one or more disease-specific risk factors. Such risk factors are in one embodiment at least one environmental risk factor. Representative environmental factors are natural products, minerals or other chemicals which are known to affect, or contemplated to affect, the risk of developing the specific disease or trait. Other environmental risk factors are risk factors related to lifestyle, including but not limited to food and drink habits, geographical location of main habitat, and occupational risk factors. In another embodiment, the risk factors comprise at least one additional genetic risk factor.

As an example of a simple test for correlation would be a Fisher-exact test on a two by two table. Given a cohort of chromosomes the two by two table is constructed out of the number of chromosomes that include both of the markers or haplotypes, one of the markers or haplotypes but not the other and neither of the markers or haplotypes. Other statistical tests of association known to the skilled person are also contemplated and are also within scope of the invention.

In other embodiments of the invention, an individual who is at a decreased susceptibility (i.e., at a decreased risk) for prostate cancer is an individual in whom at least one specific allele at one or more polymorphic marker or haplotype conferring decreased susceptibility for prostate cancer is identified. The marker alleles and/or haplotypes conferring decreased risk are also said to be protective. In one aspect, the protective marker or haplotype is one that confers a significant decreased risk (or susceptibility) of prostate cancer. In one embodiment, significant decreased risk is measured as a relative risk (or odds ratio) of less than 0.9, less than 0.8, less than 0.7, less than 0.6, less than 0.5, less than 0.4, less than 0.3, less than 0.2 and less than 0.1. In one particular embodiment, significant decreased risk is less than 0.7. In another embodiment, significant decreased risk is less than 0.5. In yet another embodiment, significant decreased risk is less than 0.3. In another embodiment, the decrease in risk (or susceptibility) is at least 20%, including but not limited to at least 25%, at least 30%, at least 35%, at least 40%, at least 45%, at least 50%, at least 55%, at least 60%, at least 65%, at least 70%, at least 75%, at least 80%, at least 85%, at least 90%, at least 95% and at least 98%. In one particular embodiment, a significant decrease in risk is at least about 30%. In another embodiment, a significant decrease in risk is at least about 50%. In another embodiment, the decrease in risk is at least about 70%. Other cutoffs or ranges as deemed suitable by the person skilled in the art to characterize the invention are however also contemplated, and those are also within scope of the present invention.

A genetic variant associated with a disease or a trait (e.g. prostate cancer) can be used alone to predict the risk of the disease for a given genotype. For a biallelic marker, such as a SNP, there are 3 possible genotypes: homozygote for the at risk variant, heterozygote, and non carrier of the at risk variant. Risk associated with variants at multiple loci can be used to estimate overall risk. For multiple SNP variants, there are k possible genotypes $k=3^n \times 2^p$; where n is the number autosomal loci and p the number of gonosomal (sex chromosomal) loci. Overall risk assessment calculations usually assume that the relative risks of different genetic variants multiply, i.e. the overall risk (e.g., RR or OR) associated with a particular genotype combination is the product of the risk values for the genotype at each locus. If the risk presented is the relative risk for a person, or a specific genotype for a person, compared to a reference population with matched gender and ethnicity, then the combined risk—is the product of the locus specific risk values—and which also corresponds to an overall risk estimate compared with the population. If the risk for a person is based on a comparison to non-carriers of the at risk allele, then the combined risk corresponds to an estimate that compares the person with a given combination of genotypes at all loci to a group of individuals who do not carry risk variants at any of those loci. The group of non-carriers of any at risk variant has the lowest estimated risk and has a combined risk, compared with itself (i.e., non-carriers) of 1.0, but has an overall risk, compare with the population, of less than 1.0. It should be noted that the group of non-carriers can potentially be very small, especially for large number of loci, and in that case, its relevance is correspondingly small.

The multiplicative model is a parsimonious model that usually fits the data of complex traits reasonably well. Deviations from multiplicity have been rarely described in the context of common variants for common diseases, and if reported are usually only suggestive since very large sample sizes are usually required to be able to demonstrate statistical interactions between loci.

By way of an example, let us consider a total of eight variants that have been described to associate with prostate cancer (Gudmundsson, J., et al., Nat Genet. 39:631-7 (2007), Gudmundsson, J., et al., Nat Genet. 39:977-83 (2007); Yeager, M., et al, Nat Genet. 39:645-49 (2007), Amundadottir, L., et al., Nat Genet. 38:652-8 (2006); Haiman, C. A., et al., Nat Genet. 39:638-44 (2007)) (see also Table 20 herein). Seven of these loci are on autosomes, and the remaining locus is on chromosome X. The total number of theoretical genotypic combinations is then $3^7 \times 2^1=4374$. Some of those genotypic classes are very rare, but are still possible, and should be considered for overall risk assessment, as illustrated by the data shown in Table 20 herein. It is likely that the multiplicative model applied in the case of multiple genetic variant will also be valid in conjugation with non-genetic risk variants assuming that the genetic variant does not clearly correlate with the "environmental" factor. In other words, genetic and non-genetic at-risk variants can be assessed under the multiplicative model to estimate combined risk, assuming that the non-genetic and genetic risk factors do not interact.

Linkage Disequilibrium

The natural phenomenon of recombination, which occurs on average once for each chromosomal pair during each meiotic event, represents one way in which nature provides variations in sequence (and biological function by consequence). It has been discovered that recombination does not occur randomly in the genome; rather, there are large variations in the frequency of recombination rates, resulting in small regions of high recombination frequency (also called recombination hotspots) and larger regions of low recombination frequency, which are commonly referred to as Linkage Disequilibrium (LD) blocks (Myers, S. et al., *Biochem Soc Trans* 34:526-530 (2006); Jeffreys, A. J., et al., *Nature Genet.* 29:217-222 (2001); May, C. A., et al., *Nature Genet.* 31:272-275 (2002)).

Linkage Disequilibrium (LD) refers to a non-random assortment of two genetic elements. For example, if a particular genetic element (e.g., "alleles" of a polymorphic marker) occurs in a population at a frequency of 0.50 (50%) and another occurs at a frequency of 0.50 (50%), then the predicted occurrence of a person's having both elements is 0.25 (25%), assuming a random distribution of the elements. However, if it is discovered that the two elements occur together at a frequency higher than 0.25, then the elements are said to be in linkage disequilibrium since they tend to be inherited together at a higher rate than what their independent allele frequencies would predict. Roughly speaking, LD is generally correlated with the frequency of recombination events between the two elements. Allele frequencies can be determined in a population by genotyping individuals in a population and determining the occurrence of each allele in the population. For populations of diploids, e.g., human populations, individuals will typically have two alleles or allelic combinations for each genetic element (e.g., a marker, haplotype or gene).

Many different measures have been proposed for assessing the strength of linkage disequilibrium (LD). Most capture the strength of association between pairs of biallelic sites. Two important pairwise measures of LD are $r^2$ (sometimes denoted $\Delta^2$) and |D'|. Both measures range from 0 (no disequilibrium) to 1 ('complete' disequilibrium), but their interpretation is slightly different. |D'| is defined in such a way that it is equal to 1 if just two or three of the possible haplotypes are present, and it is <1 if all four possible haplotypes are present. So, a value of |D'| that is <1 indicates that historical recombination may have occurred between two sites (recurrent mutation can also cause |D'| to be <1, but for single nucleotide polymorphisms (SNPs) this is usually regarded as being less likely than recombination). The measure $r^2$ represents the statistical correlation between two sites, and takes the value of 1 if only two haplotypes are present.

The $r^2$ measure is arguably the most relevant measure for association mapping, because there is a simple inverse relationship between $r^2$ and the sample size required to detect association between susceptibility loci and SNPs. These measures are defined for pairs of sites, but for some applications a determination of how strong LD is across an entire region that contains many polymorphic sites might be desirable (e.g., testing whether the strength of LD differs significantly among loci or across populations, or whether there is more or less LD in a region than predicted under a particular model). Measuring LD across a region is not straightforward, but one approach is to use the measure r, which was developed in population genetics. Roughly speaking, r measures how much recombination would be required under a particular population model to generate the LD that is seen in the data. This type of method can potentially also provide a statistically rigorous approach to the problem of determining whether LD data provide evidence for the presence of recombination hotspots. For the methods described herein, a significant $r^2$ value can be at least 0.1 such as at least 0.1, 0.15, 0.2, 0.25, 0.3, 0.35, 0.4, 0.45, 0.5, 0.55, 0.6, 0.65, 0.7, 0.75, 0.8, 0.85, 0.9, 0.91, 0.92, 0.93, 0.94, 0.95, 0.96, 0.97, 0.98, or at least 0.99. In one preferred embodiment, the significant $r^2$ value can be at least 0.2. Alternatively, linkage disequilibrium as described herein, refers to linkage disequilibrium characterized by values of |D'| of at least 0.2, such as 0.3, 0.4, 0.5, 0.6, 0.7, 0.8, 0.85, 0.9, 0.95, 0.96, 0.97, 0.98, or at least 0.99. Thus, linkage disequilibrium represents a correlation between alleles of distinct markers. It is measured by correlation coefficient or |D'| ($r^2$ up to 1.0 and |D'| up to 1.0). In certain embodiments, linkage disequilibrium is defined in terms of values for both the $r^2$ and |D'| measures. In one such embodiment, a significant linkage disequilibrium is defined as $r^2>0.1$ and |D'|>0.8. In another embodiment, a significant linkage disequilibrium is defined as $r^2>0.2$ and |D'|>0.9. Other combinations and permutations of values of $r^2$ and |D'| for determining linkage disequilibrium are also contemplated, and are also within the scope of the invention. Linkage disequilibrium can be determined in a single human population, as defined herein, or it can be determined in a collection of samples comprising individuals from more than one human population. In one embodiment of the invention, LD is determined in a sample from one or more of the HapMap populations (caucasian, african, japanese, chinese), as defined (http colon-slash-slash www.hapmap.org). In one such embodiment, LD is determined in the CEU population of the HapMap samples. In another embodiment, LD is determined in the YRI population. In yet another embodiment, LD is determined in samples from the Icelandic population.

If all polymorphisms in the genome were independent at the population level (i.e., no LD), then every single one of them would need to be investigated in association studies, to assess all the different polymorphic states. However, due to linkage disequilibrium between polymorphisms, tightly linked polymorphisms are strongly correlated, which reduces the number of polymorphisms that need to be investigated in an association study to observe a significant association. Another consequence of LD is that many polymorphisms may give an association signal due to the fact that these polymorphisms are strongly correlated.

Genomic LD maps have been generated across the genome, and such LD maps have been proposed to serve as framework for mapping disease-genes (Risch, N. & Merkiangas, K, *Science* 273:1516-1517 (1996); Maniatis, N., et al., *Proc Natl Acad Sci USA* 99:2228-2233 (2002); Reich, D E et al, *Nature* 411:199-204 (2001)).

It is now established that many portions of the human genome can be broken into series of discrete haplotype blocks containing a few common haplotypes; for these blocks, linkage disequilibrium data provides little evidence indicating recombination (see, e.g., Wall., J. D. and Pritchard, J. K., *Nature Reviews Genetics* 4:587-597 (2003); Daly, M. et al., *Nature Genet.* 29:229-232 (2001); Gabriel, S. B. et al., *Science* 296:2225-2229 (2002); Patil, N. et al., *Science* 294:1719-1723 (2001); Dawson, E. et al., *Nature* 418:544-548 (2002); Phillips, M. S. et al., *Nature Genet.* 33:382-387 (2003)).

There are two main methods for defining these haplotype blocks: blocks can be defined as regions of DNA that have limited haplotype diversity (see, e.g., Daly, M. et al., *Nature Genet.* 29:229-232 (2001); Patil, N. et al., *Science* 294:1719-1723 (2001); Dawson, E. et al., *Nature* 418:544-548 (2002); Zhang, K. et al., *Proc. Natl. Acad. Sci. USA* 99:7335-7339 (2002)), or as regions between transition zones having extensive historical recombination, identified using linkage disequilibrium (see, e.g., Gabriel, S. B. et al., *Science* 296:2225-2229 (2002); Phillips, M. S. et al., *Nature Genet.* 33:382-387 (2003); Wang, N. et al., *Am. J. Hum. Genet.* 71:1227-1234 (2002); Stumpf, M. P., and Goldstein, D. B., *Curr. Biol.* 13:1-8 (2003)). More recently, a fine-scale map of recombination rates and corresponding hotspots across the human genome has been generated (Myers, S., et al., *Science* 310: 321-32324 (2005); Myers, S. et al., *Biochem Soc Trans* 34:526530 (2006)). The map reveals the enormous variation in recombination across the genome, with recombination rates as high as 10-60 cM/Mb in hotspots, while closer to 0 in intervening regions, which thus represent regions of limited haplotype diversity and high LD. The map can therefore be used to define haplotype blocks/LD blocks as regions flanked by recombination hotspots. As used herein, the terms "haplotype block" or "LD block" includes blocks defined by any of the above described characteristics, or other alternative methods used by the person skilled in the art to define such regions.

Haplotype blocks (LD blocks) can be used to map associations between phenotype and haplotype status, using single markers or haplotypes comprising a plurality of markers. The main haplotypes can be identified in each haplotype block, and then a set of "tagging" SNPs or markers (the smallest set of SNPs or markers needed to distinguish among the haplotypes) can then be identified. These tagging SNPs or markers can then be used in assessment of samples from groups of individuals, in order to identify association between phenotype and haplotype. If desired, neighboring haplotype blocks can be assessed concurrently, as there may also exist linkage disequilibrium among the haplotype blocks.

It has thus become apparent that for any given observed association to a polymorphic marker in the genome, it is likely that additional markers in the genome also show association. This is a natural consequence of the uneven distribution of LD across the genome, as observed by the large variation in recombination rates. The markers used to detect association thus in a sense represent "tags" for a genomic region (i.e., a haplotype block or LD block) that is associating with a given disease or trait, and as such are useful for use in the methods and kits of the present invention. One or more causative (functional) variants or mutations may reside within the region found to be associating to the disease or trait. Such variants may confer a higher relative risk (RR) or odds ratio (OR) than observed for the tagging markers used to detect the association. The present invention thus refers to the markers used for detecting association to the disease, as described herein, as well as markers in linkage disequilibrium with the markers. Thus, in certain embodiments of the invention, markers that are in LD with the markers and/or haplotypes of the invention, as described herein, may be used as surrogate markers. The surrogate markers have in one embodiment relative risk (RR) and/or odds ratio (OR) values smaller than for the markers or haplotypes initially found to be associating with the disease, as described herein. In other embodiments, the surrogate markers have RR or OR values greater than those initially determined for the markers initially found to be associating with the disease, as described herein. An example of such an embodiment would be a rare, or relatively rare (such as <10% allelic population frequency) variant in LD with a more common variant (>10% population frequency) initially found to be associating with the disease, such as the variants described herein. Identifying and using such markers for detecting the association discovered by the inventors as described herein can be performed by routine methods well known to the person skilled in the art, and are therefore within the scope of the present invention.

Determination of Haplotype Frequency

The frequencies of haplotypes in patient and control groups can be estimated using an expectation-maximization algorithm (Dempster A. et al., *J. R. Stat. Soc. B*, 39:1-38 (1977)). An implementation of this algorithm that can handle missing genotypes and uncertainty with the phase can be used. Under the null hypothesis, the patients and the controls are assumed to have identical frequencies. Using a likelihood approach, an alternative hypothesis is tested, where a candidate at-risk-haplotype, which can include the markers described herein, is allowed to have a higher frequency in patients than controls, while the ratios of the frequencies of other haplotypes are assumed to be the same in both groups. Likelihoods are maximized separately under both hypotheses and a corresponding 1-df likelihood ratio statistic is used to evaluate the statistical significance.

To look for at-risk and protective markers and haplotypes within a linkage region, for example, association of all possible combinations of genotyped markers is studied, provided those markers span a practical region. The combined patient and control groups can be randomly divided into two sets, equal in size to the original group of patients and controls. The marker and haplotype analysis is then repeated and the most significant p-value registered is determined. This randomization scheme can be repeated, for example, over 100 times to construct an empirical distribution of p-values. In a preferred embodiment, a p-value of <0.05 is indicative of a significant marker and/or haplotype association.

Haplotype Analysis

One general approach to haplotype analysis involves using likelihood-based inference applied to NEsted MOdels (Gretarsdottir S., et al., *Nat. Genet.* 35:131-38 (2003)). The method is implemented in the program NEMO, which allows for many polymorphic markers, SNPs and microsatellites. The method and software are specifically designed for case-control studies where the purpose is to identify haplotype groups that confer different risks. It is also a tool for studying LD structures. In NEMO, maximum likelihood estimates, likelihood ratios and p-values are calculated directly, with the aid of the EM algorithm, for the observed data treating it as a missing-data problem.

Even though likelihood ratio tests based on likelihoods computed directly for the observed data, which have captured the information loss due to uncertainty in phase and missing genotypes, can be relied on to give valid p-values, it would still be of interest to know how much information had been lost due to the information being incomplete. The information measure for haplotype analysis is described in Nicolae and Kong (Technical Report 537, Department of Statistics, University of Statistics, University of Chicago; *Biometrics*, 60 (2):368-75 (2004)) as a natural extension of information measures defined for linkage analysis, and is implemented in NEMO.

For single marker association to a disease, the Fisher exact test can be used to calculate two-sided p-values for each individual allele. Usually, all p-values are presented unadjusted for multiple comparisons unless specifically indicated. The presented frequencies (for microsatellites, SNPs and haplotypes) are allelic frequencies as opposed to carrier frequencies. To minimize any bias due the relatedness of the patients who were recruited as families for the linkage analysis, first and second-degree relatives can be eliminated from the patient list. Furthermore, the test can be repeated for association correcting for any remaining relatedness among the patients, by extending a variance adjustment procedure described in Risch, N. & Teng, J. (*Genome Res.*, 8:1273-1288 (1998)) for sibships so that it can be applied to general familial relationships, and present both adjusted and unadjusted p-values for comparison. The differences are in general very small as expected. To assess the significance of single-marker association corrected for multiple testing we can carry out a randomization test using the same genotype data. Cohorts of patients and controls can be randomized and the association analysis redone multiple times (e.g., up to 500,000 times) and the p-value is the fraction of replications that produced a p-value for some marker allele that is lower than or equal to the p-value we observed using the original patient and control cohorts.

For both single-marker and haplotype analyses, relative risk (RR) and the population attributable risk (PAR) can be calculated assuming a multiplicative model (haplotype relative risk model) (Terwilliger, J. D. & Ott, J., *Hum. Hered.* 42:337-46 (1992) and Falk, C. T. & Rubinstein, P, *Ann. Hum. Genet.* 51 (Pt 3):227-33 (1987)), i.e., that the risks of the two alleles/haplotypes a person carries multiply. For example, if RR is the risk of A relative to a, then the risk of a person homozygote AA will be RR times that of a heterozygote Aa and $RR^2$ times that of a homozygote aa. The multiplicative model has a nice property that simplifies analysis and computations—haplotypes are independent, i.e., in Hardy-Weinberg equilibrium, within the affected population as well as within the control population. As a consequence, haplotype counts of the affecteds and controls each have multinomial distributions, but with different haplotype frequencies under the alternative hypothesis. Specifically, for two haplotypes, $h_i$ and $h_j$, $risk(h_i)/risk(h_j)=(f_i/p_i)/(f_j/p_j)$, where f and p denote, respectively, frequencies in the affected population and in the control population. While there is some power loss if the true model is not multiplicative, the loss tends to be mild except for extreme cases. Most importantly, p-values are always valid since they are computed with respect to null hypothesis.

Linkage Disequilibrium Using NEMO

LD between pairs of markers can be calculated using the standard definition of D' and $r^2$ (Lewontin, R., *Genetics* 49:49-67 (1964); Hill, W. G. & Robertson, A. *Theor. Appl. Genet.* 22:226-231 (1968)). Using NEMO, frequencies of the two marker allele combinations are estimated by maximum likelihood and deviation from linkage equilibrium is evaluated by a likelihood ratio test. The definitions of D' and $r^2$ are extended to include microsatellites by averaging over the values for all possible allele combination of the two markers weighted by the marginal allele probabilities.

Risk Assessment and Diagnostics

Within any given population, there is an absolute risk of developing a disease or trait, defined as the chance of a person developing the specific disease or trait over a specified time-period. For example, a woman's lifetime absolute risk of breast cancer is one in nine. That is to say, one woman in every nine will develop breast cancer at some point in their lives. Risk is typically measured by looking at very large numbers of people, rather than at a particular individual. Risk is often presented in terms of Absolute Risk (AR) and Relative Risk (RR). Relative Risk is used to compare risks associating with two variants or the risks of two different groups of people. For example, it can be used to compare a group of people with a certain genotype with another group having a different genotype. For a disease, a relative risk of 2 means that one group has twice the chance of developing a disease as the other group. The Risk presented is usually the relative risk for a person, or a specific genotype of a person, compared to the population with matched gender and ethnicity. Risks of two individuals of the same gender and ethnicity could be compared in a simple manner. For example, if, compared to the population, the first individual has relative risk 1.5 and the second has relative risk 0.5, then the risk of the first individual compared to the second individual is 1.5/0.5=3.

As described herein, certain polymorphic markers and haplotypes comprising such markers are found to be useful for risk assessment of prostate cancer. Risk assessment can involve the use of the markers for diagnosing a susceptibility to prostate cancer. Particular alleles of polymorphic markers are found more frequently in individuals with prostate cancer, than in individuals without diagnosis of prostate cancer. Therefore, these marker alleles have predictive value for detecting prostate cancer, or a susceptibility to prostate cancer, in an individual. Tagging markers within haplotype blocks or LD blocks comprising at-risk markers, as described herein, such as the markers of the present invention, can be used as surrogates for other markers and/or haplotypes within the haplotype block or LD block. Markers with values of $r^2$ equal to 1 are perfect surrogates for the at-risk variants, i.e. genotypes for one marker perfectly predicts genotypes for the other. Markers with smaller values of $r^2$ than 1 can also be surrogates for the at-risk variant, or alternatively represent variants with relative risk values as high as or possibly even higher than the at-risk variant. The at-risk variant identified may not be the functional variant itself, but is in this instance in linkage disequilibrium with the true functional variant. The present invention encompasses the assessment of such surrogate markers for the markers as disclosed herein. Such markers are annotated, mapped and listed in public databases, as well known to the skilled person, or can alternatively be readily identified by sequencing the region or a part of the region identified by the markers of the present invention in a group of individuals, and identify polymorphisms in the resulting group of sequences. As a consequence, the person skilled in the art can readily and without undue experimentation genotype surrogate markers in linkage disequilibrium with the markers and/or haplotypes as described herein. The tagging or surrogate markers in LD with the at-risk variants detected, also have predictive value for detecting association to prostate cancer, or a susceptibility to prostate cancer, in an individual. These tagging or surrogate markers that are in LD with the markers of the present invention can also include other markers that distinguish among haplotypes, as these similarly have predictive value for detecting susceptibility to prostate cancer.

The present invention can in certain embodiments be practiced by assessing a sample comprising genomic DNA from an individual for the presence of variants described herein to be associated with prostate cancer. Such assessment includes steps of detecting the presence or absence of at least one allele of at least one polymorphic marker, using methods well known to the skilled person and further described herein, and based on the outcome of such assessment, determine whether the individual from whom the sample is derived is at increased or decreased risk (increased or decreased susceptibility) of prostate cancer. Alternatively, the invention can be practiced utilizing a dataset comprising information about the genotype status of at least one polymorphic marker described herein to be associated with prostate cancer (or markers in linkage disequilibrium with at least one marker shown herein to be associated with prostate cancer). In other words, a dataset containing information about such genetic status, for example in the form of genotype counts at a certain polymorphic marker, or a plurality of markers (e.g., an indication of the presence or absence of certain at-risk alleles), or actual genotypes for one or more markers, can be queried for the presence or absence of certain at-risk alleles at certain polymorphic markers shown by the present inventors to be associated with prostate cancer. A positive result for a variant (e.g., marker allele) associated with prostate cancer, as shown herein, is indicative of the individual from which the dataset is derived is at increased susceptibility (increased risk) of prostate cancer.

In certain embodiments of the invention, a polymorphic marker is correlated to prostate cancer by referencing genotype data for the polymorphic marker to a look-up table that comprises correlations between at least one allele of the polymorphism and prostate cancer. In some embodiments, the table comprises a correlation for one polymorphism. In other embodiments, the table comprises a correlation for a plurality of polymorphisms. In both scenarios, by referencing to a look-up table that gives an indication of a correlation between a marker and prostate cancer, a risk for prostate cancer, or a susceptibility to prostate cancer, can be identified in the individual from whom the sample is derived. In some embodiments, the correlation is reported as a statistical measure. The statistical measure may be reported as a risk measure, such as a relative risk (RR), an absolute risk (AR) or an odds ratio (OR).

The markers and haplotypes of the invention, e.g., the markers presented in Tables 7-11, may be useful for risk assessment and diagnostic purposes, either alone or in combination. Thus, even in cases where the increase in risk by individual markers is relatively modest, e.g. on the order of 10-30%, the association may have significant implications. Thus, relatively common variants may have significant contribution to the overall risk (Population Attributable Risk is high), or combination of markers can be used to define groups of individual who, based on the combined risk of the markers, is at significant combined risk of developing the disease Thus, in one embodiment of the invention, a plurality of variants (genetic markers, biomarkers and/or haplotypes) is used for overall risk assessment. These variants are in one embodiment selected from the variants as disclosed herein. Other embodiments include the use of the variants of the present invention in combination with other variants known to be useful for diagnosing a susceptibility to prostate cancer. In such embodiments, the genotype status of a plurality of markers and/or haplotypes is determined in an individual, and the status of the individual compared with the population frequency of the associated variants, or the frequency of the variants in clinically healthy subjects, such as age-matched and sex-matched subjects. Methods known in the art, such as combined or joint risk analyses, may subsequently be used to determine the overall risk conferred based on the genotype status at the multiple loci. Assessment of risk based on such analysis may subsequently be used in the methods, uses and kits of the invention, as described herein.

As described in the above, the haplotype block structure of the human genome has the effect that a large number of variants (markers and/or haplotypes) in linkage disequilibrium with the variant originally associated with a disease or trait may be used as surrogate markers for assessing association to the disease or trait. The number of such surrogate markers will depend on factors such as the historical recombination rate in the region, the mutational frequency in the region (i.e., the number of polymorphic sites or markers in the region), and the extent of LD (size of the LD block) in the region. These markers are usually located within the physical boundaries of the LD block or haplotype block in question as defined using the methods described herein, or by other methods known to the person skilled in the art. However, sometimes marker and haplotype association is found to extend beyond the physical boundaries of the haplotype block as defined. Such markers and/or haplotypes may in those cases be also used as surrogate markers and/or haplotypes for the markers and/or haplotypes physically residing within the haplotype block as defined. As a consequence, markers and haplotypes in LD (typically characterized by $r^2$ greater than 0.1, such as $r^2$ greater than 0.2, including $r^2$ greater than 0.3, also including $r^2$ greater than 0.4) with the markers and haplotypes of the present invention are also within the scope of the invention, even if they are physically located beyond the boundaries of the haplotype block as defined herein.

For the SNP markers described herein, the opposite allele to the allele found to be in excess in patients (at-risk allele) is found in decreased frequency in prostate cancer. These markers and haplotypes in LD and/or comprising such markers, are thus protective for prostate cancer, i.e. they confer a decreased risk or susceptibility of individuals carrying these markers and/or haplotypes developing prostate cancer.

Certain variants of the present invention, including certain haplotypes, comprise, in some cases, a combination of various genetic markers, e.g., SNPs and microsatellites. Detecting haplotypes can be accomplished by methods known in the art and/or described herein for detecting sequences at polymorphic sites. Furthermore, correlation between certain haplotypes or sets of markers and disease phenotype can be verified using standard techniques. A representative example of a simple test for correlation would be a Fisher-exact test on a two by two table.

In specific embodiments, a marker allele or haplotype found to be associated with prostate cancer, (e.g., marker alleles as listed in Tables 7-11, e.g., marker alleles as listed in tables 1-6) is one in which the marker allele or haplotype is more frequently present in an individual at risk for prostate cancer (affected), compared to the frequency of its presence in a healthy individual (control), wherein the presence of the marker allele or haplotype is indicative of prostate cancer or a susceptibility to prostate cancer. In other embodiments, at-risk markers in linkage disequilibrium with one or more markers shown herein to be associated with prostate cancer (e.g., marker alleles as listed in Tables 7-11) are tagging markers that are more frequently present in an individual at risk for prostate cancer (affected), compared to the frequency of their presence in a healthy individual (control), wherein the presence of the tagging markers is indicative of increased susceptibility to prostate cancer. In a further embodiment, at-risk markers alleles (i.e. conferring increased susceptibility) in linkage disequilibrium with one or more markers found to be associated with prostate cancer (e.g., marker alleles as listed in Tables 7-11), are markers comprising one or more allele that is more frequently present in an individual at risk for prostate cancer, compared to the frequency of their presence in a healthy individual (control), wherein the presence of the markers is indicative of increased susceptibility to prostate cancer.

Study Population

In a general sense, the methods and kits of the invention can be utilized from samples containing genomic DNA from any source, i.e. any individual. In preferred embodiments, the individual is a human individual. The individual can be an adult, child, or fetus. The nucleic acid source may be any sample comprising nucleic acid material, including biological samples, or a sample comprising nucleic acid material derived therefrom. The present invention also provides for assessing markers and/or haplotypes in individuals who are members of a target population. Such a target population is in one embodiment a population or group of individuals at risk of developing prostate cancer, based on other genetic factors, biomarkers, biophysical parameters (e.g., weight, BMD, blood pressure), or general health and/or lifestyle parameters (e.g., history of cancer, e.g., prostate cancer, or related diseases, previous diagnosis of prostate cancer, family history of prostate cancer).

The invention provides for embodiments that include individuals from specific age subgroups, such as those over the age of 40, over age of 45, or over age of 50, 55, 60, 65, 70, 75, 80, or 85. Other embodiments of the invention pertain to other age groups, such as individuals aged less than 85, such as less than age 80, less than age 75, or less than age 70, 65, 60, 55, 50, 45, 40, 35, or age 30. Other embodiments relate to individuals with age at onset of the disease in any of the age ranges described in the above. In one such embodiment, the invention pertains to individuals with age at onset of prostate cancer of less than 65 years. In another such embodiment, the invention pertains to individuals with age at onset of less than 60 years. It is also contemplated that a range of ages may be relevant in certain embodiments, such as age at onset at more than age 45 but less than age 60. Other age ranges are however also contemplated, including all age ranges bracketed by the age values listed in the above. The invention furthermore relates to individuals of either sex, males or females.

The Icelandic population is a Caucasian population of Northern European ancestry. A large number of studies reporting results of genetic linkage and association in the Icelandic population have been published in the last few years. Many of those studies show replication of variants, originally identified in the Icelandic population as being associating with a particular disease, in other populations (Stacey, S. N., et al., *Nat. Genet.* May 27, 2007 (Epub ahead of print; Helgadottir, A., et al., *Science* 316:1491-93 (2007); Steinthorsdottir, V., et al., *Nat. Genet.* 39:770-75 (2007); Gudmundsson, J., et al., *Nat. Genet.* 39:631-37 (2007); Amundadottir, L. T., et al., *Nat. Genet.* 38:652-58 (2006); Grant, S. F., et al., *Nat. Genet.* 38:320-23 (2006)). Thus, genetic findings in the Icelandic population have in general been replicated in other populations, including populations from Africa and Asia.

The markers of the present invention found to be associated with prostate cancer are believed to show similar association in other human populations, as illustrated by the replication data shown in the Examples herein (Tables 1, 4a and 4b). Particular embodiments comprising individual human populations are thus also contemplated and within the scope of the invention. Such embodiments relate to human subjects that are from one or more human population including, but not limited to, Caucasian populations, European populations, American populations, Eurasian populations, Asian populations, Central/South Asian populations, East Asian populations, Middle Eastern populations, African populations, Hispanic populations, and Oceanian populations. European populations include, but are not limited to, Swedish, Norwegian, Finnish, Russian, Danish, Icelandic, Irish, Kelt, English, Scottish, Dutch, Belgian, French, German, Spanish, Portugues, Italian, Polish, Bulgarian, Slavic, Serbian, Bosnian, Chech, Greek and Turkish populations. The invention furthermore in other embodiments can be practiced in specific human populations that include Bantu, Mandenk, Yoruba, San, Mbuti Pygmy, Orcadian, Adygel, Russian, Sardinian, Tuscan, Mozabite, Bedouin, Druze, Palestinian, Balochi, Brahui, Makrani, Sindhi, Pathan, Burusho, Hazara, Uygur, Kalash, Han, Dai, Daur, Hezhen, Lahu, Miao, Oroqen, She, Tujia, Tu, Xibo, Yi, Mongolan, Naxi, Cambodian, Japanese, Yakut, Melanesian, Papuan, Karitianan, Surui, Colmbian, Maya and Pima.

In one preferred embodiment, the invention relates to populations that include black African ancestry such as populations comprising persons of African descent or lineage. Black African ancestry may be determined by self reporting as African-Americans, Afro-Americans, Black Americans, being a member of the black race or being a member of the negro race. For example, African Americans or Black Americans are those persons living in North America and having origins in any of the black racial groups of Africa. In another example, self-reported persons of black African ancestry may have at least one parent of black African ancestry or at least one grandparent of black African ancestry. In another embodiment, the invention relates to individuals of Caucasian origin.

The racial contribution in individual subjects may also be determined by genetic analysis. Genetic analysis of ancestry may be carried out using unlinked microsatellite markers such as those set out in Smith et al. (*Am J Hum Genet* 74, 1001-13 (2004)).

In certain embodiments, the invention relates to markers and/or haplotypes identified in specific populations, as described in the above. The person skilled in the art will appreciate that measures of linkage disequilibrium (LD) may give different results when applied to different populations. This is due to different population history of different human populations as well as differential selective pressures that may have led to differences in LD in specific genomic regions. It is also well known to the person skilled in the art that certain markers, e.g. SNP markers, are polymorphic in one population but not in another. The person skilled in the art will however apply the methods available and as thought herein to practice the present invention in any given human population. This may include assessment of polymorphic markers in the LD region of the present invention, so as to identify those markers that give strongest association within the specific population. Thus, the at-risk variants of the present invention may reside on different haplotype background and in different frequencies in various human populations. However, utilizing methods known in the art and the markers of the present invention, the invention can be practiced in any given human population.

Utility of Genetic Testing

The person skilled in the art will appreciate and understand that the variants described herein in general do not, by themselves, provide an absolute identification of individuals who will a priori develop prostate cancer. The variants described herein do however indicate increased and/or decreased likelihood that individuals carrying the at-risk or protective variants of the invention will ultimately develop prostate cancer. This information is however extremely valuable in itself, as outlined in more detail in the below, as it can be used to, for example, initiate preventive measures at an early stage, perform regular physical and/or mental exams to monitor the progress and/or appearance of symptoms, or to schedule exams at a regular interval to identify early symptoms, so as to be able to apply treatment at an early stage.

The knowledge of a genetic variant that confers a risk of developing cancer offers the opportunity to apply a genetic-test to distinguish between individuals with increased risk of developing the disease (i.e. carriers of the at-risk variant) and those with decreased risk of developing the disease (i.e. carriers of the protective variant, or non-carriers of the at-risk variant). The core values of genetic testing, for individuals belonging to both of the above mentioned groups, are the possibilities of being able to diagnose the disease at an early stage and provide information to the clinician about prognosis/aggressiveness of the disease in order to be able to apply the most appropriate treatment. For example, the application of a genetic test for prostate cancer (including aggressive or high Gleason grade prostate cancer, and less aggressive or low Gleason grade prostate cancer)) can provide an opportunity for the detection of the disease at an earlier stage which may lead to the application of therapeutic measures at an earlier stage, and thus can minimize the deleterious effects of the symptoms and serious health consequences conferred by cancer. Some advantages of genetic tests for cancer include:

1. To Aid Early Detection

The application of a genetic test for prostate cancer can provide an opportunity for the detection of the disease at an earlier stage which leads to higher cure rates, if found locally, and increases survival rates by minimizing regional and distant spread of the tumor. For prostate cancer, a genetic test will most likely increase the sensitivity and specificity of the already generally applied Prostate Specific Antigen (PSA) test and Digital Rectal Examination (DRE). This can lead to lower rates of false positives (thus minimize unnecessary procedures such as needle biopsies) and false negatives (thus increasing detection of occult disease and minimizing morbidity and mortality due to PCA).

2. To Determine Aggressiveness

Genetic testing can provide information about pre-diagnostic prognostic indicators and enable the identification of individuals at high or low risk for aggressive tumor types that can lead to modification in screening strategies. For example, an individual determined to be a carrier of a high risk allele for the development of aggressive prostate cancer will likely undergo more frequent PSA testing, examination and have a lower threshold for needle biopsy in the presence of an abnormal PSA value.

Furthermore, identifying individuals that are carriers of high or low risk alleles for aggressive tumor types will lead to modification in treatment strategies. For example, if prostate cancer is diagnosed in an individual that is a carrier of an allele that confers increased risk of developing an aggressive form of prostate cancer, then the clinician would likely advise a more aggressive treatment strategy such as a prostatectomy instead of a less aggressive treatment strategy.

As is known in the art, Prostate Specific Antigen (PSA) is a protein that is secreted by the epithelial cells of the prostate gland, including cancer cells. An elevated level in the blood indicates an abnormal condition of the prostate, either benign or malignant. PSA is used to detect potential problems in the prostate gland and to follow the progress of prostate cancer therapy. PSA levels above 4 ng/ml are indicative of the presence of prostate cancer (although as known in the art and described herein, the test is neither very specific nor sensitive).

In one embodiment, the method of the invention is performed in combination with (either prior to, concurrently or after) a PSA assay. In a particular embodiment, the presence of a marker or haplotype, in conjunction with the subject having a PSA level greater than 4 ng/ml, is indicative of a more aggressive prostate cancer and/or a worse prognosis. As described herein, particular markers and haplotypes are associated with high Gleason (i.e., more aggressive) prostate cancer. In another embodiment, the presence of a marker or haplotype, in a patient who has a normal PSA level (e.g., less than 4 ng/ml), is indicative of a high Gleason (i.e., more aggressive) prostate cancer and/or a worse prognosis. A "worse prognosis" or "bad prognosis" occurs when it is more likely that the cancer will grow beyond the boundaries of the prostate gland, metastasize, escape therapy and/or kill the host.

In one embodiment, the presence of a marker or haplotype is indicative of a predisposition to a somatic rearrangement (e.g., one or more of an amplification, a translocation, an insertion and/or deletion) in a tumor or its precursor. The somatic rearrangement itself may subsequently lead to a more aggressive form of prostate cancer (e.g., a higher histologic grade, as reflected by a higher Gleason score or higher stage at diagnosis, an increased progression of prostate cancer (e.g., to a higher stage), a worse outcome (e.g., in terms of morbidity, complications or death)). As is known in the art, the Gleason grade is a widely used method for classifying prostate cancer tissue for the degree of loss of the normal glandular architecture (size, shape and differentiation of glands). A grade from 1-5 is assigned successively to each of the two most predominant tissue patterns present in the examined tissue sample and are added together to produce the total or combined Gleason grade (scale of 2-10). High numbers indicate poor differentiation and therefore more aggressive cancer.

Aggressive prostate cancer is cancer that grows beyond the prostate, metastasizes and eventually kills the patient. As described herein, one surrogate measure of aggressiveness is a high combined Gleason grade. The higher the grade on a scale of 2-10 the more likely it is that a patient has aggressive disease.

As used herein and unless noted differently, the term "stage" is used to define the size and physical extent of a cancer (e.g., prostate cancer). One method of staging various cancers is the TNM method, wherein in the TNM acronym, T stands for tumor size and invasiveness (e.g., the primary tumor in the prostate); N relates to nodal involvement (e.g., prostate cancer that has spread to lymph nodes); and M indicates the presence or absence of metastates (spread to a distant site).

Methods

Methods for risk assessment of prostate cancer are described herein and are encompassed by the invention. The invention also encompasses methods of assessing an individual for probability of response to a therapeutic agent for prostate cancer, methods for predicting the effectiveness of a therapeutic agent for prostate cancer, nucleic acids, polypeptides and antibodies and computer-implemented functions. Kits for assaying a sample from a subject to detect susceptibility to prostate cancer are also encompassed by the invention.

Diagnostic and Screening Methods

In certain embodiments, the present invention pertains to methods of diagnosing, or aiding in the diagnosis of, prostate cancer or a susceptibility to prostate cancer, by detecting particular alleles at genetic markers that appear more frequently in prostate cancer subjects or subjects who are susceptible to prostate cancer. In a particular embodiment, the invention is a method of diagnosing a susceptibility to prostate cancer by detecting at least one allele of at least one polymorphic marker (e.g., the markers described herein). The present invention describes methods whereby detection of particular alleles of particular markers or haplotypes is indicative of a susceptibility to prostate cancer. Such prognostic or predictive assays can also be used to determine prophylactic treatment of a subject prior to the onset of symptoms of prostate cancer. The present invention pertains in some embodiments to methods of clinical applications of diagnosis, e.g., diagnosis performed by a medical professional. In other embodiments, the invention pertains to methods of diagnosis or determination of a susceptibility performed by a layman. Recent technological advances in genotyping technologies, including high-throughput genotyping of SNP markers, such as Molecular Inversion Probe array technology (e.g., Affymetrix GeneChip), and BeadArray Technologies (e.g., Illumina GoldenGate and Infinium assays) have made it possible for individuals to have their own genome assessed for up to one million SNPs simultaneously, at relatively little cost. The resulting genotype information, made available to the individual can be compared to information from the public literature about disease or trait (e.g., prostate cancer) risk associated with various SNPs. The diagnostic application of disease-associated alleles as described herein, can thus be performed either by the individual, through analysis of his/her genotype data, or by a health professional based on results of a clinical test. In other words, the diagnosis or assessment of a susceptibility based on genetic risk can be made by health professionals, genetic counselors or by the layman, based on information about his/her genotype and publications on various risk factors. In the present context, the term "diagnosing", "diagnose a susceptibility" and "determine a susceptibility" is meant to refer to any available diagnostic method, including those mentioned above.

In addition, in certain other embodiments, the present invention pertains to methods of diagnosing, or aiding in the diagnosis of, a decreased susceptibility to prostate cancer, by detecting particular genetic marker alleles or haplotypes that appear less frequently in prostate cancer patients than in individual not diagnosed with prostate cancer or in the general population.

As described and exemplified herein, particular marker alleles or haplotypes (e.g. markers located within LD block C02, LD block C04a, TCF2, LD block C17b and LD block C0Xa, the markers and haplotypes as listed in Tables 12-16, and markers in linkage disequilibrium therewith, e.g., the markers as listed in Tables 7-11) are associated with prostate cancer (e.g., aggressive prostate cancer). In one embodiment, the marker allele or haplotype is one that confers a significant risk or susceptibility to prostate cancer. In another embodiment, the invention relates to a method of diagnosing a susceptibility to prostate cancer in a human individual, the method comprising determining the presence or absence of at least one allele of at least one polymorphic marker in a nucleic acid sample obtained from the individual, wherein the at least one polymorphic marker is selected from the group consisting of the polymorphic markers located within LD block C02, LD block C04a, TCF2, LD block C17b and LD block C0Xa, the markers as listed in Tables 7-11, and markers in linkage disequilibrium therewith, and/or the markers as listed in Tables 11-15. In another embodiment, the invention pertains to methods of diagnosing a susceptibility to prostate cancer in a human individual, by screening for at least one marker allele or haplotype, e.g. markers located within LD block C02, LD block C04a, TCF2, LD block C17b or LD block C0Xa, and markers in linkage disequilibrium therewith. In another embodiment, the marker allele or haplotype is more frequently present in a subject having, or who is susceptible to, prostate cancer (affected), as compared to the frequency of its presence in a healthy subject (control, such as population controls). In another embodiment, the invention relates to a method of determining a susceptibility to prostate cancer in a human individual, the method comprising determining the presence or absence of at least one allele of at least one polymorphic marker in a nucleic acid sample obtained from the individual, wherein the at least one polymorphic marker is selected from the group consisting of markers rs3923603 (SEQ ID NO:1), rs4430796 (SEQ ID NO:2), rs7501939 (SEQ ID NO:3), rs1859962 (SEQ ID NO:4), D17S1350 (SEQ ID NO:5), rs5945572 (SEQ ID NO:6), rs5945605 (SEQ ID NO:7), rs2710646 (SEQ ID NO:8), rs3760511 (SEQ ID NO:56), rs7214479 (SEQ ID NO:134), rs6501445 (SEQ ID NO:146), rs983085 (SEQ ID NO:150), rs5945605 (SEQ ID NO:178) and rs721048 (SEQ ID NO:344), and markers in linkage disequilibrium therewith. In certain embodiments, the significance of association of the at least one marker allele or haplotype is characterized by a p value<0.05. In other embodiments, the significance of association is characterized by smaller p-values, such as <0.01, <0.001, <0.0001, <0.00001, <0.000001, <0.0000001, <0.00000001 or <0.000000001.

In these embodiments, the presence of the at least one marker allele or haplotype is indicative of a susceptibility to prostate cancer. These diagnostic methods involve detecting the presence or absence of at least one marker allele or haplotype that is associated with prostate cancer. The haplotypes described herein include combinations of alleles at various genetic markers (e.g., SNPs, microsatellites). The detection of the particular genetic marker alleles that make up the particular haplotypes can be performed by a variety of methods described herein and/or known in the art. For example, genetic markers can be detected at the nucleic acid level (e.g., by direct nucleotide sequencing or by other means known to the skilled in the art) or at the amino acid level if the genetic marker affects the coding sequence of a protein encoded by a prostate cancer-associated nucleic acid (e.g., by protein sequencing or by immunoassays using antibodies that recognize such a protein). The marker alleles or haplotypes of the present invention correspond to fragments of a genomic DNA sequence associated with prostate cancer. Such fragments encompass the DNA sequence of the polymorphic marker or haplotype in question, but may also include DNA segments in strong LD (linkage disequilibrium) with the marker or haplotype (for example, as determined by a value of $r^2$ greater than 0.2 and/or |D'|>0.8).

In one embodiment, diagnosis of a susceptibility to prostate cancer can be accomplished using hybridization methods, such as Southern analysis, Northern analysis, and/or in situ hybridizations (see Current Protocols in Molecular Biology, Ausubel, F. et al., eds., John Wiley & Sons, including all supplements). A biological sample from a test subject or individual (a "test sample") of genomic DNA, RNA, or cDNA is obtained from a subject suspected of having, being susceptible to, or predisposed for prostate cancer (the "test subject"). The subject can be an adult, child, or fetus. The test sample can be from any source that contains genomic DNA, such as a blood sample, sample of amniotic fluid, sample of cerebrospinal fluid, or tissue sample from skin, muscle, buccal or conjunctival mucosa, placenta, gastrointestinal tract or other organs. A test sample of DNA from fetal cells or tissue can be obtained by appropriate methods, such as by amniocentesis or chorionic villus sampling. The DNA, RNA, or cDNA sample is then examined. The presence of a specific marker allele can be indicated by sequence-specific hybridization of a nucleic acid probe specific for the particular allele. The presence of more than specific marker allele or a specific haplotype can be indicated by using several sequence-specific nucleic acid probes, each being specific for a particular allele. In one embodiment, a haplotype can be indicated by a single nucleic acid probe that is specific for the specific haplotype (i.e., hybridizes specifically to a DNA strand comprising the specific marker alleles characteristic of the haplotype). A sequence-specific probe can be directed to hybridize to genomic DNA, RNA, or cDNA. A "nucleic acid probe", as used herein, can be a DNA probe or an RNA probe that hybridizes to a complementary sequence. One of skill in the art would know how to design such a probe so that sequence specific hybridization will occur only if a particular allele is present in a genomic sequence from a test sample.

To diagnose a susceptibility to prostate cancer, a hybridization sample is formed by contacting the test sample containing an prostate cancer-associated nucleic acid, such as a genomic DNA sample, with at least one nucleic acid probe. A non-limiting example of a probe for detecting mRNA or genomic DNA is a labeled nucleic acid probe that is capable of hybridizing to mRNA or genomic DNA sequences described herein. The nucleic acid probe can be, for example, a full-length nucleic acid molecule, or a portion thereof, such as an oligonucleotide of at least 15, 30, 50, 100, 250 or 500 nucleotides in length that is sufficient to specifically hybridize under stringent conditions to appropriate mRNA or genomic DNA. For example, the nucleic acid probe can comprise all or a portion of the nucleotide sequence of LD block C02, LD block C04a, TCF2, LD block C17b and LD block C0Xa, as described herein, or all or a portion of the nucleotide sequences set forth in SEQ ID NO:1-362 herein, optionally comprising at least one allele of a marker described herein, or at least one haplotype described herein (e.g., the markers and haplotypes as listed in Tables 7-11, and markers in linkage disequilibrium therewith), or the probe can be the complementary sequence of such a sequence. In a particular embodiment, the nucleic acid probe is a portion of the nucleotide sequence of LD block C02, LD block C04a, TCF2, LD block C17b and LD block C0Xa, or all or a portion of the nucleotide sequences set forth in SEQ ID NO:1-362, as described herein, optionally comprising at least one allele of a marker described herein (e.g., the markers and haplotypes as listed in Tables 7-11, and markers in linkage disequilibrium therewith), or at least one allele contained in the haplotypes described herein, or the probe can be the complementary sequence of such a sequence. Other suitable probes for use in the diagnostic assays of the invention are described herein. Hybridization can be performed by methods well known to the person skilled in the art (see, e.g., Current Protocols in Molecular Biology, Ausubel, F. et al., eds., John Wiley & Sons, including all supplements). In one embodiment, hybridization refers to specific hybridization, i.e., hybridization with no mismatches (exact hybridization). In one embodiment, the hybridization conditions for specific hybridization are high stringency.

Specific hybridization, if present, is detected using standard methods. If specific hybridization occurs between the nucleic acid probe and the prostate cancer-associated nucleic acid in the test sample, then the sample contains the allele that is complementary to the nucleotide that is present in the nucleic acid probe. The process can be repeated for other markers of the present invention, or markers that make up a haplotype of the present invention, or multiple probes can be used concurrently to detect more than one marker alleles at a time. It is also possible to design a single probe containing more than one marker alleles of a particular haplotype (e.g., a probe containing alleles complementary to 2, 3, 4, 5 or all of the markers that make up a particular haplotype). Detection of the particular markers of the haplotype in the sample is indicative that the source of the sample has the particular haplotype (e.g., a haplotype) and therefore is susceptible to prostate cancer.

In one preferred embodiment, a method utilizing a detection oligonucleotide probe comprising a fluorescent moiety or group at its 3' terminus and a quencher at its 5' terminus, and an enhancer oligonucleotide, is employed, as described by Kutyavin et al. (*Nucleic Acid Res.* 34:e128 (2006)). The fluorescent moiety can be Gig Harbor Green or Yakima Yellow, or other suitable fluorescent moieties. The detection probe is designed to hybridize to a short nucleotide sequence that includes the SNP polymorphism to be detected. Preferably, the SNP is anywhere from the terminal residue to −6 residues from the 3' end of the detection probe. The enhancer is a short oligonucleotide probe which hybridizes to the DNA template 3' relative to the detection probe. The probes are designed such that a single nucleotide gap exists between the detection probe and the enhancer nucleotide probe when both are bound to the template. The gap creates a synthetic abasic site that is recognized by an endonuclease, such as Endonuclease IV. The enzyme cleaves the dye off the fully complementary detection probe, but cannot cleave a detection probe containing a mismatch. Thus, by measuring the fluorescence of the released fluorescent moiety, assessment of the presence of a particular allele defined by nucleotide sequence of the detection probe can be performed.

The detection probe can be of any suitable size, although preferably the probe is relatively short. In one embodiment, the probe is from 5-100 nucleotides in length. In another embodiment, the probe is from 10-50 nucleotides in length, and in another embodiment, the probe is from 12-30 nucleotides in length. Other lengths of the probe are possible and within scope of the skill of the average person skilled in the art.

In a preferred embodiment, the DNA template containing the SNP polymorphism is amplified by Polymerase Chain Reaction (PCR) prior to detection. In such an embodiment, the amplified DNA serves as the template for the detection probe and the enhancer probe.

Certain embodiments of the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example for increasing the melting temperature in regions containing a low percentage of G or C bases, in which modified A with the capability of forming three hydrogen bonds to its complementary T can be used, or for decreasing the melting temperature in regions containing a high percentage of G or C bases, for example by using modified G bases that form only two hydrogen bonds to their complementary C base in a double stranded DNA molecule. In a preferred embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

In another hybridization method, Northern analysis (see Current Protocols in Molecular Biology, Ausubel, F. et al., eds., John Wiley & Sons, supra) is used to identify the presence of a polymorphism associated with prostate cancer. For Northern analysis, a test sample of RNA is obtained from the subject by appropriate means. As described herein, specific hybridization of a nucleic acid probe to RNA from the subject is indicative of a particular allele complementary to the probe. For representative examples of use of nucleic acid probes, see, for example, U.S. Pat. Nos. 5,288,611 and 4,851,330

Additionally, or alternatively, a peptide nucleic acid (PNA) probe can be used in addition to, or instead of, a nucleic acid probe in the hybridization methods described herein. A PNA is a DNA mimic having a peptide-like, inorganic backbone, such as N-(2-aminoethyl)glycine units, with an organic base (A, G, C, T or U) attached to the glycine nitrogen via a methylene carbonyl linker (see, for example, Nielsen, P., et al., *Bioconjug. Chem.* 5:3-7 (1994)). The PNA probe can be designed to specifically hybridize to a molecule in a sample suspected of containing one or more of the marker alleles or haplotypes that are associated with prostate cancer. Hybridization of the PNA probe is thus diagnostic for prostate cancer or a susceptibility to prostate cancer.

In one embodiment of the invention, a test sample containing genomic DNA obtained from the subject is collected and the polymerase chain reaction (PCR) is used to amplify a fragment comprising one or more markers or haplotypes of the present invention. As described herein, identification of a particular marker allele or haplotype associated with prostate cancer can be accomplished using a variety of methods (e.g., sequence analysis, analysis by restriction digestion, specific hybridization, single stranded conformation polymorphism assays (SSCP), electrophoretic analysis, etc.). In another embodiment, diagnosis is accomplished by expression analysis using quantitative PCR (kinetic thermal cycling). This technique can, for example, utilize commercially available technologies, such as TaqMan® (Applied Biosystems, Foster City, Calif.), to allow the identification of polymorphisms and haplotypes. The technique can assess the presence of an alteration in the expression or composition of a polypeptide or splicing variant(s) that is encoded by a prostate cancer-associated nucleic acid. Further, the expression of the variant(s) can be quantified as physically or functionally different.

In another method of the invention, analysis by restriction digestion can be used to detect a particular allele if the allele results in the creation or elimination of a restriction site relative to a reference sequence. Restriction fragment length polymorphism (RFLP) analysis can be conducted, e.g., as described in Current Protocols in Molecular Biology, supra. The digestion pattern of the relevant DNA fragment indicates the presence or absence of the particular allele in the sample.

Sequence analysis can also be used to detect specific alleles at polymorphic sites associated with prostate cancer (e.g. the polymorphic markers and haplotypes of Tables 7-11, and markers in linkage disequilibrium therewith). Therefore, in one embodiment, determination of the presence or absence of a particular marker alleles or haplotypes comprises sequence analysis. For example, a test sample of DNA or RNA can be obtained from the test subject. PCR or other appropriate methods can be used to amplify a portion of a prostate cancer-associated nucleic acid, and the presence of a specific allele can then be detected directly by sequencing the polymorphic site (or multiple polymorphic sites) of the genomic DNA in the sample.

In another embodiment, arrays of oligonucleotide probes that are complementary to target nucleic acid sequence segments from a subject, can be used to identify polymorphisms in a prostate cancer-associated nucleic acid (e.g. the polymorphic markers and haplotypes of Tables 7-11 and markers in linkage disequilibrium therewith). For example, an oligonucleotide array can be used. Oligonucleotide arrays typically comprise a plurality of different oligonucleotide probes that are coupled to a surface of a substrate in different known locations. These oligonucleotide arrays, also described as "Genechips™," have been generally described in the art (see, e.g., U.S. Pat. No. 5,143,854, PCT Patent Publication Nos. WO 90/15070 and 92/10092). These arrays can generally be produced using mechanical synthesis methods or light directed synthesis methods that incorporate a combination of photolithographic methods and solid phase oligonucleotide synthesis methods (Fodor, S. et al., *Science*, 251:767-773 (1991); Pirrung et al., U.S. Pat. No. 5,143,854 (see also published PCT Application No. WO 90/15070); and Fodor. S. et al., published PCT Application No. WO 92/10092 and U.S. Pat. No. 5,424,186, the entire teachings of each of which are incorporated by reference herein). Techniques for the synthesis of these arrays using mechanical synthesis methods are described in, e.g., U.S. Pat. No. 5,384,261; the entire teachings of which are incorporated by reference herein. In another example, linear arrays can be utilized. Additional descriptions of use of oligonucleotide arrays for detection of polymorphisms can be found, for example, in U.S. Pat. Nos. 5,858,659 and 5,837,832, the entire teachings of both of which are incorporated by reference herein.

Other methods of nucleic acid analysis can be used to detect a particular allele at a polymorphic site associated with prostate cancer (e.g. the polymorphic markers and haplotypes of Tables 7-11, and markers in linkage disequilibrium therewith). Representative methods include, for example, direct manual sequencing (Church and Gilbert, *Proc. Natl. Acad. Sci. USA*, 81: 1991-1995 (1988); Sanger, F., et al., *Proc. Natl. Acad. Sci. USA*, 74:5463-5467 (1977); Beavis, et al., U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield, V., et al., *Proc. Natl. Acad. Sci. USA*, 86:232-236 (1989)), mobility shift analysis (Orita, M., et al., *Proc. Natl. Acad. Sci. USA*, 86:2766-2770 (1989)), restriction enzyme analysis (Flavell, R., et al, *Cell,* 15:25-41 (1978); Geever, R., et al., *Proc. Natl. Acad. Sci. USA,* 78:5081-5085 (1981)); heteroduplex analysis; chemical mismatch cleavage (CMC) (Cotton, R., et al., *Proc. Natl. Acad. Sci. USA,* 85:4397-4401 (1985)); RNase protection assays (Myers, R., et al., *Science,* 230:1242-1246 (1985); use of polypeptides that recognize nucleotide mismatches, such as *E. coli* mutS protein; and allele-specific PCR.

In another embodiment of the Invention, diagnosis or determination of prostate cancer or a susceptibility to prostate cancer can be made by examining expression and/or composition of a polypeptide encoded by prostate cancer-associated nucleic acid in those instances where the genetic marker(s) or haplotype(s) of the present invention result in a change in the composition or expression of the polypeptide. Thus, diagnosis of a susceptibility to prostate cancer can be made by examining expression and/or composition of one of these polypeptides, or another polypeptide encoded by a prostate cancer-associated nucleic acid, in those instances where the genetic marker or haplotype of the present invention results in a change in the composition or expression of the polypeptide. The haplotypes and markers of the present invention that show association to prostate cancer may play a role through their effect on one or more of these nearby genes. Possible mechanisms affecting these genes include, e.g., effects on transcription, effects on RNA splicing, alterations in relative amounts of alternative splice forms of mRNA, effects on RNA stability, effects on transport from the nucleus to cytoplasm, and effects on the efficiency and accuracy of translation.

Thus, in another embodiment, the variants (markers or haplotypes) of the invention showing association to prostate cancer affect the expression of a nearby gene. It is well known that regulatory element affecting gene expression may be located far away, even as far as tenths or even hundreds of kilobases away, from the promoter region of a gene. By assaying for the presence or absence of at least one allele of at least one polymorphic marker of the present invention, it is thus possible to assess the expression level of such nearby genes. It is thus contemplated that the detection of the markers or haplotypes of the present invention can be used for assessing expression for one or more of such genes. In one such embodiment, the gene is the TCF2 gene.

A variety of methods can be used to make such a detection, including enzyme linked immunosorbent assays (ELISA), Western blots, immunoprecipitations and immunofluorescence. A test sample from a subject is assessed for the presence of an alteration in the expression and/or an alteration in composition of the polypeptide encoded by a prostate cancer-associated nucleic acid. An alteration in expression of a polypeptide encoded by a prostate cancer-associated nucleic acid can be, for example, an alteration in the quantitative polypeptide expression (i.e., the amount of polypeptide produced). An alteration in the composition of a polypeptide encoded by a prostate cancer-associated nucleic acid is an alteration in the qualitative polypeptide expression (e.g., expression of a mutant polypeptide or of a different splicing variant). In one embodiment, diagnosis of a susceptibility to prostate cancer is made by detecting a particular splicing variant encoded by a prostate cancer-associated nucleic acid, or a particular pattern of splicing variants.

Both such alterations (quantitative and qualitative) can also be present. An "alteration" in the polypeptide expression or composition, as used herein, refers to an alteration in expression or composition in a test sample, as compared to the expression or composition of polypeptide encoded by a prostate cancer-associated nucleic acid in a control sample. A control sample is a sample that corresponds to the test sample (e.g., is from the same type of cells), and is from a subject who is not affected by, and/or who does not have a susceptibility to, prostate cancer (e.g., a subject that does not possess a marker allele or haplotype as described herein). Similarly, the presence of one or more different splicing variants in the test sample, or the presence of significantly different amounts of different splicing variants in the test sample, as compared with the control sample, can be indicative of a susceptibility to prostate cancer. An alteration in the expression or composition of the polypeptide in the test sample, as compared with the control sample, can be indicative of a specific allele in the instance where the allele alters a splice site relative to the reference in the control sample. Various means of examining expression or composition of a polypeptide encoded by a prostate cancer-associated nucleic acid can be used, including spectroscopy, colorimetry, electrophoresis, isoelectric focusing, and immunoassays (e.g., David et al., U.S. Pat. No. 4,376,110) such as immunoblotting (see, e.g., Current Protocols in Molecular Biology, particularly chapter 10, supra).

For example, in one embodiment, an antibody (e.g., an antibody with a detectable label) that is capable of binding to a polypeptide encoded by a prostate cancer-associated nucleic acid can be used. Antibodies can be polyclonal or monoclonal. An intact antibody, or a fragment thereof (e.g., Fv, Fab, Fab', $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a labeled secondary antibody (e.g., a fluorescently-labeled secondary antibody) and end-labeling of a DNA probe with biotin such that it can be detected with fluorescently-labeled streptavidin.

In one embodiment of this method, the level or amount of polypeptide encoded by a prostate cancer-associated nucleic acid in a test sample is compared with the level or amount of the polypeptide encoded by a prostate cancer-associated nucleic acid in a control sample. A level or amount of the polypeptide in the test sample that is higher or lower than the level or amount of the polypeptide in the control sample, such that the difference is statistically significant, is indicative of an alteration in the expression of the polypeptide encoded by the prostate cancer-associated nucleic acid, and is diagnostic for a particular allele or haplotype responsible for causing the difference in expression. Alternatively, the composition of the polypeptide encoded by a prostate cancer-associated nucleic acid in a test sample is compared with the composition of the polypeptide encoded by a prostate cancer-associated nucleic acid in a control sample. In another embodiment, both the level or amount and the composition of the polypeptide can be assessed in the test sample and in the control sample.

In another embodiment, the diagnosis of a susceptibility to prostate cancer is made by detecting at least one prostate cancer-associated marker allele or haplotype (e.g., the polymorphic markers and haplotypes of Tables 1-10 and markers in linkage disequilibrium therewith) in combination with an additional protein-based, RNA-based or DNA-based assay. The methods of the invention can also be used in combination with an analysis of a subject's family history and risk factors (e.g., environmental risk factors, lifestyle risk factors).

Kits

Kits useful in the methods of diagnosis comprise components useful in any of the methods described herein, including for example, hybridization probes, restriction enzymes (e.g., for RFLP analysis), allele-specific oligonucleotides, antibodies that bind to an altered polypeptide encoded by prostate cancer-associated nucleic acid (e.g., antibodies that bind to a polypeptide encoded by a genomic segment comprising at least one polymorphic marker and/or haplotype of the present invention) or to a non-altered (native) polypeptide encoded by a prostate cancer-associated nucleic acid, means for amplification of a prostate cancer-associated nucleic acid, including amplification of markers associated with prostate cancer, as described herein, means for analyzing the nucleic acid sequence of prostate cancer-associated nucleic acid, means for analyzing the amino acid sequence of a polypeptide encoded by a prostate cancer-associated nucleic acid, etc. The kits can for example include necessary buffers, nucleic acid primers for amplifying nucleic acids of the invention (e.g., one or more of the polymorphic markers as described herein), and reagents for allele-specific detection of the fragments amplified using such primers and necessary enzymes (e.g., DNA polymerase). Additionally, kits can provide reagents for assays to be used in combination with the methods of the present invention, e.g., reagents for use with other prostate cancer diagnostic assays.

In one embodiment, the invention is a kit for assaying a sample from a subject to detect prostate cancer or a susceptibility to prostate cancer in a subject, wherein the kit comprises reagents necessary for selectively detecting at least one allele of at least one polymorphism of the present invention in the genome of the individual. In a particular embodiment, the reagents comprise at least one contiguous oligonucleotide that hybridizes to a fragment of the genome of the individual comprising at least one polymorphism of the present invention (e.g., the polymorphic markers and haplotypes of Tables 7-11 and markers in linkage disequilibrium therewith). In another embodiment, the reagents comprise at least one pair of oligonucleotides that hybridize to opposite strands of a genomic segment obtained from a subject, wherein each oligonucleotide primer pair is designed to selectively amplify a fragment of the genome of the individual that includes one polymorphism, wherein the polymorphism is selected from the group consisting of the polymorphisms as defined in and polymorphic markers in linkage disequilibrium therewith. In yet another embodiment the fragment is at least 20 base pairs in size. Such oligonucleotides or nucleic acids (e.g., oligonucleotide primers) can be designed using portions of the nucleic acids flanking polymorphisms (e.g., SNPs or microsatellites) that are indicative of prostate cancer. In another embodiment, the kit comprises one or more labeled nucleic acids capable of detecting one or more specific polymorphic markers or haplotypes associated with prostate cancer, and reagents for detection of the label. Suitable labels include, e.g., a radioisotope, a fluorescent label, an enzyme label, an enzyme co-factor label, a magnetic label, a spin label, an epitope label.

In particular embodiments, the polymorphic marker or haplotype to be detected by the reagents of the kit comprises one or more markers, two or more markers, three or more markers, four or more markers or five or more markers selected from the group consisting of the markers set forth in any one of the Tables 7-15 herein. In another embodiment, the marker or haplotype to be detected comprises at least one of the markers set forth in any of the Tables 7-11 herein. In another embodiment, the marker or haplotype to be detected comprises at least one of the markers rs3923603 (SEQ ID NO:1), rs4430796 (SEQ ID NO:2), rs7501939 (SEQ ID NO:3), rs1859962 (SEQ ID NO:4), D17S1350 (SEQ ID NO:5), rs5945572 (SEQ ID NO:6), rs5945605 (SEQ ID NO:7), rs2710646 (SEQ ID NO:8), rs3760511 (SEQ ID NO:56), rs7214479 (SEQ ID NO:134), rs6501445 (SEQ ID NO:146), rs983085 (SEQ ID NO:150), rs5945605 (SEQ ID NO:178) and rs721048 (SEQ ID NO:344), or markers in linkage disequilibrium therewith.

The kit of the invention in one embodiment comprises at least one oligonucleotide probe that is from 5-100 nucleotides in length and specifically hybridizes (under stringent conditions) to all or a portion of the TCF2 gene, the LD block C02, the LD block C17b, the LD block C0Xa or the LD block C04a, and wherein at least one of said at least one oligonucleotide probes comprises a polymorphism selected from the group of polymorphisms listed in Tables 7-11, and polymorphisms in linkage disequilibrium therewith. In one embodiment, the kit further comprises at least one oligonucleotide pair for amplifying a genomic fragment comprising at least one polymorphism as set forth in SEQ ID NO:1-362, the segment being from 40-500 nucleotides in length. In another embodiment, the oligonucleotide probe comprises a detectable label. In another embodiment, the kit comprises two oligonucleotide probes, wherein one of said probes comprises at least one detectable label and a polymorphism as listed in any of the Tables 7-11. In another embodiment, one of said probes comprises one detectable label, a quencher and a polymorphism as listed in any of the Tables 7-11.

In another embodiment, the invention relates to a kit for assessing susceptibility to prostate cancer, the kit comprising at least one oligonucleotide, from 15 to 200 nucleotides in length, that specifically hybridizes to a nucleotide molecule comprising at least one polymorphic marker as set forth in any of the Tables 7-11, and polymorphic markers in linkage disequilibrium therewith.

In one preferred embodiment, the kit for detecting the markers of the invention comprises a detection oligonucleotide probe, that hybridizes to a segment of template DNA containing a SNP polymorphisms to be detected, an enhancer oligonucleotide probe and an endonuclease. As explained in the above, the detection oligonucleotide probe comprises a fluorescent moiety or group at its 3' terminus and a quencher at its 5' terminus, and an enhancer oligonucleotide, is employed, as described by Kutyavin et al. (*Nucleic Acid Res.* 34:e128 (2006)). The fluorescent moiety can be Gig Harbor Green or Yakima Yellow, or other suitable fluorescent moieties. The detection probe is designed to hybridize to a short nucleotide sequence that includes the SNP polymorphism to be detected. Preferably, the SNP is anywhere from the terminal residue to −6 residues from the 3' end of the detection probe. The enhancer is a short oligonucleotide probe which hybridizes to the DNA template 3' relative to the detection probe. The probes are designed such that a single nucleotide gap exists between the detection probe and the enhancer nucleotide probe when both are bound to the template. The gap creates a synthetic abasic site that is recognized by an endonuclease, such as Endonuclease IV. The enzyme cleaves the dye off the fully complementary detection probe, but cannot cleave a detection probe containing a mismatch. Thus, by measuring the fluorescence of the released fluorescent moiety, assessment of the presence of a particular allele defined by nucleotide sequence of the detection probe can be performed.

The detection probe can be of any suitable size, although preferably the probe is relatively short. In one embodiment, the probe is from 5-100 nucleotides in length. In another embodiment, the probe is from 10-50 nucleotides in length, and in another embodiment, the probe is from 12-30 nucleotides in length. Other lengths of the probe are possible and within scope of the skill of the average person skilled in the art.

In a preferred embodiment, the DNA template containing the SNP polymorphism is amplified by Polymerase Chain Reaction (PCR) prior to detection, and primers for such amplification are included in the reagent kit. In such an embodiment, the amplified DNA serves as the template for the detection probe and the enhancer probe.

In one embodiment, the DNA template is amplified by means of Whole Genome Amplification (WGA) methods, prior to assessment for the presence of specific polymorphic markers as described herein. Standard methods well known to the skilled person for performing WGA may be utilized, and are within scope of the invention. In one such embodiment, reagents for performing WGA are included in the reagent kit.

Certain embodiments of the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example for increasing the melting temperature in regions containing a low percentage of G or C bases, in which modified A with the capability of forming three hydrogen bonds to its complementary T can be used, or for decreasing the melting temperature in regions containing a high percentage of G or C bases, for example by using modified G bases that form only two hydrogen bonds to their complementary C base in a double stranded DNA molecule. In a preferred embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

In one of such embodiments, the presence of the marker or haplotype is indicative of a susceptibility (increased susceptibility or decreased susceptibility) to prostate cancer. In another embodiment, the presence of the marker or haplotype is indicative of response to a prostate cancer therapeutic agent. In another embodiment, the presence of the marker or haplotype is indicative of prognosis of prostate cancer. In yet another embodiment, the presence of the marker or haplotype is indicative of progress of treatment of prostate cancer. Such treatment may include intervention by surgery, medication or by other means (e.g., lifestyle changes).

In a further aspect of the present invention, a pharmaceutical pack (kit) is provided, the pack comprising a therapeutic agent and a set of instructions for administration of the therapeutic agent to humans diagnostically tested for one or more variants of the present invention, as disclosed herein. The therapeutic agent can be a small molecule drug, an antibody, a peptide, an antisense or RNAi molecule, or other therapeutic molecules. In one embodiment, an individual identified as a carrier of at least one variant of the present invention is instructed to take a prescribed dose of the therapeutic agent. In one such embodiment, an individual identified as a homozygous carrier of at least one variant of the present invention is instructed to take a prescribed dose of the therapeutic agent. In another embodiment, an individual identified as a non-carrier of at least one variant of the present invention is instructed to take a prescribed dose of the therapeutic agent.

In certain embodiments, the kit further comprises a set of instructions for using the reagents comprising the kit.

Therapeutic Agents

Variants of the present invention (e.g., the markers and/or haplotypes of the invention, e.g., the markers listed in Tables 7-11) can also be used to identify novel therapeutic targets for prostate cancer. For example, genes containing, or in linkage disequilibrium with, variants (markers and/or haplotypes) associated with prostate cancer (e.g., TCF2), or their products, as well as genes or their products that are directly or indirectly regulated by or interact with these variant genes or their products, can be targeted for the development of therapeutic agents to treat prostate cancer, or prevent or delay onset of symptoms associated with prostate cancer. Therapeutic agents may comprise one or more of, for example, small non-protein and non-nucleic acid molecules, proteins, peptides, protein fragments, nucleic acids (DNA, RNA), PNA (peptide nucleic acids), or their derivatives or mimetics which can modulate the function and/or levels of the target genes or their gene products.

The nucleic acids and/or variants of the invention, or nucleic acids comprising their complementary sequence, may be used as antisense constructs to control gene expression in cells, tissues or organs. The methodology associated with antisense techniques is well known to the skilled artisan, and is described and reviewed in *Antisense Drug Technology: Principles, Strategies, and Applications*, Crooke, ed., Marcel Dekker Inc., New York (2001). In general, antisense nucleic acid molecules are designed to be complementary to a region of mRNA expressed by a gene, so that the antisense molecule hybridizes to the mRNA, thus blocking translation of the mRNA into protein. Several classes of antisense oligonucleotide are known to those skilled in the art, including cleavers and blockers. The former bind to target RNA sites, activate intracellular nucleases (e.g., RnaseH or Rnase L), that cleave the target RNA. Blockers bind to target RNA, inhibit protein translation by steric hindrance of the ribosomes. Examples of blockers include nucleic acids, morpholino compounds, locked nucleic acids and methylphosphonates (Thompson, *Drug Discovery Today*, 7:912-917 (2002)). Antisense oligonucleotides are useful directly as therapeutic agents, and are also useful for determining and validating gene function, for example by gene knock-out or gene knock-down experiments. Antisense technology is further described in Layery et al., *Curr. Opin. Drug Discov. Devel.* 6:561-569 (2003), Stephens et al., *Curr. Opin. Mol. Ther.* 5:118-122 (2003), Kurreck, *Eur. J. Biochem.* 270:1628-44 (2003), Dias et al., *Mol. Cancer. Ter.* 1:347-55 (2002), Chen, *Methods Mol. Med.* 75:621-636 (2003), Wang et al., *Curr. Cancer Drug Targets* 1:177-96 (2001), and Bennett, *Antisense Nucleic Acid Drug. Dev.* 12:215-24 (2002)

The variants described herein can be used for the selection and design of antisense reagents that are specific for particular variants. Using information about the variants described herein, antisense oligonucleotides or other antisense molecules that specifically target mRNA molecules that contain one or more variants of the invention can be designed. In this manner, expression of mRNA molecules that contain one or more variant of the present invention (markers and/or haplotypes) can be inhibited or blocked. In one embodiment, the antisense molecules are designed to specifically bind a particular allelic form (i.e., one or several variants (alleles and/or haplotypes)) of the target nucleic acid, thereby inhibiting translation of a product originating from this specific allele or haplotype, but which do not bind other or alternate variants at the specific polymorphic sites of the target nucleic acid molecule.

As antisense molecules can be used to inactivate mRNA so as to inhibit gene expression, and thus protein expression, the molecules can be used to treat a disease or disorder, such as prostate cancer. The methodology can involve cleavage by means of ribozymes containing nucleotide sequences complementary to one or more regions in the mRNA that attenuate the ability of the mRNA to be translated. Such mRNA regions include, for example, protein-coding regions, in particular protein-coding regions corresponding to catalytic activity, substrate and/or ligand binding sites, or other functional domains of a protein.

The phenomenon of RNA interference (RNAi) has been actively studied for the last decade, since its original discovery in *C. elegans* (Fire et al., *Nature* 391:806-11 (1998)), and in recent years its potential use in treatment of human disease has been actively pursued (reviewed in Kim & Rossi, *Nature Rev. Genet.* 8:173-204 (2007)). RNA interference (RNAi), also called gene silencing, is based on using double-stranded RNA molecules (dsRNA) to turn off specific genes. In the cell, cytoplasmic double-stranded RNA molecules (dsRNA) are processed by cellular complexes into small interfering RNA (siRNA). The siRNA guide the targeting of a protein-RNA complex to specific sites on a target mRNA, leading to cleavage of the mRNA (Thompson, *Drug Discovery Today*, 7:912-917 (2002)). The siRNA molecules are typically about 20, 21, 22 or 23 nucleotides in length. Thus, one aspect of the invention relates to isolated nucleic acid molecules, and the use of those molecules for RNA interference, i.e. as small interfering RNA molecules (siRNA). In one embodiment, the isolated nucleic acid molecules are 18-26 nucleotides in length, preferably 19-25 nucleotides in length, more preferably 20-24 nucleotides in length, and more preferably 21, 22 or 23 nucleotides in length.

Another pathway for RNAi-mediated gene silencing originates in endogenously encoded primary microRNA (pri-miRNA) transcripts, which are processed in the cell to generate precursor miRNA (pre-miRNA). These miRNA molecules are exported from the nucleus to the cytoplasm, where they undergo processing to generate mature miRNA molecules (miRNA), which direct translational inhibition by recognizing target sites in the 3' untranslated regions of mRNAs, and subsequent mRNA degradation by processing P-bodies (reviewed in Kim & Rossi, *Nature Rev. Genet.* 8:173-204 (2007)).

Clinical applications of RNAi include the incorporation of synthetic siRNA duplexes, which preferably are approximately 20-23 nucleotides in size, and preferably have 3' overlaps of 2 nucleotides. Knockdown of gene expression is established by sequence-specific design for the target mRNA. Several commercial sites for optimal design and synthesis of such molecules are known to those skilled in the art.

Other applications provide longer siRNA molecules (typically 25-30 nucleotides in length, preferably about 27 nucleotides), as well as small hairpin RNAs (shRNAs; typically about 29 nucleotides in length). The latter are naturally expressed, as described in Amarzguioui et al. (*FEBS Lett.* 579:5974-81 (2005)). Chemically synthetic siRNAs and shR- NAs are substrates for in vivo processing, and in some cases provide more potent gene-silencing than shorter designs (Kim et al., *Nature Biotechnol.* 23:222-226 (2005); Siolas et al., *Nature Biotechnol.* 23:227-231 (2005)). In general siRNAs provide for transient silencing of gene expression, because their intracellular concentration is diluted by subsequent cell divisions. By contrast, expressed shRNAs mediate long-term, stable knockdown of target transcripts, for as long as transcription of the shRNA takes place (Marques et al., *Nature Biotechnol.* 23:559-565 (2006); Brummelkamp et al., *Science* 296: 550-553 (2002)).

Since RNAi molecules, including siRNA, miRNA and shRNA, act in a sequence-dependent manner, the variants of the present invention (e.g., the markers and haplotypes set forth in Tables 7-11) can be used to design RNAi reagents that recognize specific nucleic acid molecules comprising specific alleles and/or haplotypes (e.g., the alleles and/or haplotypes of the present invention), while not recognizing nucleic acid molecules comprising other alleles or haplotypes. These RNAi reagents can thus recognize and destroy the target nucleic acid molecules. As with antisense reagents, RNAi reagents can be useful as therapeutic agents (i.e., for turning off disease-associated genes or disease-associated gene variants), but may also be useful for characterizing and validating gene function (e.g., by gene knock-out or gene knock-down experiments).

Delivery of RNAi may be performed by a range of methodologies known to those skilled in the art. Methods utilizing non-viral delivery include cholesterol, stable nucleic acid-lipid particle (SNALP), heavy-chain antibody fragment (Fab), aptamers and nanoparticles. Viral delivery methods include use of lentivirus, adenovirus and adeno-associated virus. The siRNA molecules are in some embodiments chemically modified to increase their stability. This can include modifications at the 2' position of the ribose, including 2'-O-methylpurines and 2'-fluoropyrimidines, which provide resistance to Rnase activity. Other chemical modifications are possible and known to those skilled in the art.

The following references provide a further summary of RNAi, and possibilities for targeting specific genes using RNAi: Kim & Rossi, *Nat. Rev. Genet.* 8:173-184 (2007), Chen & Rajewsky, *Nat. Rev. Genet.* 8: 93-103 (2007), Reynolds, et al., *Nat. Biotechnol.* 22:326-330 (2004), Chi et al., *Proc. Natl. Acad. Sci. USA* 100: 6343-6346 (2003), Vickers et al., *J. Biol. Chem.* 278:7108-7118 (2003), Agami, *Curr. Opin. Chem. Biol.* 6:829-834 (2002), Layery, et al., *Curr. Opin. Drug Discov. Devel.* 6:561-569 (2003), Shi, *Trends Genet.* 19:9-12 (2003), Shuey et al., *Drug Discov. Today* 7:1040-46 (2002), McManus et al., *Nat. Rev. Genet.* 3:737-747 (2002), Xia et al., *Nat. Biotechnol.* 20:1006-10 (2002), Plasterk et al., *curr. Opin. Genet. Dev.* 10:562-7 (2000), Bosher et al., *Nat. Cell Biol.* 2:E31-6 (2000), and Hunter, *Curr. Biol.* 9:R440-442 (1999).

A genetic defect leading to increased predisposition or risk for development of a disease, including prostate cancer, or a defect causing the disease, may be corrected permanently by administering to a subject carrying the defect a nucleic acid fragment that incorporates a repair sequence that supplies the normal/wild-type nucleotide(s) at the site of the genetic defect. Such site-specific repair sequence may concompass an RNA/DNA oligonucleotide that operates to promote endogenous repair of a subject's genomic DNA. The administration of the repair sequence may be performed by an appropriate vehicle, such as a complex with polyethelenimine, encapsulated in anionic liposomes, a viral vector such as an adenovirus vector, or other pharmaceutical compositions suitable for promoting intracellular uptake of the administered nucleic acid. The genetic defect may then be overcome, since the chimeric oligonucleotides induce the incorporation of the normal sequence into the genome of the subject, leading to expression of the normal/wild-type gene product. The replacement is propagated, thus rendering a permanent repair and alleviation of the symptoms associated with the disease or condition.

The present invention provides methods for identifying compounds or agents that can be used to treat prostate cancer. Thus, the variants of the invention are useful as targets for the identification and/or development of therapeutic agents. Such methods may include assaying the ability of an agent or compound to modulate the activity and/or expression of a nucleic acid that includes at least one of the variants (markers and/or haplotypes) of the present invention, or the encoded product of the nucleic acid. This in turn can be used to identify agents or compounds that inhibit or alter the undesired activity or expression of the encoded nucleic acid product. Assays for performing such experiments can be performed in cell-based systems or in cell-free systems, as known to the skilled person. Cell-based systems include cells naturally expressing the nucleic acid molecules of interest, or recombinant cells that have been genetically modified so as to express a certain desired nucleic acid molecule.

Variant gene expression in a patient can be assessed by expression of a variant-containing nucleic acid sequence (for example, a gene containing at least one variant of the present invention, which can be transcribed into RNA containing the at least one variant, and in turn translated into protein), or by altered expression of a normal/wild-type nucleic acid sequence due to variants affecting the level or pattern of expression of the normal transcripts, for example variants in the regulatory or control region of the gene. Assays for gene expression include direct nucleic acid assays (mRNA), assays for expressed protein levels, or assays of collateral compounds involved in a pathway, for example a signal pathway. Furthermore, the expression of genes that are up- or down-regulated in response to the signal pathway can also be assayed. One embodiment includes operably linking a reporter gene, such as luciferase, to the regulatory region of the gene(s) of interest.

Modulators of gene expression can in one embodiment be identified when a cell is contacted with a candidate compound or agent, and the expression of mRNA is determined. The expression level of mRNA in the presence of the candidate compound or agent is compared to the expression level in the absence of the compound or agent. Based on this comparison, candidate compounds or agents for treating prostate cancer can be identified as those modulating the gene expression of the variant gene. When expression of mRNA or the encoded protein is statistically significantly greater in the presence of the candidate compound or agent than in its absence, then the candidate compound or agent is identified as a stimulator or up-regulator of expression of the nucleic acid. When nucleic acid expression or protein level is statistically significantly less in the presence of the candidate compound or agent than in its absence, then the candidate compound is identified as an inhibitor or down-regulator of the nucleic acid expression.

The invention further provides methods of treatment using a compound identified through drug (compound and/or agent) screening as a gene modulator (i.e. stimulator and/or inhibitor of gene expression).

Methods of Assessing Probability of Response to Therapeutic Agents, Methods of Monitoring Progress of Treatment and Methods of Treatment As is known in the art, individuals can have differential responses to a particular therapy (e.g., a therapeutic agent or therapeutic method). Pharmacogenomics addresses the issue of how genetic variations (e.g., the variants (markers and/or haplotypes) of the present invention) affect drug response, due to altered drug disposition and/or abnormal or altered action of the drug. Thus, the basis of the differential response may be genetically determined in part. Clinical outcomes due to genetic variations affecting drug response may result in toxicity of the drug in certain individuals (e.g., carriers or non-carriers of the genetic variants of the present invention), or therapeutic failure of the drug. Therefore, the variants of the present invention may determine the manner in which a therapeutic agent and/or method acts on the body, or the way in which the body metabolizes the therapeutic agent. The therapeutic agent is in a preferred embodiment a therapeutic agent for prostate cancer. In certain embodiments, the therapeutic agent is an agent for hormonal therapy, such as an antiandrogen (e.g., flutamide, bicalutamide, nilutamide, cyproterone acetate), an andrenal androgen blocker such as ketoconazole or aminoglutethimide, a GnRH antagonist such as abarelix, a GnRH agonist such as leuprolide, goserelin, triptorelin, or buserelin, or an agent for chemotherapy, such as docetaxel, or a bisphosphonate such as zoledronic acid.

Accordingly, in one embodiment, the presence of a particular allele at a polymorphic site or haplotype is indicative of a different, e.g. a different response rate, to a particular treatment modality. This means that a patient diagnosed with prostate cancer, and carrying a certain allele at a polymorphic or haplotype of the present invention (e.g., the at-risk and protective alleles and/or haplotypes of the invention) would respond better to, or worse to, a specific therapeutic, drug and/or other therapy used to treat the disease. Common treatment modalities for prostate cancer include surgery (prostatectomy), radiation therapy, cryosurgery, and high intensity focused ultrasound (HIFU). Therefore, the presence or absence of the marker allele or haplotype could aid in deciding what treatment should be used for a the patient. For example, for a newly diagnosed patient, the presence of a marker or haplotype of the present invention may be assessed (e.g., through testing DNA derived from a blood sample, as described herein). If the patient is positive for a marker allele or haplotype at (that is, at least one specific allele of the marker, or haplotype, is present), then the physician recommends one particular therapy, while if the patient is negative for the at least one allele of a marker, or a haplotype, then a different course of therapy may be recommended (which may include recommending that no immediate therapy, other than serial monitoring for progression of the disease, be performed). Thus, the patient's carrier status could be used to help determine whether a particular treatment modality should be administered. The value lies within the possibilities of being able to diagnose the disease at an early stage, to select the most appropriate treatment, and provide information to the clinician about prognosis/aggressiveness of the disease in order to be able to apply the most appropriate treatment.

The present invention also relates to methods of monitoring progress or effectiveness of a treatment for prostate cancer, including medication, surgery (prostatectomy), radiation therapy, cryosurgery, and high intensity focused ultrasound (HIFU). This can be done based on the genotype and/or haplotype status of the markers and haplotypes of the present invention, i.e., by assessing the absence or presence of at least one allele of at least one polymorphic marker as disclosed herein, or by monitoring expression of genes that are associated with the variants (markers and/or haplotypes) of the present invention. The risk gene mRNA or the encoded polypeptide can be measured in a tissue sample (e.g., a peripheral blood sample, or a biopsy sample). Expression levels and/or mRNA levels can thus be determined before and during treatment to monitor its effectiveness. Alternatively, or concomitantly, the genotype and/or haplotype status of at least one risk variant for prostate cancer, as presented herein, is determined before and during treatment to monitor its effectiveness.

Alternatively, biological networks or metabolic pathways related to the markers and haplotypes of the present invention can be monitored by determining mRNA and/or polypeptide levels. This can be done for example, by monitoring expression levels or polypeptides for several genes belonging to the network and/or pathway, in samples taken before and during treatment. Alternatively, metabolites belonging to the biological network or metabolic pathway can be determined before and during treatment. Effectiveness of the treatment is determined by comparing observed changes in expression levels/metabolite levels during treatment to corresponding data from healthy subjects.

In a further aspect, the markers of the present invention can be used to increase power and effectiveness of clinical trials. Thus, individuals who are carriers of at least one at-risk variant of the present invention, i.e. individuals who are carriers of at least one allele of at least one polymorphic marker conferring increased risk of developing prostate cancer may be more likely to respond to a particular treatment modality. In one embodiment, individuals who carry at-risk variants for gene(s) in a pathway and/or metabolic network for which a particular treatment (e.g., small molecule drug) is targeting, are more likely to be responders to the treatment. In another embodiment, individuals who carry at-risk variants for a gene, which expression and/or function is altered by the at-risk variant, are more likely to be responders to a treatment modality targeting that gene, its expression or its gene product. This application can improve the safety of clinical trials, but can also enhance the chance that a clinical trial will demonstrate statistically significant efficacy, which may be limited to a certain sub-group of the population. Thus, one possible outcome of such a trial is that carriers of certain genetic variants, e.g., the markers and haplotypes of the present invention, are statistically significantly likely to show positive response to the therapeutic agent, i.e. experience alleviation of symptoms associated with prostate cancer when taking the therapeutic agent or drug as prescribed.

In a further aspect, the markers and haplotypes of the present invention can be used for targeting the selection of pharmaceutical agents for specific individuals. Personalized selection of treatment modalities, lifestyle changes or combination of the two, can be realized by the utilization of the at-risk variants of the present invention. Thus, the knowledge of an individual's status for particular markers of the present invention, can be useful for selection of treatment options that target genes or gene products affected by the at-risk variants of the invention. Certain combinations of variants may be suitable for one selection of treatment options, while other gene variant combinations may target other treatment options. Such combination of variant may include one variant, two variants, three variants, or four or more variants, as needed to determine with clinically reliable accuracy the selection of treatment module.

Computer-Implemented Aspects

The present invention also relates to computer-implemented functions using the polymorphic markers and haplotypes described herein to be associated with prostate cancer. Such functions can be useful for storing, manipulating or otherwise analyzing genotype data that is useful in the methods of the invention.

One such aspect relates to computer-readable media. In general terms, such medium has capabilities of storing (i)

identifier information for at least one polymorphic marker or a haplotype; (ii) an indicator of the frequency of at least one allele of said at least one marker, or the frequency of a haplotype, in individuals with prostate cancer; and an indicator of the frequency of at least one allele of said at least one marker, or the frequency of a haplotype, in a reference population. The reference population can be a disease-free population of individuals. Alternatively, the reference population is a random sample from the general population, and is thus representative of the population at large. The frequency indicator may be a calculated frequency, a count of alleles and/or haplotype copies, or normalized or otherwise manipulated values of the actual frequencies that are suitable for the particular medium.

Additional information about the individual can be stored on the medium, such as ancestry information, information about sex, physical attributes or characteristics (including height and weight), biochemical measurements (such as blood pressure, blood is lipid levels, history of previous disease diagnosis (such as cancer, e.g., prostate cancer), family history of cancer, e.g., prostate cancer), or other useful information that is desirable to store or manipulate in the context of the genotype status of a particular individual.

The invention furthermore relates to an apparatus that is suitable for determination or manipulation of genetic data useful for determining a susceptibility to prostate cancer in a human individual. Such an apparatus can include a computer-readable memory, a routine for manipulating data stored on the computer-readable memory, and a routine for generating an output that includes a measure of the genetic data. Such measure can include values such as allelic or haplotype frequencies, genotype counts, sex, age, phenotype information, values for odds ratio (OR) or relative risk (RR), population attributable risk (PAR), or other useful information that is either a direct statistic of the original genotype data or based on calculations based on the genetic data.

The markers and haplotypes shown herein to be associated with increased susceptibility (e.g., increased risk) of prostate cancer, are in certain embodiments useful for interpretation and/or analysis of genotype data. Thus in certain embodiments, an identification of an at-risk allele for prostate cancer, as shown herein, or an allele at a polymorphic marker in LD with any one of the markers shown herein to be associated with prostate cancer, is indicative of the individual from whom the genotype data originates is at increased risk of prostate cancer. In one such embodiment, genotype data is provided for at least one polymorphic marker shown herein to be associated with prostate cancer, or a marker in linkage disequilibrium therewith. The genotype data is subsequently made available to the individual from whom the data originates, for example via a user interface accessible over the internet, together with an interpretation of the genotype data, e.g., in the form of a risk measure (such as an absolute risk (AR), risk ratio (RR) or odds ratio (OR)) for the disease (e.g., prostate cancer), based on the known association between the at least one marker and prostate cancer, as shown herein. In another embodiment, at-risk markers identified in a genotype dataset derived from an individual are assessed and results from the assessment of the risk conferred by the presence of such at-risk variants in the dataset are made available to the individual, for example via a secure web interface, or by other communication means. The results of such risk assessment can be reported in numeric form (e.g., by risk values, such as absolute risk, relative risk, and/or an odds ratio, or by a percentage increase in risk compared with a reference), by graphical means, or by other means suitable to illustrate the risk to the individual from whom the genotype data is derived.

In particular embodiments, the results of risk assessment is made available to a third party, e.g., a physician, other healthcare worker or genetic counselor.

Markers Useful in Various Aspects of the Invention

The above-described methods and applications can all be practiced with the markers and haplotypes of the invention that have in more detail been described herein in general terms as being useful for assessing susceptibility to prostate cancer. Thus, these applications can in certain embodiments be reduced to practice using any one, or a plurality of, markers located within, or in linkage disequilibrium with LD block C02, LD block C04a, the TCF2 gene, LD block C17b and/or LD block C0Xa, as defined herein. In other embodiments, the at least one marker is selected from the markers set forth in Tables 7-11, and markers in linkage disequilibrium therewith. In other embodiments, the at least one marker is selected from the markers set forth in tables 11-16. In other embodiments, the at least one marker is selected from marker rs3923603 (SEQ ID NO:1), rs4430796 (SEQ ID NO:2), rs7501939 (SEQ ID NO:3), rs1859962 (SEQ ID NO:4), D17S1350 (SEQ ID NO:5), rs5945572 (SEQ ID NO:6), rs5945605 (SEQ ID NO:7), rs2710646 (SEQ ID NO:8), rs3760511 (SEQ ID NO:56), rs7214479 (SEQ ID NO:134), rs6501445 (SEQ ID NO:146), rs983085 (SEQ ID NO:150), rs5945605 (SEQ ID NO:178) and rs721048 (SEQ ID NO:344), optionally including markers in linkage disequilibrium therewith.

In one embodiment, the at least one polymorphic marker is selected from rs2710646 (SEQ ID NO:8) and rs721048 (SEQ ID NO:344), and markers in linkage disequilibrium therewith. In one such embodiment, the at least one marker is selected from the markers set forth in Table 11. In another embodiment, the at least one polymorphic marker is rs3923603 (SEQ ID NO:1), or markers in linkage disequilibrium therewith. In one embodiment, the at least one polymorphic marker is selected from the markers set forth in Table 7. In another embodiment, the at least one polymorphic marker is rs7501939 (SEQ ID NO:3), or markers in linkage disequilibrium therewith. In one such embodiment, the at least one polymorphic marker is selected from the group of markers set forth in Table 8. In yet another embodiment, the at least one polymorphic marker is rs1859962 (SEQ ID NO:4), or markers in linkage disequilibrium therewith. In one such embodiment, the at least one polymorphic marker is selected from the group of markers set forth in Table 9. In a further embodiment, the at least one polymorphic marker is rs5945572 (SEQ ID NO:6), or markers in linkage disequilibrium therewith. In one embodiment, the at least one polymorphic marker is selected from the group of markers set forth in Table 10. In yet another embodiment the at least one polymorphic marker is selected from markers associated with the TCF2 gene by values of the linkage disequilibrium measure $r^2$ of greater than 0.2. In one such embodiment, the at least one polymorphic marker is selected from the markers set forth in Table 13.

In one embodiment, the presence of any one of allele A in marker rs3923603, allele C in rs7501939, allele G in rs1859962, allele A in rs5945572, allele A in rs2710646, allele C in rs3760511, allele A in rs4430796, allele T in rs7214479, allele A in rs6501455, allele C in rs983085, allele T in rs5945605, or allele A in rs721048 is indicative of increased susceptibility to prostate cancer.

Nucleic Acids and Polypeptides

The nucleic acids and polypeptides described herein can be used in any methods or kits as described herein. An "isolated" nucleic acid molecule, as used herein, is one that is separated from nucleic acids that normally flank the gene or nucleotide sequence (as in genomic sequences) and/or has been completely or partially purified from other transcribed sequences (e.g., as in an RNA library). For example, an isolated nucleic acid of the invention can be substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system or reagent mix. In other circumstances, the material can be purified to essential homogeneity, for example as determined by polyacrylamide gel electrophoresis (PAGE) or column chromatography (e.g., HPLC). An isolated nucleic acid molecule of the invention can comprise at least about 50%, at least about 80% or at least about 90% (on a molar basis) of all macromolecular species present. With regard to genomic DNA, the term "isolated" also can refer to nucleic acid molecules that are separated from the chromosome with which the genomic DNA is naturally associated. For example, the isolated nucleic acid molecule can contain less than about 250 kb, 200 kb, 150 kb, 100 kb, 75 kb, 50 kb, 25 kb, 10 kb, 5 kb, 4 kb, 3 kb, 2 kb, 1 kb, 0.5 kb or 0.1 kb of the nucleotides that flank the nucleic acid molecule in the genomic DNA of the cell from which the nucleic acid molecule is derived.

The nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells or heterologous organisms, as well as partially or substantially purified DNA molecules in solution. "Isolated" nucleic acid molecules also encompass in vivo and in vitro RNA transcripts of the DNA molecules of the present invention. An isolated nucleic acid molecule or nucleotide sequence can include a nucleic acid molecule or nucleotide sequence that is synthesized chemically or by recombinant means. Such isolated nucleotide sequences are useful, for example, in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue), such as by Northern blot analysis or other hybridization techniques.

The invention also pertains to nucleic acid molecules that hybridize under high stringency hybridization conditions, such as for selective hybridization, to a nucleotide sequence described herein (e.g., nucleic acid molecules that specifically hybridize to a nucleotide sequence containing a polymorphic site associated with a haplotype described herein). In certain embodiments, the invention includes variants that hybridize under high stringency hybridization and wash conditions (e.g., for selective hybridization) to a nucleotide sequence that comprises the nucleotide sequence of any one of SEQ ID NO:1-362, as set forth herein. In other embodiments, the invention includes variants that hybridize under high stringency hybridization and wash conditions (e.g., for selective hybridization) to a nucleotide sequence that comprises the nucleotide sequence of LD block C02, LD block C04a, the nucleotide sequence encoding the TCF2 gene or a fragment thereof, LD block C17b, or LD block C0Xa (or a nucleotide sequence comprising the complement of any one of SEQ ID NO:1-362, the nucleotide sequence of LD block C02, LD block C04a, the nucleotide sequence encoding the TCF2 gene or a fragment thereof, LD block C17b, or LD block C0Xa). In another embodiment, the variant comprises a nucleotide sequence containing at least one polymorphic marker or haplotype of the present invention (e.g., the markers and haplotypes disclosed in any one of Tables 7-11, and markers in linkage disequilibrium therewith).

Such nucleic acid molecules can be detected and/or isolated by allele- or sequence-specific hybridization (e.g., under high stringency conditions). Stringency conditions and methods for nucleic acid hybridizations are explained on pages 2.10.1-2.10.16 and pages 6.3.1-6.3.6 in *Current Protocols in Molecular Biology* (Ausubel, F. et al., "Current Protocols in Molecular Biology", John Wiley & Sons, (1998)), and Kraus, M. and Aaronson, S., *Methods Enzymol.,* 200:546-556 (1991), the entire teachings of which are incorporated by reference herein.

The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences (i.e., % identity of identical positions/total # of positions× 100). In certain embodiments, the length of a sequence aligned for comparison purposes is at least 30%, at least 40%, at least 50%, at least 60%, at least 70%, at least 80%, at least 90%, or at least 95%, of the length of the reference sequence. The actual comparison of the two sequences can be accomplished by well-known methods, for example, using a mathematical algorithm. A non-limiting example of such a mathematical algorithm is described in Karlin, S, and Altschul, S., *Proc. Natl. Acad. Sci. USA,* 90:5873-5877 (1993). Such an algorithm is incorporated into the NBLAST and XBLAST programs (version 2.0), as described in Altschul, S. et al., *Nucleic Acids Res.,* 25:3389-3402 (1997). When utilizing BLAST and Gapped BLAST programs, the default parameters of the respective programs (e.g., NBLAST) can be used. See the website on the world wide web at ncbi.nlm.nih.gov. In one embodiment, parameters for sequence comparison can be set at score=100, wordlength=12, or can be varied (e.g., W=5 or W=20).

Other examples include the algorithm of Myers and Miller, CABIOS (1989), ADVANCE and ADAM as described in Torellis, A. and Robotti, C., *Comput. Appl. Biosci.* 10:3-5 (1994); and FASTA described in Pearson, W. and Lipman, D., *Proc. Natl. Acad. Sci. USA,* 85:2444-48 (1988).

In another embodiment, the percent identity between two amino acid sequences can be accomplished using the GAP program in the GCG software package (Accelrys, Cambridge, UK).

The present invention also provides isolated nucleic acid molecules that contain a fragment or portion that hybridizes under highly stringent conditions to a nucleic acid that comprises, or consists of, the nucleotide sequence of any one of SEQ ID NO:1-362, LD block C02, LD block C04a, the nucleotide sequence encoding the TCF2 gene or a fragment thereof, LD block C17b, or LD block C0Xa (or a nucleotide sequence comprising the complement of the nucleotide sequence of any one of SEQ ID NO:1-362, LD block C02, LD block C04a, the nucleotide sequence encoding the TCF2 gene or a fragment thereof, LD block C17b, or LD block C0Xa), wherein the nucleotide sequence comprises at least one polymorphic allele contained in the haplotypes (e.g., haplotypes) described herein. The nucleic acid fragments of the invention are at least about 15, at least about 18, 20, 23 or 25 nucleotides, and can be 30, 40, 50, 100, 200, 500, 1000, 10,000 or more nucleotides in length.

The nucleic acid fragments of the invention are used as probes or primers in assays such as those described herein. "Probes" or "primers" are oligonucleotides that hybridize in a base-specific manner to a complementary strand of a nucleic acid molecule. In addition to DNA and RNA, such probes and primers include polypeptide nucleic acids (PNA), as described in Nielsen, P. et al., *Science* 254:1497-1500 (1991). A probe or primer comprises a region of nucleotide sequence that hybridizes to at least about 15, typically about 20-25, and in certain embodiments about 40, 50 or 75, consecutive nucleotides of a nucleic acid molecule comprising a contiguous nucleotide sequence from any one of SEQ ID NO:1-362, LD block C02, LD block C04a, the nucleotide sequence encoding the TCF2 gene or a fragment thereof, LD block C17b, or LD block C0Xa (or a nucleotide sequence comprising the complement of the nucleotide sequence of any one of SEQ ID NO:1-362, LD block C02, LD block C04a, the nucleotide sequence encoding the TCF2 gene or a fragment thereof, LD block C17b, or LD block C0Xa) and may in one embodiment comprise at least one allele contained in one or more markers and haplotypes described herein (e.g., the markers and haplotypes of Tables 7-11, or markers in linkage disequilibrium therewith), and the complement thereof. In particular embodiments, a probe or primer can comprise 100 or fewer nucleotides; for example, in certain embodiments from 6 to 50 nucleotides, or, for example, from 12 to 30 nucleotides. In other embodiments, the probe or primer is at least 70% identical, at least 80% identical, at least 85% identical, at least 90% identical, or at least 95% identical, to the contiguous nucleotide sequence or to the complement of the contiguous nucleotide sequence. In another embodiment, the probe or primer is capable of selectively hybridizing to the contiguous nucleotide sequence or to the complement of the contiguous nucleotide sequence. Often, the probe or primer further comprises a label, e.g., a radioisotope, a fluorescent label, an enzyme label, an enzyme co-factor label, a magnetic label, a spin label, an epitope label.

The nucleic acid molecules of the invention, such as those described above, can be identified and isolated using standard molecular biology techniques well known to the skilled person. The amplified DNA can be labeled (e.g., radiolabeled) and used as a probe for screening a cDNA library derived from human cells. The cDNA can be derived from mRNA and contained in a suitable vector. Corresponding clones can be isolated, DNA can obtained following in vivo excision, and the cloned insert can be sequenced in either or both orientations by art-recognized methods to identify the correct reading frame encoding a polypeptide of the appropriate molecular weight. Using these or similar methods, the polypeptide and the DNA encoding the polypeptide can be isolated, sequenced and further characterized.

In general, the isolated nucleic acid sequences of the invention can be used as molecular weight markers on Southern gels, and as chromosome markers that are labeled to map related gene positions. The nucleic acid sequences can also be used to compare with endogenous DNA sequences in patients to identify prostate cancer or a susceptibility to prostate cancer, and as probes, such as to hybridize and discover related DNA sequences or to subtract out known sequences from a sample (e.g., subtractive hybridization). The nucleic acid sequences can further be used to derive primers for genetic fingerprinting, to raise anti-polypeptide antibodies using immunization techniques, and/or as an antigen to raise anti-DNA antibodies or elicit immune responses.

Antibodies

Polyclonal antibodies and/or monoclonal antibodies that specifically bind one form of the gene product of any gene associated with the variants shown herein to be associated with increased risk of prostate cancer (e.g., TCF2), but not to the other form of the gene product, are also provided. Antibodies are also provided which bind a portion of either the variant or the reference gene product that contains the polymorphic site or sites. The term "antibody" as used herein refers to immunoglobulin molecules and immunologically active portions of immunoglobulin molecules, i.e., molecules that contain antigen-binding sites that specifically bind an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind to a polypeptide of the invention. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., polypeptide of the invention or a fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, *Nature* 256:495-497 (1975), the human B cell hybridoma technique (Kozbor et al., *Immunol. Today* 4: 72 (1983)), the EBV-hybridoma technique (Cole et al., *Monoclonal Antibodies and Cancer Therapy*, Alan R. Liss, 1985, Inc., pp. 77-96) or trioma techniques. The technology for producing hybridomas is well known (see generally *Current Protocols in Immunology* (1994) Coligan et al., (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., *Current Protocols in Immunology, supra*; Galfre et al., *Nature* 266:55052 (1977); R. H. Kenneth, in *Monoclonal Antibodies: A New Dimension In Biological Analyses*, Plenum Publishing Corp., New York, N.Y. (1980); and Lerner, *Yale J. Biol. Med.* 54:387-402 (1981)). Moreover, the ordinarily skilled worker will appreciate that there are many variations of such methods that also would be useful.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., *Bio/Technology* 9: 1370-1372 (1991); Hay et al., *Hum. Antibod. Hybridomas* 3:81-85 (1992); Huse et al., *Science* 246: 1275-1281 (1989); and Griffiths et al., *EMBO J.* 12:725-734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate a polypeptide of the invention by standard techniques, such as affinity chromatography or immunoprecipitation. A polypeptide-specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. The antibody can be coupled to a detectable substance to facilitate its detection. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies may also be useful in pharmacogenomic analysis. In such embodiments, antibodies against variant proteins encoded by nucleic acids according to the invention, such as variant proteins that are encoded by nucleic acids that contain at least one polymorphic marker of the invention, can be used to identify individuals that require modified treatment modalities.

Antibodies can furthermore be useful for assessing expression of variant proteins in disease states, such as in active stages of a disease, or in an individual with a predisposition to a disease related to the function of the protein, in particular prostate cancer. Antibodies specific for a variant protein of the present invention that is encoded by a nucleic acid that comprises at least one polymorphic marker or haplotype as described herein can be used to screen for the presence of the variant protein, for example to screen for a predisposition to prostate cancer as indicated by the presence of the variant protein.

Antibodies can be used in other methods. Thus, antibodies are useful as diagnostic tools for evaluating proteins, such as variant proteins of the invention, in conjunction with analysis by electrophoretic mobility, isoelectric point, tryptic or other protease digest, or for use in other physical assays known to those skilled in the art. Antibodies may also be used in tissue typing. In one such embodiment, a specific variant protein has been correlated with expression in a specific tissue type, and antibodies specific for the variant protein can then be used to identify the specific tissue type.

Subcellular localization of proteins, including variant proteins, can also be determined using antibodies, and can be applied to assess aberrant subcellular localization of the protein in cells in various tissues. Such use can be applied in genetic testing, but also in monitoring a particular treatment modality. In the case where treatment is aimed at correcting the expression level or presence of the variant protein or aberrant tissue distribution or developmental expression of the variant protein, antibodies specific for the variant protein or fragments thereof can be used to monitor therapeutic efficacy.

Antibodies are further useful for inhibiting variant protein function, for example by blocking the binding of a variant protein to a binding molecule or partner. Such uses can also be applied in a therapeutic context in which treatment involves inhibiting a variant protein's function. An antibody can be for example be used to block or competitively inhibit binding, thereby modulating (i.e., agonizing or antagonizing) the activity of the protein. Antibodies can be prepared against specific protein fragments containing sites required for specific function or against an intact protein that is associated with a cell or cell membrane. For administration in vivo, an antibody may be linked with an additional therapeutic payload, such as radionuclide, an enzyme, an immunogenic epitope, or a cytotoxic agent, including bacterial toxins (diphtheria or plant toxins, such as ricin). The in vivo half-life of an antibody or a fragment thereof may be increased by pegylation through conjugation to polyethylene glycol.

The present invention further relates to kits for using antibodies in the methods described herein. This includes, but is not limited to, kits for detecting the presence of a variant protein in a test sample. One preferred embodiment comprises antibodies such as a labelled or labelable antibody and a compound or agent for detecting variant proteins in a biological sample, means for determining the amount or the presence and/or absence of variant protein in the sample, and means for comparing the amount of variant protein in the sample with a standard, as well as instructions for use of the kit.

The present invention will now be exemplified by the following non-limiting examples.

EXEMPLIFICATION

Example 1

Identification of Markers and LD Block Regions Associated with Prostate Cancer

Patients Involved in the Genetics Study

A population based list of all prostate cancer patients that were diagnosed with prostate cancer in Iceland from 1955 to 2005 form the basis for this study. Patients have been invited to join the study since 2001 on an ongoing basis. As of October 2006, blood samples from 1564 prostate cancer patients have been collected. Genomic DNA from 1455 of those samples, as well as samples from 7034 control individuals was extracted and genotyped.

Genotyping

A genome-wide scan of 1455 Icelandic individuals diagnosed with Prostate Cancer and 7034 population controls was performed using Infinium HumanHap300 SNP chips from Illumina for assaying approximately 317,000 single nucleotide polymorphisms (SNPs) on a single chip (Illumina, San Diego, Calif., USA). SNP genotyping for replication in other case-control cohorts was carried using the Centaurus platform (Nanogen).

Statistical Methods for Association and Haplotype Analysis

For single marker association to the disease, Fisher exact test was used to calculate a two-sided P-value for each individual allele. When presenting the results, we used allelic frequencies rather than carrier frequencies for SNPs and haplotypes. Haplotype analyses were performed using a computer program we developed at deCODE called NEMO (NEsted MOdels) (Gretarsdóttir, et al., *Nat Genet.* 2003 October; 35(2):131-8). NEMO was used both to study marker-marker association and to calculate linkage disequilibrium (LD) between markers, and for case-control haplotype analysis. With NEMO, haplotype frequencies are estimated by maximum likelihood and the differences between patients and controls are tested using a generalized likelihood ratio test. The maximum likelihood estimates, likelihood ratios and P-values are computed with the aid of the EM-algorithm directly for the observed data, and hence the loss of information due to the uncertainty with phase and missing genotypes is automatically captured by the likelihood ratios, and under most situations, large sample theory can be used to reliably determine statistical significance. The relative risk (RR) of an allele or a haplotype, i.e., the risk of an allele compared to all other alleles of the same marker, is calculated assuming the multiplicative model (Terwilliger, J. D. & Ott, J. A haplotype-based 'haplotype relative risk' approach to detecting allelic associations. *Hum. Hered.* 42, 337-46 (1992) and Falk, C. T. & Rubinstein, P. Haplotype relative risks: an easy reliable way to construct a proper control sample for risk calculations. *Ann. Hum. Genet.* 51 (Pt 3), 227-33 (1987)), together with the population attributable risk (PAR). When controls are considered unaffected (i.e., disease-free), the relative risk is replaced by an estimate for the odds ratio (OR) of the particular marker allele or haplotype.

In the haplotype analysis, it may be useful to group haplotypes together and test the group as a whole for association to the disease. This is possible to do with NEMO. A model is defined by a partition of the set of all possible haplotypes, where haplotypes in the same group are assumed to confer the same risk while haplotypes in different groups can confer different risks. A null hypothesis and an alternative hypothesis are said to be nested when the latter corresponds to a finer partition than the former. NEMO provides complete flexibility in the partition of the haplotype space. In this way, it is possible to test multiple haplotypes jointly for association and to test if different haplotypes confer different risk. As a measure of LD, we use two standard definitions of LD, D' and $R^2$ (Lewontin, R., *Genetics,* 49:49-67 (1964) and Hill, W. G. and A. Robertson, *Theor. Appl. Genet.,* 22:226-231 (1968)) as they provide complementary information on the amount of LD. For the purpose of estimating D' and $R^2$, the frequencies of all two-marker allele combinations are estimated using maximum likelihood methods and the deviation from linkage disequilibrium is evaluated using a likelihood ratio test. The standard definitions of D' and $R^2$ are extended to include microsatellites by averaging over the values for all possible allele combinations of the two markers weighted by the marginal allele probabilities.

The number of possible haplotypes that can be constructed out of the dense set of markers genotyped over the whole genome is very large and even though the number of haplotypes that are actually observed in the patient and control cohort is much smaller, testing all of those haplotypes for association to the disease is a formidable task. It should be noted that we do not restrict our analysis to haplotypes constructed from a set of consecutive markers, as some markers may be very mutable and might split up an otherwise well conserved haplotype constructed out of surrounding markers Results As described herein (Example 1 and Example 2), we have identified five loci that confer an increased risk for particular cancers (e.g., prostate cancer (e.g., aggressive prostate cancer)). In all cases, the loci were identified in a genomewide scan in Icelandic prostate cancer material. Follow-up genotyping was performed in other cohorts to verify the signals. The five loci are located on three different chromosomes: One locus is on chromosome 2 (2p 15), one locus is on chromosome 4 (4q31.21), two loci are on chromosome 17 (17q12 and 17q24.3) and one locus is on chromosome X (Xp11.22). Particular markers and haplotypes, associated with an increased risk of prostate cancer, from these five loci were initially found to be associated with prostate cancer, as depicted in the below. Allele codes for SNPs are as follows: 1=A, 2=C, 3=G, 4=T, and X=any allele.

Locus C02 on Chromosome 2p15

Table 1 shows data for the association of marker rs2710646 to prostate cancer. The original finding in Icelandic cases (1,487 cases and 11,208 controls) is characterized by an Odds Ratio (OR) of 1.16 and a nominal p-value of 0.003 (Table 1). This finding was replicated in cohorts from Holland, Spain and in a cohort of European Americans from Chicago. While the results from the replication cohorts are not statistically significant by themselves, the overall result for the combined cohorts is highly significant (Table 1), illustrating the significance of the finding of association to this chromosomal region.

The rs2710646 marker is located within a region denoted herein as LD block C02, between positions 62,767,002 and 63,881,002 on chromosome 2.

Locus C04a on Chromosome 4q31.21

As indicated in Table 1, the 1 allele of marker rs3923603 on chromosome 4q31.21 (also called rs3923603 1 allele) was found to be associated with an increased risk of prostate cancer. The marker is located in what we call LD block C04a between positions 145601002 and 145805005 bp (NCBI Build 34); the location of the marker is indicated in Table 2. The original finding has been replicated in cohorts from Holland, Spain and the US (European Americans from Chicago), thus providing further support for the significance of the association, with overall p-value of $1.3 \times 10^{-5}$ (Table 1).

Locus C0Xa on Chromosome Xp11.22

As indicated in Table 1, markers s5945572 and rs5945605 on chromosome Xp11.22, have been found to be associated with an increased risk of prostate cancer. The markers are located in what we call LD block C0Xa between positions 50033978 and 50259000 bp (NCBI Build 34), and location of the markers is indicated in Table 2. The original finding has been replicated in cohorts from Holland, Spain and the US (European Americans from Chicago), thus providing further support for the significance of the association, with overall p-value of $1.3 \times 10^{-5}$ (Table 1).

The opposite alleles to the ones at risk of SNP markers rs5945572 1 allele show significant protection to prostate cancer in carriers.

TABLE 1

Combined association results for the following loci: 2p15, 4q31.21, and Xp11.23 for prostate cancer in Iceland, the Netherlands, Spain and US

| Location | Study population (N cases/N controls) Variant (allele) | Frequency Cases | Controls | OR | P value |
|---|---|---|---|---|---|
| 4q31.21 | Iceland (1,499/11,281) | | | | |
| | SG04S719/rs3923603 (A) Holland (974/1450) | 0.461 | 0.432 | 1.12 | 0.0048 |
| | SG04S719/rs3923603 (A) Spain (453/1,057) | 0.430 | 0.400 | 1.13 | 0.040 |
| | SG04S719/rs3923603 (A) European Americans Chicago (526/503) | 0.390 | 0.360 | 1.13 | 0.12 |
| | SG04S719/rs3923603 (A) Combining all above | 0.379 | 0.330 | 1.24 | 0.020 |
| 2p15 | SG04S719/rs3923603 (A) Iceland (1,487/11,208) | — | 0.381 | 1.14 | $1.30 \times 10^{-5}$ |
| | SG02S799/rs2710646 (A) Holland (997/1459) | 0.228 | 0.203 | 1.16 | 0.0031 |
| | SG02S799/rs2710646 (A) Spain (455/1,067) | 0.206 | 0.186 | 1.14 | 0.082 |
| | SG02S799/rs2710646 (A) European Americans Chicago (663/529) | 0.232 | 0.206 | 1.17 | 0.11 |
| | SG02S799/rs2710646 (A) Combining all above | 0.196 | 0.167 | 1.21 | 0.070 |
| Xp11.22 | SG02S799/rs2710646 (A) Iceland (1,499/11,280) | — | 0.190 | 1.16 | $3.13 \times 10^{-5}$ |
| | SG0XS73/rs5945572 (A) SG0XS83/rs5945605 (T) Holland (999/1,462) | 0.412 0.389 | 0.374 0.345 | 1.18 1.21 | $3.53 \times 10^{-3}$ $1.76 \times 10^{-3}$ |
| | SG0XS73/rs5945572 (A) SG0XS83/rs5945605 (T) Spain (456/1,077) | 0.39 0.372 | 0.348 0.335 | 1.21 1.17 | 0.024 0.048 |
| | SG0XS73/rs5945572 (A) SG0XS83/rs5945605 (T) Chicago (527/506) | 0.421 0.404 | 0.368 0.353 | 1.28 1.29 | 0.023 0.024 |
| | SG0XS73/rs5945572 (A) SG0XS83/rs5945605 (T) All excluding Iceland | 0.409 0.35 | 0.358 0.287 | 1.25 1.25 | 0.069 0.078 |
| | SG0XS73/rs5945572 (A) SG0XS83/rs5945605 (T) All combined (3,481/14,325) | — — | 0.358 0.325 | 1.23 1.22 | $2.62 \times 10^{-4}$ $6.59 \times 10^{-4}$ |
| | SG0XS73/rs5945572 (A) SG0XS83/rs5945605 (T) | — — | 0.362 0.33 | 1.21 1.22 | $3.34 \times 10^{-6}$ $3.75 \times 10^{-6}$ |

Table 2 shows the genomic location of anchor SNP and microsatellite markers from the five chromosomal regions (loci) discussed herein (see SEQ ID NO:1-7). Location of the markers is given with respect to NCBI Build34 of the human genome assembly. The relative position of the markers in basepair position (Build 34 NCBI) is indicated. Further discussion of Chromosome 17 loci are found in Example 2 herein.

TABLE 2

Genomic position of anchor markers

| Locus | Name (SEQ ID NO) | Position Build 34 |
|---|---|---|
| Chromosome 4q31.21 | rs3923603 (SEQ ID NO: 1) | 145688956 |
| Chromosome 17q12 | rs4430796 (SEQ ID NO: 2) | 36293590 |
| Chromosome 17q12 | rs7501939 (SEQ ID NO: 3) | 36296706 |
| Chromosome 17q24.3 | rs1859962 (SEQ ID NO: 4) | 69705876 |
| Chromosome 17q24.3 | D17S1350 (SEQ ID NO: 5) | 69685886-69686068* |
| Chromosome Xp11.22 | rs5945572 (SEQ ID NO: 6) | 50146489 |
| Chromosome Xp11.22 | rs5945605 (SEQ ID NO: 7) | 50107288 |
| Chromosome 2p15 | rs2710646 (SEQ ID NO: 8) | 63109413 |

*The interval of an amplimer of the microsatellite D17S1350 is given

Example 2

Two Sequence Variants Conferring Risk of Prostate Cancer Identified on Chromosome 17 and One of them, in TCF2, Shown to be Protective Against Type 2 Diabetes Prostate cancer is the most common non-dermatological cancer of males worldwide, and the second leading cause of cancer-related death in men from western industrialized countries[1]. Firmly established risk factors for this type of malignancy are age, ethnicity and family history. In addition diet, lifestyle, and circulating androgens may have impact on the risk. Despite a large body of evidence for a genetic component to the risk of prostate cancer, the variants on 8q24 are the only common sequence variants reported so far that account for substantial proportion of the cases[2-5].

In the present study we began with a genome-wide SNP association study to search for sequence variants conferring risks of prostate cancer using Icelandic cases and controls. We expanded the data from a study previously reported[3], by increasing the number of cases and controls from 1,453 to 1,501, and 3,064 to 11,290, respectively. This corresponds to an approximately 34% increase in effective sample size. After quality filtering, 310,520 SNPs from the Illumina Hap300 chip were tested for association to prostate cancer (see Methods). The results were adjusted for relatedness by applying the method of genomic control[6]. Apart from the variants on 8q24[2,3] and SNPs correlated with them, no other SNPs achieved genome-wide significance. However, we assumed that a properly designed follow-up strategy would lead to the identification of additional susceptibility variants for prostate cancer.

Like others[7], we believe that results from family-based linkage studies should be taken into account when evaluating the association results of a genome-wide study. However, instead of using linkage scores to formally weight the statistical significance of different SNPs[7], we used them to prioritize follow-up studies. The long arm of chromosome 17 has been reported in several linkage studies of prostate cancer[8-10] but no susceptibility variants have yet been found[11-13]. Hence we decided to first focus our efforts on this region.

Six SNPs on chromosome 17q, having the lowest P values ($<5 \times 10^{-4}$) and ranking from 68 to 100 among the most significantly associated SNPs in our genome-wide analysis, were selected for further analysis (FIG. 1). These SNPs mapped to two distinct regions on chromosome 17q that are both within a region with LOD scores ranging approximately between 1 and 2 but outside the proposed 10 cM candidate gene region reported in a recent linkage analysis[10]. One locus was on 17q12 (rs7501939 and rs3760511), encompassing the 5' end of the TCF2 (HNF1β) gene, where the linkage disequilibrium (LD) is weak (based on the Utah CEPH (CEU) HapMap data set). The second locus is in a gene poor area on 17q24.3 (rs1859962, rs7214479, rs6501455 and rs983085) where all four SNPs fall within a strong LD-block (based on the CEU HapMap data set). The two loci are separated by approximately 33 Mb and no LD was observed between the two of them.

We genotyped 5 of the 6 SNPs in three prostate cancer case-control groups of European ancestry from the Netherlands, Spain and the United States (US) (Table 3). The assay for rs983085 on 17q24.3 failed in genotyping but this SNP is almost perfectly correlated with rs6501455 ($r^2=0.99$) and is therefore expected to give comparable results. For each of the replication study groups, the observed effect of 4 of the 5 SNPs were in the same direction as in Iceland. One SNP, rs6501455, showed an opposite effect in the Chicago group. In general, the Dutch samples showed the strongest effects, while the results for the Spanish group were the weakest. When results from all four case-control groups were combined, two SNPs achieved genome-wide significance, rs7501939 allele C (rs7501939 C) at 17q12 (allele specific odds ratio (OR)=1.19, P=$4.7 \times 10^{-9}$) and rs1859962 allele G (rs1859962 G) at 17q24.3 (OR=1.20, P=$2.5 \times 10^{-1}$) (Table 2). In an effort to refine the signal at the 17q12 locus, we selected three markers (rs4239217, rs757210, rs4430796) that were in the same LD block as rs7501939 and were substantially correlated with it ($r^2>0.5$) based on the Hapmap CEU data. After genotyping these three refinement SNPs in the different case and control groups, one of them, rs4430796, showed an association to prostate cancer that was even stronger than that of rs7501939. Specifically, with all groups combined, allele A of rs4430796 had an OR of 1.22 with a P of $1.4 \times 10^{-11}$ (Table 4a). A joint analysis showed that the effects of rs7501939 and rs3760511 were no longer significant after adjusting for rs4430796 (P=0.88 and 0.58 respectively), while rs4430796 remained significant after adjusting for both rs7501939 and rs3760511 (P=0.0042). At 17q24.3, our attempt at refining the signal did not result with any SNP that was more significant than rs1859962. Among the Illumina SNPs, rs7114479 and rs6501455 were not significant (P>0.75) with adjustment for the effect of rs1859962, whereas, rs1859962 remained significant after adjusting for the other two SNPs (P=$7.4 \times 10^{-4}$). Henceforth, our focus is mainly on rs4430796 at 17q12 and rs1859962 at 17q24.3. However, at 17q12, since rs7501539 is the most significant among Illumina SNPs and was a part of the original genome-wide scan, we include it in the discussion when appropriate. We also recommend that all replication effort should include at least these three SNPs.

For cases diagnosed at age 65 or younger, the observed OR from the combined analysis was slightly higher, or 1.30 for rs4430796 A, and 1.27 for rs1859962 G. For each copy of the at-risk alleles, patients were diagnosed 2 and 5 months earlier, for rs4430796 and rs1859962 respectively. This observation however, was not statistically significant (P=0.40 and 0.06 for rs4430796 and rs1859962 respectively) and therefore, its confirmation requires further investigation.

The Cancer Genetic Markers of Susceptibility study group (CGEMS), has made results from a genome-wide association analysis of prostate cancer publicly available (https colon-slash-slash cgems.cancer.gov slash). For rs4430796 A allele, the P values range between $4.0\times10^{-4}$ and $1.7\times10^{-3}$ depending on the type of analysis performed, and for rs1859962 G the P values range between 0.027 and 0.048. The OR was about 1.2 for both variants which is comparable to the results we find (Table 4). These results from an independent investigation make our observation even more compelling and provide further support for the notion that similar effects could be expected in other populations of European descent.

No interaction was observed between the risk variants on 17q12 and 17q24.3; a multiplicative or log-additive model provided an adequate fit for the joint risk of rs4430796 and rs1859962. Genotype specific ORs were estimated for each locus individually (Table 3). Based on results from all four groups, a multiplicative model for the genotype risk provided an adequate fit for rs4430796 at 17q12. For rs1859962 at the 17q24.3 locus however, the full model provided a significantly better fit than the multiplicative model (P=0.006), a result mainly driven by the Icelandic samples. Specifically, the estimated OR of 1.33 for a heterozygous carrier of rs1859962 G was substantially higher than the 1.20 estimate implied by a multiplicative model. The corresponding PAR was also higher, 21% instead of 16%.

The SNPs rs7501939 and rs4430796 on 17q12 are located in the first and second intron of the TCF2 gene, respectively, which encodes a transcription factor playing an important role in embryonic development of the kidney, pancreas and liver. To the best of our knowledge, genetic variants in TCF2 have not previously been implicated in the risk of prostate cancer but germline mutations have been identified in renal carcinoma[14] and epigenetic inactivation by methylation has been found in ovarian cancer and various cancer cell lines[15]. RNA expression analysis demonstrated expression of TCF2 in both normal and tumor prostate tissue (data not shown). More than 50 different exonic TCF2 mutations have been reported in individuals with renal cysts, maturity-onset diabetes of the young, type 5 (MODY5), pancreatic atrophy, and genital tract abnormalities[16,17]. We sequenced all 9 exons of TCF2 in 200 Icelandic prostate cancer cases and 200 controls without detecting any mutations explaining our association signal (data not shown).

Evidence has been reported for association of type 2 diabetes mellitus (T2D) to common SNPs in five of the six known MODY genes[18,19], including TCF2[19,20]. Interestingly, several epidemiological studies have demonstrated an inverse relationship between T2D and the risk of prostate cancer (see Kasper et al.[21] and references therein). A recent meta-analysis estimated the relative risk of prostate cancer to be 0.84 (95% CI, 0.71-0.92) among diabetes patients[21]. We therefore, decided to investigate a potential association between T2D and the SNPs in TCF2 showing the strongest association to prostate cancer in our data.

The Illumina SNP rs7501939 was typed in 1,380 T2D patients among whom the males were not known to have prostate cancer (according to a nation-wide list of prostate cancer cases diagnosed from 1955 to 2006 held by the Icelandic Cancer Registry). When compared to 9,940 controls neither known to have prostate cancer nor T2D, rs7501939 C showed a protective effect against T2D (OR=0.88, P=0.0045) in these samples. For the same samples, allele A of the refinement SNP rs4430796 gave a comparable result (OR=0.86, P=0.0021). To validate this association, we typed both rs7501939 and rs4430796 in samples from seven additional T2D case-control groups of European-, African-, and Asian ancestry. In all seven case-control groups, rs7501939 C and rs4430796 A showed a negative association to the disease (i.e. OR<1.0) even though some of the estimated effects were very modest and individually non-significant. Three case-control groups (Denmark A, Philadelphia, and West Africans) showed a significant association (P<0.05) and one other group (Hong Kong) gave a marginally significant result (P between 0.05 and 0.10). Combining results from all eight T2D case-control groups, including the Icelandic, gave an OR of 0.91 ($P=9.2\times10^{-7}$) for rs7501939 C, and an OR of 0.91 ($P=2.7\times10^{-7}$) for rs4430796 A (Table 4). Our analysis of the data does not indicate any differential association by gender of rs7501939 or rs4430796 to T2D. In a joint analysis, the effect of rs7501939 was no longer significant after adjusting for rs4430796 (P=0.41), while rs4430796 remained significant with adjustment for rs7501939 (P=0.016). It is noted that the latter was mainly driven by the data from West Africa where the correlation between the two SNPs ($r^2=0.22$ in HapMap Yoruban samples), is substantially lower than that in Caucasians ($r^2=0.77$ in HapMap CEU samples). Still these results are consistent with what was observed for prostate cancer. For T2D, a very recent report[20] describes similar findings (OR=0.89, $P=5\times10^{-6}$) for allele G of the SNP rs757210 that is located in the second intron of TCF2 and is substantially correlated with rs4430796 A (D'=0.96; $r^2=0.62$; based on the CEU HapMap data set). This reinforces the finding that one or more variants in TCF2 that confer risk to prostate cancer are protective for T2D. To eliminate the concern that the associations of rs7501939 and rs4430796 to prostate cancer were in part a by-product of an association to T2D, we repeated the prostate cancer association analysis after removing all known diabetics from the Icelandic prostate cancer case-control group. For the resulting 1,444 cases and 9,917 controls, the association for rs7501939 C and rs4430796 A was practically unchanged; rs7501939 had an OR of 1.16 for the Icelandic samples alone ($P=4.0\times10^{-4}$), and 1.19 ($P=1.1\times10^{-8}$) when results of all four case-control groups were combined; whereas rs4430796 had an OR of 1.18 ($P=1.9\times10^{-4}$) in the Icelandic samples and an OR of 1.21 ($P=2.1\times10^{-10}$) in the combined group.

The more distal SNP, rs1859962, on chromosome 17q24.3 is in a 177.5 kb LD-block spanning from 66,579 Mb to 66,757 Mb, (NCBI Build 35), based on the CEU HapMap group. One mRNA (BC039327) and several unspliced ESTs have been localized to this region, but no known genes (www.genome.ucsc.edu, May 2004 Assembly). RT-PCR analysis of various cDNA libraries, including those derived from the prostate, revealed detectable expression of the BC039327 mRNA only in a testis library (data not shown), which was in line with previously reported results[22]. The closest telomeric gene, located ~900 kb away from the LD-block, is SOX9 a SRY related (Sex determining Region Y) transcription factor known to be important for sex determination[23]. SOX9 is expressed in normal prostate basal cells, and is probably involved in regulating androgen receptor expression in prostate cells[24]. Various rearrangement breakpoints have been described that affect the expression of SOX9 and lead to a skeletal malformation syndrome called campomelic dysplasia (CD)[25]. One such translocation breakpoint has been described within the LD-block containing the rs1859962[22]. This translocation is thought to remove a potential cis-acting regulatory element (SOX9cre1) for SOX9 leading to altered expression of SOX9[26]. Overexpression of SOX9 has been shown to suppress growth and tumorigenicity of a prostate tumor cell line[27], suggesting that SOX9 might act as a tumor suppressor gene.

In summary, two common variants on chromosome 17q, rs4430796 A and rs1859962 G, were identified to contribute to the risk of prostate cancer in four populations of European descent. Together, based on the combined results, these two variants have an estimated joint PAR of about 36%, which is substantial from a public health point of view. The large PAR is a consequence of the high frequencies of these variants. However, as their relative risks, as estimated by the ORs, are not high, the sibling risk ratio accounted for by them is only approximately 1.009 each and 1.018 jointly. As a consequence, they could only explain a very small fraction of the familial clustering of the disease and could only generate very modest linkage scores. The same is true for the identified variants in the 8q24 region[2-5]. Hence, it is expected that many more prostate cancer susceptibility variants in the genome remain to be discovered and some of these might also reside in the chromosome 17 linkage region. The vicinity of the TCF2 and SOX9 genes to the variants on 17q could implicate them in the pathogenesis of prostate cancer. Perhaps the most intriguing finding in this study is the discovery of a variant, rs4430796 A, in TCF2 that is associated with increased risk of prostate cancer, but reduced risk of T2D in individuals of European, African and Asian descent. The discovery of a genetic variant in the TCF2 gene, which accounts for at least part of the inverse relationship between these two diseases, provides a step towards an understanding of the complex biochemical checks and balances that result from the pleiotropic impact of singular genetic variants. Previous explanations of the well established inverse relationship between prostate cancer and T2D have centered on the impact of the metabolic and hormonal environment of diabetic men. However, we note that the protective effect of both the TCF2 SNPs against T2D is too modest for its impact on prostate cancer risk to be merely a by-product of its impact on T2D. Indeed, we favor the notion that the primary functional impact of rs4430796 (or a strongly correlated presently unknown variant) is on one or more metabolic or hormonal pathways important for the normal functioning of individuals throughout their lives that incidentally modulate the risk of developing prostate cancer and T2D late in life. Further investigation of the functional impact of the TCF2 variants, both in normal individuals and those with prostate cancer and T2D, may provide knowledge that can be used not only for treatment of these diseases, but no less importantly, for their prevention.

Methods

Icelandic Study Population.

Men diagnosed with prostate cancer were identified based on a nationwide list from the Icelandic Cancer Registry (ICR) that contained all 3,886 Icelandic prostate cancer patients diagnosed from Jan. 1, 1955, to Dec. 31, 2005. The Icelandic prostate cancer sample collection included 1,615 patients (diagnosed from December 1974 to December 2005) who were recruited from November 2000 until June 2006 out of the 1,968 affected individuals who were alive during the study period (a participation rate of about 82%). A total of 1,541 patients were included in a genome wide SNP genotyping effort, using the Infinium II assay method and the Sentrix HumanHap300 BeadChip (Illumina, San Diego, Calif., USA). Thereof, 1,501 (97%) were successfully genotyped according to our quality control criteria and used in the present case-control association analysis. The mean age at diagnosis for the consenting patients was 71 years (median 71 years) and the range was from 40 to 96 years, while the mean age at diagnosis was 73 years for all prostate cancer patients in the ICR. The median time from diagnosis to blood sampling was 2 years (range 0 to 26 years). The 11,290 controls (5,010 males and 6,280 females) used in this study consisted of 758 controls randomly selected from the Icelandic genealogical database and 10,532 individuals from other ongoing genome-wide association studies at deCODE. Specifically, around 1,400 from studies on T2D; about 1,600 from studies on breast cancer; 1,800 from studies on myocardial infarction, and studies on colon cancer, anxiety, addiction, schizophrenia and infectious diseases provided around 700-1,000 controls each. The controls had a mean age of 66 years (median 67) and the range was from 22 to 102 years (see Amundadottir et al. 2 for a more detailed description of the Icelandic study population). The male controls were absent from the nationwide list of prostate cancer patients according to the ICR.

The study was approved by the Data Protection Commission of Iceland and the National Bioethics Committee of Iceland. Written informed consent was obtained from all patients, relatives and controls. Personal identifiers associated with medical information and blood samples were encrypted with a third-party encryption system as previously described[28].

Dutch, Spanish, and U.S. Study Populations.

The total number of Dutch prostate cancer cases in this study was 1,013 of which 999 (98%) were successfully genotyped. The Dutch study population was comprised of two recruitment-sets of prostate cancer cases; Group-A was comprised of 390 hospital-based cases recruited from January 1999 to June 2006 at the Urology Outpatient Clinic of the Radboud University Nijmegen Medical Centre (RUNMC); Group-B consisted of 623 cases recruited from June 2006 to December 2006 through a population-based cancer registry held by the Comprehensive Cancer Centre IKO. Both groups were of self-reported European descent. The average age at diagnosis for patients in Group-A was 63 years (median 63 years) and the range was from 43 to 83 years. The average age at diagnosis for patients in Group-B was 65 years (median 66 years) and the range was from 43 to 75 years. The 1,466 control individuals were cancer free and were matched for age with the cases. They were recruited within a project entitled "The Nijmegen Biomedical Study", in the Netherlands. This is a population-based survey conducted by the Department of Epidemiology and Biostatistics and the Department of Clinical Chemistry of the RUNMC, in which 9,371 individuals participated from a total of 22,500 age and sex stratified, randomly selected inhabitants of Nijmegen. Control individuals from the Nijmegen Biomedical Study were invited to participate in a study on gene-environment interactions in multifactorial diseases, such as cancer. All the 1,466 participants in the present study are of self-reported European descent and were fully informed about the goals and the procedures of the study. The study protocol was approved by the Institutional Review Board of Radboud University and all study subjects gave written informed consent.

The Spanish study population consisted of 464 prostate cancer cases of which 456 (98%) were successfully genotyped. The cases were recruited from the Oncology Department of Zaragoza Hospital in Zaragoza, Spain, from June 2005 to September 2006. All patients were of self-reported European descent. Clinical information including age at onset, grade and stage was obtained from medical records. The average age at diagnosis for the patients was 69 years (median 70 years) and the range was from 44 to 83 years. The 1,078 Spanish control individuals were approached at the University Hospital in Zaragoza, Spain, and were confirmed to be prostate cancer free before they were included in the study. Study protocols were approved by the Institutional Review Board of Zaragoza University Hospital. All subjects gave written informed consent.

The Chicago study population consisted of 557 prostate cancer cases of which 537 (96%) were successfully genotyped. The cases were recruited from the Pathology Core of Northwestern University's Prostate Cancer Specialized Program of Research Excellence (SPORE) from May 2002 to September 2006. The average age at diagnosis for the patients was 60 years (median 59 years) and the range was from 39 to 87 years. The 514 European American controls were recruited as healthy control subjects for genetic studies at the University of Chicago and Northwestern University Medical School, Chicago, US. Study protocols were approved by the Institutional Review Boards of Northwestern University and the University of Chicago. All subjects gave written informed consent.

Statistical Analysis

Association Analysis.

All Icelandic case- and control-samples were assayed with the Infinium HumanHap300 SNP chip (Illumina, San Diego, Calif., USA). This chip contains 317,503 SNPs and provides about 75% genomic coverage in the Utah CEPH (CEU) HapMap samples for common SNPs at $r^2 \geq 0.8$. For the association analysis, 310,520 SNPs were used since, 6,983 SNPs were deemed unusable due to reasons that include being monomorphic, having low yield (<95%) and failure of Hardy-Weinberg equilibrium (HWE). Samples with a call rate below 98% were excluded from the analysis. Single SNP genotyping for the five SNPs reported here and the four case-control groups was carried out by deCODE Genetics in Reykjavik, Iceland applying the Centaurus (Nanogen) platform to all populations studied. The concordance rate of genotypes from the Illumina platform compared to the Centaurus platform, for the 5 SNPs genotyped by both methods in 1,501 cases and 758 controls form Iceland, turned out to be >99.5%.

For SNPs that were in strong LD, whenever the genotype of one SNP was missing for an individual, the genotypes of the correlated SNP were used to provide partial information through a likelihood approach as we have done before[2]. This ensured that results presented herein were always based on the same number of individuals, allowing meaningful comparisons of results for highly correlated SNPs. A likelihood procedure described in a previous publication[29] and implemented in the NEMO software was used for the association analyses. An attempt was made to genotype all individuals and all SNPs reported herein (Tables 4-5). For each of the SNPs, the yield was higher than 95% in every group. The only exception was in the case of the refinement marker rs4430796 which was not a part of the Human Hap 300 chip. There, using a single SNP assay to genotype, attempts were made for 1,883 of the 11,290 Icelandic controls (yielding 1,860), and in all Icelandic cases and all individuals from the replication groups. Most importantly, for the 17q12 locus, we note that when we evaluated the significance of one SNP (e.g. rs4430796, rs7501939 or rs3760511) with adjustment for one or two other SNPs, whether we used all 11,289 Icelandic controls that had genotypes for at least one of the three markers in Table 4a and handled the missing data by applying a likelihood approach as mentioned above, or by applying logistic regression to only individuals that had genotypes for all three markers, the resulting P values are very similar. We tested the association of an allele to prostate cancer using a standard likelihood ratio statistic that, if the subjects were unrelated, would have asymptotically a chi-square distribution with one degree of freedom under the null hypothesis. Allele-specific ORs and associated P values were calculated assuming a multiplicative model for the two chromosomes of an individual[30]. For each of the four case-control groups there was no significant deviation from HWE in the controls (P>0.01). When estimating genotype specific OR (Table 5) genotype frequencies in the population were estimated assuming HWE. We feel that this estimate is more stable than an estimate calculated using the observed genotype counts in controls directly. It is however noted that these two approaches gave very similar estimates in this instance. Results from multiple case-control groups were combined using a Mantel-Haenszel model[31] in which the groups were allowed to have different population frequencies for alleles, haplotypes and genotypes but were assumed to have common relative risks. All four of the European sample groups include both male and female controls. No significant difference between male and female controls was detected for SNPs presented in Table 2 and 3 for each of the groups after correction for the number of tests performed. We note that for all the three significant variants (rs7501939, rs4430796 and rs1859962) reported in Table 2, no significant differences in frequencies were detected among the disease groups (see description of Icelandic study population) that make up the Icelandic genome wide control sets (P=0.30, 0.55 and 0.88 respectively). The T2D individuals were removed when this test was performed for rs7501939 and rs4430796. A linear regression was used to estimate the relationship between age at onset for prostate cancer and number of copies of at-risk alleles, for rs7501939 and rs1859962, carried by cases and using group as an indicator.

To investigate potential interaction between rs7501939 C and rs1859962 G located at 17q12 and 17q24.3, respectively, we performed two analyses. First we checked for the absence of significant correlation between those alleles among cases. Secondly, by using a logistic regression we demonstrated that the interaction term is not significant (P=0.57).

We note that for the SNP rs757210, Winckler et. al[20] report the results for allele A. However, in the main text we provide their corresponding results for the other one (allele G of rs757210) because that allele was the one positively correlated to allele C of rs7501939 reported by us.

Correction for Relatedness and Genomic Control.

Some of the individuals in the Icelandic case-control groups were related to each other, causing the aforementioned chi-square test statistic to have a mean>1 and median> $(0.675)^2$. We estimated the inflation factor in 2 ways: (i) using a previously described procedure where we simulated genotypes through the genealogy of 708,683 Icelanders[32] and (ii) by calculating the average of the 310,520 chi-square statistics, which was a method of genomic control[6] to adjust for both relatedness and potential population stratification. The inflation factors, estimated by (i) and (ii), were 1.084 and 1.098, respectively. The differences among these 2 estimates were not statistically significant. Results presented are based on adjusting the chi-square statistics by dividing each of them by 1.098.

TABLE 3

Characteristics of prostate cancer cases and controls from four sources

| Study Population | Cases | Controls | Aggressive[a] (%) | Mean age at diagnosis (range) | Age at diagnosis <65 years (%) |
|---|---|---|---|---|---|
| Iceland | 1,501 | 11,290 | 50 | 70.8 (40-96) | 22 |
| Nijmegen, the Netherlands | 999 | 1,466 | 47 | 64.2 (43-83) | 52 |
| Zaragoza, Spain | 456 | 1,078 | 37 | 69.3 (44-83) | 19 |
| Chicago, U.S. | 537 | 514 | 48 | 59.6 (39-87) | 70 |
| Total: | 3,493 | 14,348 | | | |

[a]Aggressive is determined here as cancers with Gleason scores of 7 or higher AND/OR Stage of T3 or higher AND/OR node positive disease AND/OR metastatic disease.

TABLE 4a

Association results for SNPs on 17q and prostate cancer in Iceland, the Netherlands, Spain and the US

| Location | Variant (allele) | Study population (N cases/N controls) Frequency Cases | Controls | OR (95% CI) | P value |
|---|---|---|---|---|---|
| 17q12 | Iceland (1,501/11,289) | | | | |
| | rs7501939 (C) | 0.615 | 0.578 | 1.17 (1.08-1.27) | $1.8 \times 10^{-4}$ |
| | rs3760511 (C) | 0.384 | 0.348 | 1.17 (1.08-1.27) | $1.6 \times 10^{-4}$ |
| | rs4430796 (A) | 0.558 | 0.512 | 1.20 (1.11-1.31) | $1.4 \times 10^{-5}$ |
| | The Netherlands (997/1,464) | | | | |
| | rs7501939 (C) | 0.648 | 0.589 | 1.29 (1.15-1.45) | $2.4 \times 10^{-5}$ |
| | rs3760511 (C) | 0.362 | 0.338 | 1.11 (0.99-1.25) | 0.086 |
| | rs4430796 (A) | 0.568 | 0.508 | 1.28 (1.14-1.43) | $3.1 \times 10^{-5}$ |
| | Spain (456/1,078) | | | | |
| | rs7501939 (C) | 0.583 | 0.566 | 1.07 (0.92-1.26) | 0.37 |
| | rs3760511 (C) | 0.277 | 0.257 | 1.11 (0.93-1.32) | 0.25 |
| | rs4430796 (A) | 0.469 | 0.454 | 1.06 (0.91-1.24) | 0.45 |
| | Chicago (536/514) | | | | |
| | rs7501939 (C) | 0.637 | 0.588 | 1.15 (1.03-1.47) | 0.021 |
| | rs3760511 (C) | 0.347 | 0.294 | 1.28 (1.06-1.54) | $9.4 \times 10^{-3}$ |
| | rs4430796 (A) | 0.563 | 0.477 | 1.41 (1.19-1.67) | $9.4 \times 10^{-5}$ |
| | All excluding Iceland (1,989/3,056)[a] | | | | |
| | rs7501939 (C) | — | 0.581 | 1.21 (1.12-1.32) | $5.6 \times 10^{-6}$ |
| | rs3760511 (C) | — | 0.296 | 1.15 (1.05-1.25) | $2.4 \times 10^{-3}$ |
| | rs4430796 (A) | — | 0.480 | 1.24 (1.14-1.35) | $2.02 \times 10^{-7}$ |
| | All combined (3,490/14,345)[a] | | | | |
| | rs7501939 (C) | — | 0.580 | 1.19 (1.12-1.26) | $4.7 \times 10^{-9}$ |
| | rs3760511 (C) | — | 0.309 | 1.16 (1.09-1.23) | $1.4 \times 10^{-6}$ |
| | rs4430796 (A) | — | 0.488 | 1.22 (1.15-1.30) | $1.4 \times 10^{-11}$ |

All P values shown are two-sided. Shown are the corresponding numbers of cases and controls (N), allelic frequencies of variants in affected and control individuals, the allelic odds-ratio (OR) with 95% confidence interval (CI 95%) and P values based on the multiplicative model.
[a]For the combined study populations, the reported control frequency was the average, unweighted control frequency of the individual populations, while the OR and the P value were estimated using the Mantel-Haenszel model.

TABLE 4b

Association results for SNPs on 17q and prostate cancer in Iceland, the Netherlands, Spain and the US

| Location | Variant (allele) | Study population (N cases/N controls) Frequency Cases | Controls | OR (95% CI) | P value |
|---|---|---|---|---|---|
| 17q24.3 | Iceland (1,501/11,290) | | | | |
| | rs1859962 (G) | 0.489 | 0.453 | 1.16 (1.07-1.26) | $3.1 \times 10^{-4}$ |
| | rs7214479 (T) | 0.451 | 0.415 | 1.16 (1.07-1.26) | $3.3 \times 10^{-4}$ |

TABLE 4b-continued

Association results for SNPs on 17q and prostate cancer in Iceland, the Netherlands, Spain and the US

| Location | Study population (N cases/N controls) Variant (allele) | Frequency Cases | Frequency Controls | OR (95% CI) | P value |
|---|---|---|---|---|---|
| | rs6501455 (A) | 0.538 | 0.501 | 1.16 (1.07-1.26) | $3.0 \times 10^{-4}$ |
| | rs983085 (C)[b] | 0.542 | 0.504 | 1.16 (1.07-1.26) | $2.0 \times 10^{-4}$ |
| | The Netherlands (999/1,466) | | | | |
| | rs1859962 (G) | 0.522 | 0.456 | 1.30 (1.16-1.46) | $6.8 \times 10^{-6}$ |
| | rs7214479 (T) | 0.474 | 0.428 | 1.20 (1.07-1.35) | $1.5 \times 10^{-3}$ |
| | rs6501455 (A) | 0.544 | 0.488 | 1.25 (1.12-1.40) | $1.1 \times 10^{-4}$ |
| | Spain (456/1,078) | | | | |
| | rs1859962 (G) | 0.512 | 0.476 | 1.15 (0.99-1.35) | 0.071 |
| | rs7214479 (T) | 0.455 | 0.426 | 1.13 (0.96-1.32) | 0.14 |
| | rs6501455 (A) | 0.581 | 0.552 | 1.13 (0.97-1.32) | 0.13 |
| | Chicago (537/510) | | | | |
| | rs1859962 (G) | 0.513 | 0.456 | 1.25 (1.06-1.49) | $9.8 \times 10^{-3}$ |
| | rs7214479 (T) | 0.460 | 0.416 | 1.20 (1.01-1.42) | 0.041 |
| | rs6501455 (A) | 0.549 | 0.586 | 0.86 (0.72-1.02) | 0.083 |
| | All excluding Iceland (1,992/3,054)[a] | | | | |
| | rs1859962 (G) | — | 0.463 | 1.25 (1.15-1.35) | $8.3 \times 10^{-8}$ |
| | rs7214479 (T) | — | 0.423 | 1.18 (1.09-1.28) | $7.0 \times 10^{-5}$ |
| | rs6501455 (A) | — | 0.542 | 1.12 (1.05-1.20) | $6.2 \times 10^{-3}$ |
| | All combined (3,493/14,344)[a] | | | | |
| | rs1859962 (G) | — | 0.460 | 1.20 (1.14-1.27) | $2.5 \times 10^{-10}$ |
| | rs7214479 (T) | — | 0.421 | 1.17 (1.10-1.24) | $8.1 \times 10^{-8}$ |
| | rs6501455 (A) | — | 0.532 | 1.14 (1.08-1.21) | $6.9 \times 10^{-6}$ |

All P values shown are two-sided. Shown are the corresponding numbers of cases and controls (N), allelic frequencies of variants in affected and control individuals, the allelic odds-ratio (OR) with 95% confidence interval (95% CI) and P values based on the multiplicative model.

[a]For the combined study populations, the reported control frequency was the average, unweighted control frequency of the individual populations, while the OR and the P value were estimated using the Mantel-Haenszel model.

[b]The SNPs, rs983085 and rs6501455 were almost perfectly correlated ($r^2 = 0.99$) but rs983085 failed in genotyping in the non-Icelandic groups.

TABLE 5

Model-free estimates of the genotype odds ratio of rs4430796 (A) at 17q12 and rs1859962 (G) at 17q24.3.

| Study group Variant (allele) | Allelic OR | Genotype odds ratio[a] 00 | 0X (95% CI) | XX (95% CI) | P value[b] | P value[c] | PAR |
|---|---|---|---|---|---|---|---|
| Iceland | | | | | | | |
| rs4430796 (A) | 1.20 | 1 | 1.12 (0.97-1.29) | 1.40 (1.19-1.64) | 0.31 | $8.3 \times 10^{-5}$ | 0.14 |
| rs1859962 (G) | 1.16 | 1 | 1.35 (1.18-1.54) | 1.33 (1.13-1.57) | $3.4 \times 10^{-3}$ | $2.3 \times 10^{-5}$ | 0.19 |
| All except Iceland | | | | | | | |
| rs4430796 (A) | 1.24 | 1 | 1.34 (1.18-1.52) | 1.56 (1.32-1.84) | 0.12 | $4.5 \times 10^{-7}$ | 0.23 |
| rs1859962 (G) | 1.25 | 1 | 1.32 (1.17-1.49) | 1.57 (1.33-1.84) | 0.24 | $2.9 \times 10^{-7}$ | 0.22 |
| All combined | | | | | | | |
| rs4430796 (A) | 1.22 | 1 | 1.24 (1.13-1.36) | 1.48 (1.32-1.66) | 0.57 | $2.0 \times 10^{-10}$ | 0.19 |
| rs1859962 (G) | 1.20 | 1 | 1.33 (1.21-1.44) | 1.45 (1.29-1.62) | $6.0 \times 10^{-3}$ | $5.1 \times 10^{-11}$ | 0.21 |

[a]Genotype odds ratios for heterozygous-(0X) and homozygous carriers (XX) compared with non-carriers (00).
[b]Test of the multiplicative model (the null hypothesis) versus the full model, one degree of freedom.
[c]Test of no effect (the null hypothesis) versus the full model, two degrees of freedom. PAR, population attributable risk, OR, odds ratio, CI 95%, 95% confidence interval.

TABLE 6

Association results for SNPs in the TCF2 gene on 17q12 and type 2 diabetes

| Location | Study population (N cases/N controls) Variant (allele) | Frequency Cases | Frequency Controls | OR (95% CI) | P value |
|---|---|---|---|---|---|
| 17q12 | Iceland[a] (1,380/9,940) | | | | |
| | rs7501939 (C) | 0.549 | 0.582 | 0.88 (0.80-0.96) | 0.0045 |
| | rs4430796 (A) | 0.482 | 0.521 | 0.86 (0.78-0.95) | 0.0021 |
| | Denmark A (264/596) | | | | |
| | rs7501939 (C) | 0.525 | 0.593 | 0.76 (0.62-0.93) | 0.0088 |
| | rs4430796 (A) | 0.452 | 0.530 | 0.73 (0.60-0.90) | 0.0032 |
| | Denmark B (1,365/4,843) | | | | |
| | rs7501939 (C) | 0.579 | 0.596 | 0.93 (0.85-1.02) | 0.11 |
| | rs4430796 (A) | 0.507 | 0.528 | 0.92 (0.85-1.00) | 0.062 |
| | Philadelphia, US (457/967) | | | | |
| | rs7501939 (C) | 0.569 | 0.613 | 0.83 (0.71-0.98) | 0.028 |
| | rs4430796 (A) | 0.477 | 0.527 | 0.82 (0.70-0.96) | 0.013 |
| | Scotland (3,741/3,718) | | | | |
| | rs7501939 (C) | 0.607 | 0.615 | 0.97 (0.91-1.03) | 0.31 |
| | rs4430796 (A) | 0.517 | 0.526 | 0.97 (0.91-1.03) | 0.29 |
| | The Netherlands (367/915) | | | | |
| | rs7501939 (C) | 0.563 | 0.579 | 0.94 (0.79-1.11) | 0.46 |
| | rs4430796 (A) | 0.494 | 0.506 | 0.95 (0.79-1.14) | 0.58 |
| | Hong Kong (1,495/993) | | | | |
| | rs7501939 (C) | 0.768 | 0.791 | 0.87 (0.76-1.00) | 0.054 |
| | rs4430796 (A) | 0.731 | 0.754 | 0.89 (0.78-1.01) | 0.073 |
| | West Africa[b] (867/1,115) | | | | |
| | rs7501939 (C) | 0.400 | 0.437 | 0.87 (0.77-0.99) | 0.042 |
| | rs4430796 (A) | 0.271 | 0.313 | 0.80 (0.69-0.92) | 0.0024 |
| | All groups combined exclud. Iceland | | | | |
| | rs7501939 (C) | — | — | 0.91 (0.87-0.95) | $3.4 \times 10^{-5}$ |
| | rs4430796 (A) | — | — | 0.92 (0.88-0.95) | $1.8 \times 10^{-5}$ |
| | All groups combined (9,936/23,087) | | | | |
| | rs7501939 (C) | — | — | 0.91 (0.87-0.94) | $9.2 \times 10^{-7}$ |
| | rs4430796 (A) | — | — | 0.91 (0.87-0.94) | $2.7 \times 10^{-7}$ |

All P values shown are two-sided. Shown are the corresponding numbers of cases and controls (N), allelic frequencies of variants in affected and control individuals, the allelic odds-ratio (OR) with 95% confidence interval (95% CI) and P values based on the multiplicative model.
[a]Known prostate cancer patients have been excluded from the Icelandic T2D cases and controls
[b]Results for the 5 West African tribes have been combined using a Mantel-Haenszel method. The frequency of the variant in West African cases and controls is the weighted average over the 5 tribes.

REFERENCES

1. Parkin, D. M., Bray, F., Ferlay, J. & Pisani, P. Global cancer statistics, 2002. *CA Cancer J Clin* 55, 74-108 (2005).
2. Amundadottir, L. T. et al. A common variant associated with prostate cancer in European and African populations. *Nat Genet* 38, 652-8 (2006).
3. Gudmundsson, J. A second cancer susceptibility variant at 8q24 identified through a genome-wide association study. *Nature Genetics* 39 (2007).
4. Haiman, C. A. et al. Multiple regions within 8q24 independently affect risk for prostate cancer. *Nat Genet* 39 (2007).
5. Yeager, M. et al. Genome-wide association study of prostate cancer identifies a second risk locus at 8q24. *Nat Genet* 39 (2007).
6. Devlin, B. & Roeder, K. Genomic Control for association studies. *Biometrics* 55, 997-1004 (1999).
7. Roeder, K., Bacanu, S. A., Wasserman, L. & Devlin, B. Using linkage genome scans to improve power of association in genome scans. *Am J Hum Genet.* 78, 243-52 Epub 2006 Jan. 3 (2006).
8. Lange, E. M. et al. Genome-wide scan for prostate cancer susceptibility genes using families from the University of Michigan prostate cancer genetics project finds evidence for linkage on chromosome 17 near BRCA1. *Prostate* 57, 326-34 (2003).
9. Xu, J. et al. A combined genomewide linkage scan of 1,233 families for prostate cancer-susceptibility genes conducted by the international consortium for prostate cancer genetics. *Am J Hum Genet* 77, 219-29 (2005).
10. Lange, E. M. et al. Fine-mapping the putative chromosome 17q21-22 prostate cancer susceptibility gene to a 10 cM region based on linkage analysis. *Hum Genet* 121, 49-55 (2007).
11. Zuhike, K. A. et al. Truncating BRCA1 mutations are uncommon in a cohort of hereditary prostate cancer families with evidence of linkage to 17q markers. *Clin Cancer Res* 10, 5975-80 (2004).
12. Kraft, P. et al. Genetic variation in the HSD17B1 gene and risk of prostate cancer. *PLoS Genet* 1, e68 (2005).
13. White, K. A., Lange, E. M., Ray, A. M., Wojno, K. J. & Cooney, K. A. Prohibitin mutations are uncommon in pros- 13. tate cancer families linked to chromosome 17q. *Prostate Cancer Prostatic Dis* 9, 298-302 (2006).
14. Rebouissou, S. et al. Germline hepatocyte nuclear factor 1alpha and 1beta mutations in renal cell carcinomas. *Hum Mol Genet.* 14, 603-14 (2005).
15. Terasawa, K. et al. Epigenetic inactivation of TCF2 in ovarian cancer and various cancer cell lines. *Br J Cancer* 94, 914-21 (2006).
16. Bellanne-Chantelot, C. et al. Large genomic rearrangements in the hepatocyte nuclear factor-1beta (TCF2) gene are the most frequent cause of maturity-onset diabetes of the young type 5. *Diabetes* 54, 3126-32 (2005).
17. Edghill, E. L., Bingham, C., Ellard, S. & Hattersley, A. T. Mutations in hepatocyte nuclear factor-1beta and their related phenotypes. *J Med Genet* 43, 84-90 (2006).
18. Silander, K. et al. Genetic variation near the hepatocyte nuclear factor-4 alpha gene predicts susceptibility to type 2 diabetes. *Diabetes* 53, 1141-9 (2004).
19. Bonnycastle, L. L. et al. Common variants in maturity-onset diabetes of the young genes contribute to risk of type 2 diabetes in Finns. *Diabetes* 55, 2534-40 (2006).
20. Winckler, W. et al. Evaluation of Common Variants in the Six Known Maturity-Onset Diabetes of the Young (MODY) Genes for Association With Type 2 Diabetes. *Diabetes* 56, 685-93 (2007).
21. Kasper, J. S. & Giovannucci, E. A meta-analysis of diabetes mellitus and the risk of prostate cancer. *Cancer Epidemiol Biomarkers Prev* 15, 2056-62 (2006).
22. Hill-Harfe, K. L. et al. Fine mapping of chromosome 17 translocation breakpoints> or =900 Kb upstream of SOX9 in acampomelic campomelic dysplasia and a mild, familial skeletal dysplasia. *Am J Hum Genet* 76, 663-71 (2005).
23. Koopman, P. Sex determination: a tale of two Sox genes. *Trends Genet* 21, 367-70 (2005).
24. Wang, H. et al. SOX9 is expressed in normal prostate basal cells and regulates androgen receptor expression in prostate cancer cells. *Cancer Res* 67, 528-36 (2007).
25. Leipoldt, M. et al. Two novel translocation breakpoints upstream of SOX9 define borders of the proximal and distal breakpoint cluster region in campomelic dysplasia. *Clin Genet* 71, 67-75 (2007).
26. Velagaleti, G. V. et al. Position effects due to chromosome breakpoints that map approximately 900 Kb upstream and approximately 1.3 Mb downstream of SOX9 in two patients with campomelic dysplasia. *Am J Hum Genet* 76, 652-62 (2005).
27. Drivdahl, R. et al. Suppression of growth and tumorigenicity in the prostate tumor cell line M12 by overexpression of the transcription factor SOX9. *Oncogene* 23, 4584-93 (2004).
28. Gulcher, J. R., Kristjansson, K., Gudbjartsson, H. & Stefansson, K. Protection of privacy by third-party encryption in genetic research in Iceland. *Eur J Hum Genet* 8, 739-42 (2000).
29. Gretarsdottir, S. et al. The gene encoding phosphodiesterase 4D confers risk of ischemic stroke. *Nat Genet.* 35, 131-8 (2003).
30. Falk, C. T. & Rubinstein, P. Haplotype relative risks: an easy reliable way to construct a proper control sample for risk calculations. *Ann Hum Genet* 51 (Pt 3), 227-33 (1987).
31. Mantel, N. & Haenszel, W. Statistical aspects of the analysis of data from retrospective studies of disease. *J Natl Cancer Inst.* 22, 719-48 (1959).
32. Grant, S. F. et al. Variant of transcription factor 7-like 2 (TCF7L2) gene confers risk of type 2 diabetes. *Nat Genet.* 38, 320-3 Epub 2006 Jan. 15 (2006).

Example 3

Surrogate Markers in Regions Showing Association to Prostate Cancer

There are several SNP markers at each locus, either within or close by the LD block in which the anchor SNP is located, that are in strong LD with the SNP markers listed in the above.

The following therefore contains tables and markers lists that are within the scope of the invention. The tables thus list markers that are in LD, as determined by values of $r^2$ in the HapMap CEU population, of greater than 0.2. The tables furthermore list all markers within the LD blocks defined by the present invention. The markers that have been genotyped and assessed by the HapMap do not represent a full coverage of all relevant markers in the regions defined by the invention as being associating with Prostate Cancer. It is thus possible that other markers, such as the markers listed in the below, can be suitably used to assess susceptibility to Prostate Cancer, as described herein.

TABLE 7

SNPs from Chromosome 4q31.21 (within +/− 500 kb of marker rs3923603 in NCBI Build 35), correlated with rs3923603 by $R^2 > 0.2$. The SNPs were identified in the Caucasian CEU HapMap Release 22 dataset (http colon-slash-slash www.hapmap.org).

| Marker | SEQ ID NO | D' | $R^2$ | P-value | Location Build 34 | Location Build 35 |
|---|---|---|---|---|---|---|
| rs6857262 | 343 | 0.609387 | 0.228352 | 1.59E−06 | 145603677 | 145245500 |
| rs6857303 | 9 | 0.651749 | 0.245545 | 4.02E−07 | 145613415 | 145255238 |
| rs7665923 | 10 | 0.616231 | 0.222462 | 7.95E−07 | 145620837 | 145262660 |
| rs11725211 | 11 | 0.596965 | 0.211993 | 2.63E−06 | 145629733 | 145271556 |
| rs13103731 | 12 | 0.600312 | 0.205637 | 2.89E−06 | 145634114 | 145275937 |
| rs11736498 | 13 | 0.616231 | 0.222462 | 7.95E−07 | 145635911 | 145277734 |
| rs11723763 | 14 | 0.616231 | 0.222462 | 7.95E−07 | 145635923 | 145277746 |
| rs6831817 | 15 | 0.601493 | 0.201387 | 0.00001 | 145655091 | 145296914 |
| rs13134172 | 16 | 1 | 0.583822 | 2.33E−20 | 145676737 | 145318560 |
| rs10015396 | 17 | 1 | 1 | 5.98E−34 | 145677193 | 145319016 |
| rs4269130 | 18 | 1 | 1 | 4.05E−34 | 145679051 | 145320874 |
| rs4289393 | 19 | 1 | 0.410609 | 1.47E−15 | 145679688 | 145321511 |
| rs6812128 | 20 | 1 | 0.426434 | 5.10E−15 | 145679891 | 145321714 |
| rs7695923 | 21 | 1 | 0.962477 | 2.03E−32 | 145695407 | 145337230 |
| rs4599356 | 22 | 1 | 1 | 1.88E−34 | 145701080 | 145342903 |
| rs7700104 | 344 | 1 | 1 | 1.88E−34 | 145701236 | 145343059 |
| rs4240360 | 345 | 1 | 1 | 1.88E−34 | 145703019 | 145344842 |

TABLE 7-continued

SNPs from Chromosome 4q31.21 (within +/− 500 kb of marker rs3923603 in NCBI Build 35), correlated with rs3923603 by $R^2 > 0.2$. The SNPs were identified in the Caucasian CEU HapMap Release 22 dataset (http colon-slash-slash www.hapmap.org).

| Marker | SEQ ID NO | D' | $R^2$ | P-value | Location Build 34 | Location Build 35 |
|---|---|---|---|---|---|---|
| rs7692784 | 23 | 0.881426 | 0.304643 | 7.51E−10 | 145707723 | 145349546 |
| rs4303930 | 24 | 0.881426 | 0.304643 | 7.51E−10 | 145713152 | 145354975 |
| rs10012731 | 25 | 0.871279 | 0.299448 | 4.18E−09 | 145714018 | 145355841 |
| rs4417920 | 27 | 0.873144 | 0.280005 | 5.98E−09 | 145717918 | 145359741 |
| rs4505762 | 28 | 0.872158 | 0.296753 | 4.74E−09 | 145718312 | 145360135 |
| rs4583707 | 29 | 0.881426 | 0.304643 | 7.51E−10 | 145718503 | 145360326 |
| rs4425324 | 30 | 0.838714 | 0.361322 | 2.16E−10 | 145719771 | 145361594 |
| rs13127749 | 31 | 0.827215 | 0.53055 | 1.22E−15 | 145722949 | 145364772 |
| rs4518185 | 32 | 0.74467 | 0.226665 | 8.95E−07 | 145723537 | 145365360 |
| rs4549337 | 33 | 0.711728 | 0.212389 | 1.19E−06 | 145724777 | 145366600 |
| rs4390989 | 34 | 0.714302 | 0.226767 | 4.20E−07 | 145725942 | 145367765 |
| rs4305469 | 35 | 0.73105 | 0.239544 | 8.48E−08 | 145726592 | 145368415 |
| rs7658605 | 36 | 0.711728 | 0.212389 | 1.19E−06 | 145728645 | 145370468 |
| rs6828217 | 37 | 0.73105 | 0.239544 | 8.48E−08 | 145739816 | 145381639 |
| rs12505797 | 39 | 0.73105 | 0.239544 | 8.48E−08 | 145751840 | 145393663 |
| rs12503177 | 40 | 0.73105 | 0.239544 | 8.48E−08 | 145751969 | 145393792 |
| rs4482709 | 41 | 0.711728 | 0.212389 | 1.19E−06 | 145752289 | 145394112 |
| rs4320096 | 42 | 0.720957 | 0.238928 | 4.38E−07 | 145752702 | 145394525 |
| rs13144823 | 43 | 0.711728 | 0.212389 | 1.19E−06 | 145754060 | 145395883 |
| rs11100843 | 44 | 0.784071 | 0.458305 | 3.28E−13 | 145755309 | 145397132 |
| rs7679401 | 45 | 0.729175 | 0.247715 | 1.03E−07 | 145759776 | 145401599 |
| rs7684835 | 46 | 0.713635 | 0.235294 | 6.39E−07 | 145760207 | 145402030 |
| rs11943703 | 47 | 0.821897 | 0.281314 | 1.08E−08 | 145761006 | 145402829 |
| rs12509569 | 48 | 0.701656 | 0.205626 | 2.56E−06 | 145763289 | 145405112 |
| rs12510585 | 346 | 0.711728 | 0.212389 | 1.19E−06 | 145770366 | 145412189 |
| rs7689179 | 49 | 0.705517 | 0.398424 | 1.37E−11 | 145773276 | 145415099 |
| rs10002827 | 50 | 0.506653 | 0.208441 | 0.000013 | 145790721 | 145432544 |

TABLE 8

SNPs from Chromosome 17q12 (within +/− 500 kb of marker rs7501939 in NCBI Build 35), correlated with rs7501939 by $R^2 > 0.2$. The SNPs were identified in the Caucasian CEU HapMap Release 22 dataset (http colon-slash-slash www.hapmap.org).

| Marker | SEQ ID NO | D' | $R^2$ | P-value | Location Build 34 | Location Build 35 |
|---|---|---|---|---|---|---|
| rs1016990 | 51 | 0.50554 | 0.229681 | 2.18E | 36284465 | 33163028 |
| rs3744763 | 52 | 0.60072 | 0.315757 | 4.11E | 36286435 | 33164998 |
| rs2005705 | 347 | 0.855936 | 0.641047 | 2.19E | 36291850 | 33170413 |
| rs757210 | 53 | 0.963829 | 0.81187 | 1.86E | 36292065 | 33170628 |
| rs4430796 | 2 | 1 | 0.765625 | 2.13E | 36293590 | 33172153 |
| rs4239217 | 54 | 0.965889 | 0.902185 | 6.03E | 36294537 | 33173100 |
| rs7405696 | 348 | 1 | 0.558059 | 4.17E | 36297585 | 33176148 |
| rs3760511 | 55 | 1 | 0.291667 | 9.22E | 36301863 | 33180426 |
| rs7213769 | 56 | 0.75348 | 0.218821 | 6.62E | 36310716 | 33189279 |

TABLE 9

SNPs from Chromosome 17q24.3 within +/− 500 kb of marker rs1859962 in NCBI Build 35), correlated with rs1859962 by $R^2 > 0.2$. The SNPs were identified in the Caucasian CEU HapMap Release 22 dataset (http colon-slash-slash www.hapmap.org).

| Marker | SEQ ID No: | D' | R2 | P-value | Location Build 34 | Location Build 35 |
|---|---|---|---|---|---|---|
| rs4793330 | 57 | 0.632925 | 0.229843 | 1.41E−06 | 69667720 | 66582192 |
| rs1861690 | 58 | 0.624718 | 0.240049 | 1.86E−07 | 69669376 | 66583848 |
| rs7222314 | 59 | 0.966081 | 0.933295 | 1.68E−31 | 69702061 | 66616533 |
| rs17765344 | 349 | 1 | 1 | 1.90E−37 | 69703997 | 66618469 |
| rs8071558 | 60 | 1 | 1 | 1.90E−37 | 69704796 | 66619268 |
| rs8072254 | 350 | 1 | 1 | 1.90E−37 | 69704939 | 66619411 |
| rs984434 | 61 | 1 | 1 | 1.90E−37 | 69705250 | 66619722 |
| rs11650165 | 62 | 1 | 0.633803 | 1.75E−22 | 69706741 | 66621213 |
| rs991429 | 63 | 1 | 1 | 1.90E−37 | 69706896 | 66621368 |
| rs4793528 | 64 | 1 | 0.633803 | 1.75E−22 | 69707896 | 66622368 |
| rs9674957 | 65 | 1 | 0.633803 | 1.75E−22 | 69708221 | 66622693 |
| rs8077906 | 66 | 1 | 0.543014 | 2.20E−19 | 69709356 | 66623828 |
| rs8066875 | 67 | 1 | 0.543014 | 2.20E−19 | 69710700 | 66625172 |

TABLE 9-continued

SNPs from Chromosome 17q24.3 within +/− 500 kb of marker rs1859962 in NCBI Build 35), correlated with rs1859962 by $R^2 > 0.2$. The SNPs were identified in the Caucasian CEU HapMap Release 22 dataset (http colon-slash-slash www.hapmap.org).

| Marker | SEQ ID No: | D' | R2 | P-value | Location Build 34 | Location Build 35 |
| --- | --- | --- | --- | --- | --- | --- |
| rs9889335 | 68 | 1 | 1 | 7.79E−37 | 69712269 | 66626741 |
| rs4328484 | 69 | 1 | 0.633803 | 1.75E−22 | 69713353 | 66627825 |
| rs8068266 | 70 | 1 | 0.966667 | 3.12E−35 | 69714058 | 66628530 |
| rs4793529 | 351 | 1 | 0.966667 | 3.12E−35 | 69715759 | 66630231 |
| rs7217652 | 71 | 0.950239 | 0.500909 | 2.23E−15 | 69716604 | 66631076 |
| rs6501437 | 72 | 1 | 0.736328 | 1.23E−25 | 69717095 | 66631567 |
| rs6501438 | 73 | 1 | 0.729608 | 2.40E−25 | 69717283 | 66631755 |
| rs8079315 | 74 | 1 | 0.736328 | 6.95E−26 | 69717978 | 66632450 |
| rs2367256 | 75 | 1 | 0.72559 | 8.37E−25 | 69718409 | 66632881 |
| rs2190697 | 76 | 1 | 0.723359 | 1.57E−24 | 69718464 | 66632936 |
| rs4366746 | 77 | 1 | 0.703014 | 3.43E−24 | 69718754 | 66633226 |
| rs4366747 | 78 | 1 | 0.707267 | 9.94E−25 | 69718766 | 66633238 |
| rs2159034 | 79 | 1 | 0.7114 | 5.03E−25 | 69718878 | 66633350 |
| rs1013999 | 80 | 1 | 0.707267 | 1.73E−24 | 69719058 | 66633530 |
| rs4793530 | 81 | 1 | 0.7114 | 5.03E−25 | 69722386 | 66636858 |
| rs11654749 | 82 | 0.599655 | 0.281972 | 1.87E−08 | 69722729 | 66637201 |
| rs11653132 | 83 | 0.630676 | 0.353293 | 3.94E−10 | 69726955 | 66641427 |
| rs4300694 | 84 | 0.583272 | 0.249279 | 3.84E−07 | 69727959 | 66642431 |
| rs8076830 | 85 | 1 | 0.7114 | 5.03E−25 | 69729032 | 66643504 |
| rs9900242 | 86 | 0.607515 | 0.286639 | 1.44E−08 | 69732754 | 66647226 |
| rs9908442 | 352 | 0.607515 | 0.286639 | 1.44E−08 | 69735071 | 66649543 |
| rs4793334 | 353 | 0.56962 | 0.257808 | 1.60E−07 | 69735105 | 66649577 |
| rs2058083 | 87 | 0.607515 | 0.286639 | 1.44E−08 | 69735526 | 66649998 |
| rs2058084 | 354 | 0.607515 | 0.286639 | 1.44E−08 | 69736140 | 66650612 |
| rs2058085 | 88 | 0.607515 | 0.286639 | 1.44E−08 | 69736170 | 66650642 |
| rs1468481 | 89 | 1 | 0.340617 | 1.37E−12 | 69737102 | 66651574 |
| rs9915190 | 355 | 0.607515 | 0.286639 | 1.44E−08 | 69739751 | 66654223 |
| rs2041114 | 90 | 1 | 0.7114 | 5.03E−25 | 69741740 | 66656212 |
| rs723338 | 91 | 1 | 0.7114 | 5.03E−25 | 69742536 | 66657008 |
| rs2041115 | 92 | 1 | 0.709159 | 9.41E−25 | 69743550 | 66658022 |
| rs8064263 | 93 | 1 | 0.7114 | 8.79E−25 | 69743953 | 66658425 |
| rs9897865 | 94 | 1 | 0.7114 | 5.03E−25 | 69744199 | 66658671 |
| rs11656242 | 95 | 0.685791 | 0.454632 | 1.88E−13 | 69744645 | 66659117 |
| rs9897358 | 96 | 1 | 0.707267 | 1.73E−24 | 69744665 | 66659137 |
| rs11651123 | 97 | 0.685791 | 0.454632 | 1.88E−13 | 69744714 | 66659186 |
| rs11657298 | 98 | 0.685791 | 0.454632 | 1.88E−13 | 69744759 | 66659231 |
| rs11651469 | 99 | 0.847433 | 0.586131 | 7.42E−18 | 69745642 | 66660114 |
| rs11650501 | 100 | 0.847433 | 0.586131 | 7.42E−18 | 69745681 | 66660153 |
| rs719615 | 101 | 0.710626 | 0.471507 | 9.37E−14 | 69747033 | 66661505 |
| rs1558119 | 102 | 0.68918 | 0.470673 | 1.02E−13 | 69749095 | 66663567 |
| rs12150098 | 103 | 0.685791 | 0.454632 | 1.88E−13 | 69752957 | 66667429 |
| rs9910829 | 104 | 1 | 0.7114 | 5.03E−25 | 69756700 | 66671172 |
| rs7220274 | 105 | 1 | 0.7114 | 5.03E−25 | 69756890 | 66671362 |
| rs17224833 | 106 | 1 | 0.7114 | 5.03E−25 | 69757598 | 66672070 |
| rs2108534 | 107 | 1 | 0.726354 | 4.96E−24 | 69758023 | 66672495 |
| rs2108535 | 108 | 0.715546 | 0.497408 | 4.04E−14 | 69758268 | 66672740 |
| rs8182284 | 109 | 0.667129 | 0.419797 | 1.12E−11 | 69758514 | 66672986 |
| rs8182286 | 110 | 1 | 0.7114 | 8.79E−25 | 69758677 | 66673149 |
| rs4793533 | 111 | 1 | 0.7114 | 8.79E−25 | 69761594 | 66676066 |
| rs8069925 | 112 | 1 | 0.7114 | 5.03E−25 | 69761985 | 66676457 |
| rs8068189 | 113 | 0.813444 | 0.558734 | 7.88E−17 | 69762018 | 66676490 |
| rs9901508 | 114 | 1 | 0.7114 | 5.03E−25 | 69762322 | 66676794 |
| rs9907418 | 115 | 1 | 0.7114 | 5.03E−25 | 69762342 | 66676814 |
| rs2367263 | 116 | 1 | 0.687204 | 3.34E−24 | 69763411 | 66677883 |
| rs1859964 | 117 | 1 | 0.687204 | 3.34E−24 | 69763694 | 66678166 |
| rs1859965 | 118 | 1 | 0.682793 | 6.60E−24 | 69764218 | 66678690 |
| rs6501446 | 119 | 1 | 0.687204 | 3.34E−24 | 69765181 | 66679653 |
| rs4793534 | 120 | 0.648752 | 0.40685 | 4.45E−12 | 69765416 | 66679888 |
| rs4239156 | 121 | 1 | 0.687204 | 3.34E−24 | 69765504 | 66679976 |
| rs4793335 | 122 | 0.679827 | 0.431951 | 9.14E−13 | 69765814 | 66680286 |
| rs2097984 | 123 | 0.673634 | 0.410059 | 4.12E−12 | 69768349 | 66682821 |
| rs11654068 | 124 | 0.71603 | 0.434667 | 2.65E−12 | 69769659 | 66684131 |
| rs8079962 | 125 | 0.958736 | 0.654018 | 6.44E−21 | 69769825 | 66684297 |
| rs6501447 | 356 | 0.958736 | 0.654018 | 6.44E−21 | 69770221 | 66684693 |
| rs2886914 | 126 | 0.67655 | 0.427544 | 1.52E−12 | 69770936 | 66685408 |
| rs8076811 | 127 | 1 | 0.633405 | 1.85E−20 | 69772530 | 66687002 |
| rs17178251 | 128 | 0.647061 | 0.404731 | 8.59E−12 | 69774002 | 66688474 |
| rs17765644 | 357 | 0.679827 | 0.431951 | 9.14E−13 | 69776615 | 66691087 |
| rs9913988 | 358 | 1 | 0.687204 | 3.34E−24 | 69777181 | 66691653 |
| rs758106 | 129 | 1 | 0.687204 | 3.34E−24 | 69778126 | 66692598 |
| rs740408 | 130 | 0.66562 | 0.399756 | 2.17E−11 | 69778219 | 66692691 |
| rs4570900 | 131 | 0.673728 | 0.403728 | 1.72E−10 | 69783489 | 66697961 |

TABLE 9-continued

SNPs from Chromosome 17q24.3 within +/− 500 kb of marker
rs1859962 in NCBI Build 35), correlated with rs1859962 by $R^2 > 0.2$.
The SNPs were identified in the Caucasian CEU
HapMap Release 22 dataset (http colon-slash-slash www.hapmap.org).

| Marker | SEQ ID No: | D' | R2 | P-value | Location Build 34 | Location Build 35 |
|---|---|---|---|---|---|---|
| rs4611499 | 132 | 0.640666 | 0.400741 | 6.36E−12 | 69785892 | 66700364 |
| rs7214479 | 133 | 0.958736 | 0.654018 | 6.44E−21 | 69788072 | 66702544 |
| rs1008348 | 134 | 0.655348 | 0.429398 | 9.50E−13 | 69788439 | 66702911 |
| rs6501449 | 135 | 0.828717 | 0.514834 | 2.28E−14 | 69789968 | 66704440 |
| rs6501451 | 136 | 1 | 0.687204 | 3.34E−24 | 69790254 | 66704726 |
| rs6501452 | 137 | 0.826939 | 0.553522 | 1.68E−14 | 69790410 | 66704882 |
| rs11870732 | 138 | 0.648752 | 0.40685 | 4.45E−12 | 69792364 | 66706836 |
| rs17178370 | 139 | 0.666131 | 0.413925 | 6.76E−12 | 69792664 | 66707136 |
| rs7225025 | 140 | 0.79739 | 0.519604 | 6.69E−15 | 69794797 | 66709269 |
| rs17178377 | 141 | 0.681069 | 0.450817 | 3.20E−13 | 69795256 | 66709728 |
| rs11655744 | 142 | 1 | 0.675693 | 7.14E−23 | 69796179 | 66710651 |
| rs2367266 | 143 | 1 | 0.687204 | 3.34E−24 | 69797110 | 66711582 |
| rs1107305 | 144 | 0.769646 | 0.495603 | 1.89E−14 | 69797766 | 66712238 |
| rs6501455 | 145 | 0.809767 | 0.535236 | 4.42E−16 | 69798934 | 66713406 |
| rs7209505 | 146 | 0.958131 | 0.646852 | 2.29E−20 | 69800787 | 66715259 |
| rs2190463 | 147 | 0.958736 | 0.654018 | 6.44E−21 | 69804591 | 66719063 |
| rs2190456 | 148 | 0.749106 | 0.473517 | 2.05E−12 | 69808489 | 66722961 |
| rs983085 | 149 | 0.774954 | 0.507149 | 3.61E−15 | 69809184 | 66723656 |
| rs6501459 | 150 | 0.648752 | 0.40685 | 4.45E−12 | 69810578 | 66725050 |
| rs4793538 | 151 | 0.635 | 0.392093 | 3.88E−11 | 69813051 | 66727523 |
| rs2158905 | 152 | 0.774114 | 0.50285 | 6.37E−15 | 69813164 | 66727636 |
| rs2190457 | 153 | 0.652378 | 0.421393 | 2.62E−12 | 69813532 | 66728004 |
| rs11655567 | 154 | 0.774954 | 0.507149 | 3.61E−15 | 69813810 | 66728282 |
| rs7225458 | 155 | 0.648752 | 0.40685 | 4.45E−12 | 69815469 | 66729941 |
| rs10401004 | 156 | 0.917182 | 0.587347 | 3.76E−18 | 69815879 | 66730351 |
| rs917278 | 157 | 0.770798 | 0.474348 | 2.58E−14 | 69819048 | 66733520 |
| rs1978203 | 158 | 0.772049 | 0.481569 | 1.74E−14 | 69819792 | 66734264 |
| rs1978204 | 159 | 0.807013 | 0.514618 | 4.54E−15 | 69820068 | 66734540 |
| rs737956 | 160 | 0.914232 | 0.592181 | 5.02E−18 | 69820991 | 66735463 |
| rs737957 | 161 | 0.913582 | 0.572582 | 8.18E−17 | 69821032 | 66735504 |
| rs8075481 | 162 | 0.918433 | 0.595451 | 1.08E−18 | 69821319 | 66735791 |
| rs7224058 | 163 | 0.638679 | 0.396624 | 1.04E−11 | 69822902 | 66737374 |
| rs7215307 | 164 | 0.601503 | 0.352766 | 3.72E−09 | 69823490 | 66737962 |
| rs4793541 | 165 | 0.774954 | 0.507149 | 3.61E−15 | 69824718 | 66739190 |
| rs7221080 | 166 | 0.776722 | 0.504519 | 3.49E−15 | 69827095 | 66741567 |
| rs8064388 | 167 | 0.772049 | 0.481569 | 1.74E−14 | 69828140 | 66742612 |
| rs9906756 | 168 | 0.916614 | 0.57259 | 5.80E−18 | 69833167 | 66747639 |
| rs17178530 | 169 | 0.769449 | 0.479973 | 3.18E−14 | 69833235 | 66747707 |
| rs17765886 | 170 | 0.763227 | 0.477295 | 2.28E−13 | 69833328 | 66747800 |
| rs8070461 | 171 | 0.910313 | 0.547145 | 1.24E−16 | 69837995 | 66752467 |
| rs9891216 | 172 | 0.874632 | 0.520827 | 4.65E−16 | 69840055 | 66754527 |

TABLE 10

SNPs from Chromosome Xp11.22
(within +/− 1500 kb of rs5945572 in NCBI Build 35),
correlated with rs5945572 by $R^2 > 0.2$.
The SNPs were identified in the Caucasian CEU HapMap
Release 22 dataset (http colon-slash-slash www.hapmap.org).

| Marker | SEQ ID No: | D' | $R^2$ | P-value | Location Build 34 | Location Build 35 |
|---|---|---|---|---|---|---|
| rs972635 | 173 | 0.881031 | 0.424148 | 6.97E−12 | 50084494 | 51184428 |
| rs1875754 | 174 | 0.881031 | 0.424148 | 6.97E−12 | 50095192 | 51195126 |
| rs4907772 | 175 | 0.881031 | 0.424148 | 6.97E−12 | 50098347 | 51198281 |
| rs5945605 | 7 | 1 | 0.76906 | 2.30E−23 | 50107288 | 51207222 |
| rs5945606 | 177 | 1 | 0.757565 | 1.68E−22 | 50107963 | 51207897 |
| rs5945569 | 178 | 1 | 0.874668 | 3.64E−26 | 50110017 | 51209951 |
| rs5987418 | 179 | 1 | 0.870142 | 2.86E−25 | 50114019 | 51213953 |
| rs4907790 | 180 | 1 | 0.876757 | 3.46E−26 | 50114517 | 51214451 |
| rs5945607 | 181 | 1 | 0.874668 | 5.64E−26 | 50116514 | 51216448 |
| rs11798651 | 183 | 1 | 0.835656 | 7.47E−25 | 50118401 | 51218335 |
| rs5945609 | 184 | 1 | 0.874668 | 3.64E−26 | 50119272 | 51219206 |
| rs5945610 | 185 | 1 | 0.874668 | 3.64E−26 | 50119351 | 51219285 |
| rs10284147 | 186 | 1 | 0.805955 | 1.72E−24 | 50121302 | 51221236 |
| rs1327301 | 187 | 1 | 0.919246 | 1.83E−28 | 50126863 | 51226797 |
| rs1327302 | 188 | 1 | 1 | 2.99E−33 | 50127421 | 51227355 |
| rs1327304 | 189 | 1 | 1 | 2.99E−33 | 50130982 | 51230916 |

TABLE 10-continued

SNPs from Chromosome Xp11.22
(within +/− 1500 kb of rs5945572 in NCBI Build 35),
correlated with rs5945572 by $R^2 > 0.2$.
The SNPs were identified in the Caucasian CEU HapMap
Release 22 dataset (http colon-slash-slash www.hapmap.org).

| Marker | SEQ ID No: | D' | $R^2$ | P-value | Location Build 34 | Location Build 35 |
|---|---|---|---|---|---|---|
| rs5987421 | 359 | 1 | 1 | 2.07E−32 | 50143296 | 51243230 |
| rs5945617 | 190 | 1 | 1 | 2.99E−33 | 50144027 | 51243961 |
| rs5945618 | 191 | 1 | 1 | 2.99E−33 | 50145357 | 51245291 |
| rs12854262 | 192 | 1 | 0.226378 | 1.56E−07 | 50154146 | 51254080 |
| rs5945619 | 193 | 1 | 0.923404 | 2.93E−29 | 50158478 | 51258412 |
| rs5945620 | 194 | 0.884106 | 0.44477 | 5.44E−12 | 50159476 | 51259410 |
| rs1891702 | 195 | 1 | 0.923404 | 2.93E−29 | 50162267 | 51262201 |
| rs4907792 | 196 | 1 | 0.923404 | 2.93E−29 | 50165589 | 51265523 |
| rs2384958 | 197 | 1 | 0.923404 | 2.93E−29 | 50166203 | 51266137 |
| rs1936038 | 198 | 1 | 0.887734 | 3.12E−27 | 50168227 | 51268161 |
| rs5945573 | 199 | 1 | 0.887734 | 5.37E−28 | 50171156 | 51271090 |
| rs4907796 | 200 | 1 | 0.887734 | 5.37E−28 | 50178055 | 51277989 |
| rs4907775 | 201 | 1 | 0.887734 | 5.37E−28 | 50180006 | 51279940 |
| rs6614426 | 202 | 1 | 0.887734 | 5.37E−28 | 50181230 | 51281164 |
| rs1970956 | 203 | 1 | 0.887734 | 5.37E−28 | 50185184 | 51285118 |
| rs1970957 | 204 | 1 | 0.887734 | 5.37E−28 | 50185256 | 51285190 |
| rs2153993 | 205 | 1 | 0.887734 | 5.37E−28 | 50186545 | 51286479 |
| rs6614428 | 206 | 1 | 0.887734 | 5.37E−28 | 50188982 | 51288916 |
| rs1541241 | 208 | 1 | 0.887734 | 5.37E−28 | 50204595 | 51304529 |
| rs1541240 | 209 | 1 | 0.887734 | 5.37E−28 | 50204917 | 51304851 |
| rs1592303 | 210 | 1 | 0.887734 | 3.12E−27 | 50207088 | 51307022 |
| rs1110404 | 211 | 0.884106 | 0.44477 | 5.44E−12 | 50216553 | 51316487 |
| rs1110405 | 212 | 0.884106 | 0.44477 | 5.44E−12 | 50216780 | 51316714 |
| rs1343272 | 214 | 1 | 0.887734 | 5.37E−28 | 50224746 | 51324680 |
| rs5987438 | 215 | 1 | 0.887734 | 1.82E−26 | 50225787 | 51325721 |
| rs6614317 | 216 | 1 | 0.887734 | 3.12E−27 | 50226607 | 51326541 |
| rs1936037 | 217 | 1 | 0.887734 | 5.37E−28 | 50227182 | 51327116 |
| rs1936036 | 218 | 1 | 0.887734 | 5.37E−28 | 50227627 | 51327561 |
| rs3131302 | 219 | 0.884106 | 0.44477 | 5.44E−12 | 50227660 | 51327594 |
| rs1361837 | 220 | 1 | 0.887734 | 5.37E−28 | 50229870 | 51329804 |
| rs1936035 | 221 | 1 | 0.887734 | 5.37E−28 | 50233065 | 51332999 |
| rs4457126 | 222 | 1 | 0.887734 | 5.37E−28 | 50234705 | 51334639 |
| rs4308906 | 223 | 1 | 0.887734 | 5.37E−28 | 50235272 | 51335206 |
| rs4907781 | 225 | 0.884106 | 0.44477 | 5.44E−12 | 50255769 | 51355703 |
| rs5945650 | 226 | 1 | 0.853659 | 7.16E−27 | 50257193 | 51357127 |
| rs7064708 | 227 | 1 | 0.887734 | 5.37E−28 | 50259241 | 51359175 |
| rs1936034 | 228 | 1 | 0.887734 | 5.37E−28 | 50259756 | 51359690 |
| rs5945651 | 229 | 1 | 0.887734 | 5.37E−28 | 50260300 | 51360234 |
| rs1541238 | 230 | 1 | 0.887734 | 5.37E−28 | 50260441 | 51360375 |
| rs1984280 | 231 | 0.920236 | 0.808522 | 1.48E−22 | 50261077 | 51361011 |
| rs2721996 | 232 | 0.839241 | 0.264711 | 1.17E−07 | 50261165 | 51361099 |
| rs5945653 | 233 | 0.835532 | 0.255508 | 1.71E−07 | 50261315 | 51361249 |
| rs5945578 | 234 | 0.851627 | 0.563801 | 1.49E−14 | 50261944 | 51361878 |
| rs3955398 | 235 | 0.847168 | 0.539639 | 8.51E−14 | 50263639 | 51363573 |
| rs1419039 | 236 | 0.851627 | 0.563801 | 1.49E−14 | 50264982 | 51364916 |
| rs1419038 | 237 | 0.850283 | 0.571894 | 7.80E−14 | 50266006 | 51365940 |
| rs5987446 | 238 | 0.852174 | 0.549149 | 6.02E−14 | 50268126 | 51368060 |
| rs1419040 | 239 | 0.851627 | 0.563801 | 1.49E−14 | 50268841 | 51368775 |
| rs6614454 | 240 | 0.85229 | 0.562357 | 1.49E−14 | 50269140 | 51369074 |
| rs1541242 | 241 | 0.835532 | 0.255508 | 1.71E−07 | 50270359 | 51370293 |
| rs12688960 | 360 | 0.851627 | 0.563801 | 1.49E−14 | 50271345 | 51371279 |
| rs6521823 | 242 | 0.851627 | 0.563801 | 1.49E−14 | 50271564 | 51371498 |
| rs5987447 | 243 | 0.851627 | 0.563801 | 1.49E−14 | 50274370 | 51374304 |
| rs5945579 | 244 | 0.851627 | 0.563801 | 1.49E−14 | 50276001 | 51375935 |
| rs7057039 | 245 | 0.851627 | 0.563801 | 1.49E−14 | 50279417 | 51379351 |
| rs2185880 | 246 | 0.851627 | 0.563801 | 1.49E−14 | 50289478 | 51389412 |
| rs5987448 | 247 | 0.851627 | 0.563801 | 1.49E−14 | 50294562 | 51394496 |
| rs11091750 | 248 | 0.851627 | 0.563801 | 1.49E−14 | 50296878 | 51396812 |
| rs4907804 | 249 | 0.851627 | 0.563801 | 1.49E−14 | 50301057 | 51400991 |
| rs5945659 | 361 | 0.851627 | 0.563801 | 1.49E−14 | 50304407 | 51404341 |
| rs5945664 | 251 | 0.851627 | 0.563801 | 1.49E−14 | 50310726 | 51410660 |
| rs5945667 | 252 | 0.835532 | 0.255508 | 1.71E−07 | 50314369 | 51414303 |
| rs12558898 | 253 | 0.851627 | 0.563801 | 1.49E−14 | 50314532 | 51414466 |
| rs5945586 | 254 | 0.850882 | 0.562821 | 2.98E−14 | 50315435 | 51415369 |
| rs5945668 | 255 | 0.850882 | 0.562821 | 2.98E−14 | 50315732 | 51415666 |
| rs5945587 | 256 | 0.846183 | 0.492698 | 1.68E−13 | 50316246 | 51416180 |
| rs4544871 | 259 | 0.835849 | 0.254063 | 1.70E−07 | 50324147 | 51424081 |
| rs4473816 | 260 | 0.846183 | 0.492698 | 1.68E−13 | 50327396 | 51427330 |
| rs5945590 | 261 | 0.846183 | 0.492698 | 1.68E−13 | 50354050 | 51453984 |
| rs5945677 | 262 | 0.845164 | 0.491515 | 3.33E−13 | 50354977 | 51454911 |
| rs12394792 | 263 | 0.846183 | 0.492698 | 1.68E−13 | 50357758 | 51457692 |

TABLE 10-continued

SNPs from Chromosome Xp11.22
(within +/− 1500 kb of rs5945572 in NCBI Build 35),
correlated with rs5945572 by $R^2 > 0.2$.
The SNPs were identified in the Caucasian CEU HapMap
Release 22 dataset (http colon-slash-slash www.hapmap.org).

| Marker | SEQ ID No: | D' | $R^2$ | P-value | Location Build 34 | Location Build 35 |
| --- | --- | --- | --- | --- | --- | --- |
| rs5951067 | 264 | 0.846183 | 0.492698 | 1.68E−13 | 50385612 | 51485546 |
| rs4986571 | 265 | 0.846183 | 0.492698 | 1.68E−13 | 50391482 | 51491416 |
| rs5951072 | 266 | 0.846183 | 0.492698 | 1.68E−13 | 50396019 | 51495953 |
| rs6614493 | 267 | 0.846183 | 0.492698 | 1.68E−13 | 50398854 | 51498788 |
| rs5951074 | 268 | 0.846183 | 0.492698 | 1.68E−13 | 50400135 | 51500069 |
| rs11796743 | 269 | 0.816525 | 0.215395 | 1.92E−06 | 50403001 | 51502935 |
| rs974285 | 270 | 0.846183 | 0.492698 | 1.68E−13 | 50403465 | 51503399 |
| rs976556 | 271 | 0.846183 | 0.492698 | 1.68E−13 | 50407247 | 51507181 |
| rs3910588 | 272 | 0.846183 | 0.492698 | 1.68E−13 | 50410609 | 51510543 |
| rs3910587 | 273 | 0.846183 | 0.492698 | 1.68E−13 | 50410688 | 51510622 |
| rs1439461 | 274 | 0.816525 | 0.215395 | 1.92E−06 | 50415032 | 51514966 |
| rs2118952 | 275 | 0.846183 | 0.492698 | 1.68E−13 | 50419995 | 51519929 |
| rs4986558 | 276 | 0.845347 | 0.509733 | 1.30E−13 | 50425927 | 51525861 |
| rs5991819 | 277 | 0.846183 | 0.492698 | 1.68E−13 | 50428058 | 51527992 |
| rs5991820 | 278 | 0.809912 | 0.201932 | 4.54E−06 | 50430926 | 51530860 |
| rs2118951 | 281 | 0.846183 | 0.492698 | 1.68E−13 | 50435735 | 51535669 |
| rs12844657 | 282 | 0.846183 | 0.492698 | 1.68E−13 | 50439534 | 51539468 |
| rs11796701 | 283 | 0.816525 | 0.215395 | 1.92E−06 | 50440140 | 51540074 |
| rs9887648 | 284 | 0.844693 | 0.484514 | 3.99E−13 | 50440655 | 51540589 |
| rs12010969 | 285 | 0.844693 | 0.484514 | 3.99E−13 | 50441124 | 51541058 |
| rs5991822 | 286 | 0.809912 | 0.201932 | 4.54E−06 | 50443963 | 51543897 |
| rs5991733 | 287 | 0.895028 | 0.238037 | 6.89E−07 | 50444078 | 51544012 |
| rs12393443 | 288 | 0.816525 | 0.215395 | 1.92E−06 | 50444898 | 51544832 |
| rs5991824 | 290 | 0.893717 | 0.240881 | 8.45E−07 | 50452223 | 51552157 |
| rs4986559 | 291 | 0.846183 | 0.492698 | 1.68E−13 | 50455432 | 51555366 |
| rs7890241 | 292 | 0.846183 | 0.492698 | 1.68E−13 | 50457039 | 51556973 |
| rs4986553 | 293 | 0.846183 | 0.492698 | 1.68E−13 | 50463601 | 51563535 |
| rs5991735 | 294 | 0.846183 | 0.492698 | 1.68E−13 | 50469690 | 51569624 |
| rs5951078 | 295 | 0.846183 | 0.492698 | 1.68E−13 | 50470079 | 51570013 |
| rs5951079 | 296 | 0.846183 | 0.492698 | 1.68E−13 | 50472457 | 51572391 |
| rs4986554 | 297 | 0.846183 | 0.492698 | 1.68E−13 | 50480142 | 51580076 |
| rs1439460 | 298 | 0.846183 | 0.492698 | 1.68E−13 | 50490087 | 51590021 |
| rs5951064 | 299 | 0.846183 | 0.492698 | 1.68E−13 | 50490488 | 51590422 |
| rs5951083 | 300 | 0.846183 | 0.492698 | 1.68E−13 | 50497103 | 51597037 |
| rs7061919 | 301 | 0.730286 | 0.311359 | 4.35E−07 | 50498017 | 51597951 |
| rs7056700 | 302 | 0.845232 | 0.48289 | 3.96E−13 | 50498182 | 51598116 |
| rs12853137 | 303 | 0.844696 | 0.480044 | 7.80E−13 | 50498563 | 51598497 |
| rs12353683 | 304 | 0.758564 | 0.432039 | 9.01E−12 | 50502290 | 51602224 |
| rs7880576 | 305 | 0.846183 | 0.492698 | 1.68E−13 | 50509785 | 51609719 |
| rs4133299 | 306 | 0.846183 | 0.492698 | 1.68E−13 | 50517515 | 51617449 |
| rs5991738 | 307 | 0.846183 | 0.492698 | 1.68E−13 | 50517932 | 51617866 |
| rs1992271 | 308 | 0.846183 | 0.492698 | 1.68E−13 | 50526679 | 51626613 |
| rs5991739 | 309 | 0.846183 | 0.492698 | 1.68E−13 | 50527775 | 51627709 |
| rs4986555 | 362 | 0.840674 | 0.488384 | 6.28E−13 | 50528742 | 51628676 |
| rs1048437 | 310 | 0.846183 | 0.492698 | 1.68E−13 | 50532933 | 51632867 |
| rs5951087 | 311 | 0.846183 | 0.492698 | 1.68E−13 | 50535789 | 51635723 |
| rs7053197 | 312 | 0.846183 | 0.492698 | 1.68E−13 | 50542948 | 51642882 |
| rs5991707 | 313 | 0.846183 | 0.492698 | 1.68E−13 | 50547611 | 51647545 |
| rs11796891 | 314 | 0.816525 | 0.215395 | 1.92E−06 | 50550769 | 51650703 |
| rs5951091 | 315 | 0.758564 | 0.432039 | 9.01E−12 | 50565385 | 51665319 |
| rs7053327 | 316 | 0.758564 | 0.432039 | 9.01E−12 | 50570716 | 51670650 |
| rs7051319 | 317 | 0.758564 | 0.432039 | 9.01E−12 | 50575195 | 51675129 |
| rs5991744 | 318 | 0.758564 | 0.432039 | 9.01E−12 | 50577864 | 51677798 |
| rs11796974 | 319 | 0.758564 | 0.432039 | 9.01E−12 | 50583935 | 51683869 |
| rs4074722 | 320 | 0.758564 | 0.432039 | 9.01E−12 | 50595795 | 51695729 |
| rs4986557 | 322 | 0.756348 | 0.424039 | 2.02E−11 | 50611457 | 51711391 |
| rs6614515 | 323 | 0.717503 | 0.401207 | 9.50E−11 | 50611949 | 51711883 |
| rs4131729 | 324 | 0.718465 | 0.404427 | 4.94E−11 | 50614000 | 51713934 |
| rs5991762 | 325 | 0.71325 | 0.388331 | 2.35E−10 | 50614415 | 51714349 |
| rs11798798 | 326 | 0.788135 | 0.451822 | 9.61E−12 | 50629527 | 51729461 |
| rs5991776 | 328 | 0.711179 | 0.395165 | 1.72E−10 | 50640447 | 51740381 |
| rs5951070 | 329 | 0.718465 | 0.404427 | 4.94E−11 | 50640665 | 51740599 |
| rs11797967 | 330 | 0.718465 | 0.404427 | 4.94E−11 | 50643312 | 51743246 |
| rs5991804 | 332 | 0.718465 | 0.404427 | 4.94E−11 | 50659859 | 51759793 |
| rs5991805 | 333 | 0.718465 | 0.404427 | 4.94E−11 | 50662313 | 51762247 |
| rs12845073 | 334 | 0.718465 | 0.404427 | 4.94E−11 | 50664330 | 51764264 |
| rs12851025 | 335 | 0.709544 | 0.390431 | 1.96E−10 | 50664341 | 51764275 |

TABLE 10-continued

SNPs from Chromosome Xp11.22
(within +/− 1500 kb of rs5945572 in NCBI Build 35),
correlated with rs5945572 by $R^2 > 0.2$.
The SNPs were identified in the Caucasian CEU HapMap
Release 22 dataset (http colon-slash-slash www.hapmap.org).

| Marker | SEQ ID No: | D' | $R^2$ | P-value | Location Build 34 | Location Build 35 |
|---|---|---|---|---|---|---|
| rs5991812 | 337 | 0.718465 | 0.404427 | 4.94E−11 | 50670300 | 51770234 |
| rs5951109 | 338 | 0.718465 | 0.404427 | 4.94E−11 | 50675936 | 51775870 |
| rs5951114 | 339 | 0.718465 | 0.404427 | 4.94E−11 | 50692450 | 51792384 |
| rs4986573 | 340 | 0.718465 | 0.404427 | 4.94E−11 | 50695908 | 51795842 |

TABLE 11

All SNP markers, from Chromosome 2p, located between 62684001 bp
and 64597002 bp (Build 35), having correlation with rs2710646 of
$R^2 > 0.2$ or higher in the Caucasian CEU HapMap samples
(http colon-slash-slash www.hapmap.org).

| SNP1 | SNP2 | Location SNP2 | D' | $R^2$ | P-value |
|---|---|---|---|---|---|
| rs2710646 | rs13417654 | 62772272 | 0.494791 | 0.210174 | 0.000141 |
| rs2710646 | rs17025954 | 62779758 | 0.810584 | 0.552754 | 5.02E−10 |
| rs2710646 | rs901529 | 62792002 | 1 | 0.414444 | 1.02E−11 |
| rs2710646 | rs10192894 | 62813470 | 1 | 0.220126 | 3.08E−08 |
| rs2710646 | rs360808 | 62902009 | 1 | 0.308176 | 5.94E−10 |
| rs2710646 | rs7591708 | 62996584 | 1 | 0.308176 | 5.94E−10 |
| rs2710646 | rs17432497 | 63001871 | 1 | 1 | 1.43E−20 |
| rs2710646 | rs12713469 | 63034461 | 1 | 0.254487 | 6.07E−09 |
| rs2710646 | rs13410889 | 63062312 | 1 | 0.261713 | 4.46E−09 |
| rs2710646 | rs721048 | 63106265 | 1 | 1 | 1.43E−20 |
| rs2710646 | rs2553041 | 63212880 | 1 | 1 | 1.43E−20 |
| rs2710646 | rs17657646 | 63241156 | 1 | 0.209486 | 0.000202 |
| rs2710646 | rs10173115 | 63330054 | 1 | 0.205138 | 6.51E−10 |
| rs2710646 | rs17408652 | 63365024 | 0.918367 | 0.779745 | 6.98E−15 |
| rs2710646 | rs7568224 | 63365530 | 0.918367 | 0.779745 | 6.98E−15 |
| rs2710646 | rs17408841 | 63372508 | 0.917558 | 0.721288 | 4.99E−14 |
| rs2710646 | rs2421862 | 63376507 | 0.918367 | 0.779745 | 6.98E−15 |
| rs2710646 | rs13431765 | 63392263 | 0.916528 | 0.672205 | 4.32E−13 |
| rs2710646 | rs17408988 | 63393109 | 1 | 0.22813 | 2.09E−08 |
| rs2710646 | rs7605319 | 63398029 | 0.917396 | 0.722519 | 8.98E−14 |
| rs2710646 | rs13387839 | 63403105 | 0.890749 | 0.434253 | 3.92E−08 |
| rs2710646 | rs12151606 | 63404709 | 0.905052 | 0.381039 | 2.49E−08 |
| rs2710646 | rs2421822 | 63412016 | 1 | 0.236507 | 1.40E−08 |
| rs2710646 | rs13417792 | 63421734 | 0.917396 | 0.722519 | 8.98E−14 |
| rs2710646 | rs10203263 | 63428935 | 0.834075 | 0.597236 | 2.46E−11 |
| rs2710646 | rs6718609 | 63434343 | 0.836335 | 0.646667 | 2.73E−12 |
| rs2710646 | rs1850984 | 63439476 | 0.916748 | 0.670777 | 2.40E−13 |
| rs2710646 | rs13422328 | 63440711 | 0.918352 | 0.778589 | 7.84E−15 |
| rs2710646 | rs17432775 | 63440997 | 0.917581 | 0.72281 | 4.45E−14 |
| rs2710646 | rs2699396 | 63463324 | 1 | 0.240506 | 1.20E−08 |
| rs2710646 | rs1607203 | 63468803 | 0.910807 | 0.459722 | 3.36E−10 |
| rs2710646 | rs2677436 | 63470469 | 0.909889 | 0.43738 | 6.75E−10 |
| rs2710646 | rs2677438 | 63470610 | 0.910807 | 0.459722 | 3.36E−10 |
| rs2710646 | rs2699388 | 63470671 | 0.910807 | 0.459722 | 3.36E−10 |
| rs2710646 | rs2677439 | 63471532 | 0.909889 | 0.43738 | 6.75E−10 |
| rs2710646 | rs970278 | 63472088 | 0.909889 | 0.43738 | 6.75E−10 |
| rs2710646 | rs2945032 | 63472734 | 0.909889 | 0.43738 | 6.75E−10 |
| rs2710646 | rs1607205 | 63475042 | 0.909889 | 0.43738 | 6.75E−10 |
| rs2710646 | rs2030188 | 63483847 | 0.908851 | 0.414564 | 1.45E−09 |
| rs2710646 | rs12713476 | 63484384 | 0.909889 | 0.43738 | 6.75E−10 |
| rs2710646 | rs6725694 | 63485436 | 0.908851 | 0.414564 | 1.45E−09 |
| rs2710646 | rs10207356 | 63486549 | 0.90978l | 0.434899 | 7.58E−10 |
| rs2710646 | rs10173637 | 63486655 | 0.911723 | 0.48437 | 1.58E−10 |
| rs2710646 | rs7596446 | 63486740 | 0.911723 | 0.48437 | 1.58E−10 |
| rs2710646 | rs2421881 | 63487219 | 0.911723 | 0.48437 | 1.58E−10 |
| rs2710646 | rs4416201 | 63487371 | 0.909889 | 0.43738 | 6.75E−10 |
| rs2710646 | rs4671470 | 63488447 | 0.911357 | 0.457872 | 2.33E−10 |
| rs2710646 | rs4671471 | 63488458 | 0.909781 | 0.434899 | 7.58E−10 |
| rs2710646 | rs11684108 | 63488821 | 0.910709 | 0.457239 | 3.78E−10 |
| rs2710646 | rs12713477 | 63489156 | 0.908851 | 0.414564 | 1.45E−09 |
| rs2710646 | rs1517405 | 63490102 | 0.908851 | 0.414564 | 1.45E−09 |
| rs2710646 | rs6724044 | 63490289 | 0.909781 | 0.434899 | 7.58E−10 |
| rs2710646 | rs4671473 | 63490468 | 0.909781 | 0.434899 | 7.58E−10 |

TABLE 11-continued

All SNP markers, from Chromosome 2p, located between 62684001 bp
and 64597002 bp (Build 35), having correlation with rs2710646 of
$R^2 > 0.2$ or higher in the Caucasian CEU HapMap samples
(http colon-slash-slash www.hapmap.org).

| SNP1 | SNP2 | Location SNP2 | D' | $R^2$ | P-value |
|---|---|---|---|---|---|
| rs2710646 | rs4671474 | 63490638 | 0.909781 | 0.434899 | 7.58E−10 |
| rs2710646 | rs6545984 | 63491667 | 0.910807 | 0.459722 | 3.36E−10 |
| rs2710646 | rs4611627 | 63492530 | 0.909889 | 0.43738 | 6.75E−10 |
| rs2710646 | rs11125957 | 63493006 | 0.909889 | 0.43738 | 6.75E−10 |
| rs2710646 | rs6744720 | 63495567 | 0.908851 | 0.414564 | 1.45E−09 |
| rs2710646 | rs6748030 | 63495983 | 0.909889 | 0.43738 | 6.75E−10 |
| rs2710646 | rs6705776 | 63496021 | 0.909889 | 0.43738 | 6.75E−10 |
| rs2710646 | rs4428008 | 63497049 | 0.909889 | 0.43738 | 6.75E−10 |
| rs2710646 | rs4560098 | 63497112 | 0.909889 | 0.43738 | 6.75E−10 |
| rs2710646 | rs11691718 | 63499148 | 0.908851 | 0.414564 | 1.45E−09 |
| rs2710646 | rs4671476 | 63499173 | 0.908851 | 0.414564 | 1.45E−09 |
| rs2710646 | rs7591562 | 63499636 | 0.908851 | 0.414564 | 1.45E−09 |
| rs2710646 | rs6545986 | 63499651 | 0.908851 | 0.414564 | 1.45E−09 |
| rs2710646 | rs12713478 | 63500870 | 0.908851 | 0.414564 | 1.45E−09 |
| rs2710646 | rs6708847 | 63502115 | 0.908851 | 0.414564 | 1.45E−09 |
| rs2710646 | rs6709115 | 63502393 | 0.908851 | 0.414564 | 1.45E−09 |
| rs2710646 | rs12994711 | 63502769 | 0.908608 | 0.409551 | 1.83E−09 |
| rs2710646 | rs11675647 | 63502971 | 0.908608 | 0.409551 | 1.83E−09 |
| rs2710646 | rs6713500 | 63503565 | 0.90703 | 0.412904 | 2.89E−09 |
| rs2710646 | rs2090479 | 63504395 | 0.908851 | 0.414564 | 1.45E−09 |
| rs2710646 | rs6734468 | 63505103 | 0.908851 | 0.414564 | 1.45E−09 |
| rs2710646 | rs6706180 | 63505335 | 0.908851 | 0.414564 | 1.45E−09 |
| rs2710646 | rs1517404 | 63512091 | 0.908851 | 0.414564 | 1.45E−09 |
| rs2710646 | rs1400688 | 63513070 | 0.908354 | 0.404437 | 2.32E−09 |
| rs2710646 | rs1400687 | 63513300 | 0.908851 | 0.414564 | 1.45E−09 |
| rs2710646 | rs1517401 | 63515241 | 0.909889 | 0.43738 | 6.75E−10 |
| rs2710646 | rs1400686 | 63517041 | 0.909889 | 0.43738 | 6.75E−10 |
| rs2710646 | rs6545988 | 63517266 | 0.909889 | 0.43738 | 6.75E−10 |
| rs2710646 | rs6708627 | 63518460 | 0.909889 | 0.43738 | 6.75E−10 |
| rs2710646 | rs6545989 | 63519801 | 0.905708 | 0.501477 | 5.81E−10 |
| rs2710646 | rs4671480 | 63522022 | 0.909889 | 0.43738 | 6.75E−10 |
| rs2710646 | rs4671481 | 63522061 | 0.909889 | 0.43738 | 6.75E−10 |
| rs2710646 | rs7558922 | 63523226 | 0.909889 | 0.43738 | 6.75E−10 |
| rs2710646 | rs7585664 | 63523250 | 0.738118 | 0.357933 | 1.39E−07 |
| rs2710646 | rs7599736 | 63523390 | 0.909889 | 0.43738 | 6.75E−10 |
| rs2710646 | rs7559137 | 63523402 | 0.909889 | 0.43738 | 6.75E−10 |
| rs2710646 | rs6545991 | 63523597 | 0.909889 | 0.43738 | 6.75E−10 |
| rs2710646 | rs10169292 | 63527769 | 0.909889 | 0.43738 | 6.75E−10 |
| rs2710646 | rs4671484 | 63529274 | 0.909889 | 0.43738 | 6.75E−10 |
| rs2710646 | rs13021322 | 63533124 | 0.888132 | 0.200734 | 6.26E−06 |
| rs2710646 | rs11691192 | 63535613 | 0.885133 | 0.206097 | 8.03E−06 |
| rs2710646 | rs11686044 | 63535866 | 0.909889 | 0.43738 | 6.75E−10 |
| rs2710646 | rs11691357 | 63535983 | 0.909889 | 0.43738 | 6.75E−10 |
| rs2710646 | rs7561802 | 63536600 | 0.909889 | 0.43738 | 6.75E−10 |
| rs2710646 | rs6545997 | 63536680 | 0.909889 | 0.43738 | 6.75E−10 |
| rs2710646 | rs11687645 | 63536903 | 0.889708 | 0.209097 | 4.24E−06 |
| rs2710646 | rs6717060 | 63543142 | 0.907789 | 0.393501 | 2.98E−09 |
| rs2710646 | rs10209822 | 63546981 | 0.909558 | 0.429859 | 9.59E−10 |
| rs2710646 | rs1996401 | 63548282 | 0.888894 | 0.204698 | 5.35E−06 |
| rs2710646 | rs1517409 | 63549616 | 0.910075 | 0.458982 | 6.78E−10 |
| rs2710646 | rs2176418 | 63550326 | 0.910807 | 0.459722 | 3.36E−10 |
| rs2710646 | rs2176417 | 63553128 | 0.908731 | 0.412069 | 1.63E−09 |
| rs2710646 | rs2421886 | 63553846 | 0.909781 | 0.434899 | 7.58E−10 |

TABLE 11-continued

All SNP markers, from Chromosome 2p, located between 62684001 bp and 64597002 bp (Build 35), having correlation with rs2710646 of $R^2 > 0.2$ or higher in the Caucasian CEU HapMap samples (http colon-slash-slash www.hapmap.org).

| SNP1 | SNP2 | Location SNP2 | D' | $R^2$ | P-value |
|---|---|---|---|---|---|
| rs2710646 | rs908622 | 63554219 | 0.908851 | 0.414564 | 1.45E-09 |
| rs2710646 | rs11125967 | 63559326 | 0.909781 | 0.434899 | 7.58E-10 |
| rs2710646 | rs1829261 | 63561691 | 0.908731 | 0.412069 | 1.63E-09 |
| rs2710646 | rs2176416 | 63564789 | 0.908851 | 0.414564 | 1.45E-09 |
| rs2710646 | rs11883730 | 63566764 | 0.907789 | 0.393501 | 2.98E-09 |
| rs2710646 | rs11894445 | 63566882 | 0.909781 | 0.434899 | 7.58E-10 |
| rs2710646 | rs1922421 | 63567326 | 0.907789 | 0.393501 | 2.98E-09 |
| rs2710646 | rs6546001 | 63568353 | 0.908851 | 0.414564 | 1.45E-09 |
| rs2710646 | rs6546002 | 63568363 | 0.908608 | 0.409551 | 1.83E-09 |
| rs2710646 | rs7558796 | 63571642 | 0.908731 | 0.412069 | 1.63E-09 |
| rs2710646 | rs13011799 | 63571784 | 0.908851 | 0.414564 | 1.45E-09 |
| rs2710646 | rs7571697 | 63572139 | 0.908851 | 0.414564 | 1.45E-09 |
| rs2710646 | rs932172 | 63577431 | 0.908851 | 0.414564 | 1.45E-09 |
| rs2710646 | rs932171 | 63577476 | 0.908851 | 0.414564 | 1.45E-09 |
| rs2710646 | rs6741817 | 63577509 | 0.908851 | 0.414564 | 1.45E-09 |
| rs2710646 | rs4671494 | 63579532 | 0.907789 | 0.393501 | 2.98E-09 |
| rs2710646 | rs2292795 | 63579964 | 0.908851 | 0.414564 | 1.45E-09 |
| rs2710646 | rs2292794 | 63580306 | 0.908851 | 0.414564 | 1.45E-09 |
| rs2710646 | rs908621 | 63580576 | 0.908851 | 0.414564 | 1.45E-09 |
| rs2710646 | rs2421887 | 63580753 | 0.908851 | 0.414564 | 1.45E-09 |
| rs2710646 | rs2901580 | 63580808 | 0.901703 | 0.407314 | 7.51E-09 |
| rs2710646 | rs12618974 | 63581977 | 0.908851 | 0.414564 | 1.45E-09 |
| rs2710646 | rs7599208 | 63597004 | 0.888894 | 0.204698 | 5.35E-06 |
| rs2710646 | rs4671503 | 63611625 | 0.636105 | 0.225385 | 0.000026 |
| rs2710646 | rs4671505 | 63618837 | 0.633016 | 0.215614 | 0.00004 |
| rs2710646 | rs1356390 | 63644159 | 0.636105 | 0.225385 | 0.000026 |
| rs2710646 | rs6546005 | 63646605 | 0.636105 | 0.225385 | 0.000026 |
| rs2710646 | rs6736411 | 63648594 | 0.636105 | 0.225385 | 0.000026 |
| rs2710646 | rs7608470 | 63666012 | 0.631327 | 0.210567 | 0.000044 |
| rs2710646 | rs2028887 | 63690757 | 0.636105 | 0.225385 | 0.000026 |
| rs2710646 | rs10176522 | 63696967 | 0.636105 | 0.225385 | 0.000026 |
| rs2710646 | rs6546007 | 63699329 | 0.636105 | 0.225385 | 0.000026 |
| rs2710646 | rs989527 | 63701325 | 0.636105 | 0.225385 | 0.000026 |
| rs2710646 | rs1867849 | 63701466 | 0.636105 | 0.225385 | 0.000026 |
| rs2710646 | rs1446565 | 63706109 | 0.631955 | 0.22009 | 0.00004 |
| rs2710646 | rs1446564 | 63706216 | 0.636105 | 0.225385 | 0.000026 |
| rs2710646 | rs10865338 | 63707043 | 0.632602 | 0.222098 | 0.000037 |
| rs2710646 | rs10168545 | 63708818 | 0.636105 | 0.225385 | 0.000026 |
| rs2710646 | rs9789351 | 63715148 | 0.635516 | 0.223463 | 0.000028 |
| rs2710646 | rs7576316 | 63715656 | 0.636105 | 0.225385 | 0.000026 |
| rs2710646 | rs964903 | 63716082 | 0.631327 | 0.210567 | 0.000044 |
| rs2710646 | rs1031221 | 63717344 | 0.636105 | 0.225385 | 0.000026 |
| rs2710646 | rs6546009 | 63720276 | 0.636105 | 0.225385 | 0.000026 |
| rs2710646 | rs2421952 | 63724367 | 0.636105 | 0.225385 | 0.000026 |
| rs2710646 | rs7570031 | 63766799 | 0.636105 | 0.225385 | 0.000026 |
| rs2710646 | rs7584404 | 63768876 | 0.636105 | 0.225385 | 0.000026 |
| rs2710646 | rs12105140 | 63771752 | 0.636105 | 0.225385 | 0.000026 |
| rs2710646 | rs959195 | 63778659 | 0.636105 | 0.225385 | 0.000026 |
| rs2710646 | rs2028884 | 63786682 | 0.588019 | 0.264196 | 0.000016 |
| rs2710646 | rs10469944 | 63791206 | 0.636105 | 0.225385 | 0.000026 |
| rs2710646 | rs10469945 | 63791310 | 0.636105 | 0.225385 | 0.000026 |
| rs2710646 | rs6546018 | 63791956 | 0.636105 | 0.225385 | 0.000026 |
| rs2710646 | rs6546019 | 63791974 | 0.636105 | 0.225385 | 0.000026 |
| rs2710646 | rs1446569 | 63792848 | 0.636105 | 0.225385 | 0.000026 |
| rs2710646 | rs2305157 | 63797319 | 0.636105 | 0.225385 | 0.000026 |
| rs2710646 | rs1255 | 63800468 | 0.636105 | 0.225385 | 0.000026 |
| rs2710646 | rs7606045 | 63801062 | 0.636105 | 0.225385 | 0.000026 |
| rs2710646 | rs964880 | 63801466 | 0.636105 | 0.225385 | 0.000026 |
| rs2710646 | rs2604613 | 63807310 | 0.636105 | 0.225385 | 0.000026 |
| rs2710646 | rs262472 | 63808150 | 0.636105 | 0.225385 | 0.000026 |
| rs2710646 | rs262473 | 63808347 | 0.636105 | 0.225385 | 0.000026 |
| rs2710646 | rs262493 | 63819600 | 0.636105 | 0.225385 | 0.000026 |
| rs2710646 | rs190519 | 63832959 | 0.636105 | 0.225385 | 0.000026 |
| rs2710646 | rs262501 | 63833191 | 0.636105 | 0.225385 | 0.000026 |
| rs2710646 | rs196125 | 63833802 | 0.634912 | 0.221525 | 0.000031 |
| rs2710646 | rs262502 | 63834257 | 0.636105 | 0.225385 | 0.000026 |
| rs2710646 | rs262503 | 63834971 | 0.636105 | 0.225385 | 0.000026 |
| rs2710646 | rs262504 | 63835769 | 0.636105 | 0.225385 | 0.000026 |
| rs2710646 | rs262505 | 63836320 | 0.636105 | 0.225385 | 0.000026 |
| rs2710646 | rs262476 | 63845141 | 0.636105 | 0.225385 | 0.000026 |

LD Structure at Associating Loci

The LD structure of the markers and haplotypes that associates with prostate cancer, in five chromosomal regions, was assessed using HAPMAP data release 19, except for the Chromosome Xp11.22 region, for which the necessary data was not available. For this region, the LD structure was derived from our own analysis of the samples described herein. Regions characterized by high $r^2$ and/or |D'|-values are characteristic of each LD block, and increased recombination rates between adjacent markers are characteristic of the boundaries between LD blocks (leading to rapidly decreasing $r^2$ and |D'|-values). Thus, in general, regions of high LD structure are seen as genomic "blocks" (LD blocks), within which individual markers are in strong LD as indicated by high $r^2$ and |D'|-values.

Analysis of the LD structure in the regions of the present invention defines boundaries within which markers showing association to prostate cancer are residing. It is possible that markers residing within the LD block regions as defined herein and not listed in Tables 7-11 are also associated with the markers disclosed herein to be associated with prostate cancer (e.g., the markers of Table 1, Table 4a and Table 4b), since such markers are in linkage disequilibrium with the anchor markers listed in Table 2. The reason is that not all markers residing within the regions have been tested explicitly for association to prostate cancer, but the presence of the LD blocks as defined herein and the association of markers presented herein (e.g., the markers disclosed in Table 1, Table 4a and Table 4b) suggests that additional markers within the regions and in LD with the anchor markers of Table 2 are also associated with prostate cancer. Tables 12-16 provides a list of publicly known SNP markers in the four regions discussed herein (i.e., LD block C02, LD block C04a, the TCF gene, LD block C17b and LD block COX), based on the public SNP database dbSNP 125, and locations are according to NCBI Build 34).

TABLE 12

Public SNPs from dbSNP Build125 in the LD block C04a region

| Name | Location (Bld 34) |
|---|---|
| rs6537253 | 145602078 |
| rs4434191 | 145602079 |
| rs6844670 | 145602426 |
| rs4643761 | 145602575 |
| rs4557214 | 145602736 |
| rs11723371 | 145603437 |
| rs11727098 | 145603582 |
| rs28634998 | 145603675 |
| rs6857262 | 145603677 |
| rs11735662 | 145603753 |
| rs4130880 | 145604778 |
| rs7682756 | 145605488 |
| rs4535287 | 145606058 |
| rs4350961 | 145606671 |
| rs4613516 | 145606947 |
| rs3936169 | 145607497 |
| rs3936168 | 145607514 |
| rs12500422 | 145607801 |
| rs13143530 | 145607817 |
| rs4469024 | 145607978 |
| rs1132787 | 145608173 |
| rs11728240 | 145608328 |
| rs5862686 | 145608835 |
| rs13125760 | 145609468 |
| rs11279505 | 145609583 |
| rs5029339 | 145609593 |
| rs10031592 | 145609868 |
| rs4425323 | 145611159 |
| rs11100830 | 145611270 |
| rs4645174 | 145611287 |

TABLE 12-continued

Public SNPs from dbSNP Build125 in the LD block C04a region

| Name | Location (Bld 34) |
|---|---|
| rs6845104 | 145611416 |
| rs4374581 | 145611437 |
| rs4484241 | 145611703 |
| rs4393951 | 145611767 |
| rs2069004 | 145611792 |
| rs12108462 | 145612569 |
| rs10699715 | 145613243 |
| rs6857303 | 145613415 |
| rs12645789 | 145613755 |
| rs6537254 | 145614238 |
| rs10701183 | 145614266 |
| rs10643140 | 145614267 |
| rs6848116 | 145614813 |
| rs11354655 | 145614848 |
| rs10024775 | 145615212 |
| rs6824244 | 145615607 |
| rs6537255 | 145616254 |
| rs7673888 | 145616556 |
| rs7674022 | 145616585 |
| rs7672629 | 145616629 |
| rs17292861 | 145616629 |
| rs13142034 | 145616659 |
| rs7656975 | 145616886 |
| rs6835963 | 145617286 |
| rs12505498 | 145617846 |
| rs10023823 | 145617941 |
| rs10012458 | 145618043 |
| rs28691647 | 145618141 |
| rs10023998 | 145618142 |
| rs6857144 | 145618589 |
| rs6833563 | 145618590 |
| rs10559726 | 145618700 |
| rs2667332 | 145618936 |
| rs6856326 | 145618954 |
| rs13107492 | 145618972 |
| rs10015632 | 145619049 |
| rs17849972 | 145619313 |
| rs17851030 | 145619313 |
| rs4867 | 145619313 |
| rs7658293 | 145619334 |
| rs7687256 | 145619335 |
| rs7682260 | 145619347 |
| rs17858231 | 145619347 |
| rs17845377 | 145619347 |
| rs4449373 | 145619368 |
| rs2305067 | 145619485 |
| rs4240356 | 145619877 |
| rs4465992 | 145620001 |
| rs4465993 | 145620090 |
| rs7693383 | 145620147 |
| rs4835576 | 145620725 |
| rs7665923 | 145620837 |
| rs17829577 | 145620837 |
| rs4835577 | 145620938 |
| rs7694713 | 145621010 |
| rs4835578 | 145621019 |
| rs4450876 | 145621800 |
| rs7696242 | 145621813 |
| rs4337688 | 145621833 |
| rs4473613 | 145621916 |
| rs13142547 | 145622166 |
| rs13117874 | 145622214 |
| rs4565031 | 145622386 |
| rs1143455 | 145622409 |
| rs11938324 | 145623187 |
| rs4491970 | 145623308 |
| rs1373680 | 145623345 |
| rs1373681 | 145623376 |
| rs4488896 | 145623407 |
| rs4392467 | 145623408 |
| rs1444983 | 145623467 |
| rs6537257 | 145624031 |
| rs7673432 | 145624171 |
| rs7690953 | 145624193 |
| rs28474907 | 145624990 |
| rs28711072 | 145625000 |
| rs28614033 | 145625007 |
| rs4269129 | 145625007 |
| rs28521766 | 145625051 |
| rs4574352 | 145625244 |
| rs11406104 | 145625584 |
| rs1470411 | 145625607 |
| rs1966792 | 145625831 |
| rs10627192 | 145626455 |
| rs1444984 | 145626639 |
| rs1838524 | 145626769 |
| rs4535288 | 145626931 |
| rs3733387 | 145626999 |
| rs3083547 | 145627034 |
| rs1373682 | 145627318 |
| rs4464518 | 145627385 |
| rs11490715 | 145627539 |
| rs28731264 | 145627645 |
| rs4286473 | 145627645 |
| rs11944602 | 145627857 |
| rs11931075 | 145627912 |
| rs11935363 | 145627986 |
| rs11935365 | 145627996 |
| rs4287959 | 145628759 |
| rs3194696 | 145628884 |
| rs4835164 | 145628903 |
| rs7349621 | 145628956 |
| rs3209213 | 145629060 |
| rs4835165 | 145629080 |
| rs7349651 | 145629243 |
| rs9997445 | 145629362 |
| rs7349719 | 145629368 |
| rs7349654 | 145629405 |
| rs28556782 | 145629567 |
| rs11725211 | 145629733 |
| rs4349551 | 145630504 |
| rs6419323 | 145630598 |
| rs4642187 | 145630598 |
| rs7696658 | 145630825 |
| rs10708081 | 145631282 |
| rs4432704 | 145631283 |
| rs28576209 | 145631388 |
| rs28465668 | 145631399 |
| rs4413360 | 145631434 |
| rs4314231 | 145631583 |
| rs13138562 | 145631765 |
| rs13120766 | 145631855 |
| rs28488827 | 145631856 |
| rs11731918 | 145632201 |
| rs6819027 | 145632210 |
| rs6844008 | 145632212 |
| rs4355337 | 145632220 |
| rs11100814 | 145632334 |
| rs4356869 | 145632631 |
| rs4629388 | 145632640 |
| rs4835586 | 145633205 |
| rs11942789 | 145633565 |
| rs11943717 | 145633601 |
| rs11929703 | 145633721 |
| rs11943767 | 145633732 |
| rs11929795 | 145633898 |
| rs6857265 | 145633963 |
| rs13103731 | 145634114 |
| rs11939323 | 145634277 |
| rs28798506 | 145634353 |
| rs11939410 | 145634528 |
| rs5001419 | 145635170 |
| rs5001418 | 145635172 |
| rs28594673 | 145635594 |
| rs11736498 | 145635911 |
| rs11723763 | 145635923 |
| rs4260483 | 145635979 |
| rs28444311 | 145637104 |
| rs11100831 | 145637270 |
| rs11100832 | 145637271 |

TABLE 12-continued

Public SNPs from dbSNP Build125 in the LD block C04a region

| Name | Location (Bld 34) |
|---|---|
| rs11414611 | 145637738 |
| rs11723272 | 145638003 |
| rs11935223 | 145638402 |
| rs3806773 | 145640143 |
| rs3806772 | 145640145 |
| rs28603191 | 145640380 |
| rs28533871 | 145640407 |
| rs28662181 | 145642227 |
| rs13104399 | 145642297 |
| rs7681791 | 145643041 |
| rs3856993 | 145643693 |
| rs6835623 | 145643699 |
| rs9995236 | 145643762 |
| rs7688405 | 145644032 |
| rs12499911 | 145644112 |
| rs7659783 | 145644244 |
| rs13137079 | 145644268 |
| rs4352423 | 145644491 |
| rs4336173 | 145644578 |
| rs4336174 | 145644587 |
| rs4423827 | 145644589 |
| rs4336175 | 145644680 |
| rs28813719 | 145644820 |
| rs13125462 | 145644854 |
| rs28823926 | 145645272 |
| rs13435041 | 145645302 |
| rs4264778 | 145645474 |
| rs4359850 | 145645662 |
| rs28855521 | 145646293 |
| rs10434188 | 145646406 |
| rs10452245 | 145646609 |
| rs7698193 | 145646927 |
| rs10452246 | 145647005 |
| rs6537259 | 145647005 |
| rs13141025 | 145647297 |
| rs13107394 | 145647336 |
| rs7438745 | 145647490 |
| rs7438753 | 145647552 |
| rs7697694 | 145648905 |
| rs4383568 | 145648905 |
| rs4383569 | 145648906 |
| rs7697695 | 145648906 |
| rs13149556 | 145649077 |
| rs6537260 | 145649632 |
| rs7434993 | 145649890 |
| rs387988 | 145650144 |
| rs13119218 | 145650511 |
| rs12502560 | 145651217 |
| rs28780480 | 145651580 |
| rs7677825 | 145652339 |
| rs13112639 | 145652653 |
| rs13112856 | 145652764 |
| rs7688971 | 145653983 |
| rs7690607 | 145654148 |
| rs11933261 | 145654236 |
| rs11732500 | 145654255 |
| rs7690996 | 145654353 |
| rs7441048 | 145654648 |
| rs6831817 | 145655091 |
| rs11934660 | 145655438 |
| rs9761473 | 145656207 |
| rs6838900 | 145656207 |
| rs11726939 | 145656500 |
| rs12511610 | 145656754 |
| rs10008680 | 145657300 |
| rs10008688 | 145657340 |
| rs9762726 | 145657811 |
| rs9685916 | 145657811 |
| rs6537261 | 145657811 |
| rs7440632 | 145657870 |
| rs9761977 | 145658142 |
| rs9715502 | 145658142 |
| rs9685368 | 145658142 |
| rs6419324 | 145658142 |
| rs4611868 | 145658142 |
| rs28868097 | 145659949 |
| rs13113070 | 145660719 |
| rs7667722 | 145660969 |
| rs13133352 | 145661027 |
| rs10857419 | 145661746 |
| rs12511288 | 145661773 |
| rs13121373 | 145662179 |
| rs10024232 | 145662717 |
| rs11728624 | 145662770 |
| rs7665326 | 145663306 |
| rs10030421 | 145664621 |
| rs12640478 | 145664920 |
| rs12646795 | 145665173 |
| rs10673489 | 145665318 |
| rs5862687 | 145665695 |
| rs4402988 | 145666319 |
| rs4432705 | 145666587 |
| rs6819750 | 145668098 |
| rs11930911 | 145668289 |
| rs7439316 | 145668582 |
| rs7659322 | 145668785 |
| rs4469025 | 145668987 |
| rs11727331 | 145669307 |
| rs4539990 | 145670484 |
| rs6834247 | 145670516 |
| rs4303929 | 145670685 |
| rs9999314 | 145672034 |
| rs6847842 | 145672454 |
| rs13134172 | 145676737 |
| rs10857420 | 145676917 |
| rs10015396 | 145677193 |
| rs10213243 | 145677885 |
| rs4558820 | 145678132 |
| rs12501242 | 145679032 |
| rs4269130 | 145679051 |
| rs4289393 | 145679688 |
| rs17829589 | 145679688 |
| rs6812128 | 145679891 |
| rs13124384 | 145680376 |
| rs13119039 | 145680533 |
| rs4835608 | 145680821 |
| rs11947531 | 145681127 |
| rs11939413 | 145682201 |
| rs11942047 | 145684546 |
| rs13108951 | 145685301 |
| rs13108952 | 145685303 |
| rs11100837 | 145685304 |
| rs10566048 | 145685313 |
| rs10552752 | 145686612 |
| rs12508181 | 145687014 |
| rs4388034 | 145687324 |
| rs11947279 | 145688374 |
| rs3923603 | 145688956 |
| rs7655948 | 145689137 |
| rs12506435 | 145689311 |
| rs6838200 | 145689467 |
| rs7685721 | 145689488 |
| rs11726495 | 145691192 |
| rs13115983 | 145692367 |
| rs6834013 | 145692585 |
| rs12511121 | 145695145 |
| rs7695923 | 145695407 |
| rs13350605 | 145695845 |
| rs10019883 | 145695845 |
| rs11100838 | 145696321 |
| rs4555578 | 145696570 |
| rs7439076 | 145696570 |
| rs6537263 | 145699261 |
| rs4355338 | 145699261 |
| rs4487295 | 145700803 |
| rs4599356 | 145701080 |
| rs11931990 | 145701176 |
| rs7700104 | 145701236 |
| rs6148706 | 145701460 |
| rs4491971 | 145701618 |

TABLE 12-continued

Public SNPs from dbSNP Build125 in the LD block C04a region

| Name | Location (Bld 34) |
|---|---|
| rs4554017 | 145701651 |
| rs4379017 | 145701871 |
| rs10033964 | 145702395 |
| rs4240360 | 145703019 |
| rs4835622 | 145703540 |
| rs4835623 | 145703584 |
| rs4835624 | 145703588 |
| rs13111659 | 145703666 |
| rs4434192 | 145703996 |
| rs5862688 | 145706220 |
| rs13127712 | 145706253 |
| rs13133696 | 145706387 |
| rs13128382 | 145706528 |
| rs28568288 | 145706565 |
| rs7692784 | 145707723 |
| rs13115407 | 145708097 |
| rs4585250 | 145708807 |
| rs28631892 | 145708869 |
| rs4330310 | 145708893 |
| rs12644229 | 145709867 |
| rs28410289 | 145710108 |
| rs5862689 | 145710343 |
| rs5862690 | 145710865 |
| rs5862691 | 145710867 |
| rs4459948 | 145711026 |
| rs4452381 | 145711612 |
| rs4269127 | 145711675 |
| rs5862692 | 145711719 |
| rs4345121 | 145711844 |
| rs4303930 | 145713152 |
| rs10012731 | 145714018 |
| rs4491972 | 145714914 |
| rs12501983 | 145714922 |
| rs4446264 | 145715028 |
| rs7440429 | 145715028 |
| rs11934621 | 145715496 |
| rs7440593 | 145715515 |
| rs4491973 | 145715515 |
| rs4273415 | 145715657 |
| rs7441555 | 145715657 |
| rs7436168 | 145715862 |
| rs4635767 | 145715862 |
| rs4348046 | 145715964 |
| rs7441611 | 145715964 |
| rs4368558 | 145715977 |
| rs6537264 | 145715977 |
| rs11100839 | 145716530 |
| rs6811457 | 145716935 |
| rs13123634 | 145717577 |
| rs4417920 | 145717918 |
| rs4505762 | 145718312 |
| rs4583707 | 145718503 |
| rs4505763 | 145718603 |
| rs4423828 | 145719032 |
| rs4508836 | 145719091 |
| rs4425324 | 145719771 |
| rs4513513 | 145720198 |
| rs5862693 | 145720363 |
| rs10657867 | 145720367 |
| rs6856087 | 145721074 |
| rs4635768 | 145721551 |
| rs6832605 | 145722035 |
| rs13127749 | 145722949 |
| rs7664319 | 145722998 |
| rs4518185 | 145723537 |
| rs4359851 | 145723864 |
| rs4364211 | 145723955 |
| rs11734108 | 145724015 |
| rs13102357 | 145724472 |
| rs11371652 | 145724744 |
| rs11450119 | 145724754 |
| rs4549337 | 145724777 |
| rs4377535 | 145724836 |
| rs4386552 | 145725308 |
| rs4390989 | 145725942 |
| rs4392468 | 145726328 |
| rs12513016 | 145726571 |
| rs4305469 | 145726592 |
| rs11733518 | 145727422 |
| rs11934883 | 145727853 |
| rs11934916 | 145727905 |
| rs7658605 | 145728645 |
| rs9308177 | 145728963 |
| rs5862694 | 145728965 |
| rs7669619 | 145729321 |
| rs11938336 | 145729941 |
| rs10596570 | 145730167 |
| rs11100840 | 145730920 |
| rs7349691 | 145731030 |
| rs11939769 | 145731398 |
| rs7438710 | 145731672 |
| rs7435095 | 145732055 |
| rs4321580 | 145732055 |
| rs4519751 | 145732110 |
| rs7435388 | 145732110 |
| rs6537265 | 145732883 |
| rs4271962 | 145733136 |
| rs7690710 | 145733236 |
| rs4396945 | 145733269 |
| rs7436364 | 145733269 |
| rs4626149 | 145733654 |
| rs7436751 | 145733654 |
| rs4128281 | 145733745 |
| rs4481199 | 145734205 |
| rs7437777 | 145734205 |
| rs7656927 | 145734795 |
| rs7436052 | 145736165 |
| rs7436055 | 145736179 |
| rs7440160 | 145736193 |
| rs17869776 | 145736479 |
| rs13104440 | 145737381 |
| rs9790335 | 145737381 |
| rs11100841 | 145738444 |
| rs28850043 | 145738464 |
| rs7669987 | 145739181 |
| rs6828217 | 145739816 |
| rs4337686 | 145739883 |
| rs4835625 | 145739961 |
| rs13351848 | 145741102 |
| rs10032210 | 145741102 |
| rs6842847 | 145741491 |
| rs11934451 | 145743444 |
| rs13128064 | 145743514 |
| rs6537266 | 145743640 |
| rs9759814 | 145743745 |
| rs9683786 | 145743745 |
| rs6537267 | 145743745 |
| rs13115981 | 145743879 |
| rs6844087 | 145744012 |
| rs28752136 | 145744287 |
| rs13136472 | 145744324 |
| rs6851193 | 145745138 |
| rs6820942 | 145745142 |
| rs6851649 | 145745361 |
| rs6537268 | 145745365 |
| rs13351745 | 145745437 |
| rs10031214 | 145745437 |
| rs4422370 | 145745834 |
| rs6537269 | 145745834 |
| rs7437332 | 145746190 |
| rs4317153 | 145746190 |
| rs4317154 | 145746215 |
| rs7437335 | 145746215 |
| rs28866308 | 145746499 |
| rs6811004 | 145746780 |
| rs6829222 | 145746837 |
| rs12643420 | 145747495 |
| rs10009929 | 145748272 |
| rs10007545 | 145748444 |
| rs28762778 | 145749228 |

TABLE 12-continued

Public SNPs from dbSNP Build125 in the LD block C04a region

| Name | Location (Bld 34) |
|---|---|
| rs11729636 | 145749330 |
| rs11100842 | 145749579 |
| rs28449861 | 145749755 |
| rs13122044 | 145750326 |
| rs4287960 | 145750933 |
| rs4331724 | 145751306 |
| rs7441314 | 145751306 |
| rs12505797 | 145751840 |
| rs12503177 | 145751969 |
| rs4336169 | 145752009 |
| rs4269131 | 145752089 |
| rs4482709 | 145752289 |
| rs6858517 | 145752509 |
| rs17829613 | 145752702 |
| rs4320096 | 145752702 |
| rs6832567 | 145752762 |
| rs12504257 | 145752870 |
| rs10592026 | 145752872 |
| rs10592027 | 145752894 |
| rs11937287 | 145753529 |
| rs13144823 | 145754060 |
| rs13144992 | 145754101 |
| rs13105208 | 145754596 |
| rs13123796 | 145754808 |
| rs11100843 | 145755309 |
| rs6854878 | 145755922 |
| rs7691223 | 145757447 |
| rs13123322 | 145758352 |
| rs13123791 | 145758555 |
| rs7441548 | 145758930 |
| rs4320097 | 145758930 |
| rs10303170 | 145758930 |
| rs10025195 | 145758951 |
| rs7679401 | 145759776 |
| rs7684835 | 145760207 |
| rs10389982 | 145760419 |
| rs4309786 | 145760419 |
| rs10012192 | 145760480 |
| rs13349860 | 145760480 |
| rs4315730 | 145760932 |
| rs7440973 | 145760932 |
| rs11943703 | 145761006 |
| rs11943710 | 145761056 |
| rs6537271 | 145761343 |
| rs10316731 | 145761343 |
| rs10316736 | 145761590 |
| rs7696987 | 145761590 |
| rs13119542 | 145762396 |
| rs13139062 | 145762410 |
| rs12647138 | 145762494 |
| rs12509569 | 145763289 |
| rs11732756 | 145763435 |
| rs11729387 | 145763656 |
| rs13127816 | 145763979 |
| rs13128959 | 145764559 |
| rs12506864 | 145765120 |
| rs12510816 | 145765121 |
| rs12499055 | 145765272 |
| rs13102635 | 145766677 |
| rs4482710 | 145767508 |
| rs11934670 | 145768087 |
| rs11725863 | 145768271 |
| rs7657288 | 145768833 |
| rs4491974 | 145769441 |
| rs7436838 | 145769441 |
| rs10026674 | 145770126 |
| rs12510585 | 145770366 |
| rs4613517 | 145770729 |
| rs11736774 | 145771275 |
| rs4511953 | 145771302 |
| rs13114690 | 145771507 |
| rs13118529 | 145771638 |
| rs9685252 | 145771918 |
| rs13121748 | 145772389 |
| rs7658232 | 145772816 |
| rs7689179 | 145773276 |
| rs28396349 | 145773393 |
| rs11355781 | 145773626 |
| rs7690204 | 145773833 |
| rs9994461 | 145774149 |
| rs11369908 | 145774396 |
| rs6811546 | 145774683 |
| rs10707511 | 145774786 |
| rs6828423 | 145774804 |
| rs6830134 | 145774878 |
| rs4597773 | 145775060 |
| rs4334701 | 145775065 |
| rs4334702 | 145775156 |
| rs4597774 | 145775174 |
| rs4334703 | 145775290 |
| rs4591542 | 145775330 |
| rs11933796 | 145775581 |
| rs10033430 | 145775585 |
| rs10002790 | 145775728 |
| rs7656615 | 145775752 |
| rs7661687 | 145775787 |
| rs7656994 | 145775906 |
| rs7656999 | 145775912 |
| rs7684324 | 145775965 |
| rs7667380 | 145776264 |
| rs13125988 | 145776417 |
| rs9968313 | 145776461 |
| rs12645983 | 145777082 |
| rs7692268 | 145777694 |
| rs7687270 | 145778329 |
| rs4557215 | 145778499 |
| rs4285039 | 145778579 |
| rs4293748 | 145779895 |
| rs4254717 | 145779980 |
| rs4438716 | 145780000 |
| rs5862695 | 145780041 |
| rs5862696 | 145780049 |
| rs5001226 | 145780125 |
| rs7438029 | 145780146 |
| rs11422979 | 145780186 |
| rs7700020 | 145780250 |
| rs7675261 | 145780366 |
| rs7654269 | 145780520 |
| rs11736065 | 145780534 |
| rs7654605 | 145780672 |
| rs7659591 | 145780676 |
| rs9684121 | 145780762 |
| rs7676097 | 145780790 |
| rs7682399 | 145780994 |
| rs7664876 | 145781028 |
| rs7659974 | 145781096 |
| rs7681225 | 145781158 |
| rs7681569 | 145781267 |
| rs11937859 | 145781545 |
| rs10684018 | 145781645 |
| rs7666696 | 145781928 |
| rs7666704 | 145781933 |
| rs7682836 | 145781961 |
| rs7687623 | 145781995 |
| rs7671457 | 145782025 |
| rs9968341 | 145782741 |
| rs9968343 | 145782834 |
| rs4629389 | 145782873 |
| rs11408501 | 145783292 |
| rs7673707 | 145783341 |
| rs7695068 | 145783493 |
| rs5024787 | 145783709 |
| rs5024786 | 145783723 |
| rs4642188 | 145784396 |
| rs7356365 | 145784489 |
| rs7356418 | 145784495 |
| rs7655929 | 145784862 |
| rs28609938 | 145784998 |
| rs10012765 | 145785202 |
| rs10015172 | 145785249 |

TABLE 12-continued

Public SNPs from dbSNP Build125 in the LD block C04a region

| Name | Location (Bld 34) |
|---|---|
| rs10001335 | 145785465 |
| rs7662113 | 145785675 |
| rs13112701 | 145785731 |
| rs7662334 | 145785833 |
| rs7692879 | 145785886 |
| rs11325906 | 145785926 |
| rs11734478 | 145786355 |
| rs10028883 | 145786977 |
| rs9308178 | 145787077 |
| rs9308179 | 145787249 |
| rs9308180 | 145787311 |
| rs4348047 | 145787525 |
| rs7434323 | 145787672 |
| rs4586878 | 145787686 |
| rs4277729 | 145787740 |
| rs4431168 | 145787863 |
| rs13146588 | 145788461 |
| rs4835176 | 145789014 |
| rs6857355 | 145789110 |
| rs6835878 | 145789408 |
| rs9308181 | 145789824 |
| rs9884309 | 145789933 |
| rs11100844 | 145790021 |
| rs11100845 | 145790038 |
| rs10000202 | 145790187 |
| rs10002713 | 145790578 |
| rs10002827 | 145790721 |
| rs4453896 | 145790874 |
| rs5862697 | 145790912 |
| rs4532189 | 145790951 |
| rs4269132 | 145791345 |
| rs12711416 | 145791581 |
| rs28497010 | 145791894 |
| rs4521297 | 145792370 |
| rs7674504 | 145792549 |
| rs4321581 | 145792660 |
| rs13125170 | 145792702 |
| rs28488928 | 145793471 |
| rs13127136 | 145793772 |
| rs6844385 | 145793976 |
| rs4388035 | 145794715 |
| rs6537272 | 145794726 |
| rs7677370 | 145796125 |
| rs7682562 | 145796235 |
| rs13149264 | 145796979 |
| rs11933270 | 145796986 |
| rs11933275 | 145797024 |
| rs11100846 | 145797191 |
| rs7661384 | 145798489 |
| rs6819101 | 145798948 |
| rs5862698 | 145799143 |
| rs11100847 | 145799337 |
| rs13105533 | 145799802 |
| rs28513471 | 145799903 |
| rs10050184 | 145800321 |
| rs4410481 | 145800441 |
| rs4452383 | 145800549 |
| rs4600870 | 145800662 |
| rs7438126 | 145800831 |
| rs28633544 | 145800888 |
| rs11931474 | 145800899 |
| rs11945691 | 145801121 |
| rs4374583 | 145802263 |
| rs4535289 | 145802266 |
| rs11100848 | 145802986 |
| rs6821055 | 145803625 |
| rs11935505 | 145804049 |
| rs11100849 | 145804416 |

TABLE 13

Public SNPs from dbSNP Build125 within the TCF2 gene

| Name | Location (Bld 34) |
|---|---|
| rs12942441 | 36236581 |
| rs2107135 | 36236969 |
| rs12936117 | 36237243 |
| rs2107134 | 36237340 |
| rs6607285 | 36237624 |
| rs8068197 | 36238033 |
| rs3094518 | 36238441 |
| rs3094517 | 36238485 |
| rs3094516 | 36238728 |
| rs3094515 | 36239203 |
| rs17138522 | 36239284 |
| rs17624747 | 36239704 |
| rs739753 | 36239827 |
| rs17841468 | 36240323 |
| rs11263755 | 36241071 |
| rs2057712 | 36241259 |
| rs17697931 | 36241357 |
| rs2285741 | 36241357 |
| rs7222459 | 36241398 |
| rs7223047 | 36241769 |
| rs9675203 | 36241819 |
| rs9912390 | 36241945 |
| rs10962 | 36242001 |
| rs17847516 | 36242001 |
| rs11545641 | 36242001 |
| rs17138512 | 36242148 |
| rs11545642 | 36242383 |
| rs17847515 | 36242481 |
| rs2688 | 36242481 |
| rs1058166 | 36242541 |
| rs17847514 | 36242651 |
| rs2689 | 36242651 |
| rs17847513 | 36242825 |
| rs1800929 | 36242825 |
| rs2229295 | 36242826 |
| rs8068014 | 36242878 |
| rs17847530 | 36242967 |
| rs3110641 | 36242967 |
| rs8066605 | 36243051 |
| rs3094514 | 36243787 |
| rs5820230 | 36243977 |
| rs3094513 | 36244073 |
| rs3110640 | 36244373 |
| rs3094512 | 36244490 |
| rs3110639 | 36244702 |
| rs9675152 | 36245272 |
| rs3110638 | 36245313 |
| rs11263756 | 36245370 |
| rs3049510 | 36245568 |
| rs5820231 | 36245571 |
| rs5820232 | 36245572 |
| rs1110463 | 36245608 |
| rs10619352 | 36245796 |
| rs12150371 | 36245881 |
| rs12935974 | 36246332 |
| rs7501432 | 36246343 |
| rs8065402 | 36246382 |
| rs3940262 | 36246420 |
| rs11651164 | 36246836 |
| rs11656043 | 36246841 |
| rs1859211 | 36246922 |
| rs8069279 | 36247107 |
| rs3110637 | 36247329 |
| rs3094511 | 36247607 |
| rs3110636 | 36247626 |
| rs11342001 | 36247735 |
| rs3110635 | 36248166 |
| rs10535964 | 36248170 |
| rs12450532 | 36248178 |
| rs12453114 | 36248186 |
| rs11868513 | 36248242 |
| rs11868535 | 36248331 |
| rs3110634 | 36248347 |
| rs3110633 | 36248619 |
| rs2898655 | 36248655 |

TABLE 13-continued

Public SNPs from dbSNP Build125 within the TCF2 gene

| Name | Location (Bld 34) |
|---|---|
| rs11464180 | 36248772 |
| rs3094510 | 36249319 |
| rs3110632 | 36249328 |
| rs4795211 | 36249546 |
| rs4795212 | 36249793 |
| rs9892033 | 36249981 |
| rs13341296 | 36250005 |
| rs9900653 | 36250005 |
| rs3110630 | 36250023 |
| rs4795213 | 36250781 |
| rs7406029 | 36250781 |
| rs2411156 | 36250783 |
| rs4502267 | 36250783 |
| rs4795214 | 36250783 |
| rs4635384 | 36251108 |
| rs6422978 | 36251108 |
| rs13341544 | 36251132 |
| rs9908712 | 36251132 |
| rs4795215 | 36251164 |
| rs6607286 | 36251164 |
| rs4795216 | 36251617 |
| rs6607287 | 36251617 |
| rs12449654 | 36251626 |
| rs12452659 | 36251742 |
| rs2411155 | 36252024 |
| rs2411154 | 36252106 |
| rs7211959 | 36252266 |
| rs11656817 | 36252449 |
| rs7221822 | 36253596 |
| rs1016991 | 36253703 |
| rs7207401 | 36253751 |
| rs11421312 | 36253836 |
| rs2269845 | 36254275 |
| rs2269844 | 36254364 |
| rs11350722 | 36254468 |
| rs17847522 | 36254530 |
| rs2269843 | 36254530 |
| rs9890418 | 36254543 |
| rs10083829 | 36254794 |
| rs17847520 | 36254796 |
| rs2269842 | 36254796 |
| rs13339672 | 36254852 |
| rs2269841 | 36254927 |
| rs12938438 | 36254935 |
| rs11440398 | 36254974 |
| rs2269840 | 36255022 |
| rs8070225 | 36255431 |
| rs2189303 | 36255655 |
| rs11381765 | 36255669 |
| rs8075185 | 36255766 |
| rs11381764 | 36255776 |
| rs2074430 | 36256065 |
| rs11870409 | 36256161 |
| rs2189302 | 36256433 |
| rs9905004 | 36256832 |
| rs17847519 | 36256847 |
| rs2074429 | 36256847 |
| rs2074428 | 36257209 |
| rs17138495 | 36257493 |
| rs3110619 | 36257619 |
| rs3094509 | 36257849 |
| rs12948642 | 36257978 |
| rs1008284 | 36258008 |
| rs3094508 | 36258485 |
| rs7210911 | 36258850 |
| rs8068474 | 36259195 |
| rs2189301 | 36259235 |
| rs17841466 | 36259274 |
| rs28667231 | 36259638 |
| rs3094507 | 36259748 |
| rs2107133 | 36260447 |
| rs4794757 | 36260763 |
| rs10701156 | 36260853 |
| rs17625617 | 36261045 |
| rs2158254 | 36261045 |
| rs7207680 | 36261183 |
| rs11870929 | 36261640 |
| rs10618694 | 36262621 |
| rs7221709 | 36262625 |
| rs3049485 | 36262676 |
| rs5820233 | 36262691 |
| rs28497135 | 36262846 |
| rs7222069 | 36262859 |
| rs7213333 | 36263418 |
| rs9892543 | 36263509 |
| rs2285740 | 36264278 |
| rs8065904 | 36264287 |
| rs8067619 | 36264288 |
| rs3110649 | 36265730 |
| rs17847518 | 36266362 |
| rs7225211 | 36266500 |
| rs3110648 | 36266584 |
| rs17138480 | 36266697 |
| rs3110645 | 36268726 |
| rs3110644 | 36268746 |
| rs17138478 | 36268870 |
| rs3110643 | 36269042 |
| rs3110642 | 36269170 |
| rs3110631 | 36270063 |
| rs3094506 | 36270247 |
| rs2158253 | 36270333 |
| rs3094505 | 36270455 |
| rs11649743 | 36270529 |
| rs7209295 | 36270746 |
| rs17138476 | 36271155 |
| rs17138475 | 36271223 |
| rs3110618 | 36271269 |
| rs2411153 | 36271365 |
| rs3110651 | 36271418 |
| rs3110650 | 36271455 |
| rs11263757 | 36271561 |
| rs10661407 | 36272411 |
| rs10661408 | 36272412 |
| rs718961 | 36272649 |
| rs718960 | 36272829 |
| rs8068344 | 36273116 |
| rs12942953 | 36273323 |
| rs12951345 | 36273413 |
| rs1985643 | 36274052 |
| rs4795218 | 36274060 |
| rs2097759 | 36275003 |
| rs17138469 | 36275715 |
| rs4794758 | 36275978 |
| rs7407025 | 36276360 |
| rs12450628 | 36277971 |
| rs7223387 | 36278023 |
| rs11658433 | 36278457 |
| rs8066151 | 36278854 |
| rs9914818 | 36279263 |
| rs11263758 | 36279553 |
| rs10451318 | 36279669 |
| rs2107132 | 36279752 |
| rs916895 | 36279777 |
| rs11651496 | 36279794 |
| rs916894 | 36279811 |
| rs3049482 | 36280450 |
| rs10571598 | 36280461 |
| rs9895178 | 36281866 |
| rs2107131 | 36282239 |
| rs2898654 | 36283307 |
| rs11263759 | 36283391 |
| rs11263760 | 36283392 |
| rs3786127 | 36283424 |
| rs2005706 | 36283835 |
| rs12943407 | 36283879 |
| rs2002731 | 36284080 |
| rs1016990 | 36284465 |
| rs17847529 | 36284465 |
| rs17847528 | 36284562 |
| rs17847527 | 36284588 |

TABLE 13-continued

Public SNPs from dbSNP Build125 within the TCF2 gene

| Name | Location (Bld 34) |
|---|---|
| rs17847526 | 36284832 |
| rs880411 | 36284832 |
| rs9891752 | 36284854 |
| rs880410 | 36284861 |
| rs1135579 | 36284865 |
| rs1135581 | 36284891 |
| rs1135582 | 36284892 |
| rs17847525 | 36284897 |
| rs1135583 | 36284914 |
| rs5820234 | 36284988 |
| rs9892918 | 36285339 |
| rs3744764 | 36285946 |
| rs17847524 | 36286435 |
| rs3744763 | 36286435 |
| rs17847523 | 36286796 |
| rs17847521 | 36286806 |
| rs9906451 | 36286806 |
| rs3837868 | 36288222 |
| rs7405776 | 36288572 |
| rs9901538 | 36288991 |
| rs9895048 | 36289035 |
| rs3216929 | 36289413 |
| rs4795219 | 36289813 |
| rs17138459 | 36289958 |
| rs9909673 | 36291355 |
| rs17704811 | 36291780 |
| rs2005705 | 36291850 |
| rs757211 | 36292028 |
| rs757210 | 36292065 |
| rs9912751 | 36293132 |
| rs11654969 | 36293319 |
| rs11263761 | 36293325 |
| rs4430796 | 36293590 |
| rs4520879 | 36294416 |
| rs4239217 | 36294537 |
| rs17847517 | 36295280 |
| rs11651755 | 36295390 |
| rs10908278 | 36295502 |
| rs11657964 | 36296317 |
| rs4528622 | 36296558 |
| rs7501939 | 36296706 |
| rs8064454 | 36297136 |
| rs12601991 | 36297183 |
| rs11263762 | 36297476 |
| rs7405696 | 36297585 |
| rs7502069 | 36297890 |
| rs11651052 | 36297931 |
| rs757209 | 36298383 |
| rs9901746 | 36298699 |
| rs11263763 | 36299115 |
| rs11658063 | 36299422 |
| rs12453443 | 36299671 |
| rs5820235 | 36300747 |
| rs9899145 | 36301139 |
| rs9913260 | 36301447 |
| rs9913297 | 36301489 |
| rs3760511 | 36301863 |
| rs17626423 | 36303917 |
| rs12051720 | 36304974 |
| rs17138380 | 36306536 |
| rs17626459 | 36307305 |
| rs17705019 | 36307818 |
| rs9906050 | 36307993 |
| rs11868443 | 36308036 |
| rs7502487 | 36309930 |
| rs7213769 | 36310716 |
| rs12949259 | 36311129 |
| rs11455435 | 36311670 |
| rs12603084 | 36312608 |
| rs6607289 | 36313150 |
| rs6607290 | 36313188 |
| rs11381897 | 36313460 |
| rs17138335 | 36313685 |
| rs9911288 | 36313836 |
| rs9912022 | 36314159 |
| rs10567850 | 36314686 |
| rs17841462 | 36315087 |
| rs7213140 | 36315601 |
| rs12944771 | 36315626 |
| rs11421430 | 36316133 |
| rs11434768 | 36316138 |
| rs10674983 | 36316147 |
| rs8079492 | 36316421 |
| rs12940061 | 36316538 |
| rs12940062 | 36316541 |
| rs12947560 | 36316560 |
| rs12940076 | 36316561 |
| rs7219104 | 36316592 |
| rs11371770 | 36316677 |
| rs11384996 | 36316682 |
| rs4795220 | 36317218 |
| rs4795221 | 36317219 |
| rs4795222 | 36317231 |
| rs9908105 | 36317283 |
| rs10655162 | 36317587 |
| rs4795223 | 36317777 |
| rs4794759 | 36317936 |
| rs9916121 | 36318357 |
| rs8067696 | 36318502 |
| rs12600634 | 36318598 |
| rs11650348 | 36318941 |
| rs17705177 | 36319076 |
| rs6607291 | 36319412 |
| rs6607292 | 36319632 |
| rs9902483 | 36319692 |
| rs6607293 | 36319849 |
| rs6607294 | 36320128 |
| rs6607295 | 36320209 |
| rs10565630 | 36320488 |
| rs11376515 | 36320666 |
| rs8077061 | 36320869 |
| rs8077234 | 36320994 |
| rs12941488 | 36322154 |
| rs7342854 | 36322247 |
| rs7342856 | 36322327 |
| rs7342857 | 36322332 |
| rs10653005 | 36322459 |
| rs7342879 | 36322581 |
| rs9898782 | 36322636 |
| rs12950378 | 36323462 |
| rs17138201 | 36324014 |

TABLE 14

Public SNPs from dbSNP Build125 in the LD block C17b region

| Name | Location (Bld 34) |
|---|---|
| rs7208022 | 69665297 |
| rs28578535 | 69665582 |
| rs11871999 | 69665688 |
| rs7208880 | 69665972 |
| rs11330720 | 69666003 |
| rs2367244 | 69667282 |
| rs4793526 | 69667313 |
| rs4793527 | 69667320 |
| rs4793330 | 69667720 |
| rs12945790 | 69667864 |
| rs12945793 | 69667866 |
| rs12942301 | 69667992 |
| rs8077040 | 69668296 |
| rs11077543 | 69668329 |
| rs1861689 | 69669217 |
| rs1861690 | 69669376 |
| rs12936362 | 69669543 |
| rs2367245 | 69669654 |

TABLE 14-continued

Public SNPs from dbSNP Build125 in the LD block C17b region

| Name | Location (Bld 34) |
|---|---|
| rs2367246 | 69669660 |
| rs2367247 | 69669678 |
| rs2367248 | 69669835 |
| rs4337333 | 69669883 |
| rs2367249 | 69669987 |
| rs9898686 | 69670315 |
| rs9899756 | 69670442 |
| rs17224342 | 69671371 |
| rs12938195 | 69671387 |
| rs7216999 | 69671422 |
| rs7215968 | 69671472 |
| rs7217179 | 69671523 |
| rs12941678 | 69671533 |
| rs12949308 | 69671534 |
| rs7215998 | 69671548 |
| rs12949632 | 69671634 |
| rs9906150 | 69671902 |
| rs9914841 | 69672198 |
| rs4793331 | 69672482 |
| rs7223432 | 69672957 |
| rs2216288 | 69673023 |
| rs10688256 | 69673156 |
| rs6501435 | 69673287 |
| rs28415436 | 69673851 |
| rs2080539 | 69673914 |
| rs2080540 | 69674102 |
| rs2098431 | 69674201 |
| rs12452747 | 69674232 |
| rs12950552 | 69674402 |
| rs12944225 | 69674617 |
| rs11871500 | 69674867 |
| rs9895751 | 69675048 |
| rs12944216 | 69675152 |
| rs28509409 | 69675646 |
| rs11317800 | 69675735 |
| rs28479625 | 69675789 |
| rs28479657 | 69675792 |
| rs28522706 | 69676111 |
| rs28608720 | 69676295 |
| rs11870970 | 69676459 |
| rs11077544 | 69676558 |
| rs11077545 | 69676593 |
| rs994784 | 69676759 |
| rs16976397 | 69677105 |
| rs12948425 | 69677389 |
| rs12938367 | 69677408 |
| rs7221849 | 69677626 |
| rs11366111 | 69677741 |
| rs16976399 | 69677786 |
| rs7226259 | 69677831 |
| rs7221739 | 69677904 |
| rs9892269 | 69678024 |
| rs9890229 | 69678201 |
| rs11867272 | 69678271 |
| rs8068751 | 69678391 |
| rs8082156 | 69678793 |
| rs9897691 | 69679041 |
| rs9900129 | 69679059 |
| rs9897896 | 69679093 |
| rs9898123 | 69679197 |
| rs9899952 | 69679280 |
| rs9899737 | 69679909 |
| rs9905626 | 69680150 |
| rs9905810 | 69680185 |
| rs9914290 | 69680203 |
| rs9906277 | 69680390 |
| rs9908858 | 69680454 |
| rs9915246 | 69680633 |
| rs12150666 | 69680757 |
| rs9915679 | 69680808 |
| rs9916172 | 69681232 |
| rs12449832 | 69681760 |
| rs16976401 | 69681891 |
| rs11077546 | 69681919 |
| rs12944455 | 69682075 |
| rs12943693 | 69682168 |
| rs8066397 | 69682265 |
| rs8065642 | 69682519 |
| rs12600835 | 69682551 |
| rs11652143 | 69682700 |
| rs8067786 | 69682767 |
| rs12946846 | 69682905 |
| rs2367250 | 69682988 |
| rs5821824 | 69683086 |
| rs2108533 | 69683233 |
| rs28642771 | 69683621 |
| rs9904895 | 69683894 |
| rs9909477 | 69684227 |
| rs9890292 | 69684255 |
| rs1468480 | 69684610 |
| rs17765267 | 69684681 |
| rs7220901 | 69685291 |
| rs16976403 | 69685307 |
| rs9907216 | 69685712 |
| rs7217550 | 69685774 |
| rs28626361 | 69685946 |
| rs9302930 | 69685946 |
| rs10667181 | 69685947 |
| rs9914095 | 69686290 |
| rs16967044 | 69686557 |
| rs9914833 | 69686630 |
| rs7212301 | 69687200 |
| rs9891558 | 69687202 |
| rs11650685 | 69687640 |
| rs9895083 | 69687640 |
| rs8080466 | 69689709 |
| rs12453898 | 69690615 |
| rs28525974 | 69691219 |
| rs4793332 | 69691243 |
| rs17765273 | 69691691 |
| rs17177838 | 69692020 |
| rs12450393 | 69692082 |
| rs12449659 | 69693931 |
| rs7212237 | 69694416 |
| rs4564625 | 69694649 |
| rs16976404 | 69695256 |
| rs2886910 | 69695271 |
| rs9915084 | 69695508 |
| rs9302931 | 69695924 |
| rs10852729 | 69696423 |
| rs2159033 | 69696433 |
| rs2886911 | 69696503 |
| rs28360962 | 69696584 |
| rs7214412 | 69696950 |
| rs9903422 | 69697320 |
| rs16976409 | 69697871 |
| rs2215051 | 69698130 |
| rs2367252 | 69698367 |
| rs9910903 | 69698543 |
| rs9911892 | 69698576 |
| rs2190692 | 69698699 |
| rs17177858 | 69698740 |
| rs9910199 | 69698960 |
| rs28589380 | 69698962 |
| rs7211190 | 69700285 |
| rs12948683 | 69700758 |
| rs11656228 | 69700772 |
| rs2190693 | 69700881 |
| rs2190694 | 69701296 |
| rs12452913 | 69701467 |
| rs988469 | 69701741 |
| rs7222314 | 69702061 |
| rs11077547 | 69702087 |
| rs28579214 | 69702168 |
| rs16976411 | 69702473 |
| rs2190695 | 69702639 |
| rs991528 | 69702707 |
| rs11293277 | 69703131 |
| rs17765332 | 69703865 |
| rs17765344 | 69703997 |

TABLE 14-continued

Public SNPs from dbSNP Build125 in the LD block C17b region

| Name | Location (Bld 34) |
|---|---|
| rs9908087 | 69704060 |
| rs9901566 | 69704141 |
| rs9908529 | 69704183 |
| rs8071068 | 69704466 |
| rs8071558 | 69704796 |
| rs8072254 | 69704939 |
| rs10551581 | 69705007 |
| rs984434 | 69705250 |
| rs7503885 | 69705407 |
| rs1859961 | 69705778 |
| rs1859962 | 69705876 |
| rs11650165 | 69706741 |
| rs9891981 | 69706753 |
| rs991429 | 69706896 |
| rs4793528 | 69707896 |
| rs7217073 | 69708046 |
| rs7216498 | 69708055 |
| rs9674957 | 69708221 |
| rs16976415 | 69708323 |
| rs17824498 | 69708717 |
| rs8077906 | 69709356 |
| rs8079414 | 69709642 |
| rs1859963 | 69710230 |
| rs8066875 | 69710700 |
| rs16976418 | 69710909 |
| rs11357418 | 69711779 |
| rs9916515 | 69712100 |
| rs9909964 | 69712163 |
| rs9889335 | 69712269 |
| rs9911515 | 69712481 |
| rs4328484 | 69713353 |
| rs11077548 | 69713459 |
| rs8068266 | 69714058 |
| rs16976420 | 69714103 |
| rs8072735 | 69714337 |
| rs12947919 | 69715210 |
| rs9893698 | 69715560 |
| rs4793529 | 69715759 |
| rs11273447 | 69716092 |
| rs7210934 | 69716100 |
| rs10522494 | 69716131 |
| rs6501436 | 69716413 |
| rs7217652 | 69716604 |
| rs11418718 | 69716711 |
| rs11386981 | 69716721 |
| rs6501437 | 69717095 |
| rs6501438 | 69717283 |
| rs8075884 | 69717686 |
| rs8074361 | 69717818 |
| rs8079315 | 69717978 |
| rs8065372 | 69718014 |
| rs8065379 | 69718023 |
| rs5821825 | 69718400 |
| rs2367256 | 69718409 |
| rs2190696 | 69718454 |
| rs2190697 | 69718464 |
| rs10512560 | 69718543 |
| rs4362433 | 69718720 |
| rs4366746 | 69718754 |
| rs4366747 | 69718766 |
| rs2159034 | 69718878 |
| rs2159035 | 69718906 |
| rs1014000 | 69718968 |
| rs1013999 | 69719058 |
| rs17824565 | 69719591 |
| rs17224666 | 69719603 |
| rs9783828 | 69719816 |
| rs17765410 | 69719887 |
| rs9783829 | 69720122 |
| rs9783825 | 69720137 |
| rs11270436 | 69720167 |
| rs9783826 | 69720230 |
| rs9302932 | 69720682 |
| rs2367257 | 69720807 |
| rs2886913 | 69720814 |
| rs2367258 | 69720864 |
| rs16976421 | 69721043 |
| rs4793333 | 69721433 |
| rs8081862 | 69721543 |
| rs8078088 | 69721600 |
| rs11350919 | 69721604 |
| rs6501439 | 69722007 |
| rs16976422 | 69722140 |
| rs6501440 | 69722155 |
| rs6501441 | 69722209 |
| rs12451634 | 69722235 |
| rs6501442 | 69722265 |
| rs6501443 | 69722280 |
| rs4793530 | 69722386 |
| rs7206958 | 69722630 |
| rs11654749 | 69722729 |
| rs11651706 | 69723550 |
| rs28656352 | 69724006 |
| rs8073978 | 69724076 |
| rs8074021 | 69724143 |
| rs11292707 | 69724148 |
| rs11287955 | 69724149 |
| rs9906164 | 69724526 |
| rs11871297 | 69724691 |
| rs9908315 | 69724691 |
| rs9906627 | 69724693 |
| rs11871142 | 69724693 |
| rs11871327 | 69724798 |
| rs11868971 | 69724896 |
| rs13341257 | 69725212 |
| rs9899619 | 69725212 |
| rs9907995 | 69725239 |
| rs13342491 | 69725239 |
| rs2367259 | 69725537 |
| rs9901976 | 69725541 |
| rs28526842 | 69726195 |
| rs28730401 | 69726274 |
| rs9916528 | 69726554 |
| rs11653132 | 69726955 |
| rs4621009 | 69727636 |
| rs11654295 | 69727661 |
| rs4398141 | 69727827 |
| rs4471727 | 69727839 |
| rs4300694 | 69727959 |
| rs7501691 | 69728181 |
| rs4416055 | 69728410 |
| rs2367260 | 69728428 |
| rs2367261 | 69728429 |
| rs28523317 | 69728817 |
| rs8076830 | 69729032 |
| rs16976423 | 69729222 |
| rs9906588 | 69729611 |
| rs4793531 | 69730430 |
| rs7406607 | 69730430 |
| rs4793532 | 69730574 |
| rs12103911 | 69730843 |
| rs11656229 | 69731166 |
| rs6501444 | 69731345 |
| rs7208518 | 69731608 |
| rs28379920 | 69731668 |
| rs28690329 | 69731677 |
| rs28579305 | 69731820 |
| rs11656479 | 69731840 |
| rs11656520 | 69732149 |
| rs2367262 | 69732235 |
| rs9902159 | 69732480 |
| rs9900242 | 69732754 |
| rs11653076 | 69733312 |
| rs11077549 | 69734431 |
| rs9908442 | 69735071 |
| rs4793334 | 69735105 |
| rs17178034 | 69735366 |
| rs17178041 | 69735378 |
| rs8081196 | 69735492 |
| rs2058083 | 69735526 |

TABLE 14-continued

Public SNPs from dbSNP Build125 in the LD block C17b region

| Name | Location (Bld 34) |
|---|---|
| rs6501445 | 69735966 |
| rs7224774 | 69736028 |
| rs2058084 | 69736140 |
| rs2058085 | 69736170 |
| rs7225803 | 69736320 |
| rs11654896 | 69736454 |
| rs11655964 | 69736475 |
| rs7224573 | 69736591 |
| rs11655006 | 69736706 |
| rs1468481 | 69737102 |
| rs11657344 | 69737589 |
| rs7211828 | 69737632 |
| rs9898184 | 69737774 |
| rs9906742 | 69737913 |
| rs7216323 | 69738056 |
| rs7221230 | 69738073 |
| rs9905641 | 69738678 |
| rs9907587 | 69738834 |
| rs17178062 | 69739314 |
| rs9915190 | 69739751 |
| rs8078520 | 69739851 |
| rs8065751 | 69739901 |
| rs8080251 | 69739930 |
| rs17178083 | 69739997 |
| rs2215052 | 69740781 |
| rs2159036 | 69740787 |
| rs16976429 | 69741127 |
| rs2041113 | 69741315 |
| rs16976430 | 69741428 |
| rs2041114 | 69741740 |
| rs7219029 | 69742113 |
| rs3079152 | 69742453 |
| rs5821826 | 69742455 |
| rs956218 | 69742459 |
| rs723338 | 69742536 |
| rs956219 | 69742830 |
| rs28703253 | 69742927 |
| rs28475602 | 69742956 |
| rs28514850 | 69743159 |
| rs8081602 | 69743202 |
| rs8081751 | 69743291 |
| rs8080184 | 69743366 |
| rs12602284 | 69743438 |
| rs2041115 | 69743550 |
| rs8068057 | 69743778 |
| rs28629932 | 69743843 |
| rs11351232 | 69743844 |
| rs8064263 | 69743953 |
| rs9897626 | 69744076 |
| rs9897865 | 69744199 |
| rs11656242 | 69744645 |
| rs9897358 | 69744665 |
| rs11651123 | 69744714 |
| rs11657298 | 69744759 |
| rs9906121 | 69744869 |
| rs9900302 | 69744903 |
| rs11651469 | 69745642 |
| rs11651501 | 69745681 |
| rs8068340 | 69746421 |
| rs8069493 | 69746422 |
| rs9899201 | 69746666 |
| rs719615 | 69747033 |
| rs7216402 | 69747209 |
| rs7217604 | 69747260 |
| rs7342907 | 69747289 |
| rs11275150 | 69747540 |
| rs3079153 | 69747512 |
| rs16976435 | 69747677 |
| rs7219299 | 69747878 |
| rs7222795 | 69747986 |
| rs2058086 | 69748321 |
| rs2058087 | 69748370 |
| rs9916274 | 69748656 |
| rs7209594 | 69748903 |
| rs1558119 | 69749095 |
| rs10604404 | 69752277 |
| rs10556506 | 69752280 |
| rs11077550 | 69752553 |
| rs9893104 | 69752632 |
| rs12150098 | 69752957 |
| rs4629010 | 69753318 |
| rs4316800 | 69753509 |
| rs16976438 | 69753835 |
| rs17824720 | 69753977 |
| rs7502769 | 69754543 |
| rs4445939 | 69754572 |
| rs7502789 | 69754573 |
| rs4643369 | 69754602 |
| rs1974561 | 69754631 |
| rs9747823 | 69754700 |
| rs9906649 | 69754803 |
| rs11870806 | 69755483 |
| rs12601681 | 69756532 |
| rs9909762 | 69756612 |
| rs12604060 | 69756621 |
| rs9910829 | 69756700 |
| rs7220274 | 69756890 |
| rs28519385 | 69757429 |
| rs28688838 | 69757489 |
| rs17224833 | 69757598 |
| rs9894739 | 69757976 |
| rs17765545 | 69758008 |
| rs2108534 | 69758023 |
| rs2108535 | 69758268 |
| rs8182284 | 69758514 |
| rs8182286 | 69758677 |
| rs11464001 | 69760633 |
| rs9913608 | 69760687 |
| rs8068573 | 69760970 |
| rs11867357 | 69761364 |
| rs11330058 | 69761375 |
| rs10712335 | 69761382 |
| rs10563340 | 69761524 |
| rs4793533 | 69761594 |
| rs8069925 | 69761985 |
| rs8068189 | 69762018 |
| rs9900204 | 69762079 |
| rs9901508 | 69762322 |
| rs9907418 | 69762342 |
| rs16967048 | 69762777 |
| rs2058088 | 69762984 |
| rs2367263 | 69763411 |
| rs1859964 | 69763694 |
| rs1859965 | 69764218 |
| rs6501446 | 69765181 |
| rs4793534 | 69765416 |
| rs4239156 | 69765504 |
| rs11428263 | 69765526 |
| rs4438347 | 69765529 |
| rs7224698 | 69765533 |
| rs4793335 | 69765814 |
| rs9891407 | 69766332 |
| rs9891611 | 69766373 |
| rs9891269 | 69766640 |
| rs2108536 | 69766899 |
| rs9892822 | 69766928 |
| rs11657351 | 69767747 |
| rs16976440 | 69767822 |
| rs7216882 | 69768093 |
| rs9904271 | 69768257 |
| rs2097984 | 69768349 |
| rs9893839 | 69769593 |
| rs11654068 | 69769659 |
| rs8079962 | 69769825 |
| rs6501447 | 69770221 |
| rs7206969 | 69770272 |
| rs10686630 | 69770575 |
| rs10698719 | 69770684 |
| rs2886914 | 69770936 |
| rs7217918 | 69770975 |

TABLE 14-continued

Public SNPs from dbSNP Build125 in the LD block C17b region

| Name | Location (Bld 34) |
|---|---|
| rs7214621 | 69771488 |
| rs11868953 | 69771619 |
| rs12944762 | 69772101 |
| rs9909797 | 69772305 |
| rs2367264 | 69772313 |
| rs5821827 | 69772325 |
| rs5821828 | 69772327 |
| rs8076235 | 69772505 |
| rs28432258 | 69772509 |
| rs8076811 | 69772530 |
| rs16976442 | 69772618 |
| rs1859966 | 69772866 |
| rs17178251 | 69774002 |
| rs11442732 | 69774343 |
| rs7225046 | 69775440 |
| rs17765632 | 69775827 |
| rs16976443 | 69776028 |
| rs16976444 | 69776570 |
| rs7211425 | 69776601 |
| rs17765644 | 69776615 |
| rs10652863 | 69776765 |
| rs9913988 | 69777181 |
| rs11871129 | 69777585 |
| rs3079217 | 69777970 |
| rs758106 | 69778126 |
| rs7208233 | 69778192 |
| rs740408 | 69778219 |
| rs16976445 | 69778235 |
| rs2886915 | 69779284 |
| rs28451383 | 69779302 |
| rs2003060 | 69779416 |
| rs5821829 | 69779650 |
| rs5741749 | 69779684 |
| rs28509323 | 69779683 |
| rs3079221 | 69779684 |
| rs28519699 | 69779685 |
| rs5821830 | 69779695 |
| rs17224938 | 69779866 |
| rs2215049 | 69779914 |
| rs16976446 | 69779988 |
| rs17765660 | 69780218 |
| rs7219890 | 69780630 |
| rs10401046 | 69780827 |
| rs17824822 | 69781077 |
| rs17178293 | 69781121 |
| rs11653243 | 69781437 |
| rs11658483 | 69781850 |
| rs9891648 | 69782075 |
| rs16976448 | 69782186 |
| rs9898150 | 69782318 |
| rs16976449 | 69782374 |
| rs16976451 | 69782409 |
| rs8064966 | 69782923 |
| rs9905861 | 69783360 |
| rs9906098 | 69783457 |
| rs4570900 | 69783489 |
| rs4586491 | 69783636 |
| rs4471728 | 69783657 |
| rs4632175 | 69783677 |
| rs4561513 | 69783679 |
| rs4793535 | 69784004 |
| rs10717595 | 69784340 |
| rs9908262 | 69784558 |
| rs1011729 | 69784710 |
| rs12943194 | 69784780 |
| rs1011730 | 69784868 |
| rs16976453 | 69785851 |
| rs4611499 | 69785892 |
| rs7217521 | 69786434 |
| rs16976455 | 69786902 |
| rs6501448 | 69787036 |
| rs7209698 | 69787510 |
| rs10555877 | 69787548 |
| rs11274299 | 69787737 |
| rs10528465 | 69787774 |
| rs11365486 | 69787938 |
| rs7208398 | 69787979 |
| rs7214479 | 69788072 |
| rs7214488 | 69788097 |
| rs1008348 | 69788439 |
| rs7501959 | 69788446 |
| rs2367265 | 69788490 |
| rs11394357 | 69788559 |
| rs8072259 | 69788643 |
| rs11313840 | 69789156 |
| rs6501449 | 69789968 |
| rs10301911 | 69789968 |
| rs10301948 | 69790178 |
| rs6501450 | 69790178 |
| rs6501451 | 69790254 |
| rs10300397 | 69790254 |
| rs6501452 | 69790410 |
| rs10300432 | 69790428 |
| rs6501453 | 69790428 |
| rs3079233 | 69790679 |
| rs8079118 | 69790903 |
| rs11297510 | 69791440 |
| rs9893148 | 69791554 |
| rs9893377 | 69791625 |
| rs11868131 | 69792249 |
| rs11870732 | 69792364 |
| rs16976457 | 69792601 |
| rs17178370 | 69792664 |
| rs9899791 | 69792753 |
| rs16976458 | 69793386 |
| rs9909806 | 69793630 |
| rs16976460 | 69794547 |
| rs17225050 | 69794612 |
| rs7225025 | 69794797 |
| rs9890695 | 69794933 |
| rs2215050 | 69795232 |
| rs17178377 | 69795256 |
| rs9912404 | 69795917 |
| rs11655744 | 69796179 |
| rs767203 | 69796402 |
| rs11346937 | 69797001 |
| rs2367266 | 69797110 |
| rs1107305 | 69797766 |
| rs11657389 | 69798141 |
| rs28707109 | 69798155 |
| rs9912434 | 69798171 |
| rs6501454 | 69798880 |
| rs6501455 | 69798934 |
| rs11658666 | 69799137 |
| rs6501456 | 69799230 |
| rs4872347 | 69799229 |
| rs8078490 | 69799267 |
| rs9893953 | 69800265 |
| rs7209505 | 69800787 |
| rs10617559 | 69800819 |
| rs7209069 | 69800919 |
| rs8070140 | 69801724 |
| rs4313845 | 69802271 |
| rs28605967 | 69802874 |
| rs13342783 | 69803155 |
| rs9915306 | 69803155 |
| rs9896356 | 69803211 |
| rs13342052 | 69803211 |
| rs10302248 | 69803464 |
| rs2108337 | 69803464 |
| rs8067671 | 69804287 |
| rs2190463 | 69804591 |
| rs7501860 | 69804833 |
| rs11657593 | 69805061 |
| rs9909136 | 69805273 |
| rs9906656 | 69805316 |
| rs11654355 | 69806089 |
| rs6501457 | 69806375 |
| rs8066265 | 69806421 |
| rs8066924 | 69806817 |

TABLE 14-continued

Public SNPs from dbSNP Build125 in the LD block C17b region

| Name | Location (Bld 34) |
|---|---|
| rs8079912 | 69806928 |
| rs8066934 | 69807046 |
| rs8067145 | 69807477 |
| rs2190456 | 69808489 |
| rs9905278 | 69808806 |
| rs9906357 | 69808908 |
| rs983084 | 69808989 |
| rs983085 | 69809184 |
| rs11650277 | 69809918 |
| rs7211370 | 69810208 |
| rs6501458 | 69810255 |
| rs7226171 | 69810292 |
| rs9747127 | 69810292 |
| rs6501459 | 69810578 |
| rs12602874 | 69811325 |
| rs7406314 | 69811841 |
| rs4793536 | 69811841 |
| rs4793537 | 69812013 |
| rs4793538 | 69813051 |
| rs2158905 | 69813164 |
| rs2108336 | 69813235 |
| rs2190457 | 69813532 |
| rs11655567 | 69813810 |
| rs7225458 | 69815469 |
| rs10401004 | 69815879 |
| rs11291235 | 69817206 |
| rs7215164 | 69817444 |
| rs11291234 | 69817472 |
| rs7221399 | 69817567 |
| rs9905147 | 69817884 |
| rs2190458 | 69818952 |
| rs2190459 | 69818967 |
| rs917278 | 69819048 |
| rs917279 | 69819062 |
| rs2190460 | 69819088 |
| rs8065046 | 69819379 |
| rs8065211 | 69819526 |
| rs1978203 | 69819792 |
| rs1978204 | 69820068 |
| rs5025558 | 69820721 |
| rs3079276 | 69820892 |
| rs737956 | 69820991 |
| rs737957 | 69821032 |
| rs8075168 | 69821150 |
| rs8075481 | 69821319 |
| rs9915835 | 69821324 |
| rs8080004 | 69821422 |
| rs917280 | 69821734 |
| rs737958 | 69821777 |
| rs16976475 | 69821852 |
| rs917281 | 69822040 |
| rs737959 | 69822117 |
| rs11654184 | 69822459 |
| rs7225026 | 69822798 |
| rs7223912 | 69822819 |
| rs7224058 | 69822902 |
| rs4595838 | 69823065 |
| rs4793539 | 69823390 |
| rs7215307 | 69823490 |
| rs8068921 | 69823928 |
| rs8072635 | 69824306 |
| rs4793540 | 69824317 |
| rs4793541 | 69824718 |
| rs7221540 | 69826125 |
| rs10650850 | 69826133 |
| rs6501460 | 69827034 |
| rs7221080 | 69827095 |
| rs6501461 | 69827609 |
| rs8064388 | 69828140 |
| rs9892669 | 69828141 |
| rs11650797 | 69828297 |
| rs9902909 | 69828907 |
| rs9909320 | 69829271 |
| rs9904099 | 69829611 |
| rs9901939 | 69829753 |

TABLE 14-continued

Public SNPs from dbSNP Build125 in the LD block C17b region

| Name | Location (Bld 34) |
|---|---|
| rs17178523 | 69830197 |
| rs8076167 | 69830206 |
| rs6501462 | 69830257 |
| rs8077218 | 69830507 |
| rs8067695 | 69831434 |
| rs17765868 | 69831931 |
| rs9898561 | 69831976 |
| rs9906756 | 69833167 |
| rs17178530 | 69833235 |
| rs17765886 | 69833328 |
| rs9913159 | 69833376 |
| rs17765897 | 69833724 |
| rs12946942 | 69834121 |
| rs8079036 | 69834162 |
| rs16976482 | 69834651 |
| rs16976483 | 69834805 |
| rs1558061 | 69835309 |
| rs10525593 | 69835329 |
| rs8074817 | 69835313 |
| rs10598677 | 69835341 |
| rs9302933 | 69835930 |
| rs9916542 | 69836244 |
| rs9914509 | 69836395 |
| rs9916166 | 69836431 |
| rs9895657 | 69836554 |
| rs12941471 | 69837058 |
| rs9896822 | 69837234 |
| rs8066183 | 69837705 |
| rs8071929 | 69837713 |
| rs8067475 | 69837806 |
| rs8068078 | 69837850 |
| rs8068231 | 69837908 |
| rs8070461 | 69837995 |
| rs7220325 | 69838584 |
| rs2214946 | 69839003 |
| rs9909596 | 69839116 |
| rs16976490 | 69839170 |
| rs9911506 | 69839258 |
| rs9891216 | 69840055 |
| rs9898288 | 69840121 |
| rs8064489 | 69840682 |
| rs2886917 | 69841415 |
| rs7217041 | 69841447 |
| rs9899311 | 69841854 |
| rs10512561 | 69841920 |
| rs7222044 | 69842070 |
| rs2041036 | 69842261 |
| rs2041037 | 69842312 |
| rs4505385 | 69842351 |
| rs7217933 | 69842529 |
| rs2058005 | 69842858 |

TABLE 15

Public SNPs from dbSNP Build125 chromosome in the LD block C0Xa region

| Name | Location (Bld 34) |
|---|---|
| rs12857638 | 49979931 |
| rs12836093 | 49980515 |
| rs6614396 | 49981265 |
| rs5987393 | 49981474 |
| rs12859093 | 49981492 |
| rs12558299 | 49982759 |
| rs28502527 | 49982859 |
| rs1144821 | 49983111 |
| rs7060520 | 49983249 |
| rs7062166 | 49983256 |
| rs7065932 | 49983292 |
| rs1144822 | 49987108 |

TABLE 15-continued

Public SNPs from dbSNP Build125 chromosome in the LD block C0Xa region

| Name | Location (Bld 34) |
|---|---|
| rs1144823 | 49987225 |
| rs1144824 | 49988124 |
| rs5945601 | 49988628 |
| rs28552462 | 49989770 |
| rs6614399 | 49989835 |
| rs1151713 | 49990081 |
| rs1985464 | 49990289 |
| rs5987414 | 49991462 |
| rs1151714 | 49991671 |
| rs1151715 | 49991957 |
| rs2801628 | 49992103 |
| rs2625873 | 49992433 |
| rs2625874 | 49992518 |
| rs2625875 | 49992647 |
| rs2801627 | 49992707 |
| rs12846945 | 49992824 |
| rs17846448 | 49992824 |
| rs17859498 | 49992824 |
| rs2801626 | 49992830 |
| rs2625876 | 49992887 |
| rs2801625 | 49992889 |
| rs17854662 | 49992891 |
| rs17854580 | 49992933 |
| rs17854581 | 49993026 |
| rs2801624 | 49993520 |
| rs1144825 | 49993803 |
| rs1144826 | 49993823 |
| rs1144827 | 49993865 |
| rs12841743 | 49995031 |
| rs6614400 | 49996625 |
| rs1144828 | 49999653 |
| rs1144829 | 49999901 |
| rs913224 | 49999928 |
| rs1144830 | 50000975 |
| rs1144831 | 50000982 |
| rs6614401 | 50001762 |
| rs12835732 | 50003251 |
| rs2221370 | 50005157 |
| rs2221369 | 50005159 |
| rs6614402 | 50005936 |
| rs12838483 | 50007226 |
| rs17374021 | 50007700 |
| rs3904018 | 50007700 |
| rs4262466 | 50007700 |
| rs28833510 | 50008244 |
| rs28867805 | 50008255 |
| rs6614403 | 50008283 |
| rs12848124 | 50008643 |
| rs1503779 | 50009384 |
| rs12833678 | 50009385 |
| rs12688009 | 50013288 |
| rs7882940 | 50013357 |
| rs1503782 | 50014081 |
| rs1503783 | 50014184 |
| rs28600724 | 50014523 |
| rs1887347 | 50014934 |
| rs6614404 | 50015706 |
| rs12846170 | 50017341 |
| rs7472779 | 50017631 |
| rs4623626 | 50017697 |
| rs7472906 | 50017697 |
| rs6614405 | 50018413 |
| rs6614406 | 50018734 |
| rs12835881 | 50021222 |
| rs12688145 | 50023165 |
| rs12855323 | 50023420 |
| rs12856394 | 50023702 |
| rs12856724 | 50023791 |
| rs12834749 | 50024828 |
| rs2089080 | 50025042 |
| rs4477198 | 50025042 |
| rs5987416 | 50025042 |
| rs2102224 | 50025405 |
| rs12010507 | 50026965 |
| rs12858098 | 50027751 |
| rs4524976 | 50028479 |
| rs7471245 | 50028479 |
| rs1590666 | 50028877 |
| rs4388622 | 50028877 |
| rs12847705 | 50031298 |
| rs12856477 | 50032556 |
| rs12834359 | 50032568 |
| rs1576012 | 50033094 |
| rs4514178 | 50033094 |
| rs12837176 | 50033978 |
| rs12382105 | 50034001 |
| rs6614292 | 50034001 |
| rs12843301 | 50034276 |
| rs1327300 | 50035847 |
| rs12838882 | 50036951 |
| rs12857136 | 50039647 |
| rs12834256 | 50039777 |
| rs5945568 | 50040760 |
| rs7882378 | 50041887 |
| rs12833329 | 50043125 |
| rs12838967 | 50044205 |
| rs1587771 | 50045166 |
| rs10310810 | 50045420 |
| rs6614407 | 50045420 |
| rs9780006 | 50046001 |
| rs12836459 | 50047884 |
| rs1604763 | 50049061 |
| rs4587502 | 50049061 |
| rs1604761 | 50050548 |
| rs28836241 | 50051275 |
| rs7886708 | 50051382 |
| rs1503781 | 50052580 |
| rs17003292 | 50052690 |
| rs1503780 | 50052941 |
| rs7060524 | 50054360 |
| rs7065124 | 50054921 |
| rs12838105 | 50055783 |
| rs7051438 | 50056677 |
| rs976587 | 50057233 |
| rs7062237 | 50059038 |
| rs12834337 | 50059530 |
| rs2134677 | 50059658 |
| rs12843640 | 50061819 |
| rs12837760 | 50061847 |
| rs6614293 | 50061856 |
| rs12850320 | 50062311 |
| rs2134676 | 50063491 |
| rs17854399 | 50067247 |
| rs12856054 | 50067281 |
| rs1875755 | 50068083 |
| rs2281920 | 50068474 |
| rs12849304 | 50069136 |
| rs6614408 | 50069317 |
| rs7059321 | 50070408 |
| rs12852369 | 50070648 |
| rs7059804 | 50070717 |
| rs12839592 | 50073335 |
| rs6614409 | 50074260 |
| rs2134678 | 50075721 |
| rs12859167 | 50076589 |
| rs12851320 | 50078419 |
| rs12834008 | 50082228 |
| rs17249918 | 50082583 |
| rs12836006 | 50082758 |
| rs7064156 | 50083180 |
| rs972635 | 50084494 |
| rs12688411 | 50084797 |
| rs974609 | 50086161 |
| rs974610 | 50086341 |
| rs7883508 | 50087568 |
| rs7883537 | 50087624 |
| rs12382912 | 50088010 |
| rs6614410 | 50088010 |

TABLE 15-continued

Public SNPs from dbSNP Build125 chromosome in the LD block C0Xa region

| Name | Location (Bld 34) |
|---|---|
| rs9281840 | 50088911 |
| rs4406545 | 50089273 |
| rs5987410 | 50089471 |
| rs6614294 | 50089471 |
| rs6614295 | 50089616 |
| rs3959290 | 50091659 |
| rs1142943 | 50091998 |
| rs7887005 | 50092059 |
| rs7887184 | 50092170 |
| rs12844637 | 50092562 |
| rs12844299 | 50092744 |
| rs12843029 | 50092893 |
| rs2694425 | 50092973 |
| rs2694424 | 50093036 |
| rs2036490 | 50094861 |
| rs1875754 | 50095192 |
| rs7888952 | 50098151 |
| rs4907789 | 50098153 |
| rs7392318 | 50098157 |
| rs4907771 | 50098161 |
| rs5945602 | 50098173 |
| rs4907772 | 50098347 |
| rs12558999 | 50099863 |
| rs12012935 | 50101772 |
| rs5945603 | 50105350 |
| rs12383167 | 50106377 |
| rs6614296 | 50106377 |
| rs5945604 | 50106951 |
| rs6521795 | 50106951 |
| rs5945605 | 50107288 |
| rs5945606 | 50107963 |
| rs12843813 | 50108909 |
| rs12392073 | 50109526 |
| rs5945569 | 50110017 |
| rs3074307 | 50110485 |
| rs5987418 | 50114019 |
| rs12850214 | 50114240 |
| rs4907790 | 50114517 |
| rs4907791 | 50114540 |
| rs10127382 | 50115567 |
| rs13366433 | 50115567 |
| rs12387530 | 50116011 |
| rs5987419 | 50116011 |
| rs5945607 | 50116514 |
| rs5945570 | 50116531 |
| rs11091727 | 50117893 |
| rs5945608 | 50117893 |
| rs11798651 | 50118401 |
| rs5945609 | 50119272 |
| rs5945610 | 50119351 |
| rs6614297 | 50120505 |
| rs10284146 | 50121301 |
| rs10284147 | 50121302 |
| rs12845998 | 50126071 |
| rs12846154 | 50126080 |
| rs12845472 | 50126481 |
| rs5987395 | 50126695 |
| rs5945611 | 50126796 |
| rs1327301 | 50126863 |
| rs5987396 | 50127235 |
| rs1327302 | 50127421 |
| rs12853150 | 50127455 |
| rs7061990 | 50127464 |
| rs12856096 | 50127482 |
| rs5945612 | 50128059 |
| rs7064089 | 50128196 |
| rs12836045 | 50128539 |
| rs12835169 | 50128540 |
| rs1327303 | 50130975 |
| rs1327304 | 50130982 |
| rs5945613 | 50131486 |
| rs5945614 | 50134364 |
| rs1854109 | 50135378 |
| rs10855219 | 50139404 |
| rs5945571 | 50139404 |
| rs6614413 | 50139404 |
| rs2148751 | 50139634 |
| rs4556264 | 50139634 |
| rs5945615 | 50139634 |
| rs12398483 | 50141270 |
| rs5945616 | 50141270 |
| rs12851276 | 50142316 |
| rs12395326 | 50142524 |
| rs5987420 | 50142524 |
| rs5987421 | 50143296 |
| rs5945617 | 50144027 |
| rs7064195 | 50144640 |
| rs5945618 | 50145357 |
| rs12846383 | 50145415 |
| rs5987422 | 50145612 |
| rs5945572 | 50146489 |
| rs12832410 | 50147431 |
| rs12014647 | 50150686 |
| rs11091729 | 50152331 |
| rs7066127 | 50153285 |
| rs12854262 | 50154146 |
| rs7059759 | 50154963 |
| rs12853021 | 50155066 |
| rs17854581 | 50155700 |
| rs2768104 | 50156232 |
| rs2768103 | 50156299 |
| rs28641581 | 50156884 |
| rs3209107 | 50157523 |
| rs12843829 | 50157531 |
| rs5945619 | 50158478 |
| rs5987397 | 50159109 |
| rs5987423 | 50159123 |
| rs5987424 | 50159170 |
| rs5945620 | 50159476 |
| rs5945621 | 50159687 |
| rs6652209 | 50159963 |
| rs5945622 | 50160076 |
| rs6614299 | 50161112 |
| rs6614300 | 50161195 |
| rs6614301 | 50161235 |
| rs12833914 | 50161256 |
| rs12833917 | 50161257 |
| rs11338635 | 50162083 |
| rs1891702 | 50162267 |
| rs5945623 | 50162293 |
| rs5987425 | 50163127 |
| rs4907773 | 50163450 |
| rs4381122 | 50164645 |
| rs2008216 | 50164650 |
| rs4907792 | 50165589 |
| rs7056117 | 50165629 |
| rs2384958 | 50166203 |
| rs10531904 | 50166570 |
| rs2051095 | 50166976 |
| rs28367108 | 50167055 |
| rs5987426 | 50167347 |
| rs1936038 | 50168227 |
| rs6614419 | 50168606 |
| rs5945624 | 50169734 |
| rs5945625 | 50170233 |
| rs5945626 | 50170585 |
| rs5945573 | 50171156 |
| rs28670322 | 50171546 |
| rs28618971 | 50171549 |
| rs12844177 | 50171726 |
| rs6614421 | 50171872 |
| rs1071580 | 50172086 |
| rs6521802 | 50172147 |
| rs5945627 | 50172223 |
| rs12384969 | 50172585 |
| rs11091730 | 50172689 |
| rs6614423 | 50172689 |
| rs10855221 | 50173367 |

TABLE 15-continued

Public SNPs from dbSNP Build125 chromosome in the LD block C0Xa region

| Name | Location (Bld 34) |
|---|---|
| rs5945628 | 50173367 |
| rs6614424 | 50173367 |
| rs11091731 | 50173798 |
| rs5987427 | 50173798 |
| rs6614302 | 50173798 |
| rs11091732 | 50173804 |
| rs5987428 | 50173804 |
| rs6614425 | 50173804 |
| rs12398502 | 50175022 |
| rs5945574 | 50175022 |
| rs10127076 | 50175345 |
| rs11798149 | 50175345 |
| rs5987429 | 50176499 |
| rs6521803 | 50176499 |
| rs3207585 | 50176555 |
| rs6521804 | 50176772 |
| rs5945629 | 50176878 |
| rs6521805 | 50176878 |
| rs12834343 | 50176887 |
| rs12383673 | 50177011 |
| rs6614303 | 50177011 |
| rs12383675 | 50177052 |
| rs5945630 | 50177052 |
| rs6614304 | 50177052 |
| rs12556076 | 50177154 |
| rs7064349 | 50177327 |
| rs4907793 | 50177369 |
| rs6521806 | 50177369 |
| rs12387490 | 50177404 |
| rs12556595 | 50177475 |
| rs4907794 | 50177686 |
| rs5987430 | 50177686 |
| rs4907795 | 50177874 |
| rs7876147 | 50177982 |
| rs4907796 | 50178055 |
| rs4907774 | 50178333 |
| rs12012308 | 50178919 |
| rs4907775 | 50180006 |
| rs6614426 | 50181230 |
| rs12559640 | 50181590 |
| rs12388771 | 50183690 |
| rs17003306 | 50183967 |
| rs3131307 | 50184759 |
| rs1970956 | 50185184 |
| rs1970957 | 50185256 |
| rs5945631 | 50185690 |
| rs12842085 | 50186345 |
| rs2153993 | 50186545 |

It is important to note that patterns of LD in the genome are usually not "perfect". In practical terms, this means that linkage disequilibrium between individual markers within blocks, or between entire blocks, is known to occasionally extend beyond the boundaries of LD blocks as defined. Such extended pattern of LD may comprise single markers in neighbouring or even possibly distant regions, or several markers in nearby LD blocks. In such cases, the LD blocks themselves are not "perfect" in the sense that even though the local LD pattern is strongest within the LD block as defined, weaker pattern of LD in these instances is observed beyond the LD block. Such extended pattern of LD is also within scope of the present invention, as markers displaying such LD with the markers of the invention can also be used as surrogate markers in the methods of the invention.

Discussion

As described herein, five loci on chromosome 2p15, 4q31.21, 17q12, 17q24.3 and Xp11.22 have been demonstrated to play a role in cancer (e.g., prostate cancer (e.g., aggressive prostate cancer). Particular markers and/or haplotypes at each locus, including the TCF2 gene on Chromosome 17q12, are present at a higher than expected frequency in subjects having prostate cancer. Based on the markers described herein, which are associated with a propensity for particular forms of cancer, genetic susceptibility assays (e.g., a diagnostic screening test) can be used to identify individuals at risk for cancer.

The TCF2 (HNF1beta) is the only known gene within the genomic region on chromosome 17q12 of the human genome that is found to be associated to prostate cancer. The underlying variation in markers or haplotypes associated with region and cancer may affect expression of the TCF2 gene. It is however also conceivable that the effect extends to, or is mainly limited to, nearby genes, such as DDX52, AP1GBP1, TBC1D3/TBC1D3B (PRC17), and/or other known, unknown or predicted genes within the region found on chromosome 17q12 found to be associated with prostate cancer, or in adjacent regions. Furthermore, such variation may affect RNA or protein stability or may have structural consequences, such that the region is more prone to somatic rearrangement in haplotype/allele carriers. Thus, in general, the underlying variation could affect uncharacterized genes directly linked to the markers and/or haplotypes described herein, or could influence neighbouring genes not directly linked to the markers and/or haplotypes described herein.

The region found to be associated with prostate cancer on chromosome 2, i.e. the LD block C02, contains several reported genes. These include EHBP1 (EH domain-binding protein 1, also called KIAA0903), OTX1 (homolog of orthodenticle (drosophila)), BC093752, LOC51057. EHBP1 has been found to be expressed in all tissues and specific brain regions examined except lung, pancreas, and spleen, in which expression was found to be low. NPF motifs of EHBP1 are disrupted in cortical actin structures, and depletion of EHBP1 in mouse adipocytes by small interfering RNA inhibits endocytosis, suggesting that EHBP1 functions in endocytic trafficking. OTX is a homeobox family gene related to a gene expressed in *drosophila* head termed 'orthodenticle.' OTX transcription factors bind with high affinity to TAATCC/T elements on DNA.

Example 3

Further Evidence for Sequence Variants on 2p15 and Xp11.22 Conferring Susceptibility to Prostate Cancer Further characterization of association of variants on Chr. 2p15 and Xp11.22 was performed, as shown in Tables 16 and 17. As before, allele A of the SNP rs5945572 (rs5945572 A) showed the most significant P value of markers located on the X chromosome in a GWA analysis of 23,205 Icelandic samples, with an allelic specific odds ratio (OR) of 1.21 ($P=3.36 \times 10^{-4}$) (Table 16). On chromosome 2p15, allele A of rs2710646 (rs2710646 A) had an OR of 1.16 ($P=7.79 \times 10^{-4}$) (Table 17) for all Icelandic prostate cancer cases and an OR of 1.33 ($P=3.73 \times 10^{-5}$) for patients diagnosed with aggressive disease (Table 18). By examining the Utah CEPH (CEU) HapMap data we identified numerous SNPs that are substantially correlated with either of the two anchor SNPs, rs5945572 and rs2710646 ($D' \geq 0.9$ and $r^2 > 0.4$). From this list we selected several SNPs not present on the Illumina Hap300 chip, representing different degrees of correlation with the anchor SNPs, for further genotyping in 1,500 and 800 Icelandic cases and controls, respectively. None of the additional SNPs were found to be more significantly associated to the disease than the anchor SNPs (Table 19).

We proceeded to genotype rs5945572 and rs2710646 in seven prostate cancer study groups of European descent, coming from The Netherlands, Spain, Sweden and the United States (US). However, since the TaqMan assay for rs2710646 on 2p15 failed in design we replaced it with an assay for a fully correlated SNP, rs721048 (LD-characteristics between rs2710646 and rs721048 in Icelanders and in the four HapMap populations (CEU, CHB, JPT, YRI); D'=1; $r^2 \geq 0.99$), which was used for genotyping in the replication study populations. When results from all seven case-control replication groups were combined, using all prostate cancer cases, they were highly significant for both SNPs with OR=1.24 ($P=2.57 \times 10^{-10}$) for rs5945572 A on Xp11, and OR=1.15 ($P=2.23 \times 10^{-6}$) for rs721048 A on 2p15 (Table 16 and 17). By combining these data with the Icelandic data the signals at both loci achieved genome-wide significance; rs5945572 A on Xp11.22 had an OR=1.23 ($P=3.95 \times 10^{-13}$), and rs721048 A on 2p15 had an OR=1.15 ($P=7.66 \times 10^{-9}$) (Tables 16 and 17). Removing all females (N=14,135) from the control group in the analysis of the combined groups yielded essentially identical results for both loci, (OR=1.23 and 1.15 for rs5945572 A and rs721048 A, respectively). In all of the replication groups, the observed effect for the two loci was in the same direction as in the Icelandic samples, except for rs721048 A which in the Baltimore group showed no effect (OR=1). However, a test of heterogeneity in the OR of the eight different study groups showed no significant difference for the two loci (P=0.89 and 0.19 for Xp11 and 2p15, respectively). We note that in the results released by the Cancer Genetics Markers of Susceptibility study group[5] (https colon-slash-slash cgems.cancer.gov slash data slash) the two original anchor SNPs, rs5945572 and rs2710646, show nominal, but not genome-wide, significant association to prostate cancer further supporting the data presented here.

For rs5945572 A on Xp11, the OR seen for cases with younger age at onset (≤65) or aggressive phenotype was the same as for the whole group. The frequency of rs721048 A on the other hand, was significantly higher among patients diagnosed with aggressive prostate cancer than among those with less aggressive disease (OR=1.11; $P=2.6 \times 10^{-3}$). Comparing the group of patients with aggressive tumor (N=4,787) to controls gave an allelic OR of 1.22 ($P=8.7 \times 10^{-10}$) when combined for all study groups (Table 18). Specifically, the heterozygous and homozygous carriers of rs721048 A, which are close to 31% and 4% of the general population, have a genotypic OR of 1.22 and 1.49 of being diagnosed with aggressive prostate cancer compared to the non-carriers, respectively.

However, rs721048 A, like rs5945572 A, did not show a stronger association in patients with younger age at onset of prostate cancer.

Both of the variants, rs5945572 on Xp11 and rs2710646/rs721048 on 2p15, are located within regions characterized by extended linkage disequilibrium (LD), based on the CEU HapMap results. On Xp11.22, the LD-block spans a region from about 51.001 Mb to 51.612 Mb, or 611 kb (NCBI Build 35). The 2p15 LD-region is even larger, or about 1.1 Mb (62.709 Mb to 63.782 Mb; NCBI Build 35) and contains several genes. Both of the 2p15 SNPs, rs2710646 and rs721048, are located within one of the introns of the EHBP1 gene. This gene is thought to be involved in endocytic trafficking and has not previously been implicated in cancer[6]. An RT-PCR analysis of various cDNA libraries revealed detectable expression of EHBP1 in several different tissue libraries, including those derived from the prostate (data not shown).

On Xp11, several genes have been localized to the 611 Kb region of interest but none of those have been previously linked with prostate cancer. Possible cancer candidate genes, based on previously described functions, are GSPT2 and MAGED1. GSPT2 is related to GSPT1, a gene encoding a GTP-binding protein that plays an essential role at the G1- to S-phase transition of the cell cycle. MAGED1 has been implicated in programmed cell death through a JNK- and c-Jun-dependent mitochondrial pathway[7,8]. The genes closest to the SNP rs5945572 are: NUDT10 and NUDT11, along with a single exon transcript LOC340602 with unknown function (www.genome.ucsc.edu, May 2004 Assembly). NUDT10 and 11 belong to a subgroup of phosphohydrolases that preferentially hydrolyze diphosphoinositol polyphosphates (DIPPS)[9]. It has been proposed that members of this protein superfamily may be involved in vesicle trafficking, stress responses, DNA repair and apoptosis[10,11]. RT-PCR analysis of various cDNA libraries revealed detectable expression of GSPT2, MAGED1, LOC340602, NUDT10 and 11 in several different tissue libraries, including those derived from the prostate (data not shown). Which one of these genes, if any, confers the risk identified by the association reported here remains to be shown.

Recently, several sequence variants have been identified accounting for a substantial proportion of the population attributable risk (PAR) of prostate cancer[1,2,5,12,13]. With the identification of the two variants described here, yet another piece has been added to the puzzle of prostate cancer genetic susceptibility. Both the Xp11 and the 2p15 variants are common and confer a moderate risk, resulting in an estimated PAR of about 7% and 5% in individuals of European descent, respectively (see also Table 20).

TABLE 16

Association results for rs5945572 on Xp11.22 and prostate cancer in Iceland, The Netherlands, Spain, Sweden, and the US

| Study population (N cases/N controls) Variant (allele) | Frequency Cases | Frequency Controls | OR (95% c.i.) | P value |
|---|---|---|---|---|
| Iceland(1,833/21,372)[a] | | | | |
| rs5945572 (A) | 0.414 | 0.368 | 1.21 (1.09-1.34) | $3.36 \times 10^{-4}$ |
| Holland (991/2,021) | | | | |
| rs5945572 (A) | 0.390 | 0.347 | 1.20 (1.04-1.39) | 0.015 |
| Spain (539/1,594) | | | | |
| rs5945572 (A) | 0.432 | 0.364 | 1.33 (1.10-1.61) | $3.20 \times 10^{-3}$ |

TABLE 16-continued

Association results for rs5945572 on Xp11.22 and prostate cancer
in Iceland, The Netherlands, Spain, Sweden, and the US

| Study population (N cases/N controls) Variant (allele) | Frequency Cases | Frequency Controls | OR (95% c.i.) | P value |
|---|---|---|---|---|
| Sweden (2,865/1,722) | | | | |
| rs5945572 (A) | 0.421 | 0.379 | 1.19 (1.05-1.34) | $4.84 \times 10^{-3}$ |
| Baltimore, Maryland (1,516/554) | | | | |
| rs5945572 (A) | 0.397 | 0.334 | 1.31 (1.07-1.60) | $8.39 \times 10^{-3}$ |
| Chicago, Illinois (656/503) | | | | |
| rs5945572 (A) | 0.402 | 0.354 | 1.23 (0.98-1.54) | 0.072 |
| Nashville, Tennessee (526/612) | | | | |
| rs5945572 (A) | 0.392 | 0.353 | 1.18 (0.93-1.50) | 0.18 |
| Rochester, Minnesota (1,128/500)[b] | | | | |
| rs5945572 (A) | 0.381 | 0.306 | 1.40 (1.11-1.76) | $4.39 \times 10^{-3}$ |
| All excluding Iceland (8,221/7,506)[c] | | | | |
| rs5945572 (A) | — | 0.348 | 1.24 (1.16-1.33) | $2.57 \times 10^{-10}$ |
| All combined (10,054/28,879)[c] | | | | |
| rs5945572 (A) | — | 0.351 | 1.23 (1.16-1.30) | $3.95 \times 10^{-13}$ |

All P values shown are two-sided. Shown are the corresponding numbers of cases and controls (N), allelic frequencies of variants in affected and control individuals, the allelic odds-ratio (OR) with 95% confidence interval (95% c.i.) and P values.
[a]Results presented for Iceland were adjusted for relatedness using a method of genomic control (see Supplementary Methods).
[b]Results presented for Rochester were adjusted for relatedness by applying a pedigree correction factor (see Supplementary Methods).
[c]For the combined study populations, the reported control frequency was the average, unweighted control frequency of the individual populations, while the OR and the P value were estimated using the Mantel-Haenszel model.

TABLE 17

Association results for rs721048 on 2p15 and prostate cancer
in Iceland, The Netherlands, Spain, Sweden and the US

| Study population (N cases/N controls) Variant (allele) | Frequency Cases | Frequency Controls | OR (95% c.i.) | P value |
|---|---|---|---|---|
| Iceland(1,854/21,064)[a] | | | | |
| rs2710646 (A)[b] | 0.227 | 0.202 | 1.16 (1.06-1.26) | $7.79 \times 10^{-4}$ |
| rs721048 (A) | 0.229 | 0.204 | 1.16 (1.06-1.27) | $9.22 \times 10^{-4}$ |
| The Netherlands (998/2,021) | | | | |
| rs721048 (A) | 0.205 | 0.187 | 1.12 (0.98-1.28) | 0.095 |
| Spain (548/1,616) | | | | |
| rs721048 (A) | 0.234 | 0.210 | 1.15 (0.98-1.35) | 0.088 |
| Sweden (2,849/1,731) | | | | |
| rs721048 (A) | 0.201 | 0.186 | 1.10 (0.98-1.23) | 0.090 |
| Baltimore, Maryland (1,521/557) | | | | |
| rs721048 (A) | 0.205 | 0.206 | 1.00 (0.46-2.20) | 0.99 |
| Chicago, Illinois (665/552) | | | | |
| rs721048 (A) | 0.198 | 0.168 | 1.22 (1.00-1.49) | 0.055 |
| Nashville, Tennessee (526/612) | | | | |
| rs721048 (A) | 0.240 | 0.175 | 1.49 (1.21-1.83) | $1.39 \times 10^{-4}$ |
| Rochester, Minnesota (1,132/501)[c] | | | | |
| rs721048 (A) | 0.224 | 0.184 | 1.28 (1.06-1.55) | 0.012 |

TABLE 17-continued

Association results for rs721048 on 2p15 and prostate cancer
in Iceland, The Netherlands, Spain, Sweden and the US

| Study population (N cases/N controls) Variant (allele) | Frequency Cases | Controls | OR (95% c.i.) | P value |
|---|---|---|---|---|
| All excluding Iceland (8,239/7,590)[d] | | | | |
| rs721048 (A) | — | 0.188 | 1.15 (1.09-1.22) | $2.23 \times 10^{-6}$ |
| All combined (10,093/28,654)[d] | | | | |
| rs721048 (A) | — | 0.190 | 1.15 (1.10-1.21) | $7.66 \times 10^{-9}$ |

All P values shown are two-sided. Shown are the corresponding numbers of cases and controls (N), allelic frequencies of variants in affected and control individuals, the allelic odds-ratio (OR) with 95% confidence interval (95% c.i.) and P values based on the multiplicative model.
[a] Results presented for Iceland were adjusted for relatedness using a method of genomic control (see Supplementary Methods).
[b] The SNPs rs2710646 and rs721048 are highly correlated ($r^2 = 0.99$) but rs2710646 failed in genotyping in some of the non-Icelandic groups and results are therefore only presented for this marker from the Icelandic study group.
[c] Results presented for Rochester were adjusted for relatedness by applying a pedigree correction factor (see Supplementary Methods).
[d] For the combined study populations, the reported control frequency was the average, unweighted control frequency of the individual populations, while the OR and the P value were estimated using the Mantel-Haenszel model.

REFERENCES

1. Gudmundsson, J. et al. Genome-wide association study identifies a second prostate cancer susceptibility variant at 8q24. *Nat Genet* 39, 631-7 (2007).
2. Gudmundsson, J. et al. Two variants on chromosome 17 confer prostate cancer risk, and the one in TCF2 protects against type 2 diabetes. *Nat Genet* 39, 977-83 (2007).
3. Narod, S. A. et al. The impact of family history on early detection of prostate cancer. *Nat Med* 1, 99-101 (1995).
4. Monroe, K. R. et al. Evidence of an X-linked or recessive genetic component to prostate cancer risk. *Nat Med* 1, 827-9. (1995).
5. Yeager, M. et al. Genome-wide association study of prostate cancer identifies a second risk locus at 8q24. *Nat Genet* 39, 645-649 (2007).
6. Guilherme, A. et al. EHD2 and the novel EH domain binding protein EHBP1 couple endocytosis to the actin cytoskeleton. *J Biol Chem* 279, 10593-605 (2004).
7. Salehi, A. H., Xanthoudakis, S. & Barker, P. A. NRAGE, a p75 neurotrophin receptor-interacting protein, induces caspase activation and cell death through a JNK-dependent mitochondrial pathway. *J Biol Chem* 277, 48043-50 (2002).
8. Salehi, A. H. et al. NRAGE, a novel MAGE protein, interacts with the p75 neurotrophin receptor and facilitates nerve growth factor-dependent apoptosis. *Neuron* 27, 279-88 (2000).
9. Hidaka, K. et al. An adjacent pair of human NUDT genes on chromosome X are preferentially expressed in testis and encode two new isoforms of diphosphoinositol polyphosphate phosphohydrolase. *J Biol Chem* 277, 32730-8 (2002).
10. Dubois, E. et al. In *Saccharomyces cerevisiae*, the inositol polyphosphate kinase activity of Kcs1p is required for resistance to salt stress, cell wall integrity, and vacuolar morphogenesis. *J Biol Chem* 277, 23755-63 (2002).
11. Morrison, B. H., Bauer, J. A., Kalvakolanu, D. V. & Lindner, D. J. Inositol hexakisphosphate kinase 2 mediates growth suppressive and apoptotic effects of interferon-beta in ovarian carcinoma cells. *J Biol Chem* 276, 24965-70 (2001).
12. Amundadottir, L. T. et al. A common variant associated with prostate cancer in European and African populations. *Nat Genet* 38, 652-8 (2006).
13. Haiman, C. A. et al. Multiple regions within 8q24 independently affect risk for prostate cancer. *Nat Genet* 39, 638-44 (2007).

TABLE 18

Association results for rs721048 on 2q15 and aggressive prostate
cancer in Iceland, The Netherlands, Spain, Sweden and the US

| Study population (N cases/N controls) Variant (allele) | Frequency Cases | Controls | OR (95% c.i) | P value |
|---|---|---|---|---|
| Aggressive prostate cancer[a] | | | | |
| Iceland (694/21,064)[b] | | | | |
| rs2710646 (A)[c] | 0.251 | 0.202 | 1.33 (1.16-1.52) | $3.73 \times 10^{-5}$ |
| rs721048 (A) | 0.254 | 0.205 | 1.33 (1.16-1.52) | $3.71 \times 10^{-5}$ |
| The Netherlands (466/2,021) | | | | |
| rs721048 (A) | 0.211 | 0.187 | 1.16 (0.97-1.38) | 0.095 |
| Spain (185/1,616) | | | | |
| rs721048 (A) | 0.227 | 0.210 | 1.11 (0.85-1.46) | 0.45 |

TABLE 18-continued

Association results for rs721048 on 2q15 and aggressive prostate cancer in Iceland, The Netherlands, Spain, Sweden and the US

| Study population (N cases/N controls) Variant (allele) | Frequency Cases | Controls | OR (95% c.i) | P value |
|---|---|---|---|---|
| Aggressive prostate cancer[a] | | | | |
| Sweden (1,210/1,731) | | | | |
| rs721048 (A) | 0.202 | 0.186 | 1.11 (0.97-1.27) | 0.12 |
| Baltimore, Maryland (1,003/557) | | | | |
| rs721048 (A) | 0.218 | 0.206 | 1.08 (0.90-1.30) | 0.42 |
| Chicago, Illinois (320/552) | | | | |
| rs721048 (A) | 0.208 | 0.168 | 1.30 (1.02-1.66) | 0.037 |
| Nashville, Tennessee (255/612) | | | | |
| rs721048 (A) | 0.257 | 0.175 | 1.63 (1.27-2.09) | $1.28 \times 10^{-4}$ |
| Rochester, Minnesota (654/501)[d] | | | | |
| rs721048 (A) | 0.232 | 0.184 | 1.34 (1.08-1.66) | $7.07 \times 10^{-3}$ |
| All excluding Iceland (4,093/7,590)[e] | | | | |
| rs721048 (A) | — | 0.188 | 1.19 (1.11-1.28) | $2.12 \times 10^{-6}$ |
| All combined (4,787/28,654)[e] | | | | |
| rs721048 (A) | — | 0.190 | 1.22 (1.14-1.30) | $8.68 \times 10^{-10}$ |

All P values shown are two-sided. Shown are the corresponding numbers of cases and controls (N), allelic frequencies of variants in affected and control individuals, the allelic odds-ratio (OR) with 95% confidence interval (95% c.i.) and P values based on the multiplicative model.
[a]Aggressive prostate cancer is defined here as: Gleason ≥7 and/or T3 or higher and/or node positive and/or metastatic disease
[b]Results presented for Iceland were adjusted for relatedness using a method of genomic control
[c]The SNPs rs2710646 and rs721048 are highly correlated ($r^2 = 0.99$) but rs2710646 failed in genotyping in some of the non-Icelandic groups and results are therefore only presented for this marker from the Icelandic study group.
[d]Results presented for Rochester were adjusted for relatedness by applying a pedigree correction factor.
[e]For the combined study populations, the reported control frequency was the average, unweighted control frequency of the individual populations, while the OR and the P value were estimated using the Mantel-Haenszel model.

TABLE 19

LD-characteristics and adjusted association results for markers correlated with markers rs5945572 and rs2710646

| Chromosome | Marker-1 | Marker-2 | D' | $r^2$ | P value[a] |
|---|---|---|---|---|---|
| X | rs1327304 | rs5945572 | 1.00 | 1.00 | 0.31 |
| X | rs1327301 | rs5945572 | 1.00 | 0.92 | 0.23 |
| X | rs5945650 | rs5945572 | 0.97 | 0.88 | 0.86 |
| X | rs1936034 | rs5945572 | 0.97 | 0.88 | 0.96 |
| X | rs11798651 | rs5945572 | 0.95 | 0.83 | 0.36 |
| X | rs5945607 | rs5945572 | 0.95 | 0.83 | 0.35 |
| X | rs4907790 | rs5945572 | 0.95 | 0.82 | 0.13 |
| X | rs5945606 | rs5945572 | 0.95 | 0.81 | 0.26 |
| X | rs5945605 | rs5945572 | 0.94 | 0.80 | 0.15 |
| X | rs1984280 | rs5945572 | 0.90 | 0.75 | 0.50 |
| X | rs6521795 | rs5945572 | 0.92 | 0.54 | 0.75 |
| X | rs5945620 | rs5945572 | 0.98 | 0.43 | 0.36 |
| 2 | rs2553041 | rs2710646 | 1.00 | 1.00 | 0.77 |
| 2 | rs17432497 | rs2710646 | 1.00 | 0.98 | 0.22 |
| 2 | rs13431765 | rs2710646 | 0.99 | 0.79 | 0.33 |
| 2 | rs2176418 | rs2710646 | 1.00 | 0.56 | 0.88 |
| 2 | rs6545986 | rs2710646 | 0.99 | 0.55 | 0.89 |
| 2 | rs1517405 | rs2710646 | 0.99 | 0.55 | 0.92 |
| 2 | rs959195 | rs2710646 | 0.90 | 0.47 | 0.33 |
| 2 | rs7591708 | rs2710646 | 1.00 | 0.41 | 0.60 |

Shown are P values and LD-characteristics (D' and $r^2$) from an analysis on 1,500 and 800 Icelandic patients and controls, respectively.
[a]The P-value is for the association of Marker-1 to prostate cancer and has been adjusted for Marker-2 (rs5945572 or rs2710646).

TABLE 20

Analysis of combined risk for eight SNP markers associated with prostate cancer under the multiplicative model. There are $3^7 \times 2^1 = 4374$ possible genotype combinations for the eight markers. Shown are the 20 combinations that confer the lowest risk of prostate cancer (A), the 20 combinations that confer the highest risk of prostate cancer (B), and the 20 most common combinations in the general population (C). Shown are risk estimates with respect to non-carriers of all the at-risk variants (Risk 1), risk estimates with respect to the population (Risk 2), frequency of each genotype combination (Freq), cumulative frequency based on sorting on Risk 2 and start the addition from the lowest risk combination (Cumulative Freq), and genotype combinations for the eight markers. The ratio between Risk 1 and Risk 2 values is always identical, i.e. $1/0.332 = 3.012$, since the former is calculated by reference to the genotype combination that includes non-carriers (i.e., homozygotes for the non-risk, or protective, variant) at all the markers.

A.

| OR_vs_NC Risk_1 | OR_vs_pop Risk_2 | Freq | Cumulative_Freq | C08 rs10505483 | C08 rs1447295 |
|---|---|---|---|---|---|
| 1.488 | 0.494 | 1.6986E-03 | 0.0434 | GG | CC |
| 1.476 | 0.490 | 6.0132E-03 | 0.0417 | GG | CC |
| 1.476 | 0.490 | 1.4297E-03 | 0.0357 | GG | CC |
| 1.464 | 0.486 | 1.5963E-03 | 0.0342 | GG | CC |
| 1.464 | 0.486 | 5.0612E-03 | 0.0327 | GG | CC |
| 1.461 | 0.484 | 1.4622E-03 | 0.0276 | GG | CC |
| 1.452 | 0.482 | 5.3743E-03 | 0.0261 | GG | CC |
| 1.440 | 0.478 | 1.1309E-03 | 0.0208 | GG | CC |
| 1.414 | 0.469 | 3.9367E-04 | 0.0196 | GG | CC |
| 1.403 | 0.465 | 1.3937E-03 | 0.0192 | GG | CC |
| 1.392 | 0.462 | 1.4799E-03 | 0.0178 | GG | CC |
| 1.380 | 0.458 | 1.2456E-03 | 0.0164 | GG | CC |
| 1.322 | 0.439 | 8.5747E-05 | 0.0151 | GG | CC |
| 1.270 | 0.421 | 3.1168E-03 | 0.0150 | GG | CC |
| 1.230 | 0.408 | 8.3915E-04 | 0.0119 | GG | CC |
| 1.220 | 0.405 | 2.9707E-03 | 0.0111 | GG | CC |
| 1.210 | 0.401 | 3.1545E-03 | 0.0081 | GG | CC |
| 1.200 | 0.398 | 2.6551E-03 | 0.0049 | GG | CC |
| 1.150 | 0.381 | 7.3111E-04 | 0.0023 | GG | CC |
| 1.000 | 0.332 | 1.5584E-03 | 0.0016 | GG | CC |

| OR_vs_NC Risk_1 | C17 rs1859962 | C02 rs2710646 | C17 rs4430796 | CX rs5945572 | C08 rs6983267 | C11 rs10896450 |
|---|---|---|---|---|---|---|
| 1.488 | TT | TT | GG | AA | TT | AG |
| 1.476 | TT | TT | AG | GG | TT | AG |
| 1.476 | GT | TT | GG | AA | TT | AA |
| 1.464 | TT | TT | GG | GG | TT | GG |
| 1.464 | GT | TT | AG | GG | TT | AA |
| 1.461 | TT | AT | GG | GG | GT | AA |
| 1.452 | GT | TT | GG | GG | TT | AG |
| 1.440 | GG | TT | GG | GG | TT | AA |
| 1.414 | TT | AT | GG | AA | TT | AA |
| 1.403 | TT | AT | AG | GG | TT | AA |
| 1.392 | TT | AT | GG | GG | TT | AG |
| 1.380 | GT | AT | GG | GG | TT | AA |
| 1.322 | TT | AA | GG | GG | TT | AA |
| 1.270 | TT | TT | GG | GG | GT | AA |
| 1.230 | TT | TT | GG | AA | TT | AA |
| 1.220 | TT | TT | AG | GG | TT | AA |
| 1.210 | TT | TT | GG | GG | TT | AG |
| 1.200 | GT | TT | GG | GG | TT | AA |
| 1.150 | TT | AT | GG | GG | TT | AA |
| 1.000 | TT | TT | GG | GG | TT | AA |

B.

| OR_vs_NC Risk_1 | OR_vs_pop Risk_2 | Freq | Cumulative_Freq | C08 rs10505483 | C08 rs1447295 |
|---|---|---|---|---|---|
| 53.108 | 17.618 | 3.2757E-10 | 1.0000 | AA | AA |
| 46.181 | 15.320 | 2.7930E-09 | 1.0000 | AA | AA |
| 44.257 | 14.681 | 7.6908E-10 | 1.0000 | AA | AA |
| 43.891 | 14.560 | 6.4733E-10 | 1.0000 | AA | AA |
| 43.531 | 14.441 | 6.8736E-10 | 1.0000 | AA | AA |
| 43.177 | 14.323 | 6.0835E-10 | 1.0000 | AA | AA |
| 41.817 | 13.872 | 6.5514E-10 | 1.0000 | AA | AA |
| 40.157 | 13.321 | 5.9534E-09 | 1.0000 | AA | AA |
| 38.484 | 12.766 | 6.5574E-09 | 1.0000 | AA | AA |

TABLE 20-continued

Analysis of combined risk for eight SNP markers associated with prostate cancer under the multiplicative model. There are $3^7 \times 2^1 = 4374$ possible genotype combinations for the eight markers. Shown are the 20 combinations that confer the lowest risk of prostate cancer (A), the 20 combinations that confer the highest risk of prostate cancer (B), and the 20 most common combinations in the general population (C). Shown are risk estimates with respect to non-carriers of all the at-risk variants (Risk 1), risk estimates with respect to the population (Risk 2), frequency of each genotype combination (Freq), cumulative frequency based on sorting on Risk 2 and start the addition from the lowest risk combination (Cumulative Freq), and genotype combinations for the eight markers. The ratio between Risk 1 and Risk 2 values is always identical, i.e. $1/0.332 = 3.012$, since the former is calculated by reference to the genotype combination that includes non-carriers (i.e., homozygotes for the non-risk, or protective, variant) at all the markers.

| | | | | | |
|---|---|---|---|---|---|
| 38.166 | 12.661 | 5.5193E−09 | 1.0000 | AA | AA |
| 37.853 | 12.557 | 5.8607E−09 | 1.0000 | AA | AA |
| 37.545 | 12.455 | 5.1870E−09 | 1.0000 | AA | AA |
| 36.881 | 12.234 | 4.5142E−10 | 1.0000 | AA | AA |
| 36.576 | 12.133 | 1.5198E−09 | 1.0000 | AA | AA |
| 36.363 | 12.063 | 5.5859E−09 | 1.0000 | AA | AA |
| 36.276 | 12.034 | 1.6138E−09 | 1.0000 | AA | AA |
| 36.273 | 12.033 | 3.1980E−10 | 1.0000 | AA | AA |
| 35.981 | 11.936 | 1.4283E−09 | 1.0000 | AA | AA |
| 35.976 | 11.934 | 1.3583E−09 | 1.0000 | AA | AA |
| 35.684 | 11.837 | 1.2022E−09 | 1.0000 | AA | AA |

| OR_vs_NC Risk_1 | C17 rs1859962 | C02 rs2710646 | C17 rs4430796 | CX rs5945572 | C08 rs6983267 | C11 rs10896450 |
|---|---|---|---|---|---|---|
| 53.108 | GG | AA | AA | AA | GG | GG |
| 46.181 | GG | AT | AA | AA | GG | GG |
| 44.257 | GT | AA | AA | AA | GG | GG |
| 43.891 | GG | AA | AA | AA | GG | AG |
| 43.531 | GG | AA | AG | AA | GG | GG |
| 43.177 | GG | AA | AA | GG | GG | GG |
| 41.817 | GG | AA | AA | AA | GT | GG |
| 40.157 | GG | TT | AA | AA | GG | GG |
| 38.484 | GT | AT | AA | AA | GG | GG |
| 38.166 | GG | AT | AA | AA | GG | AG |
| 37.853 | GG | AT | AG | AA | GG | GG |
| 37.545 | GG | AT | AA | GG | GG | GG |
| 36.881 | TT | AA | AA | AA | GG | GG |
| 36.576 | GT | AA | AA | AA | GG | AG |
| 36.363 | GG | AT | AA | AA | GT | GG |
| 36.276 | GT | AA | AG | AA | GG | GG |
| 36.273 | GG | AA | AA | AA | GG | AA |
| 35.981 | GT | AA | AA | GG | GG | GG |
| 35.976 | GG | AA | AG | AA | GG | AG |
| 35.684 | GG | AA | AA | GG | GG | AG |

C.

| OR_vs_NC Risk_1 | OR_vs_pop Risk_2 | Freq | Cumulative_Freq | C08 rs10505483 | C08 rs1447295 |
|---|---|---|---|---|---|
| 2.250 | 0.746 | 2.0489E−02 | 0.3088 | GG | CC |
| 1.875 | 0.622 | 1.2026E−02 | 0.1699 | GG | CC |
| 2.767 | 0.918 | 1.1033E−02 | 0.5291 | GG | CC |
| 1.844 | 0.612 | 1.0749E−02 | 0.1397 | GG | CC |
| 2.722 | 0.903 | 1.0368E−02 | 0.4943 | GG | CC |
| 2.857 | 0.948 | 1.0245E−02 | 0.5675 | GG | CC |
| 1.771 | 0.588 | 1.0245E−02 | 0.1038 | GG | CC |
| 1.859 | 0.617 | 1.0122E−02 | 0.1512 | GG | CC |
| 2.745 | 0.910 | 9.7645E−03 | 0.5151 | GG | CC |
| 2.587 | 0.858 | 9.6123E−03 | 0.4239 | GG | CC |
| 2.700 | 0.896 | 8.7269E−03 | 0.4735 | GG | CC |
| 2.306 | 0.765 | 6.4757E−03 | 0.3493 | GG | CC |
| 1.537 | 0.510 | 6.3089E−03 | 0.0583 | GG | CC |
| 2.268 | 0.753 | 6.0858E−03 | 0.3284 | GG | CC |
| 2.381 | 0.790 | 6.0132E−03 | 0.3765 | GG | CC |
| 1.476 | 0.490 | 6.0132E−03 | 0.0417 | GG | CC |
| 1.549 | 0.514 | 5.9415E−03 | 0.0643 | GG | CC |
| 2.268 | 0.752 | 5.7877E−03 | 0.3175 | GG | CC |
| 2.287 | 0.759 | 5.7313E−03 | 0.3423 | GG | CC |
| 2.156 | 0.715 | 5.6420E−03 | 0.2436 | GG | CC |
| 3.348 | 1.111 | 5.5830E−03 | 0.7050 | GG | CC |
| 3.514 | 1.166 | 5.5164E−03 | 0.7574 | GG | CC |
| 2.179 | 0.723 | 5.5164E−03 | 0.2596 | GG | CC |

TABLE 20-continued

Analysis of combined risk for eight SNP markers associated with prostate cancer under the multiplicative model. There are $3^7 \times 2^1 = 4374$ possible genotype combinations for the eight markers. Shown are the 20 combinations that confer the lowest risk of prostate cancer (A), the 20 combinations that confer the highest risk of prostate cancer (B), and the 20 most common combinations in the general population (C). Shown are risk estimates with respect to non-carriers of all the at-risk variants (Risk 1), risk estimates with respect to the population (Risk 2), frequency of each genotype combination (Freq), cumulative frequency based on sorting on Risk 2 and start the addition from the lowest risk combination (Cumulative Freq), and genotype combinations for the eight markers. The ratio between Risk 1 and Risk 2 values is always identical, i.e. $1/0.332 = 3.012$, since the former is calculated by reference to the genotype combination that includes non-carriers (i.e., homozygotes for the non-risk, or protective, variant) at all the markers.

| 2.287 | 0.759 | 5.4506E−03 | 0.3348 | GG | CC |
| 2.231 | 0.740 | 5.4391E−03 | 0.2839 | GG | CC |
| 2.342 | 0.777 | 5.3743E−03 | 0.3589 | GG | CC |
| 1.452 | 0.482 | 5.3743E−03 | 0.0261 | GG | CC |
| 1.524 | 0.506 | 5.3102E−03 | 0.0517 | GG | CC |
| 3.376 | 1.120 | 5.2578E−03 | 0.7129 | GG | CC |
| 3.457 | 1.147 | 5.1842E−03 | 0.7372 | GG | CC |

| OR_vs_NC Risk_1 | C17 rs1859962 | C02 rs2710646 | C17 rs4430796 | CX rs5945572 | C08 rs6983267 | C11 rs10896450 |
|---|---|---|---|---|---|---|
| 2.250 | GT | TT | AG | GG | GT | AG |
| 1.875 | TT | TT | AG | GG | GT | AG |
| 2.767 | GT | TT | AG | AA | GT | AG |
| 1.844 | GT | TT | GG | GG | GT | AG |
| 2.722 | GT | TT | AG | GG | GT | GG |
| 2.857 | GT | TT | AG | GG | GG | AG |
| 1.771 | GT | TT | AG | GG | TT | AG |
| 1.859 | GT | TT | AG | GG | GT | AA |
| 2.745 | GT | TT | AA | GG | GT | AG |
| 2.587 | GT | AT | AG | GG | GT | AG |
| 2.700 | GG | TT | AG | GG | GT | AG |
| 2.306 | TT | TT | AG | AA | GT | AG |
| 1.537 | TT | TT | GG | GG | GT | AG |
| 2.268 | TT | TT | AG | GG | GT | GG |
| 2.381 | TT | TT | AG | GG | GG | AG |
| 1.476 | TT | TT | AG | GG | TT | AG |
| 1.549 | TT | TT | AG | GG | GT | AA |
| 2.268 | GT | TT | GG | AA | GT | AG |
| 2.287 | TT | TT | AA | GG | GT | AG |
| 2.156 | TT | AT | AG | GG | GT | AG |
| 3.348 | GT | TT | AG | AA | GT | GG |
| 3.514 | GT | TT | AG | AA | GG | AG |
| 2.179 | GT | TT | AG | AA | TT | AG |
| 2.287 | GT | TT | AG | AA | GT | AA |
| 2.231 | GT | TT | GG | GG | GT | GG |
| 2.342 | GT | TT | GG | GG | GG | AG |
| 1.452 | GT | TT | GG | GG | TT | AG |
| 1.524 | GT | TT | GG | GG | GT | AA |
| 3.376 | GT | TT | AA | AA | GT | AG |
| 3.457 | GT | TT | AG | GG | GG | GG |

TABLE 21

SEQ ID key to markers.

| SNP | SEQ ID NO |
|---|---|
| rs3923603 | 1 |
| rs4430796 | 2 |
| rs7501939 | 3 |
| rs1859962 | 4 |
| D17S1350 | 5 |
| rs5945572 | 6 |
| rs5945605 | 7 |
| rs2710646 | 8 |
| rs6857303 | 9 |
| rs7665923 | 10 |
| rs11725211 | 11 |
| rs13103731 | 12 |
| rs11736498 | 13 |
| rs11723763 | 14 |
| rs6831817 | 15 |
| rs13134172 | 16 |
| rs10015396 | 17 |
| rs4269130 | 18 |
| rs4289393 | 19 |
| rs6812128 | 20 |
| rs7695923 | 21 |
| rs4599356 | 22 |
| rs7692784 | 23 |
| rs4303930 | 24 |

TABLE 21-continued

SEQ ID key to markers.

| SNP | SEQ ID NO |
|---|---|
| rs10012731 | 25 |
| rs6537264 | 26 |
| rs4417920 | 27 |
| rs4505762 | 28 |
| rs4583707 | 29 |
| rs4425324 | 30 |
| rs13127749 | 31 |
| rs4518185 | 32 |
| rs4549337 | 33 |
| rs4390989 | 34 |
| rs4305469 | 35 |
| rs7658605 | 36 |
| rs6828217 | 37 |
| rs7441314 | 38 |
| rs12505797 | 39 |
| rs12503177 | 40 |
| rs4482709 | 41 |
| rs4320096 | 42 |
| rs13144823 | 43 |
| rs11100843 | 44 |
| rs7679401 | 45 |
| rs7684835 | 46 |
| rs11943703 | 47 |
| rs12509569 | 48 |
| rs7689179 | 49 |
| rs10002827 | 50 |
| rs1016990 | 51 |
| rs3744763 | 52 |
| rs757210 | 53 |
| rs4239217 | 54 |
| rs3760511 | 55 |
| rs7213769 | 56 |
| rs4793330 | 57 |
| rs1861690 | 58 |
| rs7222314 | 59 |
| rs8071558 | 60 |
| rs984434 | 61 |
| rs11650165 | 62 |
| rs991429 | 63 |
| rs4793528 | 64 |
| rs9674957 | 65 |
| rs8077906 | 66 |
| rs8066875 | 67 |
| rs9889335 | 68 |
| rs4328484 | 69 |
| rs8068266 | 70 |
| rs7217652 | 71 |
| rs6501437 | 72 |
| rs6501438 | 73 |
| rs8079315 | 74 |
| rs2367256 | 75 |
| rs2190697 | 76 |
| rs4366746 | 77 |
| rs4366747 | 78 |
| rs2159034 | 79 |
| rs1013999 | 80 |
| rs4793530 | 81 |
| rs11654749 | 82 |
| rs11653132 | 83 |
| rs4300694 | 84 |
| rs8076830 | 85 |
| rs9900242 | 86 |
| rs2058083 | 87 |
| rs2058085 | 88 |
| rs1468481 | 89 |
| rs2041114 | 90 |
| rs723338 | 91 |
| rs2041115 | 92 |
| rs8064263 | 93 |
| rs9897865 | 94 |
| rs11656242 | 95 |
| rs9897358 | 96 |
| rs11651123 | 97 |
| rs11657298 | 98 |
| rs11651469 | 99 |
| rs11651501 | 100 |
| rs719615 | 101 |
| rs1558119 | 102 |
| rs12150098 | 103 |
| rs9910829 | 104 |
| rs7220274 | 105 |
| rs17224833 | 106 |
| rs2108534 | 107 |
| rs2108535 | 108 |
| rs8182284 | 109 |
| rs8182286 | 110 |
| rs4793533 | 111 |
| rs8069925 | 112 |
| rs8068189 | 113 |
| rs9901508 | 114 |
| rs9907418 | 115 |
| rs2367263 | 116 |
| rs1859964 | 117 |
| rs1859965 | 118 |
| rs6501446 | 119 |
| rs4793534 | 120 |
| rs4239156 | 121 |
| rs4793335 | 122 |
| rs2097984 | 123 |
| rs11654068 | 124 |
| rs8079962 | 125 |
| rs2886914 | 126 |
| rs8076811 | 127 |
| rs17178251 | 128 |
| rs758106 | 129 |
| rs740408 | 130 |
| rs4570900 | 131 |
| rs4611499 | 132 |
| rs7214479 | 133 |
| rs1008348 | 134 |
| rs6501449 | 135 |
| rs6501451 | 136 |
| rs6501452 | 137 |
| rs11870732 | 138 |
| rs17178370 | 139 |
| rs7225025 | 140 |
| rs17178377 | 141 |
| rs11655744 | 142 |
| rs2367266 | 143 |
| rs1107305 | 144 |
| rs6501455 | 145 |
| rs7209505 | 146 |
| rs2190463 | 147 |
| rs2190456 | 148 |
| rs983085 | 149 |
| rs6501459 | 150 |
| rs4793538 | 151 |
| rs2158905 | 152 |
| rs2190457 | 153 |
| rs11655567 | 154 |
| rs7225458 | 155 |
| rs10401004 | 156 |
| rs917278 | 157 |
| rs1978203 | 158 |
| rs1978204 | 159 |
| rs737956 | 160 |
| rs737957 | 161 |
| rs8075481 | 162 |
| rs7224058 | 163 |
| rs7215307 | 164 |
| rs4793541 | 165 |
| rs7221080 | 166 |
| rs8064388 | 167 |
| rs9906756 | 168 |
| rs17178530 | 169 |
| rs17765886 | 170 |
| rs8070461 | 171 |
| rs9891216 | 172 |
| rs972635 | 173 |
| rs1875754 | 174 |

TABLE 21-continued

SEQ ID key to markers.

| SNP | SEQ ID NO |
|---|---|
| rs4907772 | 175 |
| rs6521795 | 176 |
| rs5945606 | 177 |
| rs5945569 | 178 |
| rs5987418 | 179 |
| rs4907790 | 180 |
| rs5945607 | 181 |
| rs11091727 | 182 |
| rs11798651 | 183 |
| rs5945609 | 184 |
| rs5945610 | 185 |
| rs10284147 | 186 |
| rs1327301 | 187 |
| rs1327302 | 188 |
| rs1327304 | 189 |
| rs5945617 | 190 |
| rs5945618 | 191 |
| rs12854262 | 192 |
| rs5945619 | 193 |
| rs5945620 | 194 |
| rs1891702 | 195 |
| rs4907792 | 196 |
| rs2384958 | 197 |
| rs1936038 | 198 |
| rs5945573 | 199 |
| rs4907796 | 200 |
| rs4907775 | 201 |
| rs6614426 | 202 |
| rs1970956 | 203 |
| rs1970957 | 204 |
| rs2153993 | 205 |
| rs6614428 | 206 |
| rs6418006 | 207 |
| rs1541241 | 208 |
| rs1541240 | 209 |
| rs1592303 | 210 |
| rs1110404 | 211 |
| rs1110405 | 212 |
| rs5945643 | 213 |
| rs1343272 | 214 |
| rs5987438 | 215 |
| rs6614317 | 216 |
| rs1936037 | 217 |
| rs1936036 | 218 |
| rs3131302 | 219 |
| rs1361837 | 220 |
| rs1936035 | 221 |
| rs4457126 | 222 |
| rs4308906 | 223 |
| rs6521820 | 224 |
| rs4907781 | 225 |
| rs5945650 | 226 |
| rs7064708 | 227 |
| rs1936034 | 228 |
| rs5945651 | 229 |
| rs1541238 | 230 |
| rs1984280 | 231 |
| rs2721996 | 232 |
| rs5945653 | 233 |
| rs5945578 | 234 |
| rs3955398 | 235 |
| rs1419039 | 236 |
| rs1419038 | 237 |
| rs5987446 | 238 |
| rs1419040 | 239 |
| rs6614454 | 240 |
| rs1541242 | 241 |
| rs6521823 | 242 |
| rs5987447 | 243 |
| rs5945579 | 244 |
| rs7057039 | 245 |
| rs2185880 | 246 |
| rs5987448 | 247 |
| rs11091750 | 248 |
| rs4907804 | 249 |

TABLE 21-continued

SEQ ID key to markers.

| SNP | SEQ ID NO |
|---|---|
| rs5945658 | 250 |
| rs5945664 | 251 |
| rs5945667 | 252 |
| rs12558898 | 253 |
| rs5945586 | 254 |
| rs5945668 | 255 |
| rs5945587 | 256 |
| rs6521836 | 257 |
| rs4298665 | 258 |
| rs4544871 | 259 |
| rs4473816 | 260 |
| rs5945590 | 261 |
| rs5945677 | 262 |
| rs12394792 | 263 |
| rs5951067 | 264 |
| rs4986571 | 265 |
| rs5951072 | 266 |
| rs6614493 | 267 |
| rs5951074 | 268 |
| rs11796743 | 269 |
| rs974285 | 270 |
| rs976556 | 271 |
| rs3910588 | 272 |
| rs3910587 | 273 |
| rs1439461 | 274 |
| rs2118952 | 275 |
| rs4986558 | 276 |
| rs5991819 | 277 |
| rs5991820 | 278 |
| rs12399757 | 279 |
| rs12398578 | 280 |
| rs2118951 | 281 |
| rs12844657 | 282 |
| rs11796701 | 283 |
| rs9887648 | 284 |
| rs12010969 | 285 |
| rs5991822 | 286 |
| rs5991733 | 287 |
| rs12393443 | 288 |
| rs6521844 | 289 |
| rs5991824 | 290 |
| rs4986559 | 291 |
| rs7890241 | 292 |
| rs4986553 | 293 |
| rs5991735 | 294 |
| rs5951078 | 295 |
| rs5951079 | 296 |
| rs4986554 | 297 |
| rs1439460 | 298 |
| rs5951064 | 299 |
| rs5951083 | 300 |
| rs7061919 | 301 |
| rs7056700 | 302 |
| rs12853137 | 303 |
| rs12353683 | 304 |
| rs7880576 | 305 |
| rs4133299 | 306 |
| rs5991738 | 307 |
| rs1992271 | 308 |
| rs5991739 | 309 |
| rs1048437 | 310 |
| rs5951087 | 311 |
| rs7053197 | 312 |
| rs5991707 | 313 |
| rs11796891 | 314 |
| rs5951091 | 315 |
| rs7053327 | 316 |
| rs7051319 | 317 |
| rs5991744 | 318 |
| rs11796974 | 319 |
| rs4074722 | 320 |
| rs12388600 | 321 |
| rs4986557 | 322 |
| rs6614515 | 323 |
| rs4131729 | 324 |

TABLE 21-continued

SEQ ID key to markers.

| SNP | SEQ ID NO |
|---|---|
| rs5991762 | 325 |
| rs11798798 | 326 |
| rs12395699 | 327 |
| rs5991776 | 328 |
| rs5951070 | 329 |
| rs11797967 | 330 |
| rs12394739 | 331 |
| rs5991804 | 332 |
| rs5991805 | 333 |
| rs12845073 | 334 |
| rs12851025 | 335 |
| rs6413596 | 336 |
| rs5991812 | 337 |
| rs5951109 | 338 |
| rs5951114 | 339 |
| rs4986573 | 340 |
| rs7472562 | 341 |
| rs721048 | 342 |
| rs6857262 | 343 |
| rs7700104 | 344 |
| rs4240360 | 345 |
| rs12510585 | 346 |
| rs2005705 | 347 |
| rs7405696 | 348 |
| rs17765344 | 349 |
| rs8072254 | 350 |
| rs4793529 | 351 |
| rs9908442 | 352 |
| rs4793334 | 353 |
| rs2058084 | 354 |
| rs9915190 | 355 |
| rs6501447 | 356 |
| rs17765644 | 357 |
| rs9913988 | 358 |
| rs5987421 | 359 |
| rs12688960 | 360 |
| rs5945659 | 361 |
| rs4986555 | 362 |

The invention claimed is:

1. A method for determining a susceptibility to prostate cancer in a human individual, the method comprising analyzing nucleic acid from the human individual for the presence of at least one allele of at least one polymorphic marker, wherein the at least one allele comprises rs7501939, allele C,
   detecting the presence of allele C of polymorphic marker rs7501939 in the sample, and
   determining an increased genetic susceptibility to prostate cancer for the human individual from the presence of the at least one allele in the nucleic acid, and,
   performing at least one of a prostate specific antigen (PSA) test and a digital rectal examination (DRE) on the individual determined to have the increased genetic susceptibility.

2. The method of claim 1, wherein the analyzing of the nucleic acid comprises at least one nucleic acid analysis technique selected from: polymerase chain reaction, allele-specific hybridization, allele-specific primer extension, allele-specific amplification, nucleic acid sequencing, 5'-exonuclease digestion, molecular beacon assay, oligonucleotide ligation assay, size analysis, and single-stranded conformation analysis.

3. The method of claim 2 wherein the at least one nucleic acid analysis technique is selected from the group consisting of allele-specific probe hybridization and DNA sequencing.

4. The method of claim 1, further comprising calculating a risk measure for prostate cancer that includes a relative risk or odds ratio of at least 1.2 attributable to the presence of allele C of polymorphic marker rs7501939 in the sample, using an apparatus that comprises: a computer readable memory, a processor, and a routine stored on the computer readable memory; wherein the routine is adapted to be executed on the processor to analyze marker information for at least one human individual with respect to the at least one allele of the at least one polymorphic marker, and generate an output based on the marker information, wherein the output comprises a prostate cancer risk measure of the allele as a genetic indicator of the prostate cancer for the human individual.

5. The method of claim 1, further comprising making a communication that includes the risk measure available to the individual or to a third party.

6. The method of claim 5, wherein the communication is made available to the individual or third party by a secured internet interface.

7. The method of claim 1 wherein the human individual has not yet been diagnosed with prostate cancer.

8. A method for determining a susceptibility to prostate cancer in a human individual, the method comprising analyzing nucleic acid from the human individual for the presence of at least one allele of at least one polymorphic marker, wherein the at least one allele comprises rs4430796, allele A,
   detecting the presence of allele A of polymorphic marker rs4430796 in the sample, and
   determining an increased genetic susceptibility to prostate cancer for the human individual from the presence of the at least one allele in the nucleic acid, and,
   performing at least one of a prostate specific antigen (PSA) test and a digital rectal examination (DRE) on the individual determined to have the increased susceptibility.

9. The method of claim 8, wherein the analyzing of the nucleic acid comprises at least one nucleic acid analysis technique selected from: polymerase chain reaction, allele-specific hybridization, allele-specific primer extension, allele-specific amplification, nucleic acid sequencing, 5'-exonuclease digestion, molecular beacon assay, oligonucleotide ligation assay, size analysis, and single-stranded conformation analysis.

10. The method of claim 9 wherein the at least one nucleic acid analysis technique is selected from the group consisting of allele-specific probe hybridization and DNA sequencing.

11. The method of claim 8, further comprising calculating a risk measure for prostate cancer that includes a relative risk or odds ratio of at least 1.2 attributable to the presence of allele A of polymorphic marker rs4430796 in the sample, using an apparatus that comprises: a computer readable memory, a processor, and a routine stored on the computer readable memory; wherein the routine is adapted to be executed on the processor to analyze marker information for at least one human individual with respect to the at least one allele of the at least one polymorphic marker, and generate an output based on the marker information, wherein the output comprises a prostate cancer risk measure of the allele as a genetic indicator of the prostate cancer for the human individual.

12. The method of claim 8, further comprising making a communication that includes the risk measure available to the individual or to a third party.

13. The method of claim 12, wherein the communication is made available to the individual or third party by a secured internet interface.

14. The method of claim 8 wherein the human individual has not yet been diagnosed with prostate cancer.

* * * * *

UNITED STATES PATENT AND TRADEMARK OFFICE
CERTIFICATE OF CORRECTION

| | |
|---|---|
| PATENT NO. | : 8,865,400 B2 |
| APPLICATION NO. | : 12/442171 |
| DATED | : October 21, 2014 |
| INVENTOR(S) | : Julius Gudmundsson et al. |

It is certified that error appears in the above-identified patent and that said Letters Patent is hereby corrected as shown below:

On the Title Page:

Item (73) Assignee, line 1, "(IE)" should be -- (IS) --.

Signed and Sealed this
Seventeenth Day of November, 2015

Michelle K. Lee
*Director of the United States Patent and Trademark Office*